(12) United States Patent
Søe et al.

(10) Patent No.: US 7,906,307 B2
(45) Date of Patent: Mar. 15, 2011

(54) VARIANT LIPID ACYLTRANSFERASES AND METHODS OF MAKING

(75) Inventors: Jørn Borch Søe, Tilst (DK); Jørn Dalgaard Mikkelson, Hvidovre (DK); Arno de Kreij, Genève (CH)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 11/852,274

(22) Filed: Sep. 7, 2007

(65) Prior Publication Data

US 2008/0070287 A1 Mar. 20, 2008

Related U.S. Application Data

(63) Continuation-in-part of application No. PCT/IB2007/000558, filed on Jan. 25, 2007, and a continuation-in-part of application No. 10/911,160, filed on Aug. 2, 2004, now abandoned.

(30) Foreign Application Priority Data

| Dec. 24, 2003 | (GB) | 0330016.7 |
| Jul. 16, 2004 | (GB) | 0415999.2 |
| Aug. 17, 2007 | (GB) | 0716126.8 |

(51) Int. Cl.
| *G01N 33/53* | (2006.01) |
| *C12Q 1/34* | (2006.01) |
| *C12N 9/00* | (2006.01) |
| *C12N 9/16* | (2006.01) |
| *C12N 9/10* | (2006.01) |
| *C07K 14/00* | (2006.01) |

(52) U.S. Cl. ............ 435/193; 435/7.1; 435/18; 435/183; 435/196; 530/350

(58) Field of Classification Search .................. None
See application file for complete search history.

(56) References Cited

U.S. PATENT DOCUMENTS

| 2,888,385 | A | 5/1959 | Grandel |
| 3,260,606 | A | 7/1966 | Azuma |
| 3,368,903 | A | 2/1968 | Johnson |
| 3,520,702 | A | 7/1970 | Menzi |
| 3,634,195 | A | 1/1972 | Melachouris |
| 3,652,397 | A | 3/1972 | Pardun |
| 3,677,902 | A | 7/1972 | Aunstrup |
| 3,852,260 | A | 12/1974 | Knutsen |
| 3,973,042 | A | 8/1976 | Kosikowski |
| 4,034,124 | A | 7/1977 | Van Dam |
| 4,065,580 | A | 12/1977 | Feldman |
| 4,160,848 | A | 7/1979 | Vidal |
| 4,202,941 | A | 5/1980 | Terada |
| 4,399,218 | A | 8/1983 | Gauhl |
| 4,567,046 | A | 1/1986 | Inoue |
| 4,683,202 | A | 7/1987 | Mullis |
| 4,689,297 | A | 8/1987 | Good |
| 4,707,291 | A | 11/1987 | Thom |
| 4,707,364 | A | 11/1987 | Barach |
| 4,708,876 | A | 11/1987 | Yokoyama |
| 4,798,793 | A | 1/1989 | Eigtved |
| 4,808,417 | A | 2/1989 | Masuda |
| 4,810,414 | A | 3/1989 | Huge-Jensen |
| 4,814,331 | A | 3/1989 | Kerkenaar |
| 4,818,695 | A | 4/1989 | Eigtved |
| 4,826,767 | A | 5/1989 | Hansen |
| 4,865,866 | A | 9/1989 | Moore |
| 4,904,483 | A | 2/1990 | Christensen |
| 4,916,064 | A | 4/1990 | Derez |
| 5,112,624 | A | 5/1992 | Johna |
| 5,213,968 | A | 5/1993 | Castle |
| 5,219,733 | A | 6/1993 | Myojo |
| 5,219,744 | A | 6/1993 | Kurashige |
| 5,232,846 | A | 8/1993 | Takeda |
| 5,264,367 | A | 11/1993 | Aalrust |

(Continued)

FOREIGN PATENT DOCUMENTS

AR       331094       2/1995

(Continued)

OTHER PUBLICATIONS

Sequence alignment of database accession No. Q44268 (database: UNIProtKB/TrEMBL) with SEQ ID No. 16—2pages.*

(Continued)

*Primary Examiner* — Robert Mondesi
*Assistant Examiner* — Oluwatosin Ogunbiyi
(74) *Attorney, Agent, or Firm* — Frommer Lawrence & Haug LLP; Thomas J. Kowalski; Heather J. DiPietrantonio

(57) ABSTRACT

The present invention relates to a method for the production of a variant lipid acyltransferase comprising the steps of: (i) selecting a parent enzyme which is a lipid acyltransferase enzyme; (ii) modifying one or more amino acids to produce a variant lipid acyltransferase; (iii) testing the activity of the variant lipid acyltransferase on a galactolipid and/or phospholipid and/or triglyceride substrate; (iv) selecting a variant enzyme with enhanced activity towards galactolipids compared with the parent enzyme; (v) providing a *Bacillus licheniformis* cell; (vi) transforming the *Bacillus licheniformis* cell with a heterologous nucleotide sequence encoding said variant lipid acyltransferase; and (iii) expressing said variant lipid acyltransferase in the cell under the control of a promoter sequence. The variant lipid acyltransferase can undergo post-translations modification, truncation and/or clipping, i.e., to remove a signal peptide. In addition, the present invention further relates to the use of *Bacillus licheniformis* to express a lipid acyltransferase, a *Bacillus licheniformis* host cell comprising a heterologous lipid acyltransferase and a vector comprising a nucleotide sequence encoding a lipid acyltransferase operably linked to a promoter sequence homologous to *B. licheniformis*.

24 Claims, 45 Drawing Sheets

U.S. PATENT DOCUMENTS

| | | |
|---|---|---|
| 5,273,898 A | 12/1993 | Ishii |
| 5,288,619 A | 2/1994 | Brown |
| 5,290,694 A | 3/1994 | Nakanishi |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,677,160 A | 10/1997 | Oester |
| 5,695,802 A | 12/1997 | Van Den Ouweland |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen et al. |
| 6,180,406 B1 | 1/2001 | Stemmer |
| 6,254,645 B1 | 7/2001 | Kellis |
| 6,344,328 B1 | 2/2002 | Short |
| 6,350,604 B1 | 2/2002 | Hirayama |
| 6,358,543 B1 | 3/2002 | Soe et al. |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Søe et al. |
| 6,730,346 B2 | 5/2004 | Rey |
| 6,815,190 B1 | 11/2004 | Abo |
| 6,852,346 B2 | 2/2005 | Soe et al. |
| 6,936,289 B2 | 8/2005 | Olsen et al. |
| 6,967,035 B2 | 11/2005 | Bojsen et al. |
| 7,226,771 B2 | 6/2007 | Gramatikova et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0235106 A1 | 11/2004 | Kapeller-Libermann |
| 2004/0235119 A1 | 11/2004 | Hoppe et al. |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell |

FOREIGN PATENT DOCUMENTS

| | | |
|---|---|---|
| AR | 249546 | 12/1996 |
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 199742798 | 4/1998 |
| AU | 754470 | 11/1999 |
| BR | 8404421-7 | 4/1984 |
| CA | 805618 A | 2/1969 |
| CA | 462382 | 9/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CN | 97181706.5 | 12/1998 |
| CN | 036151 | 2/2002 |
| CN | 172509 | 6/2003 |
| DE | 2817087 | 11/1978 |
| DE | 19620649 | 11/1997 |
| DE | 69129968 | 3/1999 |
| DE | 69330066 | 10/2001 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |
| DK | 5559.215 | 10/1999 |
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | PA200300634 | 4/2003 |
| EP | 0064855 | 11/1982 |
| EP | 0010296 | 12/1982 |
| EP | 0109244 | 5/1984 |
| EP | 0130064 | 1/1985 |
| EP | 0140542 | 5/1985 |
| EP | 0167309 | 1/1986 |
| EP | 0171995 | 2/1986 |
| EP | 0205208 | 12/1986 |
| EP | 0206390 | 12/1986 |
| EP | 0 258 068 | 3/1988 |
| EP | 0257388 | 3/1988 |
| EP | 0260573 | 3/1988 |
| EP | 0334462 | 9/1989 |
| EP | 0195311 | 6/1990 |
| EP | 0375102 | 6/1990 |

| | | | | | | |
|---|---|---|---|---|---|---|
| EP | 0426211 | 5/1991 | | EP | 1 624 047 BI | 10/2006 |
| EP | 0445692 | 9/1991 | | ES | 535608 | 9/1984 |
| EP | 0449375 | 10/1991 | | ES | 535602 | 10/1984 |
| EP | 0468731 | 1/1992 | | ES | 535609 | 3/1985 |
| EP | 0513709 | 11/1992 | | GB | 1086550 | 10/1967 |
| EP | 0542351 | 5/1993 | | GB | 1442418 | 7/1976 |
| EP | 0558112 | 9/1993 | | GB | 1577933 | 10/1980 |
| EP | 0258068 | 11/1993 | | GB | 2264429 | 9/1993 |
| EP | 0238023 | 12/1993 | | GB | 0028701.1 | 11/2000 |
| EP | 0575133 | 12/1993 | | GB | 2358784 | 8/2001 |
| EP | 0580252 | 1/1994 | | GB | 0301117.8 | 1/2003 |
| EP | 0258068 | 8/1994 | | GB | 0301118.6 | 1/2003 |
| EP | 0622446 | 11/1994 | | GB | 0301119.4 | 1/2003 |
| EP | 0652289 | 5/1995 | | GB | 0301120.2 | 1/2003 |
| EP | 0654527 | 5/1995 | | GB | 0301121.0 | 1/2003 |
| EP | 0396162 | 9/1995 | | GB | 0301122.8 | 1/2003 |
| EP | 0585988 | 3/1996 | | GB | 2379165 | 3/2003 |
| EP | 0 375 102 | 4/1996 | | GB | 2267033 | 11/2003 |
| EP | 0721981 | 7/1996 | | GB | 0330016.7 | 12/2003 |
| EP | 0776604 | 6/1997 | | JP | 59183881 | 4/1960 |
| EP | 0531104 | 8/1997 | | JP | 5476892 | 6/1979 |
| EP | 0808903 | 11/1997 | | JP | 55131340 | 10/1980 |
| EP | 0682116 | 12/1997 | | JP | 60078529 | 5/1985 |
| EP | 0812910 | 12/1997 | | JP | 62118883 | 11/1985 |
| EP | 0305216 | 3/1998 | | JP | 63042691 | 8/1986 |
| EP | 0847701 | 6/1998 | | JP | 62061590 | 3/1987 |
| EP | 0548228 | 8/1998 | | JP | 62285749 | 12/1987 |
| EP | 0702712 | 12/1998 | | JP | 10203974 | 8/1988 |
| EP | 0882797 | 12/1998 | | JP | 1252294 | 10/1989 |
| EP | 0897667 | 2/1999 | | JP | 2-49593 | 2/1990 |
| EP | 0913092 | 5/1999 | | JP | 2-153997 | 6/1990 |
| EP | 0913468 | 5/1999 | | JP | 04075592 | 3/1992 |
| EP | 0321811 | 12/1999 | | JP | 6014773 | 3/1992 |
| EP | 1131416 | 6/2000 | | JP | 4121186 | 4/1992 |
| EP | 0739985 | 11/2000 | | JP | 15626492 | 6/1992 |
| EP | 1057415 | 12/2000 | | JP | 04200339 | 7/1992 |
| EP | 1071734 | 1/2001 | | JP | 4300839 | 10/1992 |
| EP | 0659049 | 3/2001 | | JP | 4327536 | 11/1992 |
| EP | 1103606 | 5/2001 | | JP | 93-700773 | 3/1993 |
| EP | 659049 | 6/2001 | | JP | 5211852 | 8/1993 |
| EP | 1108360 | 6/2001 | | JP | 6345800 | 12/1994 |
| EP | 1138763 | 10/2001 | | JP | 95-700043 | 1/1995 |
| EP | 1145637 | 10/2001 | | JP | 8268882 | 4/1995 |
| EP | 0191217 | 2/2002 | | JP | 7231788 | 9/1995 |
| EP | 0869167 | 2/2002 | | JP | 7330794 | 12/1995 |
| EP | 1193314 | 4/2002 | | JP | 8143457 | 6/1996 |
| EP | 0 746 618 | 8/2002 | | JP | 96-704602 | 8/1996 |
| EP | 1233676 | 8/2002 | | JP | 8266213 | 10/1996 |
| EP | 0648263 | 9/2002 | | JP | 9040689 | 2/1997 |
| EP | 0784674 | 9/2002 | | JP | 10155493 | 6/1998 |
| EP | 784674 | 11/2002 | | JP | 10155493 A | 6/1998 |
| EP | 1073339 | 11/2002 | | JP | 11290078 | 10/1999 |
| EP | 0869167 | 1/2003 | | JP | 2000226335 | 8/2000 |
| EP | 1073339 | 1/2003 | | JP | 2001-7012115 | 9/2001 |
| EP | 1275711 | 1/2003 | | JP | 2003-7008997 | 10/2003 |
| EP | 1285969 | 2/2003 | | JP | 3553958 | 5/2004 |
| EP | 1298205 | 4/2003 | | KR | 94-10252 | 10/1994 |
| EP | 0635053 | 6/2003 | | KR | 95-702583 | 6/1995 |
| EP | 0675944 | 6/2003 | | NL | 0784674 | 12/2002 |
| EP | 0817838 | 6/2003 | | NL | 0869167 | 1/2003 |
| EP | 1280919 | 6/2003 | | NL | 1073339 | 2/2003 |
| EP | 0746608 | 8/2003 | | NL | 0746608 | 11/2003 |
| EP | 0746618 | 8/2003 | | RU | 2140751 | 6/1997 |
| EP | 0746608 | 10/2003 | | RU | 2235775 | 11/1999 |
| EP | 1042458 | 3/2004 | | RU | 2001117497 | 6/2001 |
| EP | 0851913 | 5/2004 | | TR | 200101551 | 12/1999 |
| EP | 1262562 | 6/2004 | | WO | 88/02775 | 4/1988 |
| EP | 1433852 | 6/2004 | | WO | 88/03365 | 5/1988 |
| EP | 0977869 | 7/2004 | | WO | 89/01969 | 3/1989 |
| EP | 0743017 | 9/2004 | | WO | 89/06803 | 7/1989 |
| EP | 0675949 | 10/2004 | | WO | 91/00920 | 1/1991 |
| EP | 0880590 | 10/2004 | | WO | 91/06661 | 5/1991 |
| EP | 0897423 | 10/2004 | | WO | 91/14772 | 10/1991 |
| EP | 1466980 | 10/2004 | | WO | 92/05249 | 4/1992 |
| EP | 0839186 | 11/2004 | | WO | 92/14830 | 9/1992 |
| EP | 1162889 | 2/2005 | | WO | 92/18645 | 10/1992 |
| EP | 1559788 | 8/2005 | | WO | 93/01285 | 1/1993 |
| EP | 1363506 | 11/2005 | | WO | 93/11249 | 6/1993 |
| EP | 1 624 047 A1 | 2/2006 | | WO | 93/12812 | 7/1993 |

| | | |
|---|---|---|
| WO | 94/01541 | 1/1994 |
| WO | 94/04035 | 3/1994 |
| WO | 94/14940 | 7/1994 |
| WO | 94/14951 | 7/1994 |
| WO | 94/26883 | 11/1994 |
| WO | 95/06720 | 3/1995 |
| WO | 95/09909 | 4/1995 |
| WO | 95/22606 | 8/1995 |
| WO | 95/22615 | 8/1995 |
| WO | 95/22625 | 8/1995 |
| WO | 95/29996 | 11/1995 |
| WO | 95/30744 | 11/1995 |
| WO | WO 95/29996 | 11/1995 |
| WO | 96/09772 | 4/1996 |
| WO | 96/13578 | 5/1996 |
| WO | 96/13579 | 5/1996 |
| WO | 96/13580 | 5/1996 |
| WO | 96/27002 | 9/1996 |
| WO | 96/28542 | 9/1996 |
| WO | 96/30502 | 10/1996 |
| WO | 96/32472 | 10/1996 |
| WO | 96/39851 | 12/1996 |
| WO | 97/04079 | 2/1997 |
| WO | 97/05219 | 2/1997 |
| WO | 97/07202 | 2/1997 |
| WO | 97/11083 | 3/1997 |
| WO | 97/14713 | 4/1997 |
| WO | 97/27237 | 7/1997 |
| WO | 97/27276 | 7/1997 |
| WO | 97/41212 | 11/1997 |
| WO | 97/41735 | 11/1997 |
| WO | 97/41736 | 11/1997 |
| WO | 98/08939 | 3/1998 |
| WO | 98/14594 | 4/1998 |
| WO | 98/18912 | 5/1998 |
| WO | 98/26057 | 6/1998 |
| WO | 98/31790 | 7/1998 |
| WO | 98/41623 | 9/1998 |
| WO | 98/44804 | 10/1998 |
| WO | 98/45453 | 10/1998 |
| WO | 98/50532 | 11/1998 |
| WO | 98/51163 | 11/1998 |
| WO | 98/59028 | 12/1998 |
| WO | 99/33964 | 7/1999 |
| WO | 99/34011 | 7/1999 |
| WO | 99/37782 | 7/1999 |
| WO | 99/42566 | 8/1999 |
| WO | 99/50399 | 10/1999 |
| WO | 99/53001 | 10/1999 |
| WO | 99/53769 | 10/1999 |
| WO | 99/55883 | 11/1999 |
| WO | 00/05396 | 2/2000 |
| WO | 00/28044 | 5/2000 |
| WO | 00/32758 | 6/2000 |
| WO | 00/34450 | 6/2000 |
| WO | 00/36114 | 6/2000 |
| WO | WO 00/32758 | 6/2000 |
| WO | 00/43036 | 7/2000 |
| WO | 00/49164 | 8/2000 |
| WO | 00/58517 | 10/2000 |
| WO | 00/59307 | 10/2000 |
| WO | 00/60063 | 10/2000 |
| WO | 00/71808 | 11/2000 |
| WO | 00/75295 | 12/2000 |
| WO | 01/16308 | 3/2001 |
| WO | 01/27251 | 4/2001 |
| WO | 01/29222 | 4/2001 |
| WO | 01/34835 | 5/2001 |
| WO | 01/39602 | 6/2001 |
| WO | 01/42433 | 6/2001 |
| WO | 01/47363 | 7/2001 |
| WO | 01/66711 | 9/2001 |
| WO | 00/61771 | 10/2001 |
| WO | 01/78524 | 10/2001 |
| WO | 01/83559 | 11/2001 |
| WO | 01/83770 | 11/2001 |
| WO | 01/92502 | 12/2001 |
| WO | 02/00852 | 1/2002 |
| WO | 02/03805 | 1/2002 |
| WO | 02/06457 | 1/2002 |
| WO | 02/014490 | 2/2002 |
| WO | 02/024881 | 3/2002 |
| WO | 02/030207 | 4/2002 |
| WO | 02/055679 | 7/2002 |
| WO | 02/062973 | 8/2002 |
| WO | 02/065854 | 8/2002 |
| WO | 02/066622 | 8/2002 |
| WO | 02/094123 | 11/2002 |
| WO | 03/020923 | 3/2003 |
| WO | WO 03/020941 | 3/2003 |
| WO | 03/040091 | 5/2003 |
| WO | 03/060112 | 7/2003 |
| WO | 03/070013 | 8/2003 |
| WO | 03/089260 | 10/2003 |
| WO | WO 03/089620 | 10/2003 |
| WO | 03/097825 | 11/2003 |
| WO | 03/099016 | 12/2003 |
| WO | 03/100044 | 12/2003 |
| WO | 03/102118 | 12/2003 |
| WO | 2004/004467 | 1/2004 |
| WO | 2004/018660 | 3/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | 2004/097012 | 11/2004 |
| WO | 2004/111216 | 12/2004 |
| WO | 2005/003339 | 1/2005 |
| WO | 2005/005977 | 1/2005 |
| WO | 97/07205 | 2/2005 |
| WO | 2005/056782 | 6/2005 |
| WO | 2005/066347 | 7/2005 |
| WO | 2005/066351 | 7/2005 |
| WO | 2005/080540 | 9/2005 |
| WO | 2005/087918 | 9/2005 |
| WO | 2006/008508 | 1/2006 |
| WO | 2006/008653 | 1/2006 |
| WO | 2006/032279 | 3/2006 |
| WO | WO 2008/094847 | 8/2008 |

OTHER PUBLICATIONS

Sequence alignment of database accession No. Q44268 (database: UNIProtKB/TrEMBL) with SEQ ID No. 70—2 pages.*
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.
Roberts, et al.; "Extracellular Lipase Production by Fungi from Sunflower Seed"; Mycologia(1987); vol. 79(2); pp. 265-273.
Robertson et al, Journal of Biological Chemistry, 1994, 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in *Vigna unguiculata* leaves and influence of drought stress", Physiologia Plantarum, vol. 104, pp. 577-586, 1998.
Sahsah, Y., et al., "Purification and characterization of a soluble lipolytic acylhydrolase from Cowpea (*Vigna unguiculata* L.) leaves", Biochimica et Biophysica Acta, vol. 1215, pp. 66-73, 1994.
Saiki R.K. et al Science (1988) 239, pp. 487-491.

Saito, Kunihiko, et al., "Phospholipase B from *Penicillium notatum*", Methods in Enzymology, vol. 197.

Sakai, Norio, et al., "Human glactocerebrosidase gene: promoter analysis of the 5'-flanking region and structural organization", Biochimica et Biophysica Acta, vol. 1395, pp. 62-67, 1998.

Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.

Sambrook et al, Chapters 1, 7, 9, 11, 12 and 13—Molecular Cloning a laboratory manual, Cold Spring Harbor Laboratory Press (1989).

Sambrook, J., et al. "A Laboratory Manual, Second Edition", Plasmid Vectors, 1989.

Sanchez et al., "Solution and Interface Aggregation States of *Crotalus atrox* Venom Phospholipase A2 by Two-Photon Excitation Fluorescence Correlation Spectroscopy", Biochemistry, 2001, vol. 40, pp. 6903-6911.

Saxena, et al.; "Purification Strategies for Microbial Lipases"; Journal of Microbilogical Methods (2003); pp. 1-18.

Scheib et al.; "Stereoselectivity of Mucorales lipases toward triradyiglycerols—A simple solution to a complex problem"; Protein Science (1999); vol. 8; pp. 215-221.

Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.

Scopes, Robert K., "Section 8.4: Ultrafiltration" in *Protein Purification Principles and Practice, Third Edition* (1994) Springer-Verlag, New York, p. 267-9.

Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.

Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.

Shimada et al, J. of Bioscience and Bioengineering vol. 91, No. 6, 529-538 (2001).

Shimada et al, J. of Fermentation and Bioengineering vol. 75, No. 5, 349-352 (1993).

Shimada et al, JAOCS vol. 71, No. 9, (Sep. 1994).

Shin, et al.; "Butyl-Toyopearl 650 as a New Hydrophobic Adsorbent for Water-Soluable Enzyme Proteins"; Analytical Biochemistry(1984); vol. 138; pp. 259-261.

Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.

Si, Joan Qi; "New Enzymes for the Baking Industry"; Food Tech Europe (1996) pp. 60-64.

Sias B et al, Biochemistry, (2004), vol. 43(31), p. 10138-48.

Siew W.L. & Ng W.L. (1999) Influence of diglycerides on crystalisation of palm oil, in Journal of Science of Food and Agriculture 79:722-726.

Siew W.L. & Ng W.L. (2000) Differential scanning thermograms of palm oil triglycerides in the presence of diglycerides, in Journal of Oil Palm Research 12:107.

Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.

Skovgaard, et al.;"Comparison of Intra- and extracelluarl isozyme banding patterns of *Fusarium oxysporum*"; Mycol. Res. (1998); vol. 102(9); pp. 1077-1084.

Slotboom et al Chem. Phys. Lipids 4 (1970) 15-29.

Smith, George P.; "The Progeny of sexual PCR"; Nature; vol. 370; No. 18; Aug. 4, 1994.

Smith, Timothy L., et al., "The promoter of the glucoamylase-encoding gene of *Aspergillus niger* functions in *Ustilago maydis*", Gene. 88, 259-262, 1990.

Solares, Laura F., et al., "Enzymatic resolution of new carbonate intermediates for the synthesis of (S)-(+)-zopiclone", Tetrahedron: Asymmetry, vol. 13, 2002, pp. 2577-2582.

Sols and De Le Fuente, "On the substrate specificity of glucose oxidase", Biochem et Biophysica Acta (1957) 24:206-7.

Sonntag N.O.V. (1982a) Glycerolysis of Fats and methyl esters—status, review and critique, in Journal of American Oil Chemist Society 59:795-802A.

Soragni, Elisabetta, et al., "A nutrient-regulated, dual localization phospohilpase A2 in the symbiotic fungus" The EMBO Journal, vol. 20, No. 18, pp. 5079-5090, 2001.

Sosland, Josh, "Alive and kicking", Milling & Baking News, Feb. 24, 2004.

Soumanou, Mohamed M., et al., "Two-Step Enzymatic Reaction for the Synthesis of Pure Structured Triacylglycerides", JAOCS, vol. 75, No. 6, 1998.

Spradlin J E, Biocatalysis in Agric. Technol., ACS Symposium, 389(3), 24-43 (1989).

Sreekrishna K et al (1988) J Basic Microbiol. 28(4), 265-78.

Stadler et al., "Understanding Lipase Action and Selectivity", CCACAA, vol. 68, No. 3, pp. 649-674, 1995.

Steinstraesser, et al., "Activity of Novispirin G10 against *Pseudomonas aeruginosa* in Vitro and in Infected Burns", Antimicrobial Agents and Chemotherapy, Jun. 2002, vol. 46, No. 6, pp. 1837-1844.

Stemmer, Willem P.C.; "DNA shuffling by random fragmentation and reassembly: in vitro recombination for molecular evolution"; Proc. Natl. Acad. Sci. USA, vol. 91, pp. 10747-10751; Oct. 1994.

Stemmer, Willem P.C.; "Rapid evolution of a protein in vitro by DNA shuffling"; Affymax Research Institute, Nature, vol. 370, Aug. 4, 1994.

Sternberg, M., "Purification of Industrial Enzymes with Polyacrylic Acids", Process Biochemistry, Sep. 1976.

Strickland, James A., et al., "Inhibition of Diabrotica Larval Growth by Patatin, the Lipid Acyl Hydrolase from Potato Tubers", Plant Physiol, vol. 109, pp. 667-674, 1995.

Sudbery et al (1988) Biochem Soc Trans. 16(6), 1081-3.

Sugatani, Junko, et al., "Studies of a Phospholipase B from *Penicillium notatum* Substrate Specificity and Properties of Active Site", Biochimica et Biophysica Acta, vol. 620, 1980, pp. 372-386.

Sugimoto et al., Agric. Biol. Chem. 47(6), 1201-1206 (1983).

Sugiyama et al., "Molecular cloning of a second phospholipase B gene, caPLB2 from *Candida albicans*", Medical Mycology, vol. 37, 1999.

Svendsen, A. "Engineered lipases for practical use", Inform (1994) 5(5):619-623.

Svendsen, Allan, "Lipase protein engineering" Biochimica et Biophysica Acta, vol. 1543, 2000, pp. 223-238.

Svendsen, Allan, et al., "Biochemical properties of cloned lipases from the *Pseudomonas* family", Biochimica et Biophysica Acta, vol. 1259, 1995, pp. 9-17.

Sweigard, James A., et al., "Cloning and analysis of CUT1, a cutinase gene from *Magnaporthe grisea*", Mol. Gen. Genet., 232:174-182, 1992.

Swinkels et al (1993) Antonie van Leeuwenhoek 64, 187-201.

Sztajer H et al Acta Biotechnol, vol. 8, 1988, pp169-175.

Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.

Terasaki, Masaru, et al., "Glycerolipid Acyl Hydrolase Activity in the Brown Alga *Cladosiphon okamuranus* Tokida", Biosci. Biotechnol. Biochem., vol. 67, No. 9, pp. 1986-1989, 2003.

The New Enzyme Operatives, Ingredient Technology, 50, Aug. 1997.

Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.

Thornton et al 1988 Biochem. Et Biophys. Acta. 959, 153-159.

Tiss, Aly, et al., "Effects of Gum Arabic on Lipase Interfacial Binding and Activity", Analytical Biochemistry, vol. 294, pp. 36-43, 2001.

Toida J et al, Bioscience, Biotechnology, and Biochemistry, Jul 1995, vol. 59, No. 7, pp. 1199-1203.

Tombs and Blake, Biochim. Biophys (1982) 700:81-89.

Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.

Torossian and Bell (Biotechnol. Appl. Biochem., 1991, 13:205-211.

Tsao et al. (1973) J Supramol Struct. 1(6), 490-7.

Tsychiya, Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.

Turnbull, K.M., et al., "Early expression of grain hardness in the developing wheat endosperm", Planta, 2003, vol. 216, pp. 699-706.

Turner, Nigel A., et al., "At what temperature can enzymes maintain their catalytic activity?", Enzyme and Microbial Technology, vol. 27, 2000, pp. 108-113.

Turner, Progress in Industrial Microbiology, Martinelli and Kinghorn (eds.), Elsevier, Amsterdam, 1994, 29:641-666.

Unknown, "Appendix: Classification and Index of Fungi mentioned in the Text" in *Unknown*, p. 599-616.

Unknown, "Section I: Structure and Growth—Chapter 1: An Introduction to the Fungi" in *Unknown*.

Unknown, *Studies on Lipase* (1964) p. 21.

Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.

Uppenberg, Jonas, et al., "The Sequence, crystal structure determination and refinement of two crystal forms of lipase B from Candida antarctica", Structure 1994, vol. 2, No. 4.

Upton C et al TIBS Trends in Biochemical Sciences, Elsevier Publication (1995), vol. 20, pp. 178-179.

Uusitalo et al. (1991) J Biotechnol. 17(1), 35-49.

Uwajima T et al, Agricultural and Biological Chemistry, 43(12), pp. 2633-2634, 1979.

Uwajima T et al, Agricultural and Biological Chemistry, 44(9), pp. 2039-2045, 1980.

Uwajima T et al, Methods in Enzymology, 89(41), pp. 243-248.

Vaidehi, et al.; "Lipase Activity of Some Fungi Isolated from Groundnut"; Current Science (1984); vol. 53(23); p. 1253.

van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.

van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.

van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.

van Oort, Maarten G et al, Biochemistry 1989 9278-9285.

Vaysse et at J. of Biotechnology 53 (1997) 41-46.

Villenueva, Inform, vol. 8, No. 6, Jun. 1997.

Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.

Wahnelt S.V., Meusel D, & Tulsner M, (1991) Zur kenntnis des diglyceride influsses auf das kristallisationsverhalten von Fetten, in Fat Science Technology 4:117-121.

Waninge, Rianne, et al., "Milk membrane lipid vesicle structures studied with Cryo-TEM", Colloids and Surfaces B: Biointerfaces 31 (2003), pp. 257-264.

Warmuth et al, 1992, Bio Forum 9, 282-283.

Watanabe et al. Bio sci Biochem 63(5) 820-826, 1999.

Watanabe, Yasuo et al., "Cloning and sequencing of phospholipase B gene from the yeast *Torulaspora delbrueckii*", FEMS Microbiology Letters, vol. 124, 1994, pp. 29-34.

Webb EC Enzyme Nomenclature, 1992, p. 310.

Weber et al. J Agric Food Chem 1985, 33, 1093-1096.

Welter, et al; "Identification of Recombinant DNA"; pp. 424-431.

Wen-Chen Suen et al., "Improved activity and thermostability of *Candida antarctica* lipase B by DNA family shuffling", Protein Engineering, Design & Selection, vol. 17, No. 2, pp. 133-140, 2004.

West S.; "Olive and Other Edible Oils"; Industrial Enzymology (1996); pp. 295-299.

Whitehead, Michael, et al., "Transformation of a nitrate reductase deficient mutant of *Penicillium chrysogenum* with the corresponding *Aspergillus niger* and *A. nidulans* niaD genes", Mol Gen Genet, 216: 408-411, 1989.

Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.

Winnacker, Chapter 11, pp. 424-431 in From genes to clones: introduction to gene technology, VCH (1987).

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Witt, Wolfgang et al., "Secretion of Phospholipase B From *Saccharomyces cerevisiae*", Biochimica et Biophysica Acta, vol. 795, 1984, pp. 117-124.

Wood et al., Eds., "Biomass, Part B, Lignin, Pectin, and Chitin", Methods in Enzymology (1988) vol. 161, Academic Press, San Diego.

Xu, Jun, et al., "Intron requirement for AFP gene expression in *Trichoderma viride*", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Acker, L. "Die Lipide des Getreides, ihre Zusammense and inre Bedeutung", Getreide Mehl Brot (1974) 28:181-187.

Aisaka, Kazuo et al., "Production of Lipoprotein Lipase and Lipase by Rhizopus japonicu", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the *Pseudomonas* family", Biochimica et Biophysica Acta, vol. 1259, 1995, pp. 9-17.

Al-Obaidy, K A, Dissertation Abstracts International B (1987) vol. 47(9) 3597, order No. DA8624641, pp. 266.

Amano Enzyme Inc. (2004). Http://www.amano-enzyme.co.jp/english/productuse/oil_fat.html. Dato Jun. 21, 2004.

Amin, Neelam S., et al., "Direct transformation of site-saturation libraries in *Bacillus subtilis*", BioTechniques, Dec. 2003, 35:1134-1140.

Andersson, L., et al., "Hydrolysis of galactolipids by human pancreatic lipolytic enzymes and duidenal contents", Journal of Lipid Research, 1995, vol. 36, pp. 1392-1400.

Andreas Sander, Eberhand Eilers, Andrea Heilemann, Edith von Kreis.Fett/lipid 99 (1997) Nr. 4, 115-120.

An-I Yeh et al., "Effects of Oxido-reductants on rheological properties of wheat flour dough and comparison with some characteristics of extruded noodles", Cereal Chemistry, 1999, vol. 76, No. 5, pp. 614-620.

Archer, David B., et al., "Proteolytic degradation of heterologous proteins expressed in *Aspergillus niger*", Biotechnology Letter, vol. 14, No. 5, May 1992, pp. 357-362.

Arpigny Jean Louis et al, "Bacterial lipolytic enzymes: Classification and properties", Biochemical Journal, vol. 343, No. 1, Oct. 1, 1999, pp. 177-183, XP002375631.

August C.A.P.A. et al. "The use of genetic engineering to obtain efficient production of porcine pancreatic phospholipase A2", Biochimica et Biophysica Acta, vol. 1089, 1991, pp. 345-351.

Bailey's Industrial Oils and Fat Products, vol. 2, 4th Edition, John Wiley and Sons, New York pp. 97-173.

Balcao V.M., Pavia A.L. Malcata F.X., Enzyme Microb Technhol, May 1, 1996; 18(6):392-416.

Ballance, D.J., et al., "Transformation of *Aspergillus nidulans* by the orotidine-5'-phosphate decarboxylase gene of *Neurospora crassa*", Biochemical and biophysical Research Communications, vol. 112, No. 1, 1983, pp. 284-289.

Ballance, Molecular Industrial Mycology, Systems and Applications for Filamentous Fungi, Leong and Berka (eds.), Marcel Dekker Inc, New York 1991, pp. 1-29.

Barbesgaard, Peder et al Applied Microbiology and Biotechnology (1992) 36: 569-572.

Bateman A and Haft DH (2002) Brief Bioinform 3, 236-245.

Bateman A et al, (2002) Nucleic Acids Res. 30, 276-280.

Becker T. "Separation and Purification Processes for Recovery of Industrial Enzymes" in R.K. Singh, S.S.H. Rizvi (eds): Bioseparation processes in Foods, Marcel Dekker, New York, pp. 427-445.

Bekkers et al, The use of genetic engineering to obtain efficient production of porcine pancreatic phospholipase A2 by *Saccharomyces cerevisiae*, (1991) Biochim Biophys Acta 1089(3), 345-51.

Bentley S D et al, Complete genome sequence of the model actinomycete *Streptomyces coelicolor* A3(2), Nature vol. 417, 2002, pp. 141-147.

Berger K.G. (1990) Recent developments in palm oil. In Oleagineux 45:437-443.

Berks, Ben C., "A common export pathway for proteins binding complex redox cofactors?" Molecular Microbiology, 1996, vol. 22, pp. 393-404.

Beucage S.L. et al, (1981) Tetrahedron Letters 22, p. 1859-1869.

Bilyk, Alexander, et al., "Lipase-catalyzed triglyceride Hydrolysis in Organic Solvent", pp. 320-323, JAOCS, vol. 68, No. 5, May 1991.

Biocatalysts, Limited, Product Sheet for Lipomod(TM) 627P-L627P.

Birgitte Hugh-Jensen et al., "*Rhizomucor miehei* Triglyceride Lipase is Processed and Secreted from Transformed *Aspergillus oryzae*", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.

Bjorkling, F., et al., "Lipase Catalyzed Organic Synthesis", S. Servie (ed.), Microbial Reagents in Organic Synthesis, pp. 249-260, 1992.

Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.

Bjurlin et al. Identification of carboxylesterase activities of commercial triacylglycerol hydrolase (lipase) preparations, Eur. J. Lipid Sci. Technol. 104 (2002) 143-155.

Blain JA et al, The Nature of Mycelial Lipolytic enzymes in filamentous fungi, Fems Microbiol. Lett., 1978, vol. 3, 85-87.

Blumenthal, Cynthia Z., "Production of toxic metabolites in *Aspergillus niger, Aspergillus oryzae*, and *Trichoderma reesei*: justification of mycotoxin testing in food grade enzyme preparations derived from the three fungi", Regulatory Toxicology and Pharmacology, vol. 39, 2004, p. 214-228.

Bornscheuer U T et al, Trends in Biotechnology, Elsevier Publications, Cambridge GB, vol. 20, No. 10, Oct. 1, 2002, pp. 433-437.

Bornscheuer, Uwe T., Lipase-catalyzed syntheses of monoacylglycerols, Enzyme and Microbiol Technology, vol. 17, pp. 578-586, 1995.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Buckley J. Thomas et al, Journal of Biological Chemistry, vol. 257, No. 6, pp. 3320-3325, 1982.

Buckley, Biochemistry 1983, 22, 5490-5493.

Bulkacz J et al, Biochim. Biophys. Acta (1981) vol. 664, pp. 148-155.

Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.

Butcher, Bronwyn G., et al., Microbiology, 2002, vol. 148, pp. 3983-3992.

Buxton et al, Gene, 1985, 37:207-214.

Carriere et al, "Pancreatic Lipase Structure- Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) Nuc Acids Res Symp Ser 215-23.

Casimir C A et al Progress in Lipid Research, 2004, pp. 534-552.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.

Chakravarti DN et al, Biol. Abstracts, 1981, vol. 72, abstract No. 012592.

Cheng Cheng et al., "Transformation of *Trichoderma viride* using the *Neurospora crassa* pyr4 gene and its use in the expression of a Taka-amylase a gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from *Arabidopsis*", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of *Pseudomonas cepacia* Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science and Technology, vol. 103, 2001, pp. 333-340.

Clausen, Kim, "New enzyme for degumming", Oils and Fats International, vol. 17, No. 4, Jun. 2001, pp. 24-25.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988 (89/107/EEC).
Council Regulation (EC) No. 2991/94 May 12, 1994 Official Journal of the European Communities, Sep. 12, 1994, No. L316/2-7.
Creveld, Lucia D, et al., "Identification of Functional and Unfolding Motions of Cutinase as Obtained from Molecular Dynamics Computer Simulations", Proteins: Structure, Function, and Genetics, 33:253-264, 1998.
Cui et al., "Purification and characterization of an intracellular carboxylesterase from Arthrobacter viscosus NRRL B-1973", Enzyme and Microbial Technology, vol. 24, pp. 200-208, 1999.
Daboussi et al, Heterologous expression of the *Aspergillus nidulans* regulatory gene nirA in *Fusarium oxysporum*, (1991) Gene 109(1), 155-60.
Daboussi et al., "Transformation of seven species of filamentous fungi using the nitrate reductase gene of *Aspergillus nidulans*", Curr. Genet., 15:453-456, 1989.
Daftary, R.D., et al., "Functional Bread-Making Properties of Wheat Flour Lipids", Food Technology, vol. 22, No. 237, Mar. 1968-1979.
Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.
Dalrymple, Brian D., et al., "Three Neocallimastic patriciarum esterases associated with the degradation of complex polysaccharides are members of a new family of hydrolases", Microbiology, vol. 142, pp. 2605-2614, 1997.
Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.
Database accession No. P10480 -& Database UniProt 'Online!, Jul. 1, 1989.
Database accession No. Q44268 -& Database UniProt 'Online! Nov. 1, 1996.
Database accession No. Q9F7Y6 Database UniProt 'Online!, Mar. 1, 2001.
Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 19976, pp. 81-84.
Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.
Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.
Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.
Database UNIPROTKB Jun. 1, 2003, S. Omura et al: "putative secreted hydrolase from streptomyces avermitilis" XP002376340 retrieved from EBI, Hinxton, UK Database accession No. Q828T4 abstract.
Database UNIPROTKB May 1, 2000, S.D. Bentley et al: "Putative Secreted Hydrolase from *Streptomyces coelicolor*" XP002376339 retrieved from EBI, Hinxton, UK Database accession No. Q9S2A5 abstract.
Davies, Progress in Industrial Microbiology, Martinelli and Kinghorn (eds.), Elsevier, Amsterdam 1994, 29:525-560.
De Haas GH et al, "Purification and Properties of Phospholipase A from Porcine Pancreas" Biochim. Biophys. Acta, 1968, vol. 139, pp. 103-117.
Declaration by Clive Graham Phipps Walter (Dec C), Jul. 4, 2003.
Declaration by Dr. Jorn Borch Soe, et al. (Dec F), Dec. 2, 2003.
Declaration by Dr M Turner, Feb. 4, 2005.
Declaration by Dr Mark Turner (Dec G), Feb. 4, 2005.
Declaration by Henrik Pedersen (Dec A), Jul. 7, 2003.
Declaration by Henrik Pedersen, Masoud Rajabi Zargahi and Clive Graham Phipps Walter (Dec 2), Feb. 7, 2005.
Declaration by Janne Brunstedt (Dec D), Jul. 4, 2003.
Declaration by Kazuko Kato, Henrik Pedersen, Masoud Rajabi Zaghiri, Clive Phipps Walter, and Jann Brunstedt (Dec I), Feb. 7, 2005.
Declaration by Kim Borch, Oct. 17, 2005.
Declaration by Luise Erlandsen, Oct. 21, 2005.
Declaration by Masoud Rajabi Zargahi (Dec B), Jul. 7, 2003.
Declaration by Masoud Rajabi Zargahi (Dec E), Jul. 15, 2003.
Declaration by Tina Spendler, Sep. 14, 2005.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.
Derewenda et al, "The crystal and molecular structure of the Rhizomuxor miehei Triacylglyceride Lipase at 1.9 Å Resolution", J. Mol. Biol. 1992, 227:818-839.
Derewenda, Urszula, et al., "Catalysis at the Interface: the Anatomy of a Conformational Change in a Triglyceride Lipase", Biochemistry, vol. 31, pp. 1532-1541, 1992.
Dictionary of Biochemistry and Molecular Biology, Second Edition, p. 16.
Duan, Rul Dong, Fat Digestion and Absorption (2000), p. 25-46, publisher AOCS Press, Champaign III CODEN 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Dugi KA et al, "Human hepatic and lipoprotein lipase: the loop covering the catalytic site mediates lipase substrate specificity", Journal of Biological Chemistry (1995), vol. 270, pp. 25, 396—pp. 25, 401.
Eddine et al, "Cloning and expression analysis of NhL1, a gene encoding an extracellular lipase from the fungal pea pathogen *Nextria haematococca* MP VI (*Fusarium solani* f. sp. pisi) that is expressed in planta", Mol. Genet. Genomics (2001) 265: 215-224.
EFEMA Index of Food Emulsifiers Jan. 2004, 4th Edition.
Ellaiah et al., "Production of lipase by immobilized cells of *Aspergillus niger*", Process Biochemistry, vol. 39, 2004, pp. 525-528.
Elyk, Alexander, et al., "Lipase-Catalyzed - - -", JAOCS, vol. 08, No. 5, May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques(1991); vol. 11(5); pp. 594-596.
EPO, Mobay Chemical Corporation—Decision of the Technical Board of Appeal 3.3.1 dated July 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate *Streptomyces* sp. (MSU-2110) endophytic on *Monstera* sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.
Fernandez-Garcia et al., "The use of lipolytic and proteolytic enzymees in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, J. Chem. Technol. Biotechnol. 75, 569-576.

Finizym Technical Information, Novo Enzymes, 1981.

Fødevarenubusteriet (2003). Bekendtgørelse om indhold af transfedtsyrer I olier og fedtstoffer. Bekendtgørelse nr. 160 af Nov. 3, 2003.

Forman, Todd, "Enzymes Used in Bread Baking: An Application Update", Technical Bulletin, vol. XXVI, Issue 10, Oct. 2004.

Fox, et al.; "Isolation and some Properties of Extracellular Heat-Stable Lipases: from *Pseudomonas fluorescens* Strain Aft 36"; Journal of Dairy Research (1988); vol. 50; pp. 77-89.

Frenken N. et al (1992) Appl. Envir. Microbiol. 58 3787-3791.

Galliard T and Dennis S (1974) Phytochemistry vol. 13, pp. 1731-1735.

Galliard, "The Enzymic Breakdown of Lipids in Potato Tuber by Phospholipid- and Galactolipid- Acyl Hydrolase Activities and by Lipoxygenase", Phytochemistry, 1970, vol. 9, pp. 1725-1734.

Gan, Z. et al., "Rapid Communication—Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.

Gemel, Joanna et al., "Comparison of galactolipase activity and free fatty acid levels in chloroplasts of chill-sensitive and chill resistant plants", European Journal of Biochemistry, vol. 166, 1987.

Geus et al (1987) Nucleic Acids Research 15(9) p. 3743-3759.

Gilbert, E. Jane, et al., "Purification and properties of extracellular lipase from *Pseudomonal aeruginosa* EF2", Journal of General Microbiology, 1991, vol. 137, p. 2223-2229.

Gillian, B., Turgeon et al., "*Cochliobolus heterostrophus* using the *Aspergillus nidulans* amdS gene", Mol Gen Genet, 201: 450-453, 1985.

Graille J, Lipid Technology, vol. 5, No. 1, 1993, pp. 11-16.

Greenough et al (1996) Food Chem Toxicology 34:161-166 and PubMed abstract in respect thereof.

Greenough R J et al, Food and Chemical Toxicology, vol. 34(2), 1996, pp. 161-166.

Haas and Berka, 1991, Gene, 109:107-113.

Haas, et al., "Enzymatic Phosphatidylcholine Hydrolysis in Organic Solvents: An Examination of Selected Commercially Available Lipases", JAOCS, vol. 71, No. 5, May 1994, pp. 483-490.

Haas, et al.; "Lipases of the Genera *Rhizopus* and *Rhizomucor*. Versatile Catalysts in Nature and the Laboratory"; Food Biotechnology Micro-organisims (1995); pp. 549-588.

Hansen, Chr., Danisco and Novozymes, Apr. 3, 2002, Food Ingredients day, R&D—The main ingredients for growth.

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the *Neurospora crassa* nit-4 pathway-specific regulartory gene for nitrate assimilation in *Aspergillus nidulans*", Gene., vol. 100, pp. 237-240, 1991.

Helmsing, "Purification and Properties of Galactolipase", Biochim., Biophys., Acta, vol. 178, pp. 519-533, 1969.

Henderson, H.E., et al., "Structure-function relationships of lipoprotein lipase: mutation analysis and mutagenesis of the loop region", Journal of Lipid Research, vol. 34, 1993, pp. 1593-1602.

Henke, Erik, et al., "Activity of Lipases and Esterases towards Tertiary Alcohols: Insights into Structure-Function Relationships", Angew. Chem. Int. Ed., 2002, vol. 41, No. 17.

Hernquist L & Anjou K (1993) Diglycerides as a stabilizer of the β'-crystal form in margarines and fats, in Fette Seifen Anstrichmittel 2:64-66.

Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.

Hilton S et al, Biochemistry vol. 29, No. 38, 1990, pp. 9072-9078.

Hilton S, Buckley JT, J Biol Chem. Jan. 15, 1991; 266(2): 997-1000.

Hirayama O et al, Biochim Biophys Acta. 1975, vol. 384(1), p. 127-37.

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.

Holmquist et al., "Lipases from *Rhizomucor miehei* and Humicola lanuginosa: Modification of the Lid covering the active site alters enantioselectivity", Journal of Protein Chemistry, vol. 12, No. 6, 1993.

Holmquist et al., "Probing a Functional Role of Glu87 and Trp89 in the Lid of Humicola lanuginosa Lipase through Transesterification Reactions in Organic Solvent", Journal of Protein Chemistry, 1995, vol. 14, No. 4, pp. 217-224.

Holmquist et al., "Trp89 in the Lid of Humicola lanuginosa Lipase is Important for Efficient Hydrolysis of Tributyrin", Lipids, vol. 29, No. 9, 1994.

Horn T et al, (1980) Nuc Acids Res Symp Ser 225-232.

Hoshino, et al.; "Calcium Ion Regulates the Release of Lipase of *Fusarium oxysporum*"; J. Biochem (1991); vol. 110; pp. 457-461.

Hoshino, et al.; "Purification and Some Characteristics of Extracellular Lipase from *Fusarium oxysporum* f. sp. *lini*"; Biosci. Biotech. Biochem (1992); pp. 660-664.

Hoshino, Tamotsu, et al., "Purfication and Some Characteristics of Extracellular Lipase from *Fusarium oxysporum*", Biosci. Biotech. Biochem., vol. 56, No. 4, pp. 660-664, 1992.

Hossen, Monjur and Hernandez, Ernesto, Lipids, vol. 39, Aug. 2004, pp. 777-782.

Hou Ching T, Journal of Industrial Microbiology, vol. 13, No. 4, 1994, pp. 242-248.

Hübner et al., "Interactions at the lipid-water interface", Chemistry and physics of Lipids, vol. 96, 1998, pp. 99-123.

Hugh-Jensen, Birgitte, et al., "*Rhizomucor miehei* Triglyceride Lipase is Processed and Secreted from Transformed *Aspergillus oryzae*", Lipids, vol. 24, No. 9, pp. 1989.

Humum et al., "Enzyme Catalysed Synthesis in Ambient Temperature Ionic Liquids", Biocatalysis and Biotransformation, vol. 19, pp. 331-338.

Icard-Verniere, Christele, et al., "Effects of mixing conditions on pasta dough development on biochemical changes", Cereal Chemistry, 1999, vol. 76, No. 4, pp. 558-565.

Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.

Ikeda H et al, Nature Biotech, vol. 21, 2003, p. 526-531.

Industrial enzymology (2nd Ed.), The Macmillan press 1996.

Ishihara et al Biochimica et Biophysica Acta 388 (1975) 413-422.

Isobe and Nokihara, FEBS. Lett., 1993, 320:101-106.

Isobe K et al, Journal of Molecular Catalysis B: Enzymatic 1 (1995), pp. 37-43.

Iwai and Tsujisaka (in Lipases, Borgström and Brockman (eds.), Elsevier, Amsterdam, 1984, pp. 443-468.

Iwai, Mieko, et al., "Hydrolytic and Esterifying Actions of Crystalline Lipase of *Aspergillus niger*", Osaka Municipal Technical Research Institute, Osaka, Japan.

Izco et al. Adv Food Sci vol. 21 N 3/4, (10-116) 1999.

Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53:609-616.

jan-Willem F. A. Simons et al., "Cloning, purification and characterisation of the lipase from *Staphylococcus epidermidis*", Eur. J. Biochem., vol. 253, pp. 675-683, 1998.

Jeng-yen Lin, Matthew, "Wheat Polar Lipids- A Theseis Submitted to the Graduate Faculty of the North Dakota State University of Agriculture and Applied Science", May 1972.

Joerger et al., "Alteration of Chain Length Selectivity of a Rhizopus delemar Lipase through Site-Directed Mutagenesis", Lipids, vol. 29, No. 6, 1994, pp. 377-384.

Jong et al.; "American Type Culture Collection Catalogue of Filamentous Fungi"; Eighteenth edition (1991).
Joshi, et al.; "Specificity of Fungal Lipase in Hydrolytic Cleavage of Oil"; Acta Microbiologica Hungarica (1987); vol. 34(2); pp. 111-114.
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.
Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.
Kaniuga Z, Acta Biochim Pol. (1997), vol. 44(1), p. 21-35.
Kapur J & Sood ML, J. Parasit., 1986, vol. 72, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kawamura and Doi, J. of Bacteriology Oct. 1984, p. 442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al. Korean J Dairy Sci 15 (2): 103-117 1993.
Kim, Hyung Kwoun, et al., Expression and characterization of Ca2+-independent lipase from Bacillus pumilus B26, Biochimica et Biophysica Acta, vol. 1583, 2002, pp. 205-212.
Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, p. 107-112.
King et al, Molecular and Cell Biology of Yeasts, Walton and Yarronton (eds.), Blackie, Glasgow, 1989, pp. 107-133.
Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of Rhizopus delemar Lipase", JAOCS, vol. 74, No. 11, 1997.
Kochubei S M et al, Biophysics (1981), vol. 26(2), p. 299-304.
Kochubei S M et al, Mol Biol (Mosk) (1975), vol. 9(2), (p. 190-3) p. 150-153.
Kochubei SM et al, Mol Biol (Mosk) (1978),(vol. 1, p. 47-54) p. 32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al.; "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase a from *Candida antarctica*", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity in Lyophilized Spinach Chloroplasts", Biochimica et Biophysica Acta, 408, pp. 26-34, 1975.
Kuipers, Oscar P., et al., "Enhanced Activity and Altered Specificity of Phospholipase A2 by Deletion of a Surface Loop", Science, vol. 244, 1989.
Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.
Kuwabara, et al., "Purification and Some Properties of Water-soluble Phospholipase B from *Torulaspora delbrueckii*", J. Biochem., vol. 104, pp. 236-241, 1988.
Kuwabara, et al., "Purification and Some Properties of Water-soluble Phospholipase", Agric. Biol. Chem., vol. 52, No. 10, pp. 2451-2458, 1988.
Kweon et al., "Phospholipid Hydolysate and Antistaling Amylase Effects on Retrogradation of Starch in Bread", Journal of Food Science, vol. 59, No. 5, 1994.
Larsen N G et al, Journal of Cereal Science (1990), vol. 12(2), p. 155-164.
Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.
Leggio, Leila Lo, et al., "The 1.62 a structure of Thermoascus aurantiacus endoglucanase: completing the structural picture of subfamilies in glycoside hydrolase family 5", FEBS Letters, vol. 523, 2002, pp. 103-108.
Leidich et al., "Cloning and Disruption of caPLB1, a Phospholipase B Gene Involved in the Pathogenicity of *Candida albicans*", The Journal of Biological Chemistry, vol. 273, No. 40, oo. 26078-26086, 1998.
Li, W., et al., "Surface properties and locations of gluten proteins and lipids revealed using confocal scanning laser microscopy in bread dough", Journal of Cereal Science, vol. 39, 2004, pp. 403-411.
Lih-ling Wang et al, J Agric. Food. Chem. (1993), 41, 1000-1005.
Lima, Vera L.M., et al., "Lecithin-cholesterol acyltransferase (LCAT) as a plasma glycoprotein: an overview", Carbohydrate Polymers, vol. 55, 2004, pp. 179-191.
Lin M J Y et al, Cereal Chemistry (1974), vol. 51(1), p. 34-45.
Lin S et al, Enzyme and Microbial Technology 18 (1996), pp. 383-387.
Lipase A "Amano" 6 Assay Note and Product Specification from Armano Pharmaceutical Co Ltd Nagoya Japan, Dec. 16, 1985.
Lipase A "Amano" 6 Assay Note and Product Specification from Armano Pharmaceutical Co Ltd Nagoya Japan, Aug. 27, 1985.
Lipase A "Amano" 6 product sheet, Apr. 1, 1999.
Lipase SP677 as a Baking Enzyme, from Novo Nordisk, Denmark, Mar. 17, 1994.
Lipopan F: Keep the quality—cut your costs 2000 Novozymes A/S. www.enzymes.novo.dk/cgl-bin/bvisapi.dll/biotimes/one_article.jsp?id=16947&lang=en&t=b1.
Litthauer, Derek, et al., "*Pseudomonas luteola* lipase: a new member of the 320-residue *Pseudomonas* lipase family", Enzyme and Microbial Technology, vol. 30, pp. 209-215, 2002.
Llustenberger, Cornelia, et al., "Application of Noopazyme in Asian Noodles and Non-Durum Pasta", Cereal Food, 2002-18584-01, p. 1, vol. 11.
Llustenberger, Cornelia, et al., "Enzymes in Frozen Dough and Parbaked Bread", Cereal Food, 2001-17056-01, p. 1, vol. 19.
Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.
Lozano et al., "Over-stabilization of *Candida antarctica* lipase B by ionic liquids in ester synthesis", Biotechnology Letters, vol. 23, pp. 1529-1533, 2001.
Luzi, Paola et al, Genomics (1995), vol. 26(2), p. 407-9.
Madsen J.S. & Qvist K.B. (1997) J. Food Sci. 62, 579-582.
Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.
Maria Teres Neves Petersen, PhD, "Total Internal Reflection Fluorescence Flow System with Electrochemical Control", TIRF-EC Flow System, Sep. 2002.
Marion D et al—Chapter 6, pp. 131-p. 167 of "Interactions The Keys to Cereal Quality" 1998 ISBN 0 913250-99-6 (ed. Hamer & Hoseney).
Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of Humicola lanuginosa lipase", Protein Engineering, vol. 9, No. 6, 1996, pp. 519-524.

Martinez, Chrislaine, et al., "Engineering cysteine mutants to obtain crystallographic phases with a cutinase from *Fusarium solani pisi*", Protein Engineering, vol. 6, No. 2, pp. 157-165, 1993.

Martinez, Diego, et al., "Genome sequence of the lignocellulose degrading fungus *Phanerochaete chrysosporium* strain RP78", Nature Biology, May 2, 2004.

Mase et al., "Purification and Characterization of a new Lipase from *Fusarium* sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of *Penicillium notatum* phospholipase B deduced from the Cdna", Eur. J. Biochem., vol. 202, pp. 783-787, 1991.

Matos AR, Lipid Catabolism: Lipid Degradation, 2000, p. 779-781.

Matos, A.R., et al., "A patatin-like protein with galactolipase activity is induced by drought stress in *Vigna unguiculata* leaves", Biochemical Society Transactions, vol. 28, part 6, 2000.

Matos, AR et al, FEBS Letters, 491 (2001) p. 188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus Saitoi*"; Biotiechonology and Applied Biochemistry (1987); vol. 9, pp. 401-409.

Matthes et al, (1984) EMBO J. 3, p. 801-805.

McAuley, Katherine E., et al., "Structure of a feruloyl esterase from *Aspergillus niger*", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, No. 11, Nov. 1992.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from *Phanerochaete chrysosporium* and *Bjerkandera* sp. BOS55", Enzyme and Microbial Technology, vol. 32, 2003, pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of Thermomyces lanuginosus Lipase by Detergents", Biochemistry, vol. 44, pp. 1719-1730, 2005.

Molecular Biological Methods for Bacillus—Chapter 3 (Ed. C.R. Harwood and S.M. Cutting) 1990, John Wiley and Sons Ltd, Chichester, UK.

Molochnaya Promyshlennost 1980 No. 11 21-25, 47—abstract from Food Sci & Tech Abs.

Monographs for Emulsifiers for Foods, EFEMA Nov. 1985 2nd Edition.

Moore, Charles M., et al., "Metal ion homeostasis in *Bacillus subtilis*", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the Fusicoccum Anamorph of Botryosphaneria Ribis"; vol. Xxx, pp. 117-125; Oct.-Dec. 1987.

Morinaga et al Biotechnology (1984) 2, p. 636-639.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedrom, vol. 50, No. 7, pp. 1993-2002, 1994.

Nagano, et al.; "Cloning and Nucleotide Sequence of cDNA Encoding a Lipase from Fusarium keteroporum"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao et al, JAOCS vol. 78, No. 2, 2001.

Nagao, Toshihiro et al., "Cloning and Nucleotide Sequence of CDNA Encoding a Lipase from Fusarium heterosporum", J. Biochem., vol. 116, pp. 535-540, 1994.

Nagao, Toshihiro et al., "Expression of Lipase cDNA from Fusarium heterosporum by *Saccharomyces cereviisiae*: High-Level Production and Purification", Journal of Fermentation and Bioengineering, 1996, vol. 81, No. 6, pp. 488-492.

Nagodawithana et al., "Enzymes in Food Processing", Third Edition, 1993, Academic Press, Inc.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, p. 147-151.

Nerland A H, Journal of Fish Diseases, vol. 19, No. 2, 1996, pp. 145-150.

Néron, et al., "Effects of lipase and the phosphlipase on the lipids hydrolysis during mixing in correlation with the oxygen consumption by wheat flour dough during kneading" available at http://www.cnam.fr/biochimie.

Ness, Jon. E., et al., "DNA shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences *Candida albicans* Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nierle W et al, Fette Seifen Anstrichmittel (1981), vol. 83(10), p. 391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p. 1331-4.

Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactofipids in dough".

Novozymes Memo—Test of lipases for EP1193314B1, Jul. 6, 2005.

Novozymes Report 2002 Annual Report.

Novozymes, "Biowhitening—a new concept for steamed bread", *BioTimes*, Jan. 2005.
Novozymes, "Breakthrough: Less Fattening Fried Food" *BioTimes*, Jun. 2001, No. 2.
Novozymes, "Enzymes for dough strengthening", 2001.
Novozymes, "Lipopan F BG- application and mechanism of a new lipase for bread baking" (Draft) *Cereal Food* (2003) (Author: Drost-Lustenberger, C. et al.).
Novozymes, "Product Sheet for Lipopan F BG", *Cereal Food*, (2001).
Novozymes, "Product Sheet for Lipopan FS BG", *Cereal Food* (2002).
Novozymes, "Product Sheet for Lipopan S BG", *Cereal Food* (2002).
Novozymes, "Revolutionizing baking", *BioTimes* (2002) pp. 6-7.
Novozymes, "Strong sales for lipase that makes dough stronger" *BioTimes*, Dec. 2003.
Novozymes, "The perfect roll every time for steers", *BioTimes*, Sep. 2003.
Novozymes, "The value of innovation", *BioTimes*, Mar. 2004.
Novozymes, "The vital role of technical service in baking", *BioTimes*, Jun. 2004.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) Partial glycerides and palm oil Crystallisation, in Journal of Science and Food Agriculture 28:955.
Okiy D.A. (1978) Interaction of triglycerides and diglycerides of palm oil, in Oleagineux 33:625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.
Osman, Mohamed, et al., "Lipolytic activity of *Alternaria alternata* and *Fusarium oxysporum* and certain properties of their lipids", Microbios Letters, vol. 39, pp. 131-135, 1988.
Ostrovskaya L K et al, Dokl Akad Nauk SSSR, (vol. 186(4), p. 961-3) p. 59-61.
O'Sullivan et al, J Plant Physiol, vol. 313, (1987) p. 393-404.
Outtrup, Günther H., et al., "Properties and Application of a Thermostable Maltogenic Amylase Produced by a Strain of Bacillus Modified by Recombinant-DNA Techniques", Starch/Starke, vol. 36, No. 12, pp. 405-411.
Palomo, Jose M., et al., "Enzymatic production of (3S, 4R)-(-)-4-(4'-fluorophenyl)-6-oxo-piperidin-3-carboxylic acid using a commerical preparation of lipase A from *Candida antarctica*: the role of a contaminant esterase" Tetrahedron: Asymmetry, vol. 13, 2002, pp. 2653-2659.
Palomo, Jose M., et al., "Enzymatic resolution of (±)-glycidyl butyrate in aquenous media. Strong modulation of the properties of the lipase from *Rhizopus oryzae* via immobilization techniques", Tetrahedron: Asymmetry, vol. 15, 2004, pp. 1157-1161.
Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.
Pariza, Michael, et al., "Evaluating the safety of Microbiol Enzyme Preparations Used in Food Processing: Update for a New Century", Regulatory Toxicology and Pharmacology, vol. 33, pp. 173-186.
Patent Abstracts of Japan vol. 016, No. 528 (C-1001), Oct. 29, 1992 & JP 04 200339 A see abstract.
Patent Abstracts of Japan vol. 095, No. 001, Feb. 28, 1995 & JP 06 296467 A see abstract.
Peelman F, et al, Protein Science Mar. 1998; 7(3): 587-99.
Penninga et al, Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the Humicola lanuginosa Lipase", Biochemistry, 1998, vol. 37, pp. 12375-12383.
Peters, Günther H., et al., "Theoretical Investigation of the Dynamics of the Active Site Lid in *Rhizomucor miehei* Lipase", Biophysical Journal, vol. 71, 1996, pp. 119-129.
Philippine Patent Application Serial No. 31068.
Picon et al. Biotechnology letters vol. 17 nr 10 pp. 1051-1056.
Plijter J and JHGM Mutsaers, The surface rheological properties of dough and the influence of lipase on it, Gist-brocades, Bakery Ingredients Division, Oct. 1994.
Plou et al, J. Biotechnology 92 (2002) 55-66.
Ponte J G, Cereal Chemistry (1969), vol. 46(3), p. 325-29.
Punt and van den Hondel, Meth. Enzym., 1992, 216:447-457.
Pyler, E.J., "Baking Science and Technology Third Edition", vol. 1, 1988.
Pyler, E.J., "Baking Science and Technology Third Edition", vol. II, 1988.
Queener et al. (1994) Ann N Y Acad Sci. 721, 178-93.
Rambosek and Leach, CRC Crit. Rev. Biotechnol., 1987, 6:357-393.
Rapp, Peter, et al., "Formation of extracellular lipases by filamentous fungi, yeasts, and bacteria", Enzyme Microb. Technol., 1992, vol. 14, November.
Rapp, Peter; "Production, regulation, and some properties of lipase activity from *Fusarium oxysporum* f. sp. *vasinfectum*"; Enzyme and Microbial Technology(1995); vol. 17; pp. 832-838.
Reetz M.T., Jaeger K.E. Chem Phys Lipids. Jun. 1998; 93(1-2): 3-14.
Reetz Manfred T, Current Opinion in Chemical Biology, Apr. 2002, vol. 6, No. 2, pp. 145-150.
Reiser J et al. (1990) Adv Biochem Eng Biotechnol. 43, 75-102.
Richardson & Hyslop, pp. 371-476 in Food Chemistry, 1985, second edition, Owen R. Fennema (ed), Manel Dekker, Inc, New York and Basel.
Richardson and Hyslop, "Enzymes: XI—Enzymes Added to Foods During Processing" in *Food Chemistry*, Marcel Dekker, Inc., New York, NY 1985.
Arskog and Joergensen, "Baking performance of prior art lipases from *Candida cylindracea* and *Aspergillus foeditus* and their actiivty on galactolipids in dough", Novozymes Report 2005.
Arskog and Joergensen, "Baking performance of prior art lipases from *Humicola lanuginosa, Aspergillus tubigensis, Rhizopus delemar* and *Rhizomucor miehei*, and their activity on galactolipids in dough", Novozymes Report 2005.
U.S. Appl. No. 60/039,791, filed Mar. 4, 1997, Clausen.
U.S. Appl. No. 60/189,780, filed Mar. 16, 2000, Soe, et al.
U.S. Appl. No. 60/489,441, filed Jul. 23, 2003, Kreij.
International Dairy Federation Bulletin Document, 1979, doc. 116, p. 5.
AOCS Introduction to the Processing of Fats and Oils, American Oil Chemists Society, 1984, pp. III 16-19.
Seino et al., "Enzymatic Synthesis of Carbohydrate Esters of Fatty Acid (I) Esterification of Sucrose, Glucose, Fructose and Sorbitol", J. Am. Oil Chem. Soc., 1984, vol. 61, No. 11, pp. 1761-1765.
Verenium Corporation leaflet Purifine Enzyme, Jan. 2008.
Nerland A.H., "The Nucleotide Sequence of the Gene Encoding GCAT from *Aeromonas salmonicida* SSP. *salmonicida*", Journal of Fish Diseases, 1996, vol. 19, No. 2, pp. 145-150, XP008049669.
Nerland A.H., "Glycerophospholipid-cholesterol acyltransferase precursor", SwissProt, Feb. 11, 2005, XP002318368.

Buckley J. Thomas, "Substrate specificity of bacterial glycerophospholipid Cholesterol Acyltransferase", Biochemistry, 1982, vol. 21, pp. 6699-6703.

Sen, et al., Developments in Directed Evolution for Improving Enzyme Functions, Appl. Biochem. Biotechnol (2007) vol. 143, No. 3, p. 212-223.

Patent Abstracts of Japan; Publication No. 04-370055; Publication Date Dec. 22, 1992.

Patent Abstracts of Japan; Publication No. 07-079687; Publication Date Mar. 28, 1995.

Patent Abstracts of Japan; Publication No. 48016612; Publication Date May 23, 1973.

Delphine Briand et al., "Substrate Specificity of the Lipase from *Candida parapsilosis*" Lipids, 1995, vol. 30, No. 8, pp. 747-754.

Kin-Yu Chan et al., "Direct colorimetric Assay of Free Thiol Groups and Disulfide Bonds in Suspensions of Solubilized and Particulate Cereal Proteins", Cereal Chemistry, 1993, vol. 70, No. 1, pp. 22-26.

Roberto A. Chica et al., "Semi-rational approaches to engineering enzyme activity: combining the benefits of directed evolution and rational design", Current Opinion in Biotechnology, 2005, vol. 16, pp. 378-384.

Rebeca Garcia, et al., "Analysis and Modeling of the Ferulic Acid Oxidation by a Glucose Oxidase-Peroxidase Association. Comparison with a Hexose Oxidase-Peroxidase Association", J. Agric. Food Chem., 2004, vol. 52, pp. 3946-3953.

Anna Maria V. Garzillo et al., "Production, purification and characterization of glucose oxidase from *Penicillium variabile* P16[1]" Biotechnol. Appl. Biochem., 1995, vol. 22, pp. 169-178.

Jennifer L. Seffernick et al., "Melamine Deaminase and Atrazine Chlorohydrolase: 98 Percent Identical but Functionally Different", Journal of Bacteriology, Apr. 2001, vol. 183, No. 8, pp. 2405-2410.

Hajime Seino et al., "Enzymatic Synthesis of Carbohydrate Esters of Fatty Acid (1) Esterification of Sucrose, Glucose, Fructose and Sorbitol", JAOCS, Nov. 1984, vol. 61, No. 11.

Stryer L, Biochemistry, 1981. 2$^{nd}$ edition, W H Freeman and Co, San Francisco.

Andrzej Witkowski et al., "Conversion of a β-Ketoacyl Synthase to a Malonyl Decarboxylase by Replacement of the Active-Site Cysteine with Glutamine", Biochemistry, 1999, vol. 38, pp. 11643-11650.

\* cited by examiner

FIGURE 1 (SEQ ID No. 16)

```
  1   ADTRPAFSRI  VMFGDSLSDT  GKMYSKMRGY  LPSSPPYYEG  RFSNGPVWLE  QLTKQFPGLT
 61   IANEAEGGAT  AVAYNKISWD  PKYQVINNLD  YEVTQFLQKD  SFKPDDLVIL  WVGANDYLAY
121   GWNTEQDAKR  VRDAISDAAN  RMVLNGAKQI  LLFNLPDLGQ  NPSARSQKVV  EAVSHVSAYH
181   NKLLLNLARQ  LAPTGMVKLF  EIDKQFAEML  RDPQNFGLSD  VENPCYDGGY  VWKPFATRSV
241   STDRQLSAFS  PQERLAIAGN  PLLAQAVASP  MARRSASPLN  CEGKMFWDQV  HPTTVVHAAL
301   SERAATFIET  QYEFLAHG
```

FIGURE 2 (SEQ ID No. 1)

```
  1   MKKWFVCLLG  LVALTVQAAD  SRPAFSRIVM  FGDSLSDTGK  MYSKMRGYLP
 51   SSPPYYEGRF  SNGPVWLEQL  TKQFPGLTIA  NEAEGGATAV  AYNKISWNPK
101   YQVINNLDYE  VTQFLQKDSF  KPDDLVILWV  GANDYLAYGW  NTEQDAKRVR
151   DAISDAANRM  VLNGAKQILL  FNLPDLGQNP  SARSQKVVEA  VSHVSAYHNQ
201   LLLNLARQLA  PTGMVKLFEI  DKQFAEMLRD  PQNFGLSDVE  NPCYDGGYVW
251   KPFATRSVST  DRQLSAFSPQ  ERLAIAGNPL  LAQAVASPMA  RRSASPLNCE
301   GKMFWDQVHP  TTVVHAALSE  RAATFIANQY  EFLAH*
```

FIGURE 3 (SEQ ID No. 2)

```
  1   ivafGD$lTd  geayygdsdg  ggwgagladr  Ltallrlrar  prgvdvfnrg  isGrtsdGrl
 61   ivDalvallF  laqslglpnL  pPYLsgdflr  GANFAsagAt  Ilptsgpfli  QvqFkdfksq
121   vlelrqalgl  lqellrllpv  ldakspdlvt  imiGtNDlit  saffgpkste  sdrnvsvpef
181   kdnlrqlikr  Lrsnngarii  vlitlvilnl  gplGClPlkl  alalassknv  dasgclerln
241   eavadfneal  relaiskled  qlrkdglpdv  kgadvpyvDl  ysifqdldgi  qnpsayvyGF
301   ettkaCCGyG  gryNynrvCG  naglcnvtak  aCnpssylls  flfwDgfHps  ekGykavAea
361   l
```

FIGURE 4 (SEQ ID No. 3)

```
  1   mkkwfvcllg  lvaltvqaad  srpafsrivm  fgdslsdtgk  myskmrgylp  ssppyyegrf
 61   sngpvwleql  tnefpgltia  neaeggptav  aynkiswnpk  yqvinnldye  vtqflqkdsf
121   kpddlvilwv  gandylaygw  nteqdakrvr  daisdaanrm  vlngakeill  fnlpdlgqnp
181   sarsqkvvea  ashvsayhnq  lllnlarqla  ptgmvklfei  dkqfaemlrd  pqnfglsdqr
241   nacyggsyvw  kpfasrsast  dsqlsafnpq  erlaiagnpl  laqavaspma  arsastlnce
301   gkmfwdqvhp  ttvvhaalse  paatfiesqy  eflah
```

FIGURE 5 (SEQ ID No. 4)

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIGURE 6 (SEQ ID No. 5)

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 7 (SEQ ID No. 6)

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 8 (SEQ ID No. 7)

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIGURE 9 (SEQ ID No. 8)

```
         10         20         30         40         50         60
          |          |          |          |          |          |
MNLRQWMGAA TAALALGLAA CGGGGTDQSG NPNVAKVQRM VVFGDSLSDI GTYTPVAQAV 70         80         90        100        110        120
          |          |          |          |          |          |
GGGKFTTNPG PIWAETVAAQ LGVTLTPAVM GYATSVQNCP KAGCFDYAQG GSRVTDPNGI 130        140        150        160        170        180
          |          |          |          |          |          |
GHNGGAGALT YPVQQQLANF YAASNNTFNG NNDVVFVLAG SNDIFFWTTA AATSGSGVTP 190        200        210        220        230        240
          |          |          |          |          |          |
AIATAQVQQA ATDLVGYVKD MIAKGATQVY VFNLPDSSLT PDGVASGTTG QALLHALVGT 250        260        270        280        290        300
          |          |          |          |          |          |
FNTTLQSGLA GTSARIIDFN AQLTAAIQNG ASFGFANTSA RACDATKINA LVPSAGGSSL 310        320        330        340
          |          |          |          |
FCSANTLVAS GADQSYLFAD GVHPTTAGHR LIASNVLARL LADNVAH
```

FIGURE 10 (SEQ ID No. 19)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIGURE 11 (SEQ ID No. 10)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIGURE 12 (SEQ ID No. 11)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

FIGURE 13 (SEQ ID No. 12)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

FIGURE 14 (SEQ ID No. 13)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIGURE 15 (SEQ ID No. 14)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

FIGURE 16 (SEQ ID No. 15)

```
  1 MKKWFVCLLG LIALTVQAAD TRPAFSRIVM FGDSLSDTGK MYSKMRGYLP
 51 SSPPYYEGRF SNGPVWLEQL TKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNK
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIETQY EFLAHG*
```

FIGURE 17A

```
Alignment of pfam00657.6 consensus sequence with P10480
               *->ivafGDSlTdg...............eayygdsdgggwgagladrL
                  iv+fGDSl+d+++  ++ ++  +++++++ +++s+g   w ++l + +
    P10480   28    IVMFGDSLSDTgkmyskmrgylpssppYYEGRFSNGPVWLEQLTNEF   74 tall..rlrarprgvdvfnrgisGrtsdGrlivDalvallFlaqslglpn
               + l    + +++++++++  +n+   +
    P10480   75  PGLTiaNEAEGGPTAVAYNKISWNPK----------------------  100

LpPYLsgdflrGANFAsagAtIlptsgpfliQvqFkdfksqvlelrqalg
                                                           ++  ++
    P10480  101  ---------------------------------------YQVINN  106 llqellrllpvldakspdlvtimiGtNDlitsaffgpkstesdrnvsvpe
               l++e+ ++l +++ k+ dlv+++G+ND+      ++ ++ ++++++
    P10480  107  LDYEVTQFLQKDSFKPDDLVILWVGANDY--------LAYGWNTEQDAKR  148 fkdnlrqlikrLrsnngariivlitlvilnlgplGClPlklalalasskn
               ++d ++++++r+    nga+         ++++nl+ lG+ P+
    P10480  149  VRDAISDAANRMV-LNGAK-----EILLFNLPDLGQNPS----------  181 vdasgclerlneavadfnealrelaiskledqlrkdglpdvkgadvpyvD
               ++++ +e +  ++a++n++l +la      +ql+++g++++++++d ++++
    P10480  182  ARSQKVVEAASHVSAYHNQLLLNLA-----RQLAPTGMVKLFEIDKQFAE  226 lysifqdldgiqnpsayv.y....GFe..ttkaCCGyGgr.yNyn.rv.CG
               +   +q+++ + + +a+++++    +++ +++a+++++++  +N+++r+ ++
    P10480  227  MLRDPQNFGLSDQRNACYgGsyvwKPFaSRSASTDSQLSaFNPQeRLaIA  276 nag.l.c.nvtakaC.npssyll.sflfwDgfHpsekGykavAeal<-*
               +++ l +  ++++a++ +s+ ++++++fwD++Hp+    ++a+ e
    P10480  277  GNPlLaQaVASPMAArSASTLNCeGKMFWDQVHPTTVVHAALSEPA    322

Alignment of pfam00657.6 consensus sequence with AAG09804
               *->ivafGDSlTdg...............eayygdsdgggwgagladrL
                  iv+fGDSl+d+++  ++ ++  +++++++ +++s+g   w ++l + +
```

FIGURE 17B

```
AAG09804      28    IVMFGDSLSDTgkmyskmrgylpssppYYEGRFSNGPVWLEQLTKQF   74 tallrlrarprgvdvfnrgisGrtsdGrlivDalvallFlaqslglpnLp
                      +g+++ n  + +G+t
AAG09804      75    ----------PGLTIANEAEGGAT--------------------------   88

PYLsgdflrGANFAsagAtIlptsgpfliQvqFkdfksqvlelrqa....
                                                    ++++ + ++++ +
AAG09804      89    ----------------------------------AVAYNKISWNpkyq  102

..lgllqellrllpvldakspdlvtimiGtNDlitsaffgpkstesdrnv
                      ++l++e+ ++l +++ k+ dlv++++G+ND+       ++ ++ ++
AAG09804     103    vyNNLDYEVTQFLQKDSFKPDDLVILWVGANDY--------LAYGWNTEQ  144 svpefkdnlrqlikrLrsnngariivlitlvilnlgplGClPlklalala
                    +++++++d ++++++r+    nga+     ++++nl+ lG+ P+
AAG09804     145    DAKRVRDAISDAANRMV-LNGAK-----QILLFNLPDLGQNPS-------  181 ssknvdasgclerlneavadfnealrelaiskledqlrkdglpdvkgadv
                          ++++ +e  +  ++a++n++l +la      +ql+++g++++++++d
AAG09804     182    ----ARSQKVVEAVSHVSAYHNKLLLNLA-----RQLAPTGMVKLFEIDK  222 pyvDlysifqdldgiqnpsayv.y....GFe.ttkaCCGyGgr.yNyn.r
                    +++++   +q+++ +  ++ +++++    +++ t++ +++ +++ + +++r
AAG09804     223    QFAEMLRDPQNFGLSDVENPCYdGgyvwKPFaTRSVSTDRQLSaFSPQeR  272 v.CGnag.l.c.nvtakaC.npssyll.sflfwDgfHpsekGykavAeal
                    +  +++++  l +   ++++a++  +s   ++++++fwD++Hp+    ++a+ e+
AAG09804     273    LaIAGNPlLaQaVASPMARrSASPLNCeGKMFWDQVHPTTVVHAALSERA  322

<-*

AAG09804       -     -

Alignment of pfam00657.6 consensus sequence with NP_631558
                    *->ivafGDSlTdgeayygdsdgggwgagladrLtallrlrarprgvdvf
                         +va+GDS ++g       +g +  +++L   +  +  +  ++    +
NP_631558     42    YVALGDSYSAG---------SGVLPVDPANL----LCLRSTANYPHV    75 nrgisGrtsdGrlivD.a.l.vallFlaqslglpnLpPYLsgdflrGANF
                    + ++G++       D + +   +
NP_631558     76    IADTTGAR-----LTDvTcGaAQ---------------------------  93

AsagAtIlptsgpfliQvqFkdfksqvlelrqalgllqellrllpvldak
                                                +++       ++ +  ++  +++
NP_631558     94    --------------------------TADFTRAQYPGVAPQLDALGT   114 spdlvtimiGtNDl................itsaffgpkstesdrnvsvp
                    + dlvt+  iG+ND  ++  +  +  ++ ++      ++  + +k
NP_631558    115    GTDLVTLTIGGNDNstfinaitacgtagvlSGGKGSPCKDRHGTSFDDEI 164 efkdn..lrqlikrLrs.nngariivlitlvilnlg...........plG
                    e   +++ l++++  +r+++ +ar+ +l   ++i+++   +++   +  + G
NP_631558    165    EANTYpaLKEALLGVRArAPHARVAALGYPWITPATadpscflklplAAG  214

ClPlklalalassknvdasgclerlneavadfnealrelaiskledqlrk
                      P+                      l+  ++a  n  a+r    a
NP_631558    215    DVPY------------------LRAIQAHLNDAVRRAA----------  234 dglpdvkgadvpyvDlysifqdldgiqnpsayvyGFettkaCCGyGgryN
                                 ++  + +yvD+ ++
NP_631558    235    ------EETGATYVDFSGVSDG----------------------------  250 ynrvCGnaglcnvtakaC.npssyll.sflfwDgf...HpsekGykavAe
                               ++aC+ p +++ +  lf + + + Hp++ G +++Ae
NP_631558    251    -------------HDACeAPGTRWIePLLFGHSLvpVHPNALGERRMAE  286 al<-*
                    +
NP_631558    287    HT   288

Alignment of pfam00657.6 consensus sequence with CAC42140
                    *->ivafGDSlTdgeayygdsdgggwgagladrLtallrlrarprgvdvf
```

FIGURE 17C

```
                     +va+GDS ++g          +g +  +++L      + + + ++  +
    CAC42140    42     YVALGDSYSAG---------SGVLPVDPANL----LCLRSTANYPHV  75 nrgisGrtsdGrlivD.a.l.vallFlaqslglpnLpPYLsgdflrGANF
                  + ++G++         D + + +
    CAC42140    76  IADTTGAR-----LTDvTcGaAQ--------------------------  93

AsagAtIlptsgpfliQvqFkdfksqvlelrqalgllqellrllpvldak
                                                   +++    ++ +  ++ +++
    CAC42140    94  --------------------------TADFTRAQYPGVAPQLDALGT  114 spdlvtimiGtNDl................itsaffgpkstesdrnvsvp
                  + dlvt+ iG+ND ++  +  +  ++ +   ++  +k   ++ + +++
    CAC42140   115  GTDLVTLTIGGNDNstfinaitacgtagvlSGGKGSPCKDRHGTSFDDEI 164 efkdn..lrqlikrLrs.nngariivlitlvilnlg..........plG
                  e  +++ l++++  +r+++ +ar+ +l  ++i+++  +++    + +   G
    CAC42140   165  EANTYpaLKEALLGVRArAPHARVAALGYPWITPATadpscflklplAAG 214

ClPlklalalassknvdasgclerlneavadfnealrelaiskledqlrk
                  P+                        l+ ++a   n a+r    a
    CAC42140   215  DVPY-------------------LRAIQAHLNDAVRRAA---------- 234 dglpdvkgadvpyvDlysifqdldgiqnpsayvyGFettkaCCGyGgryN
                          ++ + +yvD+ ++
    CAC42140   235  ------EETGATYVDFSGVSDG---------------------------- 250 ynrvCGnaglcnvtakaC.npssyll.sflfwDgf...HpsekGykavAe
                                 ++aC+ p +++ + 1f + + + Hp++ G +++Ae
    CAC42140   251  --------------HDACeAPGTRWIePLLFGHSLvpVHPNALGERRMAE 286 al<-*
                  +
    CAC42140   287  HT    288
```

Alignment of pfam00657.6 consensus sequence with P41734

```
                  *->ivafGDSlTdg....eayygdsdgggwgagladrLtallrlrarprg
                     ++fGDS+T+   +++ + +   d+  ga+l + +        +r+
    P41734    6     FLLFGDSITEFafntRPIEDGKDQYALGAALVNEY---------TRK  43 vdvfnrgisGrtsdGrlivDalvallFlaqslglpnLpPYLsgdflrGAN
                  +d+   rg++G+t
    P41734   44   MDILQRGFKGYT-------------------------------------  55

FAsagAtIlptsgpfliQvqFkdfksqvlelrqalgllqellrllpvlda
                                                  +r+al++l+e+l+     +
    P41734   56   ---------------------------SRWALKILPEILKH-----E  70 kspdlvtimiGtNDlitsaffgpkstesdrnvsvpefkdnlrqlikrLrs
                  +  +  ti++G+ND+            ++ +++ v++pef+dn+rq++++++++s
    P41734   71   SNIVMATIFLGANDA---------CSAGPQSVPLPEFIDNIRQMVSLMKS 111 nngariivlitlvilnlgplGClPlklalalassknvdasgclerlneav
                  ++++ii+++++lv   ++          ++ k ++ +  + r+ne +
    P41734  112   YHIRPIIIGPGLVDREKW------------EKEKSEEIALGYFRTNENF 148 adfnealrelaiskledqlrkdglpdvkgadvpyvDlysifqdldgiqnp
                  a +  al +la             ++ +vp+v l++++fq+  +g++++
    P41734  149   AIYSDALAKLA---------------NEEKVPFVALNKAFQQEGGDAWQ 182 sayvyGFettkaCCGyGgryNynrvCGnaglcnvtakaCnpssyllsflf
                  +                                              l+
    P41734  183   Q--------------------------------------------LL 185 wDgfHpsekGykavAeal<-*
                  Dg+H+s  kGyk+++++l
    P41734  186   TDGLHFSGKGYKIFHDEL    203
```

FIGURE 18 (SEQ ID No. 25)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLTKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

FIGURE 19 (SEQ ID NO. 26)

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 20 (SEQ ID No. 27)

```
ZP_00058717
    1 mlphpagerg evgaffallv gtpqdrrlrl echetrplrg rcgcgerrvp pltlpgdgvl
   61 cttsstrdae tvwrkhlqpr pdggfrphlg vgcllagqgs pgvlwcgreg crfevcrrdt
  121 pglsrtrngd ssppfragws lppkcgeisq sarktpavpr ysllrtdrpd gprgrfvgsg
  181 praatrrrlf lgipalvlvt altlvlavpt gretlwrmwc eatqdwclgv pvdsrgqpae
  241 dgeflllspv qaatwgnyya lgdsyssgdg ardyypgtav kggcwrsana ypelvaeayd
  301 faghlsflac sgqrgyamld aidevgsqld wnsphtslvt igiggndlgf stvlktcmvr
  361 vpllldskact dqedairkrm akfettfeel isevrtrapd arilvvgypr ifpeeptgay
  421 ytltasnqrw lnetiqefnq qlaeavavhd eeiaasggvg svefvdvyha ldgheigsde
  481 pwvngvqlrd latgvtvdrs tfhpnaaghr avgervieqi etgpgrplya tfavvagatv
  541 dtlagevg
```

FIGURE 21 (SEQ ID No. 28)

```
    1 mgsgpraatr rrlflgipal vlvtaltlvl avptgretlw rmwceatqdw clgvpvdsrg
   61 qpaedgefll lspvqaatwg nyyalgdsys sgdgardyyp gtavkggcwr sanaypelva
  121 eaydfaghls flacsgqrgy amldaidevg sqldwnspht slvtigiggn dlgfstvlkt
  181 cmvrvpllds kactdqedai rkrmakfett feelisevrt rapdarilvv gyprifpeep
  241 tgayytltas nqrwlnetiq efnqqlaeav avhdeeiaas ggvgsvefvd vyhaldghei
  301 gsdepwvngv qlrdlatgvt vdrstfhpna aghravgerv ieqietgpgr plyatfavva
  361 gatvdtlage vg
```

FIGURE 22 (SEQ ID No. 29)

```
  1 mrttviaasa llllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 23 (SEQ ID No. 30)

ZP_00094165

```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk //
```

FIGURE 24 (SEQ ID No. 31)

NP_625998.

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
//
```

FIGURE 25 (SEQ ID No. 32)

NP_827753.

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
//
```

FIGURE 26

```
A.sal   1   MKKWFVCLLGLIALTVQAADTRPAFSRIVMFGDSLSDTGKMYSKMRGYLPSSPPYYEGRF  60
                +              +
A.hyd   1   MKKWFVCLLGLVALTVQAADSRPAFSRIVMFGDSLSDTGKMYSKMRGYLPSSPPYYEGRF  60

A. sal  61  SNGPVWLEQLTKQFPGLTIANEAEGGATAVAYNKISWNPKYQVINNLDYEVTQFLQKDSF 120
                        ++            +
A. hyd  61  SNGPVWLEQLTNEFPGLTIANEAEGGPTAVAYNKISWNPKYQVINNLDYEVTQFLQKDSF 120

A. sal 121  KPDDLVILWVGANDYLAYGWNTEQDAKRVRDAISDAANRMVLNGAKQILLFNLPDLGQNP 180
                                                         +
A. hyd 121  KPDDLVILWVGANDYLAYGWNTEQDAKRVRDAISDAANRMVLNGAKEILLFNLPDLGQNP 180

A. sal 181  SARSQKVVEAVSHVSAYHNKLLLNLARQLAPTGMVKLFEIDKQFAEMLRDPQNFGLSDVE 240
                       +          +                                      ++
A.hyd  181  SARSQKVVEAASHVSAYHQLLLNLARQLAPTGMVKLFEIDKQFAEMLRDPQNFGLSDQR  240

A. sal 241  NPCYDGGYVWKPFATRSVSTDRQLSAFSPQERLAIAGNPLLAQAVASPMARRSASPLNCE 300
                - ++ -     + + +                            + -
A. hyd 241  NACYGGSYVWKPFASRSASTDSQLSAFNPQERLAIAGNPLLAQAVASPMAARSASTLNCE 300

A. sal 301  GKMFWDQVHPTTVVHAALSERAATFIETQYEFLAH 335
                        +                +
A. hyd 301  GKMFWDQVHPTTVVHAALSEPAATFIESQYEFLAH 335
```

FIGURE 27 (SEQ ID No. 34)

```
ADSRPAFSRIVMFGDSLSDTGKMYSKMRGYLPSSPPYYEGRFSNGPVWLEQLTNEFPGLTIANEAEGGPTAVAYNK
ISWNPKYQVINNLDYEVTQFLQKDSFKPDDLVILWVGANDYLAYGWNTEQDAKRVRDAISDAANRMVLNGAKEILL
FNLPDLGQNPSARSQKVVEAASHVSAYHQLLLNLARQLAPTGMVKLFEIDKQFAEMLRDPQNFGLSDQRNACYGG
SYVWKPFASRSASTDSQLSAFNPQERLAIAGNPLLAQAVASPMAARSASTLNCE
GKMFWDQVHPTTVVHAALSEPAATFIESQYEFLAH
```

FIGURE 28 (SEQ ID No. 35)

```
  1   ADTRPAFSRI VMFGDSLSDT GKMYSKMRGY LPSSPPYYEG RFSNGPVWLE QLTKQFPGLT
 61   IANEAEGGAT AVAYNKISWN PKYQVINNLD YEVTQFLQKD SFKPDDLVIL WVGANDYLAY
121   GWNTEQDAKR VRDAISDAAN RMVLNGAKQI LLFNLPDLGQ NPSARSQKVV EAVSHVSAYH
181   NKLLLNLARQ LAPTGMVKLF EIDKQFAEML RDPQNFGLSD VENPCYDGGY VWKPFATRSV
241   STDRQLSAFS PQERLAIAGN PLLAQAVASP MARRSASPLN CEGKMFWDQV HPTTVVHAAL
301   SERAATFIET QYEFLAHG
```

FIGURE 29 (SEQ ID No. 36)

```
ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT
```

FIGURE 30

```
               1         10        20        30        40        50
               |---------+---------+---------+---------+---------|
       satA        ADTRPAFSRIVMFGDSLSDTGKMYSKMRGYLPSSPPYYEGRFSN--G
       R.sol   QSGNPNYAKVQRMVYFGDSLSDIGT--------YTPVAQAVGGGKFTTNPG
    Consensus  ...adnraafqRiVmFGDSLSDiGk.......YlPsaqayqeGrFsn..G 51        60        70        80        90        100
               |---------+---------+---------+---------+---------|
       satA       PVMLEQLTKQFPGLTIANEREGGATAVAYNKISMNPKYQVINNLDYEVTQ
       R.sol      PIMAETVAAQL-GYTLTPAVMGYATSVQNCPKAGCFDYAQGGSRVTDPNG
    Consensus     P!MaEqlaaQl.GlTianaaeGgATaVannkiagnfdYaqgnnrdt.$pnq 101       110       120       130       140       150
               |---------+---------+---------+---------+---------|
       satA       FLQKDSFKPDDLVILMVGANDYLAYG--HNTEQDAKRVRDAISDAANRMY
       R.sol      IGHNGGAGALTYPVQQQLANFYANSNNTFNGNNDVVFVLAGSNDIFFMTT
    Consensus     igqndgagaddlp!qqqgANdYaAsn..fNg##DakrVraainDaanrmt 151       160       170       180       190       200
               |---------+---------+---------+---------+---------|
       satA       LNGAKQILLFNLPDLGQNPSARSQKVVEAVSHVSAYHNKL-LLNLARQLA
       R.sol      AAATSGSGVTPAIATAQVQQRATDLVGYVKDMIAKGATQVYVFNLPDSSL
    Consensus     aaaakqiglfnaialaQnqqRas#lVgeakdh!aaganql.llNLarqla 201       210       220       230       240       250
               |---------+---------+---------+---------+---------|
       satA       PTGMVKLFEIDKQFAEMLRDPQNFGLSDVENPCYDGGYVHKPFATRSVST
       R.sol      TPDGVASGTTGQALLHALYGTFNTTLQSGLAGTSARIIDFNAQLTAAIQN
    Consensus     ppdgValgeidqalaeaLrdpqNfgLqdgeagcsargidfnaqaTaaIqn 251       260       270       280       290       300
               |---------+---------+---------+---------+---------|
       satA       DRQLSAFSPQERLAIAG--NPLLAQAVASPM---ARRSASPLNCEGKMFM
       R.sol      GASFGFANTSARACDATKINALVPSAGGSSLFCSANTLYASGADQSYLFA
    Consensus     daqlgaanpqaRaadNg..NaLlaqNgaSp$...RrrlaapgadNgkSFa 301       310       320       330
               |---------+---------+---------|
       satA       DQVHPTTYVNAALSERAATFIETQYEFLAN
       R.sol      DGVHPTTAGNRLIASNVLARLLA--DNVAN
    Consensus     DqVHPTTagNaaiaeraaariea..NnlAN
```

FIGURE 31A

```
                                         ▼
Pfam         *->ivafGDSltdggg...............ayygdsdgggwgagladrltsla..rlrargrgvdv
Sriml   38   YVALGDSYSSGVG.............agSYDSSSGSCKRSTKSYPALWAAS.......HTGTRF  81
Scoe1    5   YVAVGDSFTEG--...............--VGDPGPDGAFVGWADRLAVLL..ADRRPEGDFTY  47
Scoe2   10   LVAVGDSFTEG--...............--MSDLLPDGSYRGWADLLATRM...-AARSPGFRY  50
Scoe3  239   VVAFGDSITDG--...............ARSQSDANHRWTDVLAARLHEAA..GDGRDTPRYSV 283
Scoe4   75   LMMLGDSTAAG--..................------QGVHRAGQTPGALLASG..LAAVAERPVRL 113
Scoe5   66   VAAVGDSITRGFD.............acAVLSDCPEVSWATGSSAKVDSLAvrLLGKADAAEHS 116
Ahyd1   28   IVMFGDSLSDTGKmyskmrgylpssppyYEGRFSNGPVWLEQLTNEFPGLTiaNEAEGGPTAVA  91
Asal1   28   IVMFGDSLSDTGKmyskmrgylpssppyYEGRFSNGPVWLEQLTKQF----........------PGLTI  79
Ahyd2   40   IVMFGDSLSDTGKmyskmrgylpssppyYEGRFSNGPVWLEQLTKQFPGLTiaNEAEGGATAVA 103

Pfam         fnrgisGrtsdGrlvvDarlvatllFlaqflGlnlpPYLsgdflrGANFAsagAtIlgtslipflni
Sriml   82   NFTACSGAR---------------------------------------------------------  90
Scoe1   48   TNLAVRGRL---------------------------------------------------------  56
Scoe2   51   ANLAVRGKL---------------------------------------------------------  59
Scoe3  284   VNEGISGNR--------------------------------------------------------- 292
Scoe4  114   GSVAQPGAC--------------------------------------------------------- 122
Scoe5  117   WNYAVTGAR--------------------------------------------------------- 125
Ahyd1   92   YNKISWNPK--------------------------------------------------------- 100
Asal1   80   ANEAEGGAT---------------------------------------------------------  88
Ahyd2  104   YNKISWNPK--------------------------------------------------------- 112

▼
Pfam         QvqFkdfkskvlelrqa......lgllqellrlvpvldakspdlvtimiGtNDl...itvakfgpks
Sriml   91   ------------------........---TGDVLAKQLTPVNSGTDLVSITIGGNDAgfaDTMTTCNLQG 131
Scoe1   57   ------------------........---LDQIVAEQVPRVVGLAPDLVSFAAGGNDI.........I---  86
Scoe2   60   ------------------........--IGQIVDEQVDVAAAMGADVITLVGGLNDT..---------  88
Scoe3  293   -------LLTSRPGRPA......DNPSGLSRFQRDVLERTNVKAVVVVLGVNDV............ 333
Scoe4  123   ------------------......SDDLDRQVALVLAEPDRVPDICVIMVGANDV............ 153
Scoe5  126   ------------------........---MADLTAQVTRAAQREPELVAVMAGANDA.........--CR 155
Ahyd1  101   --------------YQVI......NNLDYEVTQFLQKDSFKPDDLVILWVGANDY...--------LA 137
Asal1   89   -------AVAYNKISWNpkyqvyNNLDYEVTQFLQKDSFKPDDLVILWVGANDY...--------LA 137
Ahyd2  113   --------------YQVI......NNLDYEVTQFLQKDSFKPDDLVILWVGANDY...--------LA 149

Pfam         .......tksdrnvsvpefrdnlrklikrLrsangariiilitlvllnlpl..........plGCl
Sriml  132   esaclarIAKARAYIQQTLPAQLDQVYDAIDSRAPAA-----QVVVLGYP-.............. 176
Scoe1   87   ......---RPGTDPDEVAERFELAVAALT-AAAGTVLVTTGFDTRGVP-.............----- 125
Scoe2   89   .........---LRPKCDMARVRDLLTQAVERLAPHCEQLVLMRSP-.................----- 122
Scoe3  334   .......LNSPELADRDAILTGLRTLVDRAHARGLRVVGATITPFGGYGG-........……----- 376
Scoe4  154   .......---THRMPATRSVRHLSSAVRRLR-TAGAEVVVGTCPDLGTIE-.............----- 192
Scoe5  156   .......STTSAMTPVADFRAQFEEAMATLR-KKLPKAQVYVSSIPDLKRLwsqgrtnplgkQVWKL 214
Ahyd1  138   .......YGWNTEQDAKRVRDAISDAANRMV-LNGAK-----EILLFNLP-.............----- 174
Asal1  138   .......YGWNTEQDAKRVRDAISDAANRMV-LNGAK-----QILLFNLP-.............----- 174
Ahyd2  150   .......YGWNTEQDAKRVRDAISDAANRMV-LNGAK-----QILLFNLP-.............----- 186

Pfam         pq.klalalassknvdatgclerlneavadyneаlrelaei.ek.l.q.aqlrkdglpdlkeanvpy
Sriml  177   --.RFYKLGGSCAVGLSEKSRAAINAAADDINAVTAKRA--.---.-.-.-----------ADHGFAF 219
Scoe1  126   --.---------------VLKHLRGKIATYNGHVRAIA--.---.-.-.-----------DRYGCPV 152
Scoe2  123   --.------------GRQGPVLERFRPRMEALFAVIDDLA--.---.-.-.-----------GRHGAVV 154
Scoe3  377   --.YTEARETMRQEVNEEIRSGRVFDTVVDFDKALRDPY--.---.-.-.---------------- 412
Scoe4  193   --.----------------------------RVRQPLRWLaRRaSrQlAAAQTIGAVEQGGRTVSL 227
Scoe5  215   GLcPSMLGDADSLDSAATLRRNTVRDRVADYNEVLREVC--.---.-.AkDRRCRSDDGAVHEFRFGT 273
Ahyd1  175   --.-----DLGQNPSARSQKVVEAASHVSAYHNQLLLLNLA--.---.-.-.RQLAPTGMVKLFEIDKQF 224
Asal1  175   --.-----DLGQNPSARSQKVVEAVSHVSAYHNKLLLNLA--.---.-.-.RQLAPTGMVKLFEIDKQF 224
Ahyd2  187   --.-----DLGQNPSARSQKVVEAVSHVSAYHNQLLLLNLA--.---.-.-.RQLAPTGMVKLFEIDKQF 236

Pfam         VDlysifqdldgiqnpsayv.y....GFeet.kaCCGyGgr.yNyn.rv.CGnag.l.ck.vtakaC
Sriml  220   GDVNT----------------.-....-.---------.-----.-TFAgHElCSGAPwL.HS.VT---- 242
Scoe1  153   LDLWSLRSVQDRRA------.-....-.----.----------.----.-----.-.--.------ 166
Scoe2  155   VDLYGAQSLADPRM------.-....-.-----.---------.---.------.-.---.------ 168
```

FIGURE 31B

```
Scoe3  413 ------------------------.-....-----.-----------.----.--.------.-.---.------ 413
Scoe4  228 GDLLGPEFAQNPREL-----.-....-----.-----------.----.--.------.-.---.------ 242
Scoe5  274 DQL----------------.-....-----.-----------.----.--.------.-.---.------ 276
Ahyd1  225 AEMLRDPQNFGLSDQRNACYgGsyvwKPFASrSASTDSQLSaFNPQeRLaIAGNPlLaQAvASPMAA 291
Asa11  225 AEMLRDPQNFGLSDVENPCYdGgyvwKPFATrSVSTDRQLSaFSPQeRLaIAGNPlLaQAvASPMAR 291
Ahyd2  237 AEMLRDPQNFGLSDVENPCYdGgyvwKPFATrSVSTDRQLSaFSPQeRLaIAGNPlLaQAvASPMAR 303
                                     ▼
Pfam       .dassyll.atlfwDgf.HpsekGykavAeal<-*
Sriml  243 .--------.--LPVENSyHPTANGQSKGYLPV   263
Scoe1  167 .--------.--WDADRL.HLSPEGHTRVALRA   186
Scoe2  169 .--------.--WDVDRL.HLTAEGHRRVAEAV   188
Scoe3  413 .-DPRRMRsDYDSGDHL.HPGDKGYARMGAVI    441
Scoe4  243 .--------.--FGPDNY.HPSAEGYATAAMAV   262
Scoe5  277 .--------.--SHWDWF.HPSVDGQARLAEIA   296
Ahyd1  292 rSASTLNCeGKMFWDQV.HPTTVVHAALSEPA    322
Asa11  292 rSASPLNCeGKMFWDQV.HPTTVVHAALSERA    322
Ahyd2  304 rSASPLNCeGKMFWDQV.HPTTVVHAALSERA    334
```

FIGURE 32 (SEQ ID No. 39)

```
   1 ggtggtgaac cagaacaccc ggtcgtcggc gtgggcgtcc aggtgcaggt gcaggttctt
  61 caactgctcc agcaggatgc cgccgtggcc gtgcacgatg gccttgggca ggcctgtggt
 121 ccccgacgag tacagcaccc atagcggatg gtcgaacggc agcggggtga actccagttc
 181 cgcgccttcg cccgcggctt cgaactccgc ccaggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcaccccga agtcggggga
 421 acaggacgac caggtcgcac cgatcgcggc gcaggcgagg aatgcggccg tcgcctcggc
 481 gatgttcggc aggtaggcca cgacccggtc gccggggccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg ggcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctcccctaa cgctccccgg tgacgagtg
1021 ttgtgcacca catctagcac gcgggacgcg gaaaccgtat ggagaaaaca cctacaaccc
1081 cggccggacg gtgggtttcg gccacactta ggggtcgggt gcctgcttgc cgggcagggc
1141 agtcccgggg tgctgtggtg cgggcgggag ggctgtcgct tcgaggtgtg ccggcgggac
1201 actccgggcc tcagccgtac ccgcaacggg gacagttctc ctcccttccg ggctggatgg
1261 tcccttcccc cgaaatgcgg cgagatctcc cagtcagccc ggaaaacacc cgctgtgccc
1321 aggtactctt tgcttcgaac agacaggccg gacggtccac gggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agacgctgtg gcgcatgtgg
1501 tgtgaggcca cccaggactg gtgcctgggg gtgccggtcg actcccgcgg acagcctgcg
1561 gaggacggcg agtttctgct gctttctccg gtccaggcag cgacctgggg gaactattac
1621 gcgctcgggg attcgtactc ttcggggggac ggggcccgcg actactatcc cggcaccgcg
1681 gtgaagggcg gttgctggcg gtccgctaac gcctatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact cccctcacac gtcgctggtg
1861 acgatcggga tcggcggcaa cgatctgggg ttctccacgg ttttgaagac ctgcatggtg
1921 cgggtgccgc tgctggacag caaggcgtgc acggaccagg aggacgctat ccgcaagcgg
1981 atggcgaaat tcgagacgac gtttgaagag ctcatcagcg aagtgcgcac ccgcgcgccg
2041 gacgcccgga tccttgtcgt gggctacccc cggattttttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacgagat cggctcggac
2281 gagccgtggg tgaacgggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gcccggccg tccgctctat gccactttcg cggtggtggc ggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcgttg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacggggggcg agggcgcgga catggtccag gtaagggccg tcgcggacga ggctcaccac
2821 ggcagtgccg accgcgcagg cgagggcgtt gccgccgaag tgctgccgt gctggccggg
2881 gcggatcacg tcgaagactt ccgcgtcgcc taccgccgcc gccacgggca ggatgccgcc
2941 gcccagcgct tgccgaaca ggtagatatc ggcgtcgact ccgctgtggt cgcaggcccg
```

FIGURE 33 (SEQ ID No. 40)

```
  1 vgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

Figure 34

```
Pfam           *->ivafGDSltdggg...............ayygdsdgggwgagladrltsla..rlrargrgvdv
Sriml    38       YVALGDSYSSGVG.............agSYDSSSGSCKRSTKSYPALWAAS..------HTGTRF  81
Scoe1     5       YVAVGDSFTEG--................--VGDPGPDGAFVGWADRLAVLL..ADRRPEGDFTY  47
Scoe2    10       LVAVGDSFTEG--................--MSDLLPDGSYRGWADLLATRM...--AARSPGFRY  50
Ahyd1    28       IVMFGDSLSDTCKmyskmrgylpssppyYEGRFSNGPVWLEQLTNEFPGLTiaNEAECGPTAVA  91
Asal1    28       TVMFGDSISDTGKmyskmrgylpssppyYEGRFSNGPVWLEQLTKQF----..------PGLTT  79
Ahyd2    40       IVMFGDSLSDTGKmyskmrgylpssppyYEGRFSNGPVWLEQLTKQFPGLTiaNEAEGGATAVA 103

Pfam           fnrgisGrtsdGrlvvDarlvatllFlaqflGlnlpPYLsgdflrGANFAsagAtIlgtslipflni
Sriml    82    NFTACSGAR---------------------------------------------------------  90
Scoe1    48    TNLAVRGRL---------------------------------------------------------  56
Scoe2    51    ANLAVRGKL---------------------------------------------------------  59
Ahyd1    92    YNKISWNPK--------------------------------------------------------- 100
Asal1    80    ANEAEGGAT---------------------------------------------------------  88
Ahyd2   104    YNKISWNPK--------------------------------------------------------- 112

Pfam           QvqFkdfkskvlelrqa......lgllqellrlvpvldakspdlvtimiGtNDl...itvakfgpks
Sriml    91    -----------------......---TGDVLAKQLTPVNSGTDLVSITIGGNDAgfaDTMTTCNLQG 131
Scoe1    57    -----------------......---LDQIVAEQVPRVVGLAPDLVSFAAGGNDI...------I----  86
Scoe2    60    -----------------......---IGQIVDEQVDVAAAMGADVITLVGGLNDT...----------  88
Ahyd1   101    -------------YQVI......NNLDYEVTQFLQKDSFKPDDLVILWVGANDY...---------LA 137
Asal1    89    -------AVAYNKISWNpkyqvyNNLDYEVTQFLQKDSFKPDDLVILWVGANDY...---------LA 137
Ahyd2   113    -------------YQVI......NNLDYEVTQFLQKDSFKPDDLVILWVGANDY...---------LA 149

Pfam           .......tksdrnvsvpefrdnlrklikrLrsangariiilitlvllnlplplGCl
Sriml   132    esaclarIAKARAYIQQTLPAQLDQVYDAIDSRAPAA-------QVVVLGYP------ 176
Scoe1    87    .......---RPGTDPDEVAERFELAVAALT-AAAGTVLVTTGFDTRGVP------ 125
Scoe2    89    .......---------LRPKCDMARVRDLLTQAVERLAPICEQLVLMRSP------ 122
Ahyd1   138    .......YGWNTEQDAKRVRDAISDAANRMV-LNGAK-----EILLFNLP------ 174
Asal1   138    .......YGWNTEQDAKRVRDAISDAANRMV-LNGAK-----QILLFNLP------ 174
Ahyd2   150    .......YGWNTEQDAKRVRDAISDAANRMV-LNGAK-----QILLFNLP------ 186

Pfam           pqklalalassknvdatgclerlneavadyneаlrelaeiekIqaqlrkcglpdlkeanvpy
Sriml   177    --RFYKLGGSCAVGLSEKSRAAINAAADDINAVTAKRA-------------ADHGFAF 219
Scoe1   126    ------------------VLKHLRGKIATYNGHVRAIA-----------------DRYGCPV 152
Scoe2   123    -------------GRQGPVLERFRPRMEALFAVIDDLA-----------------GRHGAVV 154
Ahyd1   175    ------DLGQNPSARSQKVVEAASIVSAYINQLLLNLA------RQLAPTGMVKLFEIDKQF 224
Asal1   175    ------DLGQNPSARSQKVVEAVSHVSAYENKLLLNLA------RQLAPTGMVKLFEIDKQF 224
Ahyd2   187    ------DLGQNPSARSQKVVEAVSHVSAYENQLLLNLA------RQLAPTGMVKLFEIDKQF 236

Pfam           VDlysifqdldgiqnpsayv.y....GFeet.kaCCGyGgr.yNyn.rv.CGnag.l.ck.vtakaC
Sriml   220    GDVNT---------------.-...-----.---------.-TFAgHElCSGAPwL.HS.VT---- 242
Scoe1   153    IDLWSLRSVQDRRA------.-...-----.---------.----.--.-----.-.--.------ 166
Scoe2   155    VDLYGAQSLADPRM------.-...-----.---------.----.--.-----.-.--.------ 168
Ahyd1   225    AEMLRDPQNFGLSDQRNACYqGsyvwKPFASrSASTDSQLSaFNPQeRLaIAGNPlLaQAvASPMAA 291
Asal1   225    AEMLRDPQNFGLSDVENPCYdGgyvwKPFATrSVSTDRQLSaFSPQeRLaIAGNPlLaQAvASPMAR 291
Ahyd2   237    AEMLRDPQNFGLSDVENPCYdGgyvwKPFATrSVSTDRQLSaFSPQeRLaIAGNPlLaQAvASPMAR 303

Pfam           .dassyll.atlfwDgf.HpsekGykavAeal<-*
Sriml   243    .-------.--LPVENSyHPTANGQSKGYLPV    263
Scoe1   167    .-------.--WDADRL.HLSPEGHTRVALRA    186
Scoe2   169    .-------.--WDVDRL.HLTAEGHRRVAEAV    188
Ahyd1   292    rSASTLNCeGKMFWDQV.HPTTVVHAALSEPA    322
Asal1   292    rSASPLNCeGKMFWDQV.HPTTVVHAALSERA    322
Ahyd2   304    rSASPLNCeGKMFWDQV.HPTTVVHAALSERA    334
```

FIGURE 35 (SEQ ID No. 42)

```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggggc ggcgggctct gtggtgcccc gcgacccccg
 181 gccccggtga gcggtgaatg aaatccggct gtaatcagca tcccgtgccc accccgtcgg
 241 ggaggtcagc gcccggagtg tctacgcagt cggatcctct cggactcggc catgctgtcg
 301 gcagcatcgc gctcccgggt cttggcgtcc ctcggctgtt ctgcctgctg tccctggaag
 361 gcgaaatgat caccggggag tgatacaccg gtggtctcat cccggatgcc cacttcggcg
 421 ccatccggca attcgggcag ctccggggtgg aagtaggtgg catccgatgc gtcggtgacg
 481 ccatagtggg cgaagatctc atcctgctcg agggtgctca ggccactctc cggatcgata
 541 tcggggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aaatggtgg tgggagccct ggtcgcggtt
 961 ccgtgggagg cgccgtgccc cgcaggatcg tcggcatcgg cggatctggc cggtaccccg
1021 cggtgaataa aatcattctg taaccttcat cacggttggt tttaggtatc cgcccctttc
1081 gtcctgaccc cgtcccccggc gcgcgggagc ccgcgggttg cggtagacag gggagacgtg
1141 gacaccatga ggacaacggt catcgcagca agcgcattac tccttctcgc cggatgcgcg
1201 gatggggccc gggaggagac cgccggtgca ccgccgggtg agtcctccgg gggcatccgg
1261 gaggagggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg ccaggggggcg
1441 gtgaccgggg atctgctcga acccaggacg ctgggggagc gcacgctgcc ggcgcaggtg
1501 gatgcgctga cggaggacac caccctggtc accctctcca tcggggggcaa tgacctcgga
1561 ttcggggagg tggcgggatg catccgggaa cggatcgccg gggagaacgc tgatgattgc
1621 gtggacctgc tgggggaaaac catcggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactgggggg atgtctccga ggcggatcgt
1801 cgttgggcgg ttgagctgac cgggcagatc aacgagaccg tgcgcgaggc ggccgaacga
1861 cacgatgccc tctttgtcct gcccgacgat gccgatgagc acaccagttg tgcaccccca
1921 cagcagcgct gggcggatat ccagggccaa cagaccgatg cctatccgct gcacccgacc
1981 tccgccggcc atgaggcgat ggccgccgcc gtccgggacg cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaagggttg ttccccgagg gtgcgcagag ccgagtccag
2221 acctgcggcc tgctccggat catgggccca accggcgatg acgatcaaca ccccccaggat
2281 cccgaaggcg ataccacggg cgacataacc ggctgttccg gtgatgatga tcgcggtccc
2341 gacctgccct gaccccgcac ccgcctccag atcctcccgg aaatcccggg tggccccctt
2401 ccagaggttg tagacacccg ccccccagtac caccagcccg gcgaccacaa ccagcaccac
2461 accccagggt tgggatagga cggtggcggt gacatcggtg gcggtctccc catcggaggt
2521 gctgccgccc cgggcgaagg tggaggtggt caccgccagg gagaagtaga ccatggccat
2581 gaccgcccc ttggcccttt ccttgaggtc ctcgcccgcc agcagctggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatcccca ggacaatgaa
2821 accacctctg gccaggtgg tcagcgcggg gtggtcctcg gcctggtcgg cagcccgttc
2881 gatcgtccgt ttcgcggatc tggtgtcgcc cttatccata gctcccattg aaccgccttg
2941 aggggtgggc ggccactgtc agggcggatt gtgatctgaa ctgtgatgtt ccatcaaccc
```

FIGURE 36 SEQ ID No. 69

```
   1 tgccggaact caagcggcgt ctagccgaac tcatgcccga aagcgcgtgg cactatcccg
  61 aagaccaggt ctcggacgcc agcgagcgcc tgatgccgc cgaaatcacg cgcgaacagc
 121 tctaccgcca gctccacgac gagctgccct atgacagtac cgtacgtccc gagaagtacc
 181 tccatcgcaa ggacggttcg atcgagatcc accagcagat cgtgattgcc cgcgagacac
 241 agcgtccgat cgtgctgggc aagggtggcg cgaagatcaa ggcgatcgga gaggccgcac
 301 gcaaggaact ttcgcaattg ctcgacacca aggtgcacct gttcctgcat gtgaaggtcg
 361 acgagcgctg ggccgacgcc aaggaaatct acgaggaaat cggcctcgaa tgggtcaagt
 421 gaagctcttc gcgcgccgct gcgccccagt acttctcgcc cttgccgggc tggctccggc
 481 ggctacggtc gcgcgggaag caccgctggc cgaaggcgcg cgttacgttg cgctgggaag
 541 ctccttcgcc gcaggtccgg gcgtggggcc caacgcgccc ggatcgcccg aacgctgcgg
 601 ccggggcacg ctcaactacc cgcacctgct cgccgaggcg ctcaagctcg atctcgtcga
 661 tgcgacctgc agcggcgcga cgacccacca cgtgctgggc ccctggaacg aggttccccc
 721 tcagatcgac agcgtgaatg gcgacacccg cctcgtcacc ctgaccatcg gcggaaacga
 781 tgtgtcgttc gtcggcaaca tcttcgccgc cgcttgcgag aagatggcgt cgcccgatcc
 841 gcgctgcggc aagtggcggg agatcaccga ggaagagtgg caggccgacg aggagcggat
 901 gcgctccatc gtacgccaga tccacgcccg cgcgcctctc gccgggtgg tggtggtcga
 961 ttacatcacg gtcctgccgc catcaggcac ttgcgctgcc atggcgattt cgccggaccg
1021 gctggcccag agccgcagcg ccgcgaaacg gcttgccggg attaccgcac gggtcgcgcg
1081 agaagagggt gcatcgctgc tcaagttctc gcatatctcg cgccggcacc atccatgctc
1141 tgccaagccc tggagcaacg gctttccgc ccggccgac gacggcatcc cggtccatcc
1201 gaaccggctc ggacatgctg aagcggcagc ggcgctggtc aagcttgtga aattgatgaa
1261 gtagctactg cactgatttc aaatagtatt gcctgtcagc tttccagccc ggattgttgc
1321 agcgcaacag aaacttgtcc gtaatggatt gatggtttat gtcgctcgca aattgccgtc
1381 gaagggaacg ggcgcgtcgc tcgttaacgt cctgggtgca gcagtgacgg agcgcgtgga
1441 tgagtgatac tggcggtgtc atcggtgtac gcgccgccat tccatgcct gtacgcgccg
//
```

FIGURE 37A (SEQ ID No. 44)

```
   1 cccggcggcc cgtgcaggag cagcagccgg cccgcgatgt cctcgggcgt cgtcttcatc
  61 aggccgtcca tcgcgtcggc gaccggcgcc gtgtagttgg cccggacctc gtcccaggtg
 121 cccgcggcga tctggcgggt ggtgcggtgc gggccgcgcc gaggggagac gtaccagaag
 181 cccatcgtca cgttctccgg ctgcggttcg ggctcgtccg ccgctccgtc cgtcgcctcg
 241 ccgagcacct tctcggcgag gtcggcgctg gtcgccgtca ccgtgacgtc ggcgccccgg
 301 ctccagcgcg agatcagcag cgtccagccg tcgccctccg ccagcgtcgc gctgcggtcg
 361 tcgtcgcggg cgatccgcag cacgcgcgcg ccgggcggca gcagcgtcgc gccggaccgt
 421 acgcggtcga tgttcgccgc gtgcgagtac ggctgctcac ccgtggcgaa acggccgagg
 481 aacagcgcgt cgacgacgtc ggacggggag tcgctgtcgt ccacgttgag ccggatcggc
 541 agggcttcgt gcgggttcac ggacatgtcg ccatgatcgg gcaccgcc gccgcgtgca
 601 cccgctttcc cgggcacgca cgacaggggc tttctcgccg tcttccgtcc gaacttgaac
 661 gagtgtcagc catttcttgg catggacact tccagtcaac gcgcgtagct gctaccacgg
 721 ttgtggcagc aatcctgcta agggaggttc catgagacgt ttccgacttg tcggcttcct
 781 gagttcgctc gtcctcgccg ccggcgccgc cctcaccggg gcagcgaccg cccaggcggc
 841 ccaacccgcc gccgccgacg gctatcggc cctcggcgac tcctactcct ccggggtcgg
 901 agcgggcagc tacatcagct cgagcggcga ctgcaagcgc agcacgaagg cccatccta
 961 cctgtgggcg gccgcccact cgccctccac gttcgacttc accgcctgtt ccggcgcccg
1021 tacgggtgat gttctctccg gacagctcgg cccgctcagc tccggcaccg gctcgtctc
1081 gatcagcatc ggcggcaacg acgccggttt cgccgacacc atgacgacct gtgtgctcca
1141 gtccgagagc tcctgcctgt cgcggatcgc caccgccgag gcgtacgtcg actcgacgct
1201 gcccgcaag ctcgacgcg tctactcgg aatcagcgac aaggcgccga acgcccacgt
1261 cgtcgtcatc ggctacccgc gcttctacaa gctcggcacc acctgcatcg gcctgtccga
1321 gaccaagcgg acggcgatca acaaggcctc cgaccacctc aacaccgtcc tcgcccagcg
```

FIGURE 37B

```
1381 cgccgccgcc cacggcttca ccttcggcga cgtacgcacc accttcaccg gccacgagct
1441 gtgctccggc agcccctggc tgcacagcgt caactggctg aacatcggcg agtcgtacca
1501 ccccaccgcg gccggccagt ccggtggcta cctgccggtc ctcaacggcg ccgcctgacc
1561 tcaggcggaa ggagaagaag aaggagcgga gggagacgag gagtgggagg ccccgcccga
1621 cggggtcccc gtccccgtct ccgtctccgt cccggtcccg caagtcaccg agaacgccac
1681 cgcgtcggac gtggcccgca ccggactccg cacctccacg cgcacggcac tctcgaacgc
1741 gccggtgtcg tcgtgcgtcg tcaccaccac gccgtcctgg cgcgagcgct cgccgcccga
1801 cgggaaggac agcgtccgcc accccggatc ggagaccgac ccgtccgcgg tcacccaccg
1861 gtagccgacc tccgcgggca gccgcccgac cgtgaacgtc gccgtgaacg cgggtgcccg
1921 gtcgtgcggc ggcggacagg cccccgagta gtgggtgcgc gagcccacca cggtcacctc
1981 caccgactgc gctgcggggc
```

FIGURE 38

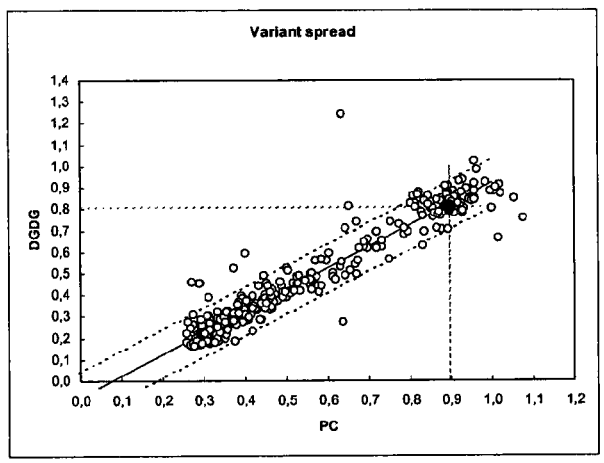

FIGURE 39 (SEQ ID No. 46)

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagccgg tgcccttctt gagcgtgacg atgtagctgc
 181 ccttgatcgc ggtgggggag ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctgggtg gggcgcacgg ctgtgggggg tgcgcgcgtc atcacgcaca cggccctgga
 421 gcgtcgtgtt ccgccctggg ttgagtaaag cctcggccat ctacggggt ggctcaaggg
 481 agttgagacc ctgtcatgag tctgacatga gcacgcaatc aacgggccg tgagcacccc
 541 ggggcgaccc cggaaagtgc cgagaagtct tggcatggac acttcctgtc aacacgcgta
 601 gctggtacga cggttacggc agagatcctg ctaaagggag gttccatgag acgttcccga
 661 attacggcat acgtgacctc actcctcctc gccgtcggct gcgccctcac cggggcagcg
 721 acggcgcagg cgtccccagc cgccgcggcc acgggctatg tggccctcgg cgactcgtac
 781 tcgtccggtg tcggcgccgg cagctacctc agctccagcg gcgactgcaa gcgcagttcg
 841 aaggcctatc cgtacctctg gcaggccgcg cattcaccct cgtcgttcag tttcatggct
 901 tgctcgggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgccgg ccaactcgac agcgtgtaca cggcgatcag cacgaaggcc
1141 ccgtcggccc atgtggccgt gctggctac ccccgcttct acaaactggg cggctcctgc
1201 ctcgcgggcc tctcggagac caagcggtcc gccatcaacg acgcggccga ctatctgaac
1261 agcgccatcg ccaagcgcgc cgccgaccac ggcttcacct tcggcgacgt caagagcacc
1321 ttcaccggcc atgagatctg ctccagcagc cctggctgc acagtctcga cctgctgaac
1381 atcggccagt cctaccaccc gaccgcggcc ggccagtccg gcggctatct gccggtcatg
1441 aacagcgtgg cctgagctcc cacggcctga attttaagg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga cacctgctt ctgctgggtc tttccgccgc
1681 tcgccgggaa ggacagcgtc ttccagcccg gatccgggac ctcgcccttc ttggtcaccc
1741 agcggtactc caccctcgacc ggcacccggc ccaccgtgaa ggtcgccgtg aacgtgggcg
1801 cctggcgcgt gggcggcggg caggcaccgg agtagtcggt gtgcacgccg gtgaccgtca
1861 ccttcacgga ctgggccggc gggtcgtcg taccgccgcc gccaccgccg cctcccggag
1921 tggagcccga gctgtggtcg cccccgccgt cggcgttgtc gtcctcgggg gttttcgaac
```

FIGURE 40

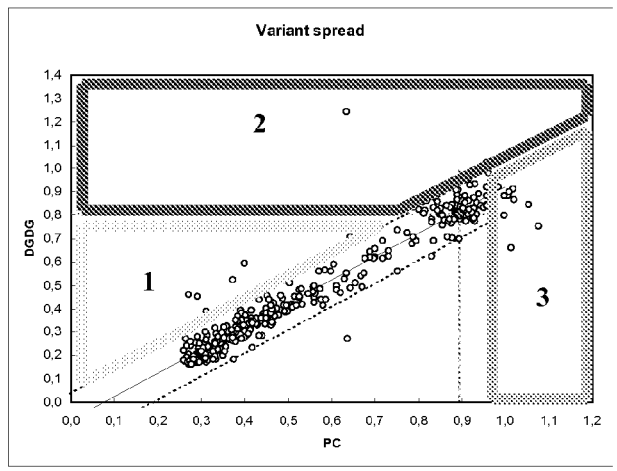

FIGURE 41 (SEQ ID No. 48)

```
1    ctgcagacac ccgccccgcc ttctcccgga tcgtcatgtt cggcgactcc ctcagcgaca
61   ccggcaagat gtactccaag atgcgcggct acctgccgtc ctccccgccg tactacgagg
121  gccgcttctc gaacggcccg gtctggctgg agcagctgac gaagcagttc cccggcctga
181  cgatcgccaa cgaggccgag gggggcgcga ccgcagtcgc ctacaacaag atctcctgga
241  acccgaagta ccaggtcatt aacaacctcg actacgaggt cacccagttc ttgcagaagg
301  actcgttcaa gcccgacgac ctggtcatcc tgtgggtggg cgccaacgac tacctggcct
361  acggttggaa cacggagcag gacgccaagc gggtgcgcga cgccatctcg gacgcggcaa
421  accgcatggt cctgaacggc gcgaagcaga tcctgctgtt caacctgccc gacctgggcc
481  agaacccgtc cgcccgctcc cagaaggtcg tcgaggccgt ctcgcacgtg tccgcctacc
541  acaacaagct gctcctcaac ctcgcccggc agctcgcccc gacgggcatg gtcaagctgt
601  tcgagatcga caagcagttc gcggagatgc tgcgcgaccc ccagaacttc ggcctgagcg
661  acgtggagaa cccgtgctac gacggcggct acgtgtggaa gccgttcgcc acccggtccg
721  tctcgaccga ccggcagctg tcggccttct cgccccagga gcgcctggcg atcgctggca
781  acccgctcct ggcacaggcg gtagcttcgc cgatggcccg ccgctcggcc tcgcccctca
841  actgcgaggg caagatgttc tgggaccagg tccaccccac caccgtggtc cacgccgccc
901  tctcggagcg cgccgccacc ttcatcgaga cccagtacga gttcctcgcc cactagtcta
961  gaggatcc
```

FIGURE 42

1. L131
2. S.avermitilis
3. T.fusca
4. Consensus

```
                    1                                              50
1   (1)   --------MRLTRSLSAASVIVFALLLALLGISPAQAAG-----------
2   (1)   --------MRRSRITAYVTSLLLAVGCALTGAATAQASPA----------
3   (1)   VGSGPRAATRRRLFLGIPALVLVTALTLVLAVPTGRETLWRMWCEATQDW
4   (1)           MRRSRFLA  ALILLTLA AL GAA ARAAP 51                                             100
1  (32)   -------------------------P-AYVALGDSYSSGNGAGSYID
2  (33)   -------------------------AAATGYVALGDSYSSGVGAGSYLS
3  (51)   CLGVPVDSRGQPAEDGEFLLLSPVQAATWGNYYALGDSYSSGDGARDYYP
4  (51)                         A A  YVALGDSYSSG GAGSY 101                                             150
1  (53)   SSGD---CHRSNNAYPARWAAANAP---SSFTFAACSGAVTTDVIN----
2  (57)   SSGD---CKRSSKAYPYLWQAAHSP---SSFSFMACSGARTGDVLA----
3 (101)   GTAVKGGCWRSANAYPELVAEAYDFA--GHLSFLACSGQRGYAMLDAIDE
4 (101)   SSGD   C RSTKAYPALWAAAHA    SSFSF ACSGARTYDVLA 151                                             200
1  (93)   --NQLGALNAST--GLVSITIGGNDAGFADAMTTCVTS------SDSTCL
2  (97)   --NQLGTLNSST--GLVSLTIGGNDAGFSDVMTTCVLQ------SDSACL
3 (149)   VGSQLDWNSPHT--SLVTIGIGGNDLGFSTVLKTCMVR------VPLLDS
4 (151)      QL  LNS T  LVSITIGGNDAGFAD MTTCVL       SDSACL 201                                             250
1 (133)   NRLATATNYINTTLLA-------RLDAVYSQIKARAPNARVVVLGYPRMY
2 (137)   SRINTAKAYVDSTLPG-------QLDSVYTAISTKAPSAHVAVLGYPRFY
3 (191)   KACTDQEDAIRKRMAKF----ETTFEELISEVRTRAPDARILVVGYPRIF
4 (201)      RIA AK YI  TLPA       RLDSVYSAI TRAP ARVVVLGYPRIY 251                                             300
1 (176)   LASNPWYCLGLSNTKRAAINTTADTLNSVISSRATAH----------GF
2 (180)   KLGG-SCLAGLSETKRSAINDAADYLNSAIAKRAADH----------GF
3 (237)   PEEPTGAYYTLTASNQRWLNETIQEFNQQLAEAVAVHDEEIAASGGVGSV
4 (251)        SG   LGLS TKRAAINDAAD LNSVIAKRAADH           GF 301                                             350
1 (215)   RFGDVRPTFNNHELFFGNDWLHSLTLP----------------VWESYH
2 (218)   TFGDVKSTFTGHEICSSSTWLHSLDLLN---------------IGQSYH
3 (287)   EFVDVYHALDGHEIGSDEPWVNGVQLRDLATG---------VTVDRSTFH
4 (301)   TFGDV  TF GHELCSA PWLHSLTLP               V  SYH 351                                             395
1 (248)   PTSTGHQSGYLPVLNANSST---------------------
2 (252)   PTAAGQSGGYLPVMNSVA-----------------------
3 (328)   PNAAGHRAVGERVIEQIETGPGRPLYATFAVVAGATVDTLAGEVG
4 (351)   PTA GHAAGYLPVLNSI T
```

FIGURE 43

SEQ ID No 17 which is the amino acid sequence of a lipid acyltransferase from *Candida parapsilosis*;

```
MRYFAIAFLL INTISAFVLA PKKPSQDDFY TPPQGYEAQP LGSILKTRNV PNPLTNVFTP VKVQNAWQLL
VRSEDTFGNP NAIVTTIIQP FNAKKDKLVS YQTFEDSGKL DCAPSYAIQY GSDISTLTTQ GEMYYISALL
DQGYYVVTPD YEGPKSTFTV GLQSGRATLN SLRATLKSGN LTGVSSDAET LLWGYSGGSL ASGWAAAIQK
EYAPELSKNL LGAALGGFVT NITATAEAVD SGPFAGIISN ALAGIGNEYP DFKNYLLKKV SPLLSITYRL
GNTHCLLDGG IAYFGKSFFS
RIIRYFPDGW DLVNQEPIKT ILQDNGLVYQ PKDLTPQIPL FIYHGTLDAI VPIVNSRKTF QQWCDWGLKS
GEYNEDLTNG HITESIVGAP AALTWIINRF NGQPPVDGCQ HNVRASNLEY PGTPQSIKNY FEAALHAILG
FDLGPDVKRD KVTLGGLLKL ERFAF
```

FIGURE 44

SEQ ID No 18 which is the amino acid sequence of a lipid acyltransferase from *Candida parapsilosis*;

```
MRYFAIAFLL INTISAFVLA PKKPSQDDFY TPPQGYEAQP LGSILKTRNV PNPLTNVFTP VKVQNAWQLL
VRSEDTFGNP NAIVTTIIQP FNAKKDKLVS YQTFEDSGKL DCAPSYAIQY GSDISTLTTQ GEMYYISALL
DQGYYVVTPD YEGPKSTFTV GLQSGRATLN SLRATLKSGN LTGVSSDAET LLWGYSGGSL ASGWAAAIQK
EYAPELSKNL LGAALGGFVT NITATAEAVD SGPFAGIISN ALAGIGNEYP DFKNYLLKKV SPLLSITYRL
GNTHCLLDGG IAYFGKSFFS RIIRYFPDGW DLVNQEPIKT ILQDNGLVYQ PKDLTPQIPL FIYHGTLDAI
VPIVNSRKTF QQWCDWGLKS GEYNEDLTNG HITESIVGAP AALTWIINRF NGQPPVDGCQ HNVRASNLEY
PGTPQSIKNY FEAALHAILG FDLGPDVKRD KVTLGGLLKL ERFAFHHHHH H
```

FIGURE 48

[Figure 48 shows a multiple sequence alignment of 1DEO, 1IVN, and P10480 with secondary structure annotations. The alignment content is not legibly transcribable from the provided image resolution.]

```
1DEO       T T V Y   L   A G D S T M A K n - - - - - - - - - - - - - - - - G G G S T N G W G E Y L
           s1s1s1s1 s1   s1s1h?h?h?                                         h1h1h1h1h1
1IVN     A D T L L   I   L G D S L S A G - - - - - - - - - - - - - Y R M S A S A A W P A L L
         s1s1s1s1   s1   s1s1h h h h                                         h1h1h1h1h1
P10480       I V     M   F G D S L S D T g k m y s k m r g y l p s p p y y e G R F S N G P V W L E Q L

1DEOm      T T V Y   L   A G D S T M A K n - - - - - - - - - - - - - - - - G G G S T N G W G E Y L
           s1s1s1s1 s1   s1s1h?h?h?                                         h1h1h1h1h1
1IVNm    A D T L L   I   L G D S L S A G - - - - - - - - - - - - - Y R M S A S A A W P A L L
         s1s1s1s1   s1   s1s1h h h h                                         h1h1h1h1h1
P10480m      I V     M   F G D S L S D T g k m y s k m r g y l p s p p y y e G R F S N G P V W L E Q L

1DEO     A S Y L S   A   T V - - - - - - - - - - - - - - - V N D A V A G R S - - A R S Y T R E G R F E N I A D V V
         h1h1h1     s2   s2                                             h3h3 h3h3h3h3h3h3h3h3h3h3h3h3
1IVN     N D K W q   s   k - - - - - - - - - - - - - - s2s2 V N A S I S G D T - - S Q Q G L A R L P A L L K Q
         h1h1h1     s2?s2?                              s2s2                              h3h3h3h3h3h3h3h3h3h3h3h3
P10480   T N E F P   G   L T i a n e a e g g p t a v a Y N K I S W N P K Y q v I N N L D Y E V T Q F L Q K D S F

1DEOm    A S Y L S   A   T V - - - - - - - - - - - - - - - V N D A V A G R S - - A R S Y T R E G R F E N I A
         h1h1h1     s2   s2                                             h3h3 h3h3h3h3h3h3h3h3h3h3
1IVNm    N D K W g   s   k - - - - - - - - - - - - - - s2s2 V N A S I S G D T - - S Q Q G L A R L P A L L
         h1h1h1     s2?s2?                              s2s2                              h3h3h3h3h3h3h3
P10480m  T N E F P   G   L T i a n e a e g g p t a v a Y N K I S W N P K     Y q v I N N L D Y E V T Q F L Q

1DEO     T A G D Y   V   I V E F G H N D G g s - - l s t d n g - - t t d c - - s g t g a E v C Y S V Y D G V N E T I L T F P
         s4s4       s4   s4                                                         s?s?s?s?s?s?h4h4h4
1IVN     H Q P R W   V   L V E L G G N D G - - ? ? - - ? ? - - ? ? - - t t - - ? ? - - - - - - - - - L R G F Q P Q Q T E
         h3 s4s4s4  s4   s4s4                                                                               h4h4h4h4
P10480   K P D D L   V   I L W V G A N D Y - - - - - - - - - - - - - - - - - - - - - - - - L A Y G W N T E Q D A K R V R

1DEOm    D   V V T   A   G D Y V I V E F G H N D G g s - - l s t d n g - - t t d c - - s g t g a E v C Y S V Y D G V N E T I
         h3h3        s4  s4s4s4s4s4                                                         s?s?s?s?s?s?s?
1IVNm    K Q H Q P       R W V L V E L G G N D - - - - - - - - - - - - - - - - - - - - - - - - - - L R G F Q P
         h3h3h3           s4s4s4s4s4                                                                        h4
P10480m  K D S F K   P   D D L V I L W V G A N D Y - - - - - - - - - - - - - - - - - - - - - - - - L A Y G W N T B Q D A

1DEO     A Y L E N   A   A K L F T - A K G A K - - - - - V I L S s5 s5 s5 - - - - - - - - N N P W E T G T F V N S P T R
         h4h4h4h4   h4   h4                s5                s5 s5                                                      
1IVN     Q T L R Q   I   L Q D V K a A N A E P l l m q i R L P A N Y G R - - - - - - - - - - - - - - - - - - - R Y
         h4h4h4h4   h4   h4h4h4h4                                                                                  h5
P10480   D A I S D   A   A N R M V - L N G A K s5s5s5 s5s?s5?s5?s5? E I L L F N L P d l g g n p S A R S Q K V V E A A S H V
```

FIGURE 50B

```
1DEOm    L T F P A   Y   L E N A A K L F T A K   G A K V I L S   Q   T P N   N P   W E T G T F V N S P T R   - R Y N E A
1IVNm    Q Q T B Q   T   L R Q I L Q D V K a A   N A E P l i m   q i R L P   A N   Y G R   - - - - - - - - -
         h4h4h4h4   h4  h4h4h4h4h4h4h4h4h4h4                     q s5?s5?s5?s5?                              h5h5h5h5h5
P10480mK R V R D   A   I S D A A N R M V L N   G A K E I L L   F N L P   d   l g   q n P S A R S Q K V V E A A S H V S A

1DEO     F V B Y A   E   L A A E V A - - - - -                                   G   V E   Y V   D H W S Y V D S I Y E T L G N A t v n
         h5h5h5h5   h5  h5h5h5h5                                                     s6  s6s6?h6h6h6h6h6h6h6h6h6h6h6h6 h h h - -
1IVN     N E A F S   A   I Y P K L A k e - - -                                   f   D V   P   L L P F F M E E V Y L K P Q   W - - - -
         h5h5h5h5   h5  h5h5h5h5h5h5h5                                               s6  s6 s6s6?   h6h6h6h6h6                  s
P10480   S A Y H N   Q   L L L N L A r q l a p                               k   e   i D   K   Q   F A   B M L R D P Q N F G L S D Q R N   a c y

1DEOm    F V B Y   A   B L A A E V A - - - - -                                           G   V E   Y V   D H   W S Y V V D S I Y E T L G N A t v n - -
         h5h5h5h5   h5  h5h5h5h5h5h5                                                          s6  s6 s6?h6h6   h6h6h6h6 h6h6h6h6h6h6  h h h - -
1IVNm    F S A I   Y   P K L A k e - - - - - -                               f s6 s6  e i   D V   P   L L   P F F   M E E V Y       L K P Q   W - -
         h5h5h5h5   h5  h5h5h5                                                                    h6 h6  h6h6                       s
P10480mY H N Q L   L   L N L A r g l a p t g   m v k l f     m v       g   p q   F A   E M   L R D P Q N F G L S D Q R N   a c y g g

1DEO     - - - - -   -   - - - - - - - - - - -                                                                                                    - -
1IVN     - - - - -   -   - - - - - - - - - - -                                                                                                    - -
P10480   g g s y v   w   k p f a s r s a s t d   s q l s a f   n p   g e   r l   a i       a g n p l l a g a   v a s p m a a r s a

1DEOm    - - - - -   -   - - - - - - - - - - -                                                                                                    - -
1IVNm    - - - - -   -   - - - - - - - - - - -                                                                                                    - -
P10480m  s y v v w k  p   f a s r s a a s t d s g   l s a f   n p   g e   r l   a i       a g n p l l a g a v a s p m a a r s a s t

1DEO     - - - - -   -   s Y F P I D H T H T S   P A G A B   V V   K A   L   A F   L L K S V L T T T S F E G
1IVN     - - - - -   -   h - - M Q D D G I H P N   R D A Q P   F F   h7 h7 h7 h7 h7 h7 h7 h2 h2 h2
         s                                 s s s                       A D   W M   A K Q
P10480   e   g k M F W D Q V H P T   T V V H   h7 h7 h7 h7   A T F   I E S Q Y E F L A H   -

1DEOm    F   Y   F F I D H T H T S P A   G A E V V V C T G T S L K S V L T T T S F E G T C
         s?s?s?s?                                 h7 h7 h7 h7 h7 h7 h7   h2 h2 h2
1IVNm    - -   - M Q D D G I H P N R D   A Q P F H   A D W M   A K Q   P L V N H D S L E
         s s                                 h7 h7 h7 h7 h7 h7 h7
P10480m1 n c e g k M F W D Q V H P T T V   V H A A L S E P A T F I B   S Q Y E F L A H -
```

FIGURE 51

```
                      10        20        30        40        50
60
        ....*....|....*....|....*....|....*....|....*....|....*....|
1IVN_A        4 LLILGDSLSAG------------------YRMSASAAWPALLNDKWqsk----
---------- 34
P10480       28
IVMFGDSLSDTgkmyskmrgylpssppyyeGRFSNGPVWLEQLTNEFPGLTianeaeggp 87

70        80        90       100       110
120
        ....*....|....*....|....*....|....*....|....*....|....*....|
1IVN_A       35 -tsvVNASISGDT-----------------------------------
SQQGLARLPALLKQHQPEW 65
P10480       88 tsvaYNKISWNPKyq---------------------------
vINNLDYEVTQFLQKDSFKPDDL 125

130       140       150       160       170
180
        ....*....|....*....|....*....|....*....|....*....|....*....|
1IVN_A       66 VLVELGGNDG--------------------------------------
LRGFQPQQTEQT 87
P10480      126 VILWVGANDY------------------------------------LA---
YGWNTEQDAKRVRDA 152

190       200       210       220       230
240
        ....*....|....*....|....*....|....*....|....*....|....*....|
1IVN_A       88 LRQILQDVKaANAEPllaqiRLPANYGR--------------------
---------- 115
P10480      153 ISDAANRMV-LNGAK------EILLFNLPdlg------------
-----qnP 180

250       260       270       280       290
300
        ....*....|....*....|....*....|....*....|....*....|....*....|
1IVN_A      116 ---------------RYNEAFSAIYPKLAke---------------
fDVPLLPFFME 142
P10480      181 SAFSQKVVEAAGHVSAYHNQLLLNLAqlaptg------------
mvklfetDKQFAEMLRD 230

310       320       330       340       350
360
        ....*....|....*....|....*....|....*....|....*....|....*....|
1IVN_A      143 EVYLKPQW-------------------------------------
---------- 150
P10480      231
PQNFGLSDQRNacyggsyvwkpfasraastdaglsafapgerlaiaqnpllaqavaspma 290

370       380       390       400
        ....*....|....*....|....*....|....*....|
1IVN_A      151 ------------MQDDGI-------HPNRDAQPFIADWM 170
P10480      291 araastlncegkMFWDQV-------SPTTVVHAALSEPA 322
```

FIGURE 52

```
                  1                                                50
    P10480   (1)  MKKWFVCLLGLVALTVQAADSRPAFSRIVMFGDSLSDTGKMYSKMRGYLP
    A. sal   (1)  -----------------ADTRPAFSRIVMFGDSLSDTGKMYSKMRGYLP
    A. hyd   (1)  -----------------ADSRPAFSRIVMFGDSLSDTGKMYSKMRGYLP
 Consensus   (1)                   AD*RPAFSRIVMFGDSLSDTGKMYSKMRGYLP
                  51                                              100
    P10480  (51)  SSPPYYEGRFSNGPVWLEQLTNEFPGLTIANEAEGGPTAVAYNKISWNPK
    A. sal  (33)  SSPPYYEGRFSNGPVWLEQLTKQFPGLTIANEAEGGATAVAYNKISWNPK
    A. hyd  (33)  SSPPYYEGRFSNGPVWLEQLTKQFPGLTIANEAEGGATAVAYNKISWNPK
 Consensus  (51)  SSPPYYEGRFSNGPVWLEQLT**FPGLTIANEAEGG*TAVAYNKISWNPK
                  101                                             150
    P10480 (101)  YQVINNLDYEVTQFLQKDSFKPDDLVILWVGANDYLAYGWNTEQDAKRVR
    A. sal  (83)  YQVINNLDYEVTQFLQKDSFKPDDLVILWVGANDYLAYGWNTEQDAKRVR
    A. hyd  (83)  YQVINNLDYEVTQFLQKDSFKPDDLVILWVGANDYLAYGWNTEQDAKRVR
 Consensus (101)  YQVINNLDYEVTQFLQKDSFKPDDLVILWVGANDYLAYGWNTEQDAKRVR
                  151                                             200
    P10480 (151)  DAISDAANRMVLNGAKEILLFNLPDLGQNPSARSQKVVEAASHVSAYHNQ
    A. sal (133)  DAISDAANRMVLNGAKQILLFNLPDLGQNPSARSQKVVEAVSHVSAYHNK
    A. hyd (133)  DAISDAANRMVLNGAKQILLFNLPDLGQNPSARSQKVVEAVSHVSAYHNQ
 Consensus (151)  DAISDAANRMVLNGAK*ILLFNLPDLGQNPSARSQKVVEA*SHVSAYHN*
                  201                                             250
    P10480 (201)  LLLNLARQLAPTGMVKLFEIDKQFAEMLRDPQNFGLSDQRNACYGGSYVW
    A. sal (183)  LLLNLARQLAPTGMVKLFEIDKQFAEMLRDPQNFGLSDVENPCYDGGYVW
    A. hyd (183)  LLLNLARQLAPTGMVKLFEIDKQFAEMLRDPQNFGLSDVENPCYDGGYVW
 Consensus (201)  LLLNLARQLAPTGMVKLFEIDKQFAEMLRDPQNFGLSD**N*CY*G*YVW
                  251                                             300
    P10480 (251)  KPFASRSASTDSQLSAFNPQERLAIAGNPLLAQAVASPMAARSASTLNCE
    A. sal (233)  KPFATRSVSTDRQLSAFSPQERLAIAGNPLLAQAVASPMARRSASPLNCE
    A. hyd (233)  KPFATRSVSTDRQLSAFSPQERLAIAGNPLLAQAVASPMARRSASPLNCE
 Consensus (251)  KPFA*RS*STD*QLSAF*PQERLAIAGNPLLAQAVASPMA*RSAS*LNCE
                  301                                336
    P10480 (301)  GKMFWDQVHPTTVVHAALSEPAATFIESQYEFLAH-
    A. sal (283)  GKMFWDQVHPTTVVHAALSERAATFIETQYEFLAHG
    A. hyd (283)  GKMFWDQVHPTTVVHAALSERAATFIANQYEFLAH-
 Consensus (301)  GKMFWDQVHPTTVVHAALSE*AATFI**QYEFLAH*
```

FIGURE 53

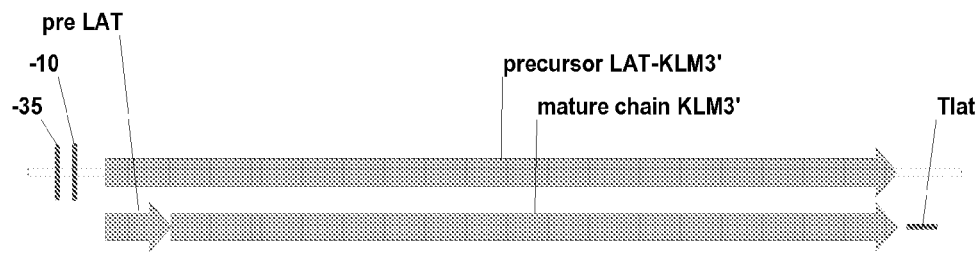

Gene construct for KLM3' expression 1225 bp

FIGURE 55

```
                                                  -35
  1   GCTTTTCTTT TGGAAGAAAA TATAGGGAAA ATGGTACTTG TTAAAAATTC GGAATATTTA
      CGAAAAGAAA ACCTTCTTTT ATATCCCTTT TACCATGAAC AATTTTTAAG CCTTATAAAT
       -10                                       M  K  Q  Q  K  R  L ·
 61   TACAATATCA TATGTTTCAC ATTGAAAGGG GAGGAGAATC ATGAAACAAC AAAAACGGCT
      ATGTTATAGT ATACAAAGTG TAACTTTCCC CTCCTCTTAG TACTTTGTTG TTTTTGCCGA
      · Y  A  R  L  L  T  L  L  F  A  L  I  F  L  L  P  H  S  A  A ·
121   TTACGCCCGA TTGCTGACGC TGTTATTTGC GCTCATCTTC TTGCTGCCTC ATTCTGCAGC
      AATGCGGGCT AACGACTGCG ACAATAAACG CGAGTAGAAG AACGACGGAG TAAGACGTCG
      · S  A  A  D  T  R  P  A  F  S  R  I  V  M  F  G  D  S  L  S ·
181   TTCAGCAGCA GATACAAGAC CGGCGTTTAG CCGGATCGTC ATGTTTGGAG ATAGCCTGAG
      AAGTCGTCGT CTATGTTCTG GCCGCAAATC GGCCTAGCAG TACAAACCTC TATCGGACTC
      · D  T  G  K  M  Y  S  K  M  R  G  Y  L  P  S  S  P  P  Y  Y ·
241   CGATACGGGC AAAATGTATA GCAAAATGAG AGGCTATCTT CCGTCAAGCC CGCCGTATTA
      GCTATGCCCG TTTTACATAT CGTTTTACTC TCCGATAGAA GGCAGTTCGG GCGGCATAAT
      · E  G  R  F  S  N  G  P  V  W  L  E  Q  L  T  K  Q  F  P  G ·
301   TGAAGGCCGC TTTAGCAATG GACCGGTCTG GCTGGAACAA CTGACGAAAC AATTTCCGGG
      ACTTCCGGCG AAATCGTTAC CTGGCCAGAC CGACCTTGTT GACTGCTTTG TTAAAGGCCC
      · L  T  I  A  N  E  A  E  G  G  A  T  A  V  A  Y  N  K  I  S ·
361   ACTGACGATC GCTAATGAAG CAGAAGGAGG AGCAACAGCG GTCGCCTATA ACAAAATCAG
      TGACTGCTAG CGATTACTTC GTCTTCCTCC TCGTTGTCGC CAGCGGATAT TGTTTTAGTC
      · W  D  P  K  Y  Q  V  I  N  N  L  D  Y  E  V  T  Q  F  L  Q ·
421   CTGGGACCCG AAATATCAGG TCATCAACAA CCTGGACTAT GAAGTCACAC AGTTTCTTCA
      GACCCTGGGC TTTATAGTCC AGTAGTTGTT GGACCTGATA CTTCAGTGTG TCAAAGAAGT
      · K  D  S  F  K  P  D  D  L  V  I  L  W  V  G  A  N  D  Y  L ·
481   GAAAGACAGC TTTAAACCGG ATGATCTGGT CATCCTTTGG GTCGGCGCCA ATGATTATCT
      CTTTCTGTCG AAATTTGGCC TACTAGACCA GTAGGAAACC CAGCCGCGGT TACTAATAGA
      · A  Y  G  W  N  T  E  Q  D  A  K  R  V  R  D  A  I  S  D  A ·
541   GGCGTATGGC TGGAACACAG AACAAGATGC CAAAAGAGTC AGAGATGCCA TCAGCGATGC
      CCGCATACCG ACCTTGTGTC TTGTTCTACG GTTTTCTCAG TCTCTACGGT AGTCGCTACG
      · A  N  R  M  V  L  N  G  A  K  Q  I  L  F  N  L  P  D  L ·
601   CGCTAATAGA ATGGTCCTGA ACGGCGCCAA ACAAATCCTG CTGTTTAACC TGCCGGATCT
      GCGATTATCT TACCAGGACT TGCCGCGGTT TGTTTAGGAC GACAAATTGG ACGGCCTAGA
      · G  Q  N  P  S  A  R  S  Q  K  V  V  E  A  V  S  H  V  S  A ·
661   GGGACAAAAT CCGAGCGCCA GAAGCCAAAA AGTCGTCGAA GCAGTCAGCC ATGTCAGCGC
      CCCTGTTTTA GGCTCGCGGT CTTCGGTTTT TCAGCAGCTT CGTCAGTCGG TACAGTCGCG
      · Y  H  N  K  L  L  L  N  L  A  R  Q  L  A  P  T  G  M  V  K ·
721   CTATCATAAC AAACTGCTGC TGAACCTGGC AAGACAATTG GCACCGACGG GAATGGTTAA
      GATAGTATTG TTTGACGACG ACTTGGACCG TTCTGTTAAC CGTGGCTGCC CTTACCAATT
      · L  F  E  I  D  K  Q  F  A  E  M  L  R  D  P  Q  N  F  G  L ·
781   ATTGTTTGAA ATTGACAAAC AGTTTGCCGA AATGCTGAGA GATCCGCAAA ATTTTGGCCT
      TAACAAACTT TAACTGTTTG TCAAACGGCT TTACGACTCT CTAGGCGTTT TAAAACCGGA
      · S  D  V  E  N  P  C  Y  D  G  G  Y  V  W  K  P  F  A  T  R ·
841   GAGCGATGTC GAAAACCCGT GCTATGATGG CGGATATGTC TGGAAACCGT TTGCCACAAG
      CTCGCTACAG CTTTTGGGCA CGATACTACC GCCTATACAG ACCTTTGGCA AACGGTGTTC
      · S  V  S  T  D  R  Q  L  S  A  F  S  P  Q  E  R  L  A  I  A ·
901   AAGCGTCAGC ACGGATAGAC AACTGTCAGC GTTTAGCCCG CAAGAAAGAC TGGCAATCGC
      TTCGCAGTCG TGCCTATCTG TTGACAGTCG CAAATCGGGC GTTCTTTCTG ACCGTTAGCG
      · G  N  P  L  L  A  Q  A  V  A  S  P  M  A  R  R  S  A  S  P ·
961   CGGAAATCCG CTTTTGGCAC AAGCAGTTGC TTCACCGATG CAAGAAGAT CAGCAAGCCC
      GCCTTTAGGC GAAAACCGTG TTCGTCAACG AAGTGGCTAC CGTTCTTCTA GTCGTTCGGG
      · L  N  C  E  G  K  M  F  W  D  Q  V  H  P  T  T  V  H  A ·
1021  GCTGAATTGC GAAGGCAAAA TGTTTTGGGA TCAGGTCCAT CCGACAACAG TTGTCCATGC
      CGACTTAACG CTTCCGTTTT ACAAAACCCT AGTCCAGGTA GGCTGTTGTC AACAGGTACG
      · A  L  S  E  R  A  A  T  F  I  E  T  Q  Y  E  F  L  A  H  G ·
1081  TGCCCTTTCA GAAAGAGCGG CGACGTTTAT CGAAACACAG TATGAATTTC TGGCCCATGG
      ACGGGAAAGT CTTTCTCGCC GCTGCAAATA GCTTTGTGTC ATACTTAAAG ACCGGGTACC
      ·stop
1141  CTGAGTTAAC AGAGGACGGA TTTCCTGAAG GAAATCCGTT TTTTTATTTT AAGCTTGGAG
      GACTCAATTG TCTCCTGCCT AAAGGACTTC CTTTAGGCAA AAAAATAAAA TTCGAACCTC
1201  ACAAGGTAAA GGATAAAACC TCGAG
      TGTTCCATTT CCTATTTTGG AGCTC
```

FIGURE 57 (SEQ ID No 49)

```
   1   ATGAAACAAC AAAAACGGCT TTACGCCCGA TTGCTGACGC TGTTATTTGC
       TACTTTGTTG TTTTTGCCGA AATGCGGGCT AACGACTGCG ACAATAAACG

51   GCTCATCTTC TTGCTGCCTC ATTCTGCAGC TTCAGCAGCA GATACAAGAC
       CGAGTAGAAG AACGACGGAG TAAGACGTCG AAGTCGTCGT CTATGTTCTG

101   CGGCGTTTAG CCGGATCGTC ATGTTGGAG ATAGCCTGAG CGATACGGGC
       GCCGCAAATC GGCCTAGCAG TACAAACCTC TATCGGACTC GCTATGCCCG

151   AAAATGTATA GCAAAATGAG AGGCTATCTT CCGTCAAGCC CGCCGTATTA
       TTTTACATAT CGTTTTACTC TCCGATAGAA GGCAGTTCGG GCGGCATAAT

201   TGAAGGCCGC TTTAGCAATG GACCGGTCTG GCTGGAACAA CTGACGAAAC
       ACTTCCGGCG AAATCGTTAC CTGGCCAGAC CGACCTTGTT GACTGCTTTG

251   AATTTCCGGG ACTGACGATC GCTAATGAAG CAGAAGGAGG AGCAACAGCG
       TTAAAGGCCC TGACTGCTAG CGATTACTTC GTCTTCCTCC TCGTTGTCGC

301   GTCGCCTATA ACAAATCAG CTGGGACCCG AAATATCAGG TCATCAACAA
       CAGCGGATAT TGTTTTAGTC GACCCTGGGC TTTATAGTCC AGTAGTTGTT

351   CCTGGACTAT GAAGTCACAC AGTTTCTTCA GAAAGACAGC TTTAAACCGG
       GGACCTGATA CTTCAGTGTG TCAAAGAAGT CTTTCTGTCG AAATTTGGCC

401   ATGATCTGGT CATCCTTTGG GTCGGCGCCA ATGATTATCT GGCGTATGGC
       TACTAGACCA GTAGGAAACC CAGCCGCGGT TACTAATAGA CCGCATACCG

451   TGGAACACAG AACAAGATGC CAAAAGAGTC AGAGATGCCA TCAGCGATGC
       ACCTTGTGTC TTGTTCTACG GTTTTCTCAG TCTCTACGGT AGTCGCTACG

501   CGCTAATAGA ATGGTCCTGA ACGGCGCCAA ACAAATCCTG CTGTTTAACC
       GCGATTATCT TACCAGGACT TGCCGCGGTT TGTTTAGGAC GACAAATTGG

551   TGCCGGATCT GGGACAAAAT CCGAGCGCCA GAAGCCAAAA AGTCGTCGAA
       ACGGCCTAGA CCCTGTTTTA GGCTCGCGGT CTTCGGTTTT TCAGCAGCTT

601   GCAGTCAGCC ATGTCAGCGC CTATCATAAC AAACTGCTGC TGAACCTGGC
       CGTCAGTCGG TACAGTCGCG GATAGTATTG TTTGACGACG ACTTGGACCG

651   AAGACAATTG GCACCGACGG GAATGGTTAA ATTGTTTGAA ATTGACAAAC
       TTCTGTTAAC CGTGGCTGCC CTTACCAATT TAACAAACTT TAACTGTTTG

701   AGTTTGCCGA AATGCTGAGA GATCCGCAAA ATTTTGGCCT GAGCGATGTC
       TCAAACGGCT TTACGACTCT CTAGGCGTTT TAAAACCGGA CTCGCTACAG

751   GAAAACCCGT GCTATGATGG CGGATATGTC TGGAAACCGT TTGCCACAAG
       CTTTTGGGCA CGATACTACC GCCTATACAG ACCTTTGGCA AACGGTGTTC

801   AAGCGTCAGC ACGGATAGAC AACTGTCAGC GTTTAGCCCG CAAGAAAGAC
       TTCGCAGTCG TGCCTATCTG TTGACAGTCG CAAATCGGGC GTTCTTTCTG

851   TGGCAATCGC CGGAAATCCG CTTTTGGCAC AAGCAGTTGC TTCACCGATG
       ACCGTTAGCG GCCTTTAGGC GAAAACCGTG TTCGTCAACG AAGTGGCTAC

901   GCAAGAAGAT CAGCAAGCCC GCTGAATTGC GAAGGCAAAA TGTTTTGGGA
       CGTTCTTCTA GTCGTTCGGG CGACTTAACG CTTCCGTTTT ACAAAACCCT

951   TCAGGTCCAT CCGACAACAG TTGTCCATGC TGCCCTTTCA GAAAGAGCGG
       AGTCCAGGTA GGCTGTTGTC AACAGGTACG ACGGGAAAGT CTTTCTCGCC

1001   CGACGTTTAT CGAAACACAG TATGAATTTC TGGCCCATGG CTGA
       GCTGCAAATA GCTTTGTGTC ATACTTAAAG ACCGGGTACC GACT
```

FIGURE 58 (SEQ ID No. 50)

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCGCTTC
181  TCCAACGGGC CCGTCTGGCT GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC CGGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCGG CAACCCGCTG
841  CTGGCCCAGG CCGTCGCCAG CCCCATGGCT GCCCGCAGCG CCAGCACCCT CAACTGTGAG
901  GGCAAGATGT TCTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

FIGURE 59 (SEQ ID No. 51)

```
  1  ATGAAAAAAT GGTTTGTTTG TTTATTGGGG TTGATCGCGC TGACAGTTCA GGCAGCCGAC
 61  ACTCGCCCCG CCTTCTCCCG GATCGTGATG TTCGGCGACA GCCTCTCCGA TACCGGCAAA
121  ATGTACAGCA AGATGCGCGG TTACCTCCCC TCCAGCCCGC CCTACTATGA GGGCCGTTTC
181  TCCAACGGAC CCGTCTGGCT GGAGCAGCTG ACCAAGCAGT TCCCGGGTCT GACCATCGCC
241  AACGAAGCGG AAGGCGGTGC CACTGCCGTG GCTTACAACA AGATCTCCTG GAATCCCAAG
301  TATCAGGTCT ACAACAACCT GGACTACGAG GTCACCCAGT TCTTGCAGAA AGACAGCTTC
361  AAGCCGGACG ATCTGGTGAT CCTCTGGGTC GGTGCCAATG ACTATCTGGC ATATGGCTGG
421  AATACGGAGC AGGATGCCAA GCGAGTTCGC GATGCCATCA GCGATGCGGC CAACCGCATG
481  GTACTGAACG GTGCCAAGCA GATACTGCTG TTCAACCTGC CGGATCTGGG CCAGAACCCG
541  TCAGCCCGCA GTCAGAAGGT GGTCGAGGCG GTCAGCCATG TCTCCGCCTA TCACAACAAG
601  CTGCTGCTGA ACCTGGCACG CCAGCTGGCC CCCACCGGCA TGGTAAAGCT GTTCGAGATC
661  GACAAGCAAT TTGCCGAGAT GCTGCGTGAT CCGCAGAACT TCGGCCTGAG CGACGTCGAG
721  AACCCCTGCT ACGACGGCAG CTATGTGTGG AAGCCGTTTG CCACCCGCAG CGTCAGCACC
781  GACCGCCAGC TCTCCGCCTT CAGTCCGCAG GAACGCCTCG CCATCGCCGG CAACCCGCTG
841  CTGGCACAGG CCGTTGCCAG TCCTATGGCC CGCCGCAGCG CCAGCCCCCT CAACTGTGAG
901  GGCAAGATGT TCTGGGATCA GGTACACCCG ACCACTGTCG TGCACGCAGC CCTGAGCGAG
961  CGCGCCGCCA CCTTCATCGA GACCCAGTAC GAGTTCCTCG CCCACGGATG A
```

FIGURE 60 (SEQ ID No. 52)

```
  1  ATGCCGAAGC CTGCCCTTCG CCGTGTCATG ACCGCGACAG TCGCCGCCGT CGGCACGCTC
 61  GCCCTCGGCC TCACCGACGC CACCGCCCAC GCCGCGCCCG CCCAGGCCAC TCCGACCCTG
121  GACTACGTCG CCCTCGGCGA CAGCTACAGC GCCGGCTCCG GCGTCCTGCC CGTCGACCCC
181  GCCAACCTGC TCTGTCTGCG CTCGACGGCC AACTACCCCC ACGTCATCGC GGACACGACG
241  GGCGCCCGCC TCACGGACGT CACCTGCGGC GCCGCGCAGA CCGCCGACTT CACGCGGGCC
301  CAGTACCCGG GCGTCGCACC CCAGTTGGAC GCGCTCGGCA CCGGCACGGA CCTGGTCACG
361  CTCACCATCG GCGGCAACGA CAACAGCACC TTCATCAACG CCATCACGGC TGCGGCACG
421  GCGGGTGTCC TCAGCGGCGG CAAGGGCAGC CCTGCAAGG ACAGGCACGG CACCTCCTTC
481  GACGACGAGA TCGAGGCCAA CACGTACCCC GGCAAGAACA AGGCGCTGCT CGGCGTCCGC
541  GCCAGGGCTC CCCACGCCAG GGTGGCGGCT CTCGGCTACC CGTGGATCAC CCCGGCCACC
601  GCCGACCCGT CCTGCTTCCT GAAGCTCCCC CTCGCCGCCG GTGACGTGCC CTACCTGCGG
661  GCCATCCAGG CACACCTCAA CGACGCGGTC CGGCGGCCG CCGAGGAGAC CGGAGCCACC
721  TACGTGGACT TCTCCGGGGT GTCCGACGGC CACGACGCCT GCGAGGCCCC CGGCACCCGC
781  TGGATCGAAC CGCTGCTCTT CGGGCACAGC CTCGTTCCCG TCCACCCCAA CGCCCTGGGC
841  GAGCGGCGCA TGGCCGAGCA CACGATGGAC GTCCTCGGCC TGGACTGA
```

FIGURE 61 (SEQ ID No. 53)

```
  1  TCAGTCCAGG CCGAGGACGT CCATCGTGTG CTCGGCCATG CGCCGCTCGC CCAGGGCGTT
 61  GGGGTGGACG GGAACGAGGC TGTGCCCGAA GAGCAGCGGT TCGATCCAGC GGGTGCCGGG
121  GGCCTCGCAG GCGTCGTGGC CGTCGGACAC CCCGGAGAAG TCCACGTAGG TGGCTCCGGT
181  CTCCTCGGCG GCCCGCCGGA CCGCGTCGTT GAGGTGTGCC TGGATGGCCC GCAGGTAGGG
241  CACGTCACCG GCGGCGAGGG GGAGCTTCAG GAAGCAGGAC GGGTCGGCGC TGGCCGGGGT
301  GATCCACGGG TAGCCGAGAG CCGCCACCCT GGCGTGGGGA GCCCTGGCGC GGACGCCGAG
361  CAGCGCCTCC TTGAGCGCGG GGTACGTGTT GGCCTCGATC TCGTCGTCGA AGGAGGTGCC
421  GTGCCTGTCC TTGCAGGGGC TGCCCTTGCC GCCGCTGAGG ACACCCGCCC TGCCGCAGGC
481  CGTGATGGCG TTGATGAAGG TGCTGTTGTC GTTGCCGCCG ATGGTGAGCG TGACCAGGTC
541  CGTGCCGGTG CCGAGCGCGT CCAACTGGGG TGCGACGCCC GGGTACTGGG CCCGCGTGAA
601  GTCGGCGGTC TGCGCGGCGC CGCAGGTGAC GTCCGTGAGG CGGGCGCCCC TCGTGTCCGC
661  GATGACGTGG GGGTAGTTGG CCGTCGAGCG CAGACAGAGC AGGTTGGCGG GGTCGACGGG
721  CAGGACGCCG GAGCCGGCGC TGTAGCTGTC GCCGAGGCGG ACGTAGTCCA GGGTCGGAGT
781  GGCCTGGGCG GCGCGGCGT GGGCGGTGGC GTCGGTGAGG CCGAGGGCGA GCGTGCCGAC
841  GGCGGCGACT GTCGCGGTCA TGACACGGCG AAGGGCAGGC TTCGGCAT
```

FIGURE 62 (SEQ ID No. 54)

```
  1  ATGGATTACG AGAAGTTTCT GTTATTTGGG GATTCCATTA CTGAATTTGC TTTTAATACT
 61  AGGCCCATTG AAGATGGCAA AGATCAGTAT GCTCTTGGAG CCGCATTAGT CAACGAATAT
121  ACGAGAAAAA TGGATATTCT TCAAAGAGGG TTCAAAGGGT ACACTTCTAG ATGGGCGTTG
181  AAAATACTTC CTGAGATTTT AAAGCATGAA TCCAATATTG TCATGGCCAC AATATTTTTG
241  CCTCCCAACC ATCCATCCTC ACCACCTCCC CAAACTCTCC CCCTCCCCCA ATTTATCCAT
301  AATATTCGTC AAATGGTATC TTTGATGAAG TCTTACCATA TCCGTCCTAT TATAATAGGA
361  CCGGGGCTAG TAGATAGAGA GAAGTGGGAA AAAGAAAAAT CTGAAGAAAT AGCTCTCGGA
421  TACTTCCGTA CCAACGAGAA CTTTGCCATT TATTCCGATG CCTTAGCAAA ACTAGCCAAT
481  GAGGAAAAAG TTCCCTTCGT GGCTTTGAAT AAGGCGTTTC AACAGGAAGG TGGTGATGCT
541  TGGCAACAAC TGCTAACAGA TGGACTGCAC TTTTCCGGAA AAGGGTACAA AATTTTTCAT
601  GACGAATTAT TGAAGGTCAT TGAGACATTC TACCCCCAAT ATCATCCCAA AACATGCAG
661  TACAAACTGA AAGATTGGAG AGATGTGCTA GATGATGGAT CTAACATAAT GTCTTGA
```

FIGURE 63 (SEQ ID No. 55)

```
atgaacctgc gtcaatggat gggcgccgcc acggctgccc ttgccttggg cttggccgcg    60
tgcggggggcg gtgggaccga ccagagcggc aatcccaatg tcgccaaggt gcagccatg   120
gtggtgttcg cgacagcct gagcgatatc ggcacctaca ccccgtcgc gcaggcggtg   180
ggcggcggca agttcaccac caacccgggc cgatctggg ccgagaccgt ggccgcgcaa   240
ctgggcgtga cgctcacgcc ggcggtgatg ggctacgcca cctccgtgca gaattccccc   300
aaggccggct gcttcgacta tgcgcagggc ggctcgcgcg tgaccgatcc gaacgccatc   360
ggccacaacg gcggcgcggg ggcgctgacc taccggttc agcagcagct cgccaacttc   420
tacgcggcca gcaacaacac attcaacggc aataacgatg tcgtcttcgt gctggccggc   480
agcaacgaca ttttcttctg gaccactgcg gcggccacca gcggctccgg cgtgacgccc   540
gccattgcca cggcccaggt gcagcaggcc gcgacggacc tggtcggcta tgtcaaggac   600
atgatcgcca agggtgcgac gcaggtctac gtgttcaacc tgcccgacag cagcctgacg   660
ccggacggcg tggcaagcgg cacgaccggc caggcgctgc tgcacgcgct ggtggccacg   720
ttcaacacga cgctgcaaag cgggctggcc ggcacctcgg cgcgcatcat cgacttcaac   780
gcacaactga ccgcggcgat ccagaatggc gcctcgttcg gcttcgccaa caccacgcc   840
cgggcctgcg acgccaccaa gatcaatgcc ctggtgccga gcgccggcgg cagctcgctg   900
ttctgctcgg ccaacacgct ggtggcttcc ggtgcggacc agagctacct gttcgccgac   960
ggcgtgcacc cgaccacggc cggccatcgc ctgatcgcca gcaacgtgct ggcgccctg   1020
ctggcggata cgtcgcgca ctga                                          1044
```

FIGURE 64 (SEQ ID No. 56)

```
  1 gtgatcgggt cgtacgtggc ggtgggggac agcttcaccg agggcgtcgg cgacccggc
 61 cccgacgggg cgttcgtcgg ctgggccgac cggctcgccg tactgctcgc ggaccggcgc
121 cccgaggcc acttcacgta cacgaacctc gccgtgcgcg gcaggctcct cgaccagatc
181 gtggcggaac aggtccgcg ggtcgtcgga ctcgcgcccg acctcgtctc cttcgcggcg
241 ggcggcaacc acatcatccg gcccggcacc gatcccgacg aggtcgccga ccggttcgag
301 ctggcggtgc ccgcgctgac cgccgcggcc ggaaccgtcc tggtgaccac cgggttcgac
361 acccggggc tgcccgtcct caagcacctg cgcggcaaga tcgccacgta acgggcac
421 gtccgcgcca tcgccgaccg ctacggctgc ccggtgctcg acctgtggtc cctgcggagc
481 gtccaggacc gcagggcgtg ggacgccgac cggctgcacc tgtcgccgga cgggcacacc
541 cgggtggcgc tgccgcgggg caggccctg ggctgcgcg tcccggccga ccctgaccag
601 ccctggccgc ccctgccgcc gcgcggcacg ctcgacgtcc ggcgcgacga cgtgcactgg
661 gcgcgcgagt acctggtgcc gtggatcggg cgccggctgc ggggcgagtc ctcgggcgac
721 cacgtgacgc caaggggac gctgtcgccg gacgccatca agacgcggat cgccgcggtg
781 gcctga
```

FIGURE 65 (SEQ ID No. 57)

```
  1 atgcagacga acccgcgta caccagtctc gtcgccgtcg gcgactcctt caccgagggc
 61 atgtcggacc tgctgcccga cggctcctac cgtggctggg ccgacctcct cgccacccgg
121 atggcggccc gctcccccgg cttccggtac gccaacctgg cggtgcgcgg caagctgatc
181 ggacagatcc tcgacgagca ggtggacgtg gccgccgcca tgggagccga cgtgatcacg
241 ctggtcgcc ggctcaacga cacgctgcgg cccaagtgcg acatggcccg cgtgcgggac
301 ctgctgaccc aggccgtgga acggctcgcc ccgcactgcg agcagctggt cctgatcgcc
361 agtccggtc gccagggtcc ggtgctggag cgcttccggc ccgcatgga cgccctgttc
421 gccgtgatcc acgacctggc cgggcggcac ggcgccgtgg tcgtcgacct ctacggggcc
481 cagtcgctgc ccgaccctcg gatgtgggac gtggaccggc tgcacctgac cgccgagggc
541 caccgccggc tcgcggaggc ggtgtggcag tcgctcggcc acgagcccga cgaccccgag
601 tggacgcgc cgatcccggc gacgccgccg ccggggtggg tgacgcgcag cacgcggac
661 gtccggttcc ccggcagca cctgctgccc tggataggcc gcaggctgac cgggcgctcg
721 tccggggacc gcctgccggc caagcgcccg gacctgctgc cctacgagga ccccgcacgg
781 tga
```

FIGURE 66 (SEQ ID No. 58)

```
   1 atgaccggc gtcgtgacgg gggtgcgggg gcgcccccca ccaagcaccg tgccctgctc
  61 gcggcgatcc tcaccctgat agtggcgatc tccgcggcca tatacgccgg agcgtccgcg
 121 gacgacgca gcaggaccag cgcgctgcag gccggaggcc gtctcccacg aggagacgcc
 181 gccccgcgt ccaccggtgc ctggtgggc gcctgggcca ccgcaccggc cgcggccgag
 241 ccgggcaccc agacgaccgg cctggcgggc cgctccgtgc gcaacgtcgt ccacacctcg
 301 gtcggcggca ccggcgcgcg gatcaccctc tcgaacctgt acggcagtc cccgctgacc
 361 gtcacacacc cctcgatcgc cctggccgcc gggcccgaca ccgccgccgc gatcgccgac
 421 accatgcgcc ggctcacctt cggcgccgac gccgggtga tcatcccggc cgggggccag
 481 gtgatgagcc acaccgcccg cctcgccatc ccctacgggg cgaacgtcct cgtcaccacg
 541 tactcccca tccgtccgg gccggtgacc taccatcgc aggcccggca caccagctac
 601 ctggccgacc gcgaccgcac ggcggacgtc accgccgtcg cgtacaccac cccacgcccc
 661 tactggcgct acctgaccgc cctcgacgtg ctgagccacg aggccgacgg cacggtcgtg
 721 gcgttcggcc actccatcac cgacggcgcc cgctcgcaga gcgacgccaa ccaccgctgg
 781 accgacgtcc tcgccgcacg cctgcacgag gcggcgggcg acggccggga cacgcccgc
 841 tacagcgtcc tcaacgaggg catcagccgc aaccgctcc tgaccagcag gccgggcgg
 901 ccggccgaca cccgagcgg actgagccgg ttccagcggg acgtgctgga acgcaccaac
 961 gtcaaggccc tcgtcgtcgt cctcggcgtc aacgacgtcc tgaacagccc cgaactcgcc
1021 gaccgcgacc ccatcctgac cggcctgcgc accctcgtcg accgggcgca cgccggggga
1081 ctgcgggtcc tcggcgccac gatcacgccg ttcgcggct acggcggcta caccgaggcc
1141 cgcgagacga tgcggcagga ggtcaacgag gagatccgct ccggccgggt cttcgacacg
1201 gtcgtcgact tcgacaaggc cctgcgcgac ccgtacgacc cgccgggat cgctccgac
1261 tacgacagcc gcgaccacct gcacccggc gacaagggat acgcgcgcat cggcgcggtc
1321 atcgacctgc ccgcgctgaa gggcgcgggg ccggtcaagg cgtag
```

FIGURE 67 (SEQ ID No. 59)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcaggtgggg ggtgggcacg ccgacccggg tgccgaacgc gcagggactg
 181 tacggcggca ccctgcccac ggccggcgac ccgccgctgc ggctgatgat gctgggcgac
 241 tccacggccg ccgggcaggg cgtgcaccgg gccgggcaga cgccgggcgc gctgctggcg
 301 tccgggctcg cggcggtggc ggagcggccg gtgcggctgg ggtcggtcgc ccagccgggg
 361 gcgtgctcgg acgacctgga ccggcaggtg gcgctggtgc tcgccgagcc ggaccgggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgggcacg atcgagcggg tgcggcagcc gctgcgctgg
 601 ctggcccggc gggcctcacg gcagctcgcg gcggcacaga ccatcggcgc cgtcgagcag
 661 ggcgggcgca cggtgtcgct gggcgacctg ctgggtccgg agttcgcgca gaacccgcgg
 721 gagctcttcg gccccgacaa ctaccacccc tccgccgagg ggtacgccac ggccgcgatg
 781 gcggtactgc cctcggtgtg cgccgccgtc ggcctgtgcc cggccgacga ggagcaccgg
 841 gacgcgctgc gccgcgaggg cttcctgccg gtgccgcgcg cggccgcgga ggcggcgtcc
 901 gaggcgggta cggaggtcgc cgccgccatg cctacgggcc ctcgggggcc ctgggcgctg
 961 ctgaagcgcc ggagacggcg tcgggtgtcg gaggcggaac cgtccagccc gtccggcgtt
1021 tga
```

FIGURE 68 (SEQ ID No. 60)

```
   1 atgggtcgag ggacggacca gcggacgcgg tacggccgtc gccgggcgcg tgtcgcgctc
  61 gccgccctga ccgccgccgt cctgggcgtg ggcgtggcgg gctgcgactc cgtgggcggc
 121 gactcacccg ctccttccgg cagcccgtcg aagcggacga ggacggcgcc cgcctgggac
 181 accagcccgg cgtccgtcgc cgccgtgggc gactccatca cgcgcggctt cgacgcctgt
 241 gcggtgctgt cggactgccc ggaggtgtcg tgggcgaccg gcagcagcgc gaaggtcgac
 301 tcgctggccg tacggctgct ggggaaggcg gacgcggccg agcacagctg gaactacgcg
 361 gtcaccgggg cccggatggc ggacctgacc gctcaggtga cgcgggcggc gcagcgcgag
 421 ccggagctgg tggcggtgat ggccggggca aacgacgcgt gccggtccac gacctcggcg
 481 atgacgccgg tggcggactt ccgggcgcag ttcgaggagg cgatggccac cctgcgcaag
 541 aagctcccca aggcgcaggt gtacgtgtcg agcatcccgg acctcaagcg gctctggtcc
 601 cagggccgca ccaacccgct gggcaagcag gtgtggaagc tcggcctgtg cccgtcgatg
 661 ctgggcgacg cggactccct ggactcggcg gcgaccctgc ggcgcaacac ggtgcgcgac
 721 cgggtggcgg actacaacga ggtgctgcgg gaggtctgcg cgaaggaccg gcggtgccgc
 781 agcgacgacg gcgcggtgca cgagttccgg ttcggcacgg accagttgag ccactgggac
 841 tggttccacc cgagtgtgga cggccaggcc cggctggcgg agatcgccta ccgcgcggtc
 901 accgcgaaga atccctga
```

FIGURE 69 (SEQ ID No. 61)

```
   1 ttcatcacaa cgatgtcaca acaccggcca tccgggtcat ccctgatcgt gggaatgggt
  61 gacaagcctt cccgtgacga aagggtcctg ctacatcaga aatgacagaa atcctgctca
 121 gggaggttcc atgagactgt cccgacgcgc ggccacggcg tccgcgctcc tcctcacccc
 181 ggcgctcgcg ctcttcggcg cgagcgccgc cgtgtccgcg ccgcgaatcc aggccaccga
 241 ctacgtggcc ctcggcgact cctactcctc ggggtcggc gcgggcagct acgacagcag
 301 cagtggctcc tgtaagcgca gcaccaagtc ctaccgcc ctgtgggcc cctgcacac
 361 cggtacgcgg ttcaacttca ccgcctgttc gggcgccgc acaggagacg tgctggccaa
 421 gcagctgacc ccgtcaact ccggcaccga cctggtcagc attaccatcg cggcaacga
 481 cgcgggcttc gccgacacca tgaccacctg caacctccag ggcgagagcg cgtgcctggc
 541 gcgatcgcc aaggcgcag cctacatcca gcagacgtcg cccgccagc tggaccaggt
 601 ctacgacgcg atcgacagcc gggccccgc agcccaggtc gtcgtcctgg gctaccgcg
 661 cttctacaag ctgggcggca gctgcgccgt cggtctctcg gagaagtccc gcgcggccat
 721 caacgccgcc gccgacgaca tcaacgccgt caccgccaag cgccgcgcg accacggctt
 781 cgccttcggg gacgtcaaca cgaccttcgc cggcacgag ctgtgctccg gcgcccctg
 841 gctgcacagc gtcacccttc ccgtggagaa ctcctaccac ccacggcca acggacagtc
 901 caaggctac ctgccgtcc tgaactccg cacctgatct gcggtact ccgcccctga
 961 cgaagtcccg ccccgggcg ggcttcgcc gtaggtcgc gtaccgccgt cgcccgtcgc
1021 gccggtggcc ccgccgtacg tgccgccgcc ccggacgcg gtcggttc
```

FIGURE 70 (SEQ ID No. 62)

```
  1  ATGAAAAAAT GGTTTGTGTG TTTATTGGGA TTGGTCGCGC TGACAGTTCA
     TACTTTTTTA CCAAACACAC AAATAACCCT AACCAGCGCG ACTGTCAAGT

51  GGCAGCCGAC AGTCGCCCCG CCTTTTCCCG GATCGTGATG TTCGGCGACA
     CCGTCGGCTG TCAGCGGGGC GGAAAAGGGC CTAGCACTAC AAGCCGCTGT

101  GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151  TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201  GGAGCAGCTG ACCAAACAGT TCCCGGGTCT GACCATCGCC AACGAAGCGG
     CCTCGTCGAC TGGTTTGTCA AGGGCCCAGA CTGGTAGCGG TTGCTTCGCC

251  AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301  TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351  AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401  ACTATCTGGC CTATGGCTGG AACACGGAGC AGGATGCCAA GCGGGTTCGC
     TGATAGACCG GATACCGACC TTGTGCCTCG TCCTACGGTT CGCCCAAGCG

451  GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501  GATACTGCTG TTCAACCTGC CGGATCTGGG CCAGAACCCG TCAGCTCGCA
     CTATGACGAC AAGTTGGACG GCCTAGACCC GGTCTTGGGC AGTCGAGCGT

551  GTCAGAAGGT GGTCGAGGCG GTCAGCCATG TCTCCGCCTA TCACAACCAG
     CAGTCTTCCA CCAGCTCCGC CAGTCGGTAC AGAGGCGGAT AGTGTTGGTC

601  CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651  GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701  TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751  AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801  CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851  CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901  GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951  CCTGAGCGAG CGCGCCGCCA CCTTCATCGC GAACCAGTAC GAGTTCCTCG
     GGACTCGCTC GCGCGGCGGT GGAAGTAGCG CTTGGTCATG CTCAAGGAGC

1001 CCCAC TGA
     GGGTG ACT
```

FIGURE 71 (SEQ ID No. 63)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCG GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

FIGURE 72 (SEQ ID No. 24)

```
   1  ATGTTTAAGT TTAAAAAGAA TTTCTTAGTT GGATTATCGG CAGCTTTAAT
      TACAAATTCA AATTTTTCTT AAAGAATCAA CCTAATAGCC GTCGAAATTA

51  GAGTATTAGC TTGTTTTCGG CAACCGCCTC TGCAGCTAGC GCCGACAGCC
      CTCATAATCG AACAAAAGCC GTTGGCGGAG ACGTCGATCG CGGCTGTCGG

101  GTCCCGCCTT TTCCCGGATC GTGATGTTCG GCGACAGCCT CTCCGATACC
      CAGGGCGGAA AAGGGCCTAG CACTACAAGC CGCTGTCGGA GAGGCTATGG

151  GGCAAAATGT ACAGCAAGAT GCGCGGTTAC CTCCCCTCCA GCCCGCCCTA
      CCGTTTTACA TGTCGTTCTA CGCGCCAATG GAGGGGAGGT CGGGCGGGAT

201  CTATGAGGGC CGTTTCTCCA ACGGACCCGT CTGGCTGGAG CAGCTGACCA
      GATACTCCCG GCAAAGAGGT TGCCTGGGCA GACCGACCTC GTCGACTGGT

251  AACAGTTCCC GGGTCTGACC ATCGCCAACG AAGCGGAAGG CGGTGCCACT
      TTGTCAAGGG CCCAGACTGG TAGCGGTTGC TTCGCCTTCC GCCACGGTGA

301  GCCGTGGCTT ACAACAAGAT CTCCTGGAAT CCCAAGTATC AGGTCATCAA
      CGGCACCGAA TGTTGTTCTA GAGGACCTTA GGGTTCATAG TCCAGTAGTT

351  CAACCTGGAC TACGAGGTCA CCCAGTTCTT GCAGAAAGAC AGCTTCAAGC
      GTTGGACCTG ATGCTCCAGT GGGTCAAGAA CGTCTTTCTG TCGAAGTTCG

401  CGGACGATCT GGTGATCCTC TGGGTCGGTG CCAATGACTA TCTGGCCTAT
      GCCTGCTAGA CCACTAGGAG ACCCAGCCAC GGTTACTGAT AGACCGGATA

451  GGCTGGAACA CGGAGCAGGA TGCCAAGCGG GTTCGCGATG CCATCAGCGA
      CCGACCTTGT GCCTCGTCCT ACGGTTCGCC CAAGCGCTAC GGTAGTCGCT

501  TGCGGCCAAC CGCATGGTAC TGAACGGTGC CAAGCAGATA CTGCTGTTCA
      ACGCCGGTTG GCGTACCATG ACTTGCCACG GTTCGTCTAT GACGACAAGT

551  ACCTGCCGGA TCTGGGCCAG AACCCGTCAG CTCGCAGTCA GAAGGTGGTC
      TGGACGGCCT AGACCCGGTC TTGGGCAGTC GAGCGTCAGT CTTCCACCAG

601  GAGGCGGTCA GCCATGTCTC CGCCTATCAC AACCAGCTGC TGCTGAACCT
      CTCCGCCAGT CGGTACAGAG GCGGATAGTG TTGGTCGACG ACGACTTGGA

651  GGCACGCCAG CTGGCCCCCA CCGGCATGGT AAAGCTGTTC GAGATCGACA
      CCGTGCGGTC GACCGGGGGT GGCCGTACCA TTTCGACAAG CTCTAGCTGT

701  AGCAATTTGC CGAGATGCTG CGTGATCCGC AGAACTTCGG CCTGAGCGAC
      TCGTTAAACG GCTCTACGAC GCACTAGGCG TCTTGAAGCC GGACTCGCTG

751  GTCGAGAACC CCTGCTACGA CGGCGGCTAT GTGTGGAAGC CGTTTGCCAC
      CAGCTCTTGG GGACGATGCT GCCGCCGATA CACACCTTCG GCAAACGGTG

801  CCGCAGCGTC AGCACCGACC GCCAGCTCTC CGCCTTCAGT CCGCAGGAAC
      GGCGTCGCAG TCGTGGCTGG CGGTCGAGAG GCGGAAGTCA GGCGTCCTTG

851  GCCTCGCCAT CGCCGGCAAC CCGCTGCTGG CACAGGCCGT TGCCAGTCCT
      CGGAGCGGTA GCGGCCGTTG GCGACGACC GTGTCCGGCA ACGGTCAGGA

901  ATGGCCCGCC GCAGCGCCAG CCCCCTCAAC TGTGAGGGCA AGATGTTCTG
      TACCGGGCGG CGTCGCGGTC GGGGGAGTTG ACACTCCCGT TCTACAAGAC

951  GGATCAGGTA CACCCGACCA CTGTCGTGCA CGCAGCCCTG AGCGAGCGCG
      CCTAGTCCAT GTGGGCTGGT GACAGCACGT GCGTCGGGAC TCGCTCGCGC

1001  CCGCCACCTT CATCGCGAAC CAGTACGAGT TCCTCGCCCA CTGATGA
      GGCGGTGGAA GTAGCGCTTG GTCATGCTCA AGGAGCGGGT GACTACT
```

FIGURE 73

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPF
236  RSASPLNCEG KMFWDQVHPT TVVHAALSER AATFIETQYE FLAHG
```

VARIANT LIPID ACYLTRANSFERASES AND METHODS OF MAKING

REFERENCE TO RELATED APPLICATIONS

This application is a continuation-in-part of International Patent Application PCT/IB2007/000558 filed Jan. 25, 2007. This application is also a continuation in part of U.S. patent application Ser. No. 10/911,160 filed Aug. 2, 2004, now abandoned, which claims priority from United Kingdom Application Number GB 0330016.7 filed on 24 Dec. 2003, International Patent Application Number PCT/IB2004/000655 filed on 15 Jan. 2004 and United Kingdom Application Number GB 0415999.2 filed on 16 Jul. 2004. This application also claims priority to United Kingdom Application Number GB 0716126.8 filed 17 Aug. 2007. Reference is made to the following related applications: WO2004/064537, WO2004/064987, WO2005/066347, WO2005/066351, WO2006/008508, US 2002-0009518, US 2004-0091574, U.S. Application Ser. Nos. 60/764,430 and 60/489,441.

Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference.

FIELD OF THE PRESENT INVENTION

The present invention relates to methods of producing variant enzymes. The present invention further relates to novel variant enzymes and to the use of these novel variant enzymes.

Specifically, the present invention relates to the production of lipid acyltransferases. In particular, methods for the production of a lipid acyltransferase by expressing a lipid acyltransferase in a Bacillus host cell, preferably a B. licheniformis host cell. In addition, the present invention relates to the use of Bacillus (preferably B. licheniformis) to express a lipid acyltransferase and to a Bacillus host cell, preferably a B. licheniformis host cell, comprising in its genome a gene encoding a lipid acyltransferase.

BACKGROUND OF THE PRESENT INVENTION

Lipid acyltransferases are known to be advantageous in food applications. Lipid acyltransferases have been found to have significant acyltransferase activity in foodstuffs. This activity has surprising beneficial applications in methods of preparing foodstuffs.

For instance, WO 2004/064537 discloses a method for the in situ production of an emulsifier by use of a lipid acyltransferase and the advantages associated therewith.

Further, lipid:cholesterol acyltransferase enzymes have been known for some time (see for example Buckley—Biochemistry 1983, 22, 5490-5493). In particular, glycerophospholipid:cholesterol acyl transferases (GCATs) have been found, which like the plant and/or mammalian lecithin:cholesterol acyltransferases (LCATs), will catalyse fatty acid transfer between phosphatidylcholine and cholesterol.

Upton and Buckley (TIBS 20, May 1995, p178-179) and Brumlik and Buckley (J. of Bacteriology April 1996, p2060-2064) teach a lipase/acyltransferase from Aeromonas hydrophila which has the ability to carry out acyl transfer to alcohol receptors in aqueous media.

A putative substrate binding domain and active site of the A. hydrophila acyltransferase have been identified (see for example Thornton et al 1988 Biochem. et Biophys. Acta. 959, 153-159 and Hilton & Buckley 1991 J. Biol. Chem. 266, 997-1000) for this enzyme.

Buckley et al (J. Bacteriol 1996, 178(7) 2060-4) taught that Ser16, Asp116 and His291 are essential amino acids which must be retained for enzyme activity to be maintained.

Robertson et al (J. Biol. Chem. 1994, 269, 2146-50) taught some specific mutations, namely Y226F, Y230F, Y30F, F13S, S18G, S18V, of the A. hydrophila acyltransferase, none of which are encompassed by the present invention.

Accordingly, there is a need for a method for the commercial production of lipid acyltransferases, including variant lipid acyltransferases.

However, generally genes can be difficult to express in heterologous hosts and expression of lipid acyltransferases in host cells can be problematic.

WO 2004/064537 discloses the expression of two Aeromonas lipid acyltransferases in Bacillus subtilis and Escherichia Coli. However, expression in B. subtilis is low whilst E. coli is not a GRAS organism and is, therefore, unsuitable as a host for enzymes that are to be used in the food industry.

U.S. Pat. No. 6,255,076 discloses a method of producing a polypeptide in a Bacillus host cell. However, such a method requires the use of a tandem promoter in which each promoter sequence in operably linked to a single copy of a nucleic acid sequence encoding the polypeptide sequence. Thus, there is a need in the art for an improved method for the production of lipid acyltransferases.

SUMMARY ASPECTS OF THE PRESENT INVENTION

Aspects of the present invention are presented in the claims and in the following commentary.

The present invention is predicated upon the finding of specific variants of a GDSx containing lipid acyltransferase enzyme, which variants have an increased hydrolytic activity and/or transferase activity compared with a parent enzyme. In particular, the variants according to the present invention have an enhanced hydrolytic activity towards galactolipids and/or an enhanced transferase activity using galactolipid as an acyl donor as compared with a parent enzyme. The variants according to the present invention may additionally have an enhanced ratio of activity towards galactolipids to phospholipids and/or towards galactolipids to triacylglyerides compared with a parent enzyme.

According to a first aspect the present invention provides a method of producing a variant lipid acyltransferase enzyme comprising: (a) selecting a parent enzyme which is a lipid acyltransferase enzyme characterised in that the enzyme comprises the amino acid sequence motif GDSX, wherein X is one or more of the following amino acid residues L, A, V, I, F, Y, H, Q, T N, M or S; (b) modifying one or more amino acids to produce a variant lipid acyltransferase; (c) testing the variant lipid acyltransferase for activity on a galactolipid substrate, and optionally a phospholipid substrate and/or optionally a triglyceride substrate; (d) selecting a variant enzyme with an enhanced activity towards galactolipids compared with the parent enzyme; and optionally (e) preparing a quantity of the variant enzyme.

In another aspect the present invention provides a variant lipid acyltransferase enzyme characterised in that the enzyme comprises the amino acid sequence motif GDSX, wherein X is one or more of the following amino acid residues L, A, V, I, F, Y, H, Q, T N, M or S, and wherein the variant enzyme comprises one or more amino acid modifications compared with a parent sequence at any one or more of the following amino acid residues defined in set 2 or set 4 or set 6 or set 7.

In a further aspect the present invention provides a variant lipid acyltransferase enzyme characterised in that the enzyme comprises the amino acid sequence motif GDSX, wherein X is one or more of the following amino acid residues L, A, V, I, F, Y, H, Q, T N, M or S, and wherein the variant enzyme comprises one or more amino acid modifications compared with a parent sequence at any one or more of the following amino acid residues detailed in set 2 or 4 or 6 or 7 identified by said parent sequence being structurally aligned with the structural model of P10480 defined herein, which is preferably obtained by structural alignment of P10480 crystal structure coordinates with 1IVN.PDB and/or 1DEO.PDB as taught herein.

The present invention yet further provides a variant lipid acyltransferase enzyme characterised in that the enzyme comprises the amino acid sequence motif GDSX, wherein X is one or more of the following amino acid residues L, A, V, I, F, Y, H, Q, T N, M or S, and wherein the variant enzyme comprises one or more amino acid modifications compared with a parent sequence at any one or more of the following amino acid residues identified when said parent sequence is aligned to the pfam consensus sequence (SEQ ID No. 2) and modified according to a structural model of P10480 to ensure best fit overlap (see FIG. 3) as taught in (SET 2): Ala114, Trp111, Tyr117, Pro156, Tyr179, Gln182, His180, Asn181, Met209, Leu210, Arg211, Asn215, Met285, Gln289, Val290, Asn80, Pro81, Lys82.

According to a further aspect the present invention provides a variant lipid acyltransferase enzyme wherein the variant enzyme comprises an amino acid sequence, which amino acid sequence is shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 except for one or more amino acid modifications at any one or more of the following amino acid residues identified by sequence alignment with SEQ ID No. 2: (SET 2 or 4 or 6 or 7).

In a further aspect the present invention provides a variant lipid acyltransferase enzyme wherein the variant enzyme comprises an amino acid sequence, which amino acid sequence is shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 except for one or more amino acid modifications at any one or more of the following amino acid residues identified by said parent sequence being structurally aligned with the structural model of P10480 defined herein, which is preferably obtained by structural alignment of P10480 crystal structure coordinates with 1IVN.PDB and/or 1DEO.PDB as taught herein: (SET 2 or 4 or 6 or 7).

According to a further aspect the present invention provides a variant lipid acyltransferase enzyme wherein the variant enzyme comprises an amino acid sequence, which amino acid sequence is shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 except for one or more amino acid modifications at any one or more of the following amino acid residues identified when said parent sequence is aligned to the pfam consensus sequence (SEQ ID No. 2) and modified according to a structural model of P10480 to ensure best fit overlap (see FIG. 3) as taught herein: (SET 2) Ala114, Trp111, Tyr117, Pro156, Tyr179, Gln182, His180, Asn181, Met209, Leu210, Arg211, Asn215, Met285, Gln289, Val290, Asn80, Pro81, Lys82.

According to yet a further aspect, the present invention provides a variant lipid acyltransferase enzyme whereint eh variant enzyme comprises an amino acid sequence, which amino acid sequence has undergone post-translational modification and/or truncation. In one aspect, the amino acid sequence is shown as SEQ ID No. 70.

The present invention yet further provides the use of a variant lipolytic enzyme according to the present invention or obtained by a method according to the present invention in a substrate (preferably a foodstuff) for preparing a lyso-glycolipid, for example digalactosyl monoglyceride (DGMG) or monogalactosyl monoglyceride (MGMG) by treatment of a glycolipid (e.g. digalactosyl diglyceride (DGDG) or monogalactosyl diglyceride (MGDG)) with the variant lipolytic enzyme according to the present invention or obtained by a method according to the present invention to produce the partial hydrolysis product, i.e. the lyso-glycolipid.

In a further aspect, the present invention provides the use of a variant lipolytic enzyme according to the present invention or obtained by a method according to the present invention in a substrate (preferably a foodstuff) for preparing a lyso-phospholipid, for example lysolecithin, by treatment of a phospholipid (e.g. lecithin) with the variant lipolytic enzyme according to the present invention or obtained by a method according to the present invention to produce a partial hydrolysis product, i.e a lyso-phospholipid.

In one aspect the present invention relates to a method of preparing a foodstuff the method comprising adding a variant lipolytic enzyme according to the present invention or obtained by a method according to the present invention to one or more ingredients of the foodstuff.

Another aspect of the present invention relates to a method of preparing a baked product from a dough, the method comprising adding a variant lipolytic enzyme according to the present invention or obtained by a method according to the present invention to the dough.

In another aspect of the present invention there is provided the use of a variant lipolytic enzyme according to the present invention or obtained by a method according to the present invention in a process of treating egg or egg-based products to produce lysophospholipids.

A further aspect of the present invention provides a process of enzymatic degumming of vegetable or edible oils, comprising treating the edible or vegetable oil with a variant lipolytic enzyme according to the present invention or obtained by a method according to the present invention so as to hydrolyse a major part of the polar lipids (e.g. phospholipid and/or glycolipid).

In another aspect the present invention provides the use of a variant lipolytic enzyme according to the present invention or obtained by a method according to the present invention in a process comprising treatment of a phospholipid so as to hydrolyse fatty acyl groups.

In another aspect the present invention provides the use of a variant lipolytic enzyme according to the present invention or obtained by a method according to the present invention in a process for reducing the content of a phospholipid in an edible oil, comprising treating the oil with said variant lipolytic enzyme so as to hydrolyse a major part of the phospholipid, and separating an aqueous phase containing the hydrolysed phospholipid from the oil.

There is also provided a method of preparing a variant lipolytic enzyme according to the present invention or obtained by a method according to the present invention, the method comprising transforming a host cell with a recombinant nucleic acid comprising a nucleotide sequence coding for said variant lipolytic enzyme, the host cell being capable of expressing the nucleotide sequence coding for the polypeptide of the lipolytic enzyme, cultivating the transformed host cell under conditions where the nucleic acid is expressed and harvesting the variant lipolytic enzyme.

In a further aspect the present invention relates to the use of a variant lipolytic enzyme according to the present invention or obtained by a method according to the present invention in the bioconversion of polar lipids (preferably glycolipids) to make high value products, such as carbohydrate esters and/or protein esters and/or protein subunit esters and/or a hydroxy acid ester.

The present invention yet further relates to an immobilised variant lipolytic enzyme according to the present invention or obtained by a method according to the present invention.

Aspects of the present invention are presented in the claims and in the following commentary.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same. The present invention further encompasses methods of isolating the nucleotide sequence, such as isolating from a host cell.

Other aspects concerning the amino acid sequence for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequence for use in the present invention using the same, such as expression in a host cell; including methods of transferring same, and then purifying said sequence.

One aspect of the present invention relates to a method for the production of a lipid acyltransferase comprising the steps of:
 (i) providing a host cell, preferably a *Bacillus* host cell wherein the *Bacillus* host cell is one other than *Bacillus subtilis*, preferably a *Bacillus licheniformis* cell;
 (ii) transforming the host cell, preferably the *Bacillus* host cell wherein the *Bacillus* host cell is one other than *Bacillus subtilis*, preferably the *Bacillus licheniformis* cell, with a heterologous nucleotide sequence encoding a lipid acyltransferase and
 (iii) expressing the lipid acyltransferase in the cell under the control of a promoter sequence.

In another aspect, the present invention relates to a *Bacillus* host cell wherein the *Bacillus* host cell is one other than *Bacillus subtilis*, preferably a *Bacillus licheniformis* host cell, comprising a heterologous lipid acyltransferase.

In a further aspect, the present invention relates to the use of a *Bacillus* host cell wherein the *Bacillus* host cell is one other than *Bacillus subtilis*, preferably a *Bacillus licheniformis* host cell, in the production of a heterologous lipid acyltransferase.

Suitably expression in the *Bacillus* host wherein the *Bacillus* host is one other than *Bacillus subtilis*, and preferably wherein the *Bacillus* host is *B. lichenformis*, may result in increased expression when compared to expression in *B. subtilis*.

In yet another aspect, the present invention relates to an expression vector comprising a nucleotide sequence encoding a lipid acyltransferase operably linked to one or more regulatory sequence(s) such that the regulatory sequence(s) is capable of expressing the nucleotide sequence encoding a lipid acyltransferase in a suitable host or host cell, preferably in a *Bacillus* host (or cell) wherein the *Bacillus* host (or cell) is one other than *Bacillus subtilis*, preferably in *B. licheniformis* or a *B. licheniformis* cell.

Suitably the lipid acyltransferase may be a recombinant lipid acyltransferase.

In another aspect, the lipid acyltransferase may be a lipid acyltransferase which has undergone post-translational modification and/or truncation.

For the ease of reference, these and further aspects of the present invention are now discussed under appropriate section headings. However, the teachings under each section are not necessarily limited to each particular section.

DETAILED ASPECTS OF THE PRESENT INVENTION

According to a first aspect the present invention provides a method of producing a variant lipid acyltransferase enzyme comprising: (a) selecting a parent enzyme which is a lipid acyltransferase enzyme characterised in that the enzyme comprises the amino acid sequence motif GDSX, wherein X is one or more of the following amino acid residues L, A, V, I, F, Y, H, Q, T N, M or S; (b) modifying one or more amino acids to produce a variant lipid acyltransferase; (c) testing the variant lipid acyltransferase for activity on a galactolipid substrate, and optionally a phospholipid substrate and/or optionally a triglyceride substrate; (d) selecting a variant enzyme with an enhanced activity towards galactolipids compared with the parent enzyme; and optionally (e) preparing a quantity of the variant enzyme.

The term "modifying" as used herein means adding, substituting and/or deleting. Preferably the term "modifying" means "substituting".

For the avoidance of doubt, when an amino acid is substituted in the parent enzyme it is preferably substituted with an amino acid which is different from that originally found at that position in the parent enzyme. In other words, the term "substitution" is not intended to cover the replacement of an amino acid with the same amino acid.

In another aspect the present invention provides a variant lipid acyltransferase enzyme characterised in that the enzyme comprises the amino acid sequence motif GDSX, wherein X is one or more of the following amino acid residues L, A, V, I, F, Y, H, Q, T N, M or S, and wherein the variant enzyme comprises one or more amino acid modifications compared with a parent sequence at any one or more of the following amino acid residues defined in set 2 or set 4 or set 6 or set 7.

In a further aspect the present invention provides a variant lipid acyltransferase enzyme characterised in that the enzyme comprises the amino acid sequence motif GDSX, wherein X is one or more of the following amino acid residues L, A, V, I, F, Y, H, Q, T N, M or S, and wherein the variant enzyme comprises one or more amino acid modifications compared with a parent sequence at any one or more of the following amino acid residues detailed in set 2 or 4 or 6 or 7 identified by said parent sequence being structurally aligned with the structural model of P10480 defined herein, which is preferably obtained by structural alignment of P10480 crystal structure coordinates with 1IVN.PDB and/or 1DEO.PDB as taught herein.

The present invention yet further provides a variant lipid acyltransferase enzyme characterised in that the enzyme comprises the amino acid sequence motif GDSX, wherein X is one or more of the following amino acid residues L, A, V, I, F, Y, H, Q, T N, M or S, and wherein the variant enzyme comprises one or more amino acid modifications compared with a parent sequence at any one or more of the following amino acid residues identified when said parent sequence is aligned to the pfam consensus sequence (SEQ ID No. 2) and modified according to a structural model of P10480 to ensure best fit overlap (see FIG. 3) as taught in (SET 2): Ala114, Trp111, Tyr117, Pro156, Tyr179, Gln182, His180, Asn181, Met209, Leu210, Arg211, Asn215, Met285, Gln289, Val290, Asn80, Pro81, Lys82.

According to a further aspect the present invention provides a variant lipid acyltransferase enzyme wherein the variant enzyme comprises an amino acid sequence, which amino acid sequence is shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 except for one or more amino acid modifications at any one or more of the following amino acid residues identified by sequence alignment with SEQ ID No. 2: (SET 2 or 4 or 6 or 7).

In a further aspect the present invention provides a variant lipid acyltransferase enzyme wherein the variant enzyme comprises an amino acid sequence, which amino acid sequence is shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 except for one or more amino acid modifications at any one or more of the following amino acid residuesidentified by said parent sequence being structurally aligned with the structural model of P10480 defined herein, which is preferably obtained by structural alignment of P10480 crystal structure coordinates with 1IVN.PDB and/or 1DEO.PDB as taught herein: (SET 2 or 4 or 6 or 7).

According to a further aspect the present invention provides a variant lipid acyltransferase enzyme wherein the variant enzyme comprises an amino acid sequence, which amino acid sequence is shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 except for one or more amino acid modifications at any one or more of the following amino acid residues identified when said parent sequence is aligned to the pfam consensus sequence (SEQ ID No. 2) and modified according to a structural model of P10480 to ensure best fit overlap (see FIG. 3) as taught herein: (SET 2) Ala114, Trp111, Tyr117, Pro156, Tyr179, Gln182, His180, Asn181, Met209, Leu210, Arg211, Asn215, Met285, Gln289, Val290, Asn80, Pro81, Lys82.

The present invention yet further provides the use of a variant lipolytic enzyme according to the present invention or obtained by a method according to the present invention in a substrate (preferably a foodstuff) for preparing a lyso-glycolipid, for example digalactosyl monoglyceride (DGMG) or monogalactosyl monoglyceride (MGMG) by treatment of a glycolipid (e.g. digalactosyl diglyceride (DGDG) or monogalactosyl diglyceride (MGDG)) with the variant lipolytic enzyme according to the present invention or obtained by a method according to the present invention to produce the partial hydrolysis product, i.e. the lyso-glycolipid.

In a further aspect, the present invention provides the use of a variant lipolytic enzyme according to the present invention or obtained by a method according to the present invention in a substrate (preferably a foodstuff) for preparing a lyso-phospholipid, for example lysolecithin, by treatment of a phospholipid (e.g. lecithin) with the variant lipolytic enzyme according to the present invention or obtained by a method according to the present invention to produce a partial hydrolysis product, i.e a lyso-phospholipid.

The variant lipid acyltransferase enzyme according to the present invention may in addition (or alternatively) to the modifications taught above, may comprise one of the following amino acid modifications at Ser18: S18A, L, M, F, W, K, Q, E, P, I, C, Y, H, R, N, D, T.

The variant lipid acyltransferase enzyme according to the present invention may in addition (or alternatively) to the modifications taught above, may comprise one of the following amino acid modifications at Y30: Y30A, G, L, M, W, K, Q, S, E, P, V, I, C, H, R, N, D, T.

The variant lipid acyltransferase enzyme according to the present invention may in addition (or alternatively) to the modifications taught above, may comprise one of the following amino acid modifications at Y230: Y230A, G, L, M, W, K, Q, S, E, P, V, I, C, H, R, N, D, T.

Preferably, the parent lipid acyltransferase enzyme comprises any one of the following amino acid sequences: SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70 or an amino acid sequence which has 75% or more identity with any one of the sequences shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70.

Suitably, the parent lipid acyltransferase enzyme according to the present invention comprises an amino acid sequence which has at least 80%, preferably at least 85%, more preferably at least 90%, more preferably at least 95%, more at least 98% homology with any one of the sequences shown as SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70.

Suitably, the parent lipid acyltransferase enzyme may be encoded by any one of the following nucleotide sequences: SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62, SEQ ID No. 63, SEQ ID No. 24, SEQ ID No. 36, SEQ ID No. 39, SEQ ID No. 42, SEQ ID No. 69, SEQ ID No. 44, SEQ ID No. 46 or SEQ ID No. 36 or a nucleotide sequence which has at least 75% or more identity with any one of the sequences shown as SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62, SEQ ID No. 63, SEQ ID No. 24, SEQ ID No. 36, SEQ ID No. 39, SEQ ID No. 42, SEQ ID No. 69, SEQ ID No. 44, SEQ ID No. 46 or SEQ ID No. 36.

Suitably, the nucleotide sequence may have 80% or more, preferably 90% or more, more preferably 95% or more, even more preferably 98% or more identity with any one of the sequences shown as SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62, SEQ ID No. 63, SEQ ID No. 24, SEQ ID No. 36, SEQ ID No. 39, SEQ ID No. 42, SEQ ID No. 69, SEQ ID No. 44, SEQ ID No. 46 or SEQ ID No. 36.

Preferably the method of producing a variant lipid acyltransferase enzyme further comprises one or more of the following steps:
1) structural homology mapping or
2) sequence homology alignment.

Suitably, the structural homology mapping may comprise one or more of the following steps:
i) aligning a parent sequence with a structural model (1IVN.PDB) shown in FIG. 45;
ii) selecting one or more amino acid residue within a 10 Å sphere centred on the central carbon atom of the glycerol molecule in the active site (see FIG. 46); and
iii) modifying one or more amino acids selected in accordance with step (ii) in said parent sequence.

In one embodiment preferably the amino acid residue selected in within an 9, preferably within a 8, 7, 6, 5, 4, or 3 Å sphere centred on the central carbon atom of the glycerol molecule in the active site (see FIG. 46).

Suitably, the structural homology mapping may comprise one or more of the following steps:
i) aligning a parent sequence with a structural model (1IVN. PDB) shown in FIG. 45;
ii) selecting one or more amino acids within a 10 Å sphere centred on the central carbon atom of the glycerol molecule in the active site (see FIG. 46);
iii) determining if one or more amino acid residues selected in accordance with step (ii) are highly conserved (particularly are active site residues and/or part of the GDSx motif and/or part of the GANDY (SEQ ID NO: 45) motif); and
iv) modifying one or more amino acids selected in accordance with step (ii), excluding conserved regions identified in accordance with step (iii) in said parent sequence.

In one embodiment preferably the amino acid residue selected in within an 9, preferably within a 8, 7, 6, 5, 4, or 3 Å sphere centred on the central carbon atom of the glycerol molecule in the active site (see FIG. 46).

Suitably, the sequence homology alignment may comprise one or more of the following steps:
i) selecting a first parent lipid acyltransferase;
ii) identifying a second related lipid acyltransferase having a desirable activity;
iii) aligning said first parent lipid acyltransferase and the second related lipid acyltransferase;
iv) identifying amino acid residues that differ between the two sequences; and
v) modifying one or more of the amino acid residues identified in accordance with step (iv) in said parent lipid acyltransferase.

Suitably, the sequence homology alignment may comprise one or more of the following steps:
i) selecting a first parent lipid acyltransferase;
ii) identifying a second related lipid acyltransferase having a desirable activity;
iii) aligning said first parent lipid acyltransferase and the second related lipid acyltransferase;
iv) identifying amino acid residues that differ between the two sequences;
v) determining if one or more amino acid residues selected in accordance with step (iv) are highly conserved (particularly are active site residues and/or part of the GDSx motif and/or part of the GANDY (SEQ ID NO: 45) motif); and
vi) modifying one or more of the amino acid residues identified in accordance with step (iv) excluding conserved regions identified in accordance with step (v) in said parent sequence.

Suitably, said first parent lipid acyltransferase may comprise any one of the following amino acid sequences: SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70.

Suitably, said second related lipid acyltransferase may comprise any one of the following amino acid sequences: SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 40, SEQ ID No. 29, SEQ ID No. 30, SEQ ID No. 31, SEQ ID No. 32 or SEQ ID No. 70.

According to one aspect of the present invention there is provided a method for the production of a lipid acyltransferase as described above, comprising the steps of:
(i) providing a host cell, preferably a *Bacillus* host cell wherein the *Bacillus* host cell is one other than *Bacillus subtilis*, preferably a *Bacillus licheniformis* cell;

(ii) transforming the host cell, preferably a *Bacillus* host cell wherein the *Bacillus* host cell is one other than *Bacillus subtilis*, preferably a *Bacillus licheniformis* cell, with an heterologous nucleotide sequence encoding a lipid acyltransferase; and (iii) expressing the lipid acyltransferase in the cell under the control of a promoter sequence.

Additionally, a nucleotide sequence encoding a signal peptide may be operably linked to said heterologous nucleotide sequence encoding a lipid acyltransferase.

In one aspect of the invention, there is provided a variant lipid acyltransferase enzyme having one or more modifications in comparison to a parent lipid acyltransferase enzyme having the amino acid sequence motif GDSX wherein X is one or more of amino acid residues L, A, V, I, F, Y, H, Q, T, N, M or S, wherein the variant lipid acyltransferase enzyme undergoes post-translational modification and/or truncation.

In one embodiment, such a truncated enzyme may comprise the amino acid sequence of SEQ ID NO. 70. Such variant enzymes can be made by the methods of the present invention and are subject to truncation following translation.

Thus, for example, in one aspect of the present invention a first mature variant lipid acyltransferase enzyme may have the amino acid sequence of SEQ ID No. 16 prior to post-translational modification. Following post-translational modification and/or truncation, said mature variant lipid acyltransferase may have the amino acid sequence of SEQ ID No. 70. In one aspect, at least 1 or 5 or 10 or 15 or 20 or 25 or 30 or 35 or 38 or 40 or more amino acid residues may be removed during the post-translational modification.

In one aspect of the present invention, the post-translational modification can result in the removal of amino acids from about position 235 to about position 273. In one aspect of the present invention, amino acid residue number 274 of a lipid acyltransferase having the amino acid sequence of SEQ ID No. 16 corresponds to amino acid residue number 236 of a lipid acyltransferase having the amino acid sequence of SEQ ID No. 70.

In one aspect of the present invention, there is provided nucleic acid sequences that encode a truncated lipid acyltransferase enzyme. In one embodiment, the nucleotide sequence of SEQ ID No. 49 (FIG. 57) encodes the amino acid sequence of SEQ ID No. 70.

In another aspect of the invention, said post-translational modification can be induced by methods known to those of skill in the art or such post-translational modification can occur naturally. For example, expression of SEQ ID No. 49 in *Bacillus licheniformis* would result in the expression of a protein having an amino acid sequence which has been subjected to post-translational modification. In another example, the expression of SEQ ID No. 49 in *Bacillus licheniformis* would result in the expression of a protein having the amino acid sequence shown in SEQ ID No. 70. One of skill in the art will readily recognize alternative expression systems which will also result in the expression of a post-translationally modified enzyme.

Suitably the method of the present invention may further comprise the additional step of isolating/recovering the lipid acyltransferase.

In another aspect there is provided a lipid acyltransferase enzyme having an amino acid sequence which undergoes post-translational modification. In one aspect, there is provided a lipid acyltransferase enzyme having an amino acid sequence as depicted in SEQ ID No. 70. In a further aspect, there is provided a lipid acyltransferase enzyme having an amino acid sequence that has at least 70%, or at least 80%, or at least 85%, or at least 90% or at least 95%, or at least 96%, or at least 97%, or at least 98%, or at least 99%, sequence identity to the amino acid sequence depicted in SEQ ID No. 70.

In another aspect, the present invention relates to a *Bacillus licheniformis* host cell comprising a heterologous lipid acyltransferase.

Suitably the lipid acyltransferase may be a recombinant lipid acyltransferase.

Suitably the promoter sequence used in accordance with the host cells, vectors, methods and/or uses of the present invention may be homologous to the host cell. "Homologous to the host cell" means originating within the host organism; i.e. a promoter sequence which is found naturally in the host organism. Suitably, the promoter sequence may be selected from the group consisting of a nucleotide sequence encoding: an α-amylase promoter, a protease promoter, a subtilisin promoter, a glutamic acid-specific protease promoter and a levansucrase promoter. Suitably the promoter sequence may be a nucleotide sequence encoding: the LAT (e.g. the alpha-amylase promoter from *B. lichenformis*, also known as AmyL), AprL (e.g. subtilisin Carlsberg promoter), Endo-GluC (e.g. the glutamic-acid specific promoter from *B. licheniformis*), AmyQ (e.g. the alpha amylase promoter from *B. amyloliquefaciens* alpha-amylase promoter) and SacB (e.g. the *B. subtilis* levansucrase promoter).

In one embodiment of the present invention the promoter sequence is the −35 to −10 sequence of an alpha amylase promoter, preferably the −35 to −10 sequence of a *B. licheniformis* α-amylase promoter. The "−35 to −10 sequence" describes the position relative to the transcription start site. Both the "−35" and the "−10" are boxes, i.e. a number of nucleotides, each comprising 6 nucleotides and these boxes are separated by 17 nucleotides. These 17 nucleotides are often referred to as a "spacer". This is illustrated in FIG. 55, where the −35 and the −10 boxes are underlined. For the avoidance of doubt, where "−35 to −10 sequence" is used herein it refers to a sequence from the start of the −35 box to the end of the −10 box i.e. including both the −35 box, the 17 nucleotide long spacer and the −10 box.

In some aspects, the nucleotide sequence encoding a lipid acyltransferase for use in any one of the host cells, vectors, methods and/or uses of the present invention may comprise a GDSx motif and/ or a GANDY (SEQ ID NO: 45) motif.

Preferably, the lipid acyltransferase enzyme is characterised as an enzyme which possesses acyltransferase activity and which comprises the amino acid sequence motif GDSX, wherein X is one or more of the following amino acid residues L, A, V, I, F, Y, H, Q, T, N, M or S.

Suitably, the nucleotide sequence encoding a lipid acyltransferase for use in any one of the vectors, host cells, methods and/or uses of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*. Preferably, the lipid acyltransferase is obtainable, preferably obtained, from an organism from the genus *Aeromonas*.

In some aspects of the present invention, the nucleotide sequence encoding a lipid acyltransferase for use in any one of the vectors, host cells, methods and/or uses of the present invention encodes a lipid acyltransferase that comprises an aspartic acid residue at a position corresponding to N-80 in the amino acid sequence of the *Aeromonas hydrophila* lipid acyltransferase shown as SEQ ID No. 35.

In addition or in the alternative, the nucleotide sequence encoding a lipid acyltransferase for use in any one of the vectors, host cells, methods and/or uses of the present invention encodes a lipid acyltransferase that may comprise the amino acid sequence shown as SEQ ID No. 16 or SEQ ID No. 70, or an amino acid sequence which has 75% or more homology thereto. Suitably, the nucleotide sequence encoding a lipid acyltransferase encodes a lipid acyltransferase that may comprise the amino acid sequence shown as SEQ ID No. 16 or SEQ ID No. 70.

The term "heterologous" as used herein means a sequence derived from a separate genetic source or species. A heterologous sequence is a non-host sequence, a modified sequence, a sequence from a different host cell strain, or a homologous sequence from a different chromosomal location of the host cell.

A "homologous" sequence is a sequence that is found in the same genetic source or species i.e. it is naturally occurring in the relevant species of host cell.

The term "recombinant lipid acyltransferase" as used herein means that the lipid acyltransferase has been produced by means of genetic recombination. For instance, the nucleotide sequence encoding the lipid acyltransferase has been inserted into a cloning vector, resulting in a *B. licheniformis* cell characterised by the presence of the heterologous lipid acyltransferase.

Advantages

Variants transferases of the present invention have one or more of the following advantageous properties compared with the parent enzyme:

i) an increased activity on polar lipids and/or an increased activity on polar lipids compared to triglycerides.

ii) an increased activity on galactolipids (glycolipids), such as one or more of digalactosyl diglyceride (DGDG) and/or monogalactosyl diglyceride (MGDG).

iii) an increased ratio of activity on galactolipids (glycolipids) compared to either phospholipids and/or triglycerides Preferably variants transferases of the invention have increased activity on digalactosyl diglyceride (DGDG) and/or monogalactosyl diglyceride (MGDG).

The variants transferases of the invention may also have an increased activity on triglycerides.

The variants transferases of the invention may also have an increased activity on phospholipids, such as lecithin, including phosphatidyl choline.

Variants transferases of the present invention may have decreased activity on triglycerides, and/or monoglycerides and/or diglycerides.

The term polar lipid refers to the polar lipids usually found in a dough, preferably galactolipids and phospholipids.

When used in preparation of a dough or baked product the variant transferase of the invention may result in one or more of the following unexpected technical effects in dough and/or baked products: an improved specific volume of either the dough or the baked products (for example of bread and/or of cake); an improved dough stability; an improved crust score (for example a thinner and/or crispier bread crust), an improved crumb score (for example a more homogenous crumb distribution and/or a finer crumb structure and/or a softer crumb); an improved appearance (for example a smooth surface without blisters or holes or substantially without blisters or holes); a reduced staling; an enhanced softness; an improved odour; an improved taste.

Host Cell

In one embodiment of the present invention the host cell for use in the methods and/or uses of thee present invention is a *Bacillus licheniformis* host cell.

It has been found that the use of a *Bacillus licheniformis* host cell results in increased expression of a lipid acyltransferase when compared with other organisms, such as *Bacillus subtilis*.

A lipid acyltransferase from *Aeromonas salmonicida* has been inserted into a number of conventional expression vectors, designed to be optimal for the expression in *Bacillus subtilis, Hansenula polymorpha, Schizosaccharomyces pombe* and *Aspergillus tubigensis*, respectively. Only very low levels were, however, detected in *Hansenula polymorpha, Schizosaccharomyces pombe* and *Aspergillus tubigensis*. The expression levels were below 1 µg/ml, and it was not possible to select cells which yielded enough protein to initiate a commercial production (results not shown). In contrast, *Bacillus licheniformis* was able to produce protein levels, which are attractive for an economically feasible production.

In particular, it has been found that expression in *B. licheniformis* is approximately 100-times greater than expression in *B. subtilis* under the control of aprE promoter or is approximately 100-times greater than expression in *S. lividans* under the control of an A4 promoter and fused to cellulose (results not shown herein).

In another embodiment the host cell may be any *Bacillus* cell other than *B. subtilis*. Preferably, said *Bacillus* host cell being from one of the following species: *Bacillus licheniformis; B. alkalophilus; B. amyloliquefaciens; B. circulans; B. clausii; B. coagulans; B. firmus; B. lautus; B. lentus; B. megaterium; B. pumilus* or *B. stearothermophilus*.

The term "host cell"—in relation to the present invention includes any cell that comprises either a nucleotide sequence encoding a lipid acyltransferase as defined herein or an expression vector as described above and which is used in the recombinant production of a lipid acyltransferase having the specific properties as defined herein.

Thus, a further embodiment of the present invention provides a host cell comprising (for example transformed or transfected with) a nucleotide sequence of the present invention or a nucleotide sequence that expresses a polypeptide having the specific properties as defined herein.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Suitably, in some embodiments, the host cell may be a protease deficient or protease minus strain and/or an α-amylase deficient or α-amylase minus strain.

Regulatory Sequences

In some applications, a lipid acyltransferase sequence for use in any one of the host cells, vectors, methods and/or uses of the present invention may be operably linked to a regulatory sequence which is capable of providing for the expression of the nucleotide sequence, such as by the chosen host cell (such as a *B. licheniformis* cell).

By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of regulatory regions, e.g. promoter, secretion leader and terminator regions that are not regulatory regions for the nucleotide sequence encoding the enzyme in nature.

Suitably, the nucleotide sequence of the present invention may be operably linked to at least a promoter.

Suitably, the nucleotide sequence encoding a lipid acyltransferase may be operably linked to at a nucleotide sequence encoding a terminator sequence. Examples of suitable terminator sequences for use in any one of the vectors, host cells, methods and/or uses of the present invention include: an α-amylase terminator sequence (for instance, CGGGACTTACCGAAAGAAACCATCAAT-GATGGTTTCTTTTTTGTTCATAAA—SEQ ID No. 64), an alkaline protease terminator sequence (for instance, CAA-GACTAAAGACCGTTCGCCCGTTTTG-CAATAAGCGGGCGAATCTTACATAAAA ATA—SEQ ID No. 65), a glutamic-acid specific terminator sequence (for instance, ACGGCCGTTAGATGTGACAGCCCGTTC-CAAAAGGAAGCGGGCTGTCTTCGTGTAT TATTGT—SEQ ID No. 66), a levanase terminator sequence (for instance, TCTTTTAAAGGAAAGGCTGGAATGCCCG-GCATTCCAGCCACATGATCATCGTTT—SEQ ID No. 67) and a subtilisin E terminator sequence (for instance, GCT-GACAAATAAAAAGAAGCAGGTATGGAG-GAACCTGCTTCTTTTTAC TATTATTG—SEQ ID No. 71). Suitably, the nucleotide sequence encoding a lipid acyltransferase may be operably linked to an α-amylase terminator, such as a *B. licheniformis* α-amylase terminator.

Promoter

The promoter sequence to be used in accordance with the present invention may be heterologous or homologous to the sequence encoding a lipid acyltransferase.

The promoter sequence may be any promoter sequence capable of directing expression of a lipid acyltransferase in the host cell of choice.

Suitably, the promoter sequence may be homologous to a *Bacillus* species, for example *B. licheniformis*. Preferably, the promoter sequence is homologous to the host cell of choice.

Suitable promoter sequences for use in the present invention include: the promoter of the *Bacillus licheniformis* alpha-amylase gene, the promoter of the *Bacillus licheniformis* subtilisin gene, the promoter of the *Bacillus subtilis* subtilisin gene, the promoter of the *Bacillus licheniformis* alkaline protease gene (subtilisin Carlsberg gene), the promoter of the *B. licheniformis* glutamic-acid specific protease gene, the promoter of *B. amyloliquefaciens* alpha-amylase gene; the promoter of *B. subtilis* levansucrase and a "consensus" promoter having the sequence TTGACA for the "−35" region and TATAAT for the "−10" region (i.e. the −35 to −10 promoter) of the alpha-amylase gene.

Other examples of promoters suitable for directing the transcription of a nucleic acid sequence in the methods of the present invention include: the promoter of the *Bacillus lentus* alkaline protease gene (aprH); the promoter of the *Bacillus subtilis* alpha-amylase gene (amyE); the promoter of the *Bacillus stearothermophilus* maltogenic amylase gene (amyM); the promoter of the *Bacillus licheniformis* penicillinase gene (penP); the promoters of the *Bacillus subtilis* xylA and xylB genes; and/or the promoter of the *Bacillus thuringiensis* subsp. *tenebrionis* CryIIIA gene.

In a preferred embodiment, the promoter sequence is an α-amylase promoter (such as a *Bacillus licheniformis* α-amylase promoter). Preferably, the promoter sequence comprises the −35 to −10 sequence of the *B. licheniformis* α-amylase promoter—see FIGS. 53 and 55.

Signal Peptide

The lipid acyltransferase produced by a host cell by expression of the nucleotide sequence encoding the lipid acyltransferase may be secreted or may be contained intracellularly depending on the sequence and/or the vector used.

A signal sequence may be used to direct secretion of the coding sequences through a particular cell membrane. The signal sequences may be natural or foreign to the lipid acyltransferase coding sequence. For instance, the signal peptide coding sequence may be obtained form an amylase or protease gene from a *Bacillus* species, preferably from *Bacillus licheniformis*.

Suitable signal peptide coding sequences may be obtained from one or more of the following genes: maltogenic α-amylase gene, subtilisin gene, beta-lactamase gene, neutral protease gene, prsA gene, and/or acyltransferase gene.

Preferably, the signal peptide is a signal peptide of *B. licheniformis* α-amylase, *Aeromonas* acyltransferase (for instance, mkkwfvcllglialtvqa—SEQ ID No. 21), *B. subtilis* subtilisin (for instance, mrskklwisllfaltliftmafsnmsaqa—SEQ ID No. 22) or *B. licheniformis* subtilisin (for instance, mmrkksfwfgmltafmlvftmefsdsasa—SEQ ID No. 23). Suitably, the signal peptide may be the signal peptide of *B. licheniformis* α-amylase.

However, any signal peptide coding sequence capable of directing the expressed lipid acyltransferase into the secretory pathway of a *Bacillus* host cell (preferably a *B. licheniformis* host cell) of choice may be used.

In some embodiments of the present invention, a nucleotide sequence encoding a signal peptide may be operably linked to a nucleotide sequence encoding a lipid acyltransferase of choice.

The lipid acyltransferase of choice may be expressed in a host cell as defined herein as a fusion protein.

Expression Vector

The term "expression vector" means a construct capable of in vivo or in vitro expression.

Preferably, the expression vector is incorporated in the genome of the organism, such as a *B. licheniformis* host. The term "incorporated" preferably covers stable incorporation into the genome.

The nucleotide sequence encoding a lipid acyltransferase as defined herein may be present in a vector, in which the nucleotide sequence is operably linked to regulatory sequences such that the regulatory sequences are capable of providing the expression of the nucleotide sequence by a suitable host organism (such as *B. licheniformis*), i.e. the vector is an expression vector.

The vectors of the present invention may be transformed into a suitable host cell as described above to provide for expression of a polypeptide having lipid acyltransferase activity as defined herein.

The choice of vector, e.g. plasmid, cosmid, virus or phage vector, genomic insert, will often depend on the host cell into which it is to be introduced. The present invention may cover other forms of expression vectors which serve equivalent functions and which are, or become, known in the art.

Once transformed into the host cell of choice, the vector may replicate and function independently of the host cell's genome, or may integrate into the genome itself.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein for use in any one of the vectors, host cells, other methods and/or uses of the present invention, by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Lipid Acyl Transferase

The nucleotide sequence encoding a lipid acyl transferase for use in any one of the methods, vectors and/or uses of the present invention may encode a natural lipid acyl transferase or a variant lipid acyl transferase.

For instance, the nucleotide sequence encoding a lipid acyl transferase for use in the present invention may be one as described in WO2004/064537, WO2004/064987, WO2005/066347, or WO2006/008508. These documents are incorporated herein by reference.

The term "lipid acyl transferase" as used herein preferably means an enzyme that has acyltransferase activity (generally classified as E.C. 2.3.1.x, for example 2.3.1.43), whereby the enzyme is capable of transferring an acyl group from a lipid to one or more acceptor substrates, such as one or more of the following: a sterol; a stanol; a carbohydrate; a protein; a protein subunit; a sugar alcohol, such as ascorbic acid and/or glycerol—preferably glycerol and/or a sterol, such as cholesterol.

Preferably, the nucleotide sequence encoding a lipid acyl transferase for use in any one of the vectors, host cells, methods and/or uses of the present invention encodes a lipid acyltransferase that is capable of transferring an acyl group from a phospholipid (as defined herein) to a sugar alcohol, such as ascorbic acid and/or glycerol, most preferably glycerol.

For some aspects the "acyl acceptor" according to the present invention may be any compound comprising a hydroxy group (—OH), such as for example, polyvalent alcohols, including glycerol; sterols; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water. Preferably, the "acyl acceptor" according to the present invention is a sugar alcohol, such as a polyol, most preferably glycerol. For the purpose of this invention ascorbic acid is also considered a sugar-alcohol.

The acyl acceptor is preferably not a monoglyceride.

The acyl acceptor is preferably not a diglyceride

In one aspect, the nucleotide sequence encoding a lipid acyltransferase for use in any one of the host cells, vectors, methods and/or uses of the present invention encodes a lipid acyltransferase that may, as well as being able to transfer an acyl group from a lipid to glycerol, additionally be able to transfer the acyl group from a lipid to one or more of the following: a carbohydrate, a protein, a protein subunit, sterol and/or a stanol, preferably it is capable of transferring to both a sugar alcohol, such as ascorbic acid and/or glycerol, most preferably a sterol such as cholesterol, and/or plant sterol/stanols.

Preferably, the lipid substrate upon which the lipid acyl acts is one or more of the following lipids: a phospholipid, such as a lecithin, e.g. phosphatidylcholine.

This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the nucleotide sequence encoding a lipid acyl transferase for use in any one of the host cells, vectors, methods and/or uses of the present invention encodes a lipid acyltransferase that is incapable, or substantially incapable, of acting on a triglyceride and/or a 1-monoglyceride and/or 2-monoglyceride.

For some aspects, preferably the nucleotide sequence encoding a lipid acyl transferase for use in any one of the host cells, vectors, methods and/or uses of the present invention encodes a lipid acyltransferase that does not exhibit triacylglycerol lipase activity (E.C. 3.1.1.3) or does not exhibit significant triacylglycerol lipase activity (E.C. 3.1.1.3).

The ability to hydrolyse triglyeride (E.C. 3.1.1.3 activity) may be determined by lipase activity is determined according to Food Chemical Codex (3rd Ed., 1981, pp 492-493) modified to sunflower oil and pH 5.5 instead of olive oil and pH 6.5. The lipase activity is measured as LUS (lipase units sunflower) where 1 LUS is defined as the quantity of enzyme which can release 1 [mu]mol of fatty acids per minute from sunflower oil under the above assay conditions. Alternatively the LUT assay as defined in WO9845453 may be used. This reference is incorporated herein by reference.

The nucleotide sequence encoding a lipid acyl transferase for use in any one of the host cells, vectors, methods and/or uses of the present invention may encode a lipid acyltransferase that which is substantially incapable of acting on a triglyceride may have a LUS/mg of less than 1000, for example less than 500, such as less than 300, preferably less than 200, more preferably less than 100, more preferably less than 50, more preferably less than 20, more preferably less than 10, such as less than 5, less than 2, more preferably less than 1 LUS/mg. Alternatively LUT/mg activity is less than 500, such as less than 300, preferably less than 200, more preferably less than 100, more preferably less than 50, more preferably less than 20, more preferably less than 10, such as less than 5, less than 2, more preferably less than 1 LUT/mg.

The nucleotide sequence encoding a lipid acyl transferase for use in any one of the host cells, vectors, methods and/or uses of the present invention may encode a lipid acyltransferase that which is substantially incapable of acting on a monoglyceride may be determined by using mono-oleate (M7765 1-Oleoyl-rac-glycerol 99%) in place of the sunflower oil in the LUS assay. 1 MGHU is defined as the quantity of enzyme which can release 1 [mu]mol of fatty acids per minute from monoglyceride under the assay conditions.

The nucleotide sequence encoding a lipid acyl transferase for use in any one of the host cells, vectors, methods and/or uses of the present invention encodes a lipid acyltransferase that which is substantially incapable of acting on a triglyceride may have a MGHU/mg of less than 5000, for example less than 1000, for example less than 500, such as less than 300, preferably less than 200, more preferably less than 100, more preferably less than 50, more preferably less than 20, more preferably less than 10, such as less than 5, less than 2, more preferably less than 1 MGHU/mg.

Suitably, the nucleotide sequence encoding a lipid acyltransferase for use in any one of the host cells, vectors, methods and/or uses of the present invention encodes a lipid acyltransferase that may exhibit one or more of the following phospholipase activities: phospholipase A2 activity (E.C. 3.1.1.4) and/or phospholipase A1 activity (E.C. 3.1.1.32). The lipid acyl transferase may also have phospholipase B activity (E.C 3.1.1.5).

Suitably, for some aspects the lipid acyltransferase may be capable of transferring an acyl group from a phospholipid to a sugar alcohol, preferably glycerol and/or ascorbic acid.

For some aspects, preferably the nucleotide sequence encoding a lipid acyltransferase for use any one of the host cells, vectors, methods and/or uses of the present invention encodes a lipid acyltransferase that is capable of transferring an acyl group from a phospholipid to a sterol and/or a stanol to form at least a sterol ester and/or a stanol ester.

The lipid acyltransferase may be capable of transferring an acyl group from a lipid to a polyol such as glycerol, and/or a sterol such as cholesterol or plant sterol/stanols. Thus, in one embodiment the "acyl acceptor" according to the present invention may be glycerol and/or cholesterol or plant sterol/stanols.

Suitably in the protein or protein subunit the acyl acceptor may be one or more of the following constituents of the protein or protein subunit: a serine, a threonine, a tyrosine, or a cysteine.

When the protein subunit is an amino acid, suitably the amino acid may be any suitable amino acid. Suitably the amino acid may be one or more of a serine, a threonine, a tyrosine, or a cysteine for example.

In one aspect, preferably the variant enzyme is capable of transferring an acyl group from a lipid to glycerol.

In one aspect, preferably the variant enzyme is capable of transferring an acyl group from a lipid to a hydroxy acid.

In one aspect, preferably the variant enzyme is capable of transferring an acyl group from a lipid to a polyvalent alcohol.

In one aspect, the variant lipid acyltransferase may, as well as being able to transfer an acyl group from a lipid to a sterol and/or a stanol, additionally be able to transfer the acyl group from a lipid to one or more of the following: a carbohydrate, a protein, a protein subunit, glycerol.

Preferably, the lipid substrate upon which the variant lipid acyltransferase according to the present invention acts is one or more of the following lipids: a phospholipid, such as a lecithin, e.g. phosphatidylcholine, a triacylglyceride, a cardiolipin, a diglyceride, or a glycolipid, such as digalactosyldiglyceride (DGDG) for example. This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the lipid substrate upon which the variant lipid acyltransferase acts is a phospholipid, such as lecithin, for example phosphatidylcholine.

For some aspects, preferably the lipid substrate is a glycolipid, such as DGDG for example.

Preferably the lipid substrate is a food lipid, that is to say a lipid component of a foodstuff.

Preferably, when carrying out a method according to the present invention the product (i.e. foodstuff) is produced without increasing or substantially increasing the free fatty acids in the foodstuff.

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule. Acyl transfer which results from hydrolysis requires the separation of the water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

Protocol for the Determination of % Acyltransferase Activity:

A foodstuff to which a lipid acyltransferase according to the present invention has been added may be extracted following the enzymatic reaction with $CHCl_3:CH_3OH$ 2:1 and the organic phase containing the lipid material is isolated and analysed by GLC according to the procedure detailed hereinbelow. From the GLC analysis (and if necessary HPLC analysis) the amount of free fatty acids and one or more of sterol/stanol esters; carbohydrate esters, protein esters; diglycerides; or monoglycerides are determined. A control foodstuff to which no enzyme according to the present invention has been added, is analysed in the same way.

Calculation:

From the results of the GLC (and optionally HPLC analyses) the increase in free fatty acids and sterol/stanol esters and/or carbohydrate esters and/or protein esters and/or diglycerides and/or monoglycerides can be calculated:

Δ% fatty acid=% Fatty acid(enzyme)−% fatty acid(control); Mv fatty acid=average molecular weight of the fatty acids;

A=Δ% sterol ester/Mv sterol ester (where Δ% sterol ester=% sterol/stanol ester(enzyme)−% sterol/stanol ester (control) and Mv sterol ester=average molecular weight of the sterol/stanol esters)−applicable where the acyl acceptor is a sterol and/or stanol;

B=Δ% carbohydrate ester/Mv carbohydrate ester (where Δ% carbohydrate ester=% carbohydrate ester(enzyme)−% carbohydrate ester(control) and Mv carbohydrate ester=average molecular weight of the carbohydrate ester)−applicable where the acyl acceptor is a carbohydrate;

C=Δ% protein ester/Mv protein ester (where Δ% protein ester=% protein ester(enzyme)−% protein ester(control) and Mv protein ester=average molecular weight of the protein ester)−applicable where the acyl acceptor is a protein; and D=absolute value of diglyceride and/or monoglyceride/Mv di/monoglyceride (where Δ% diglyceride and/or monoglyceride=% diglyceride and/or monoglyceride (enzyme)−% diglyceride and/or monoglyceride (control) and Mv di/monoglyceride=average molecular weight of the diglyceride and/or monoglyceride)−applicable where the acyl acceptor is glycerol.

The transferase activity is calculated as a percentage of the total enzymatic activity:

% transferase activity =

$$\frac{A^* + B^* + C^* + D^* \times 100}{A^* + B^* + C^* + D^* + \Delta \% \text{ fatty acid} / (Mv \text{ fatty acid})}$$

*- delete as appropriate.

The amino acids which fall within the terms "non-polar", "polar-uncharged", "polar-charged" are given in the table below, as are the amino acids falling within the terms "aliphatic" and "aromatic". The term "polar" refers to both "polar-uncharged" and "polar-charged" amino acids.

| ALIPHATIC | Non-polar | G A P I L V |
| --- | --- | --- |
| | Polar-uncharged | C S T M N Q |
| | Polar-charged | D E K R |
| AROMATIC | | H F W Y |

GLC Analysis

Perkin Elmer Autosystem 9000 Capillary Gas Chromatograph equipped with WCOT fused silica column 12.5 m×0.25 mm ID×0.1 μ film thickness 5% phenyl-methyl-silicone (CP Sil 8 CB from Chrompack).

Carrier gas: Helium.

Injector. PSSI cold split injection (initial temp 50° C. heated to 385° C.), volume 1.0 μl Detector FID: 395° C.

| | Oven program: | | |
| --- | --- | --- | --- |
| | 1 | 2 | 3 |
| Oven temperature, ° C. | 90 | 280 | 350 |
| Isothermal, time, min. | 1 | 0 | 10 |
| Temperature rate, ° C./min. | 15 | 4 | |

Sample preparation: 30 mg of sample was dissolved in 9 ml Heptane:Pyridin, 2:1 containing internal standard heptadecane, 0.5 mg/ml. 300 μl sample solution was transferred to a crimp vial, 300 μl MSTFA (N-Methyl-N-trimethylsilyl-trifluoraceamid) was added and reacted for 20 minutes at 60° C.

Calculation: Response factors for mono-di-triglycerides and free fatty acid were determined from Standard 2 (mono-di-triglyceride), for Cholesterol, Cholesteryl palmitate and Cholesteryl stearate the response factors were determined from pure reference material (weighing for pure material 10 mg).

For some aspects, preferably the variant lipid acyltransferase according to the present invention is incapable, or substantially incapable, of acting on a triglyceride and/or a 1-monoglyceride and/or 2-monoglyceride.

Suitably, the lipid substrate or lipid acyl donor may be one or more lipids present in one or more of the following substrates: fats, including lard, tallow and butter fat; oils including oils extracted from or derived from palm oil, sunflower oil, soya bean oil, safflower oil, cotton seed oil, ground nut oil, corn oil, olive oil, peanut oil, coconut oil, and rape seed oil. Lecithin from soya, rape seed or egg yolk is also a suitable lipid substrate. The lipid substrate may be an oat lipid or other plant based material containing galactolipids.

In one aspect the lipid acyl donor is preferably lecithin (such as phosphatidylcholine) in egg yolk.

For some aspects of the present invention, the lipid may be selected from lipids having a fatty acid chain length of from 8 to 22 carbons.

For some aspects of the present invention, the lipid may be selected from lipids having a fatty acid chain length of from 16 to 22 carbons, more preferably of from 16 to 20 carbons.

For some aspects of the present invention, the lipid may be selected from lipids having a fatty acid chain length of no greater than 14 carbons, suitably from lipids having a fatty acid chain length of from 4 to 14 carbons, suitably 4 to 10 carbons, suitably 4 to 8 carbons.

Suitably, the variant lipid acyltransferase according to the present invention may exhibit one or more of the following lipase activities: glycolipase activity (E.C. 3.1.1.26), triacylglycerol lipase activity (E.C. 3.1.1.3), phospholipase A2 activity (E.C. 3.1.1.4) or phospholipase A1 activity (E.C. 3.1.1.32). The term "glycolipase activity" as used herein encompasses "galactolipase activity".

Suitably, the variant lipid acyltransferase according to the present invention may have at least one or more of the following activities: glycolipase activity (E.C. 3.1.1.26) and/or phospholipase A1 activity (E.C. 3.1.1.32) and/or phospholipase A2 activity (E.C. 3.1.1.4).

For some aspects, the variant lipid acyltransferase according to the present invention may have at least glycolipase activity (E.C. 3.1.1.26).

Suitably, for some aspects the variant lipid acyltransferase according to the present invention may be capable of transferring an acyl group from a glycolipid and/or a phospholipid to one or more of the following acceptor substrates: a sterol, a stanol, a carbohydrate, a protein, glycerol.

For some aspects, preferably the variant lipid acyltransferase according to the present invention is capable of transferring an acyl group from a glycolipid and/or a phospholipid to a sterol and/or a stanol to form at least a sterol ester and/or a stanol ester.

For some aspects, preferably the variant lipid acyltransferase according to the present invention is capable of transferring an acyl group from a glycolipid and/or a phospholipid to a carbohydrate to form at least a carbohydrate ester.

For some aspects, preferably the variant lipid acyltransferase according to the present invention is capable of transferring an acyl group from a glycolipid and/or a phospholipid to a protein to form at least protein ester (or a protein fatty acid condensate).

For some aspects, preferably the variant lipid acyltransferase according to the present invention is capable of transferring an acyl group from a glycolipid and/or a phospholipid to glycerol to form at least a diglyceride and/or a monoglyceride.

For some aspects, preferably the variant lipid acyltransferase according to the present invention does not exhibit triacylglycerol lipase activity (E.C. 3.1.1.3).

In some aspects, the variant lipid acyltransferase may be capable of transferring an acyl group from a lipid to a sterol and/or a stanol. Thus, in one embodiment the "acyl acceptor" according to the present invention may be either a sterol or a stanol or a combination of both a sterol and a stanol.

In one embodiment suitably the sterol and/or stanol may comprise one or more of the following structural features:
a 3-beta hydroxy group or a 3-alpha hydroxy group; and/or
A:B rings in the cis position or A:B rings in the trans position or $C_5$-$C_6$ is unsaturated.

Suitable sterol acyl acceptors include cholesterol and phytosterols, for example alpha-sitosterol, beta-sitosterol, stigmasterol, ergosterol, campesterol, 5,6-dihydrosterol, brassicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, and other natural or synthetic isomeric forms and derivatives.

In one aspect of the present invention suitably more than one sterol and/or stanol may act as the acyl acceptor, suitably more than two sterols and/or stanols may act as the acyl acceptor. In other words, in one aspect of the present invention, suitably more than one sterol ester and/or stanol ester may be produced. Suitably, when cholesterol is the acyl acceptor one or more further sterols or one or more stanols may also act as the acyl acceptor. Thus, in one aspect, the present invention provides a method for the in situ production of both a cholesterol ester and at least one sterol or stanol ester in combination. In other words, the lipid acyltransferase for some aspects of the present invention may transfer an acyl group from a lipid to both cholesterol and at least one further sterol and/or at least one stanol.

In one aspect, preferably the sterol acyl acceptor is one or more of the following: alpha-sitosterol, beta-sitosterol, stigmasterol, ergosterol and campesterol.

In one aspect, preferably the sterol acyl acceptor is cholesterol. When it is the case that cholesterol is the acyl acceptor for the variant lipid acyltransferase, the amount of free cholesterol in the foodstuff is reduced as compared with the foodstuff prior to exposure to the variant lipid acyltransferase and/or as compared with an equivalent foodstuff which has not been treated with the variant lipid acyltransferase.

Suitable stanol acyl acceptors include phytostanols, for example beta-sitostanol or ss-sitostanol.

In one aspect, preferably the sterol and/or stanol acyl acceptor is a sterol and/or a stanol other than cholesterol.

In some aspects, the foodstuff prepared in accordance with the present invention may be used to reduce blood serum cholesterol and/or to reduce low density lipoprotein. Blood serum cholesterol and low density lipoproteins have both been associated with certain diseases in humans, such as atherosclerosis and/or heart disease for example. Thus, it is envisaged that the foodstuffs prepared in accordance with the present invention may be used to reduce the risk of such diseases.

Thus, in one aspect the present invention provides the use of a foodstuff according to the present invention for use in the treatment and/or prevention of atherosclerosis and/or heart disease.

In a further aspect, the present invention provides a medicament comprising a foodstuff according to the present invention.

In a further aspect, the present invention provides a method of treating and/or preventing a disease in a human or animal patient which method comprising administering to the patient an effective amount of a foodstuff according to the present invention.

Suitably, the sterol and/or the stanol "acyl acceptor" may be found naturally within the foodstuff. Alternatively, the sterol and/or the stanol may be added to the foodstuff. When it is the case that a sterol and/or a stanol is added to the foodstuff, the sterol and/or stanol may be added before, simultaneously with, and/or after the addition of the lipid acyltransferase according to the present invention. Suitably, the present invention may encompass the addition of exogenous sterols/stanols, particularly phytosterols/phytostanols, to the foodstuff prior to or simultaneously with the addition of the variant enzyme according to the present invention.

For some aspects, one or more sterols present in the foodstuff may be converted to one or more stanols prior to or at the same time as the variant lipid acyltransferase is added according to the present invention. Any suitable method for converting sterols to stanols may be employed. For example, the conversion may be carried out by chemical hydrogenation for example. The conversion may be conducted prior to the addition of the variant lipid acyltransferase in accordance with the present invention or simultaneously with the addition of the variant lipid acyltransferase in accordance with the present invention. Suitably enzymes for the conversion of sterol to stanols are taught in WO00/061771.

Suitably the present invention may be employed to produce phytostanol esters in situ in a foodstuff. Phytostanol esters have increased solubility through lipid membranes, bioavailability and enhanced health benefits (see for example WO92/99640).

In some embodiments of the present invention the stanol ester and/or the sterol ester may be a flavouring and/or a texturiser. In which instances, the present invention encompasses the in situ production of flavourings and/or texturisers.

For some aspects of the present invention, the variant lipid acyltransferase according to the present invention may utilise a carbohydrate as the acyl acceptor. The carbohydrate acyl acceptor may be one or more of the following: a monosaccharide, a disaccharide, an oligosaccharide or a polysaccharide. Preferably, the carbohydrate is one or more of the following: glucose, fructose, anhydrofructose, maltose, lactose, sucrose, galactose, xylose, xylooligosacharides, arabinose, maltooligosaccharides, tagatose, microthecin, ascopyrone P, ascopyrone T, cortalcerone.

Suitably, the carbohydrate "acyl acceptor" may be found naturally within the foodstuff. Alternatively, the carbohydrate may be added to the foodstuff. When it is the case that the carbohydrate is added to the foodstuff, the carbohydrate may be added before, simultaneously with, and/or after the addition of the variant lipid acyltransferase according to the present invention.

Carbohydrate esters can function as valuable emulsifiers in foodstuffs. Thus, when it is the case that the enzyme functions to transfer the acyl group to a sugar, the invention encompasses the production of a second in situ emulsifier in the foodstuff.

In some embodiments, the variant lipid acyltransferase may utilise both a sterol and/or stanol and a carbohydrate as an acyl acceptor.

The utilisation of a variant lipid acyltransferase which can transfer the acyl group to a carbohydrate as well as to a sterol and/or a stanol is particularly advantageous for foodstuffs comprising eggs. In particular, the presence of sugars, in particular glucose, in eggs and egg products is often seen as disadvantageous. Egg yolk may comprise up to 1% glucose. Typically, egg or egg based products may be treated with glucose oxidase to remove some or all of this glucose. However, in accordance with the present invention this unwanted sugar can be readily removed by "esterifying" the sugar to form a sugar ester.

For some aspects of the present invention, the variant lipid acyltransferase according to the present invention may utilise a protein as the acyl acceptor. Suitably, the protein may be one or more of the proteins found in a food product, for example in a dairy product and/or a meat product. By way of example only, suitable proteins may be those found in curd or whey, such as lactoglobulin. Other suitable proteins include ovalbumin from egg, gliadin, glutenin, puroindoline, lipid transfer proteins from grains, and myosin from meat.

Preferably, the lipid acyltransferase enzyme may be characterised using the following criteria:
the enzyme possesses acyl transferase activity which may be defined as ester transfer activity whereby the acyl part of an original ester bond of a lipid acyl donor is transferred to an acyl acceptor, preferably glycerol or cholesterol, to form a new ester; and
the enzyme comprises the amino acid sequence motif GDSX, wherein X is one or more of the following amino acid residues L, A, V, I, F, Y, H, Q, T, N, M or S.

Preferably, X of the GDSX motif is L or Y. More preferably, X of the GDSX motif is L. Thus, preferably the enzyme according to the present invention comprises the amino acid sequence motif GDSL (SEQ ID NO: 43).

The GDSX motif is comprised of four conserved amino acids. Preferably, the serine within the motif is a catalytic serine of the lipid acyl transferase enzyme. Suitably, the serine of the GDSX motif may be in a position corresponding to Ser-16 in *Aeromonas hydrophila* lipid acyltransferase enzyme taught in Brumlik & Buckley (Journal of Bacteriology April 1996, Vol. 178, No. 7, p 2060-2064).

To determine if a protein has the GDSX motif according to the present invention, the sequence is preferably compared with the hidden markov model profiles (HMM profiles) of the pfam database in accordance with the procedures taught in WO2004/064537 or WO2004/064987, incorporated herein by reference.

Preferably the lipid acyl transferase enzyme can be aligned using the Pfam00657 consensus sequence (for a full explanation see WO2004/064537 or WO2004/064987).

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft DH (2002) Brief Bioinform 3; 236-245.

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located at websites maintained by the Sanger Institute (UK) in conjunction with Wellcome Trust Institute, the Institut National de la Recherche Agronomique, and the Center for Genomics and Bioinformatics of the Karolinska Institutet, among others.

The database offers a search facility where one can enter a protein sequence. Using the default parameters of the database the protein sequence will then be analysed for the presence of Pfam domains. The GDSX domain is an established domain in the database and as such its presence in any query sequence will be recognised. The database will return the alignment of the Pfam00657 consensus sequence to the query sequence.

A multiple alignment, including *Aeromonas salmonicida* or *Aeromonas hydrophila* can be obtained by:
a) manual
obtain an alignment of the protein of interest with the Pfam00657 consensus sequence and obtain an alignment of P10480 with the Pfam00657 consensus sequence following the procedure described above;
or
b) through the database
After identification of the Pfam00657 consensus sequence the database offers the option to show an alignment of the query sequence to the seed alignment of the Pfam00657 consensus sequence. P10480 is part of this seed alignment and is indicated by GCAT_AERHY. Both the query sequence and P10480 will be displayed in the same window.

The *Aeromonas hydrophila* reference sequence:
The residues of *Aeromonas hydrophila* GDSX lipase are numbered in the NCBI file P10480, the numbers in this text refer to the numbers given in that file which in the present invention is used to determine specific amino acids residues which, in a preferred embodiment are present in the lipid acyltransferase enzymes of the invention.

The Pfam alignment was performed (FIG. 31 and FIG. 34):
The following conserved residues can be recognised and in a preferable embodiment may be present in the variant enzymes for use in the compositions and methods of the invention;

```
Block 1 - GDSX block
hid hid hid hid Gly Asp Ser hid
 28  29  30  31  32  33  34  35
```

```
Block 2 - GANDY block
hid Gly hid Asn Asp hid
130 131 132 133 134 135

Block 3 - HPT block
His
309
```

Where 'hid' means a hydrophobic residue selected from Met, Ile, Leu, Val, Ala, Gly, Cys, His, Lys, Trp, Tyr, Phe.

Preferably the parent and/or variant lipid acyltransferase enzyme for use in the compositions/methods of the invention can be aligned using the Pfam00657 consensus sequence.

Preferably, a positive match with the hidden markov model profile (HMM profile) of the pfam00657 domain family indicates the presence of the GDSL (SEQ ID NO: 43) or GDSX domain according to the present invention.

Preferably when aligned with the Pfam00657 consensus sequence the lipid acyltransferase for use in the methods or uses of the invention may have at least one, preferably more than one, preferably more than two, of the following, a GDSx block, a GANDY (SEQ ID NO: 45) block, a HPT block. Suitably, the lipid acyltransferase may have a GDSx block and a GANDY (SEQ ID NO: 45) block. Alternatively, the enzyme may have a GDSx block and a HPT block. Preferably the enzyme comprises at least a GDSx block. See WO2004/064537 or WO2004/064987 for further details.

Preferably, residues of the GANDY (SEQ ID NO: 45) motif are selected from GANDY (SEQ ID NO: 45), GGNDA (SEQ ID NO: 76), GGNDL (SEQ ID NO: 77), most preferably GANDY (SEQ ID NO: 45).

Preferably, when aligned with the Pfam00657 consensus sequence the enzyme for use in the methods or uses of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 1: 28hid, 29hid, 30hid, 31hid, 32gly, 33Asp, 34Ser, 35hid, 130hid, 131Gly, 132Hid, 133Asn, 134Asp, 135hid, 309His.

The pfam00657 GDSX domain is a unique identifier which distinguishes proteins possessing this domain from other enzymes.

The pfam00657 consensus sequence is presented in FIG. 3 as SEQ ID No. 2. This is derived from the identification of the pfam family 00657, database version 6, which may also be referred to as pfam00657.6 herein.

The consensus sequence may be updated by using further releases of the pfam database (for example see WO2004/064537 or WO2004/064987).

In one embodiment, the nucleotide sequence encoding a lipid acyl transferase enzyme for use in any one of the host cells, vectors, methods and/or uses of the present invention encodes a lipid acyltransferase that may be characterised using the following criteria:
  (i) the enzyme possesses acyl transferase activity which may be defined as ester transfer activity whereby the acyl part of an original ester bond of a lipid acyl donor is transferred to acyl acceptor, preferably glycerol or cholesterol, to form a new ester, preferably monoglyceride or cholesterol ester respectfully;

(ii) the enzyme comprises the amino acid sequence motif GDSX, wherein X is one or more of the following amino acid residues L, A, V, I, F, Y, H, Q, T, N, M or S.;
  (iii) the enzyme comprises His-309 or comprises a histidine residue at a position corresponding to His-309 in the *Aeromonas hydrophila* lipid acyltransferase enzyme shown in FIGS. 2 and 4 (SEQ ID No. 1 or SEQ ID No. 3).

Preferably, the amino acid residue of the GDSX motif is L.

In SEQ ID No. 3 or SEQ ID No. 1 the first 18 amino acid residues form a signal sequence. His-309 of the full length sequence, that is the protein including the signal sequence, equates to His-291 of the mature part of the protein, i.e. the sequence without the signal sequence.

In one embodiment, the nucleotide sequence encoding a lipid acyl transferase enzyme for use any one of the host cells, vectors, methods and uses of the present invention encodes a lipid acyltransferase that comprises the following catalytic triad: Ser-34, Asp-306 and His-309 or comprises a serine residue, an aspartic acid residue and a histidine residue, respectively, at positions corresponding to Ser-34, Asp-306 and His-309 in the *Aeromonas hydrophila* lipid acyl transferase enzyme shown in FIG. 4 (SEQ ID No. 3) or FIG. 2 (SEQ ID No. 1). As stated above, in the sequence shown in SEQ ID No. 3 or SEQ ID No. 1 the first 18 amino acid residues form a signal sequence. Ser-34, Asp-306 and His-309 of the full length sequence, that is the protein including the signal sequence, equate to Ser-16, Asp-288 and His-291 of the mature part of the protein, i.e. the sequence without the signal sequence. In the pfam00657 consensus sequence, as given in FIG. 3 (SEQ ID No. 2) the active site residues correspond to Ser-7, Asp-345 and His-348.

In one embodiment, the nucleotide sequence encoding a lipid acyltransferase enzyme for use any one of the host cells, vectors, methods and uses of the present invention encodes a lipid acyltransferase that may be characterised using the following criteria:
  the enzyme possesses acyl transferase activity which may be defined as ester transfer activity whereby the acyl part of an original ester bond of a first lipid acyl donor is transferred to an acyl acceptor to form a new ester; and
  the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-306 and His-309, respectively, in the *Aeromonas hydrophila* lipid acyltransferase enzyme shown in SEQ ID No. 3 or SEQ ID No. 1.

Suitably, the nucleotide sequence encoding a lipid acyltransferase enzyme for use in any one of the host cells, vectors, methods and uses of the present invention may be one of the following nucleotide sequences:
  (a) the nucleotide sequence shown as SEQ ID No. 36 (see FIG. 29);
  (b) the nucleotide sequence shown as SEQ ID No. 27 (see FIG. 20);
  (c) the nucleotide sequence shown as SEQ ID No. 39 (see FIG. 32);
  (d) the nucleotide sequence shown as SEQ ID No. 42 (see FIG. 35);
  (e) the nucleotide sequence shown as SEQ ID No. 44 (see FIG. 37);
  (f) the nucleotide sequence shown as SEQ ID No. 46 (see FIG. 39);
  (g) the nucleotide sequence shown as SEQ ID No. 48 (see FIG. 41);
  (h) the nucleotide sequence shown as SEQ ID No. 49 (see FIG. 57);

(i) the nucleotide sequence shown as SEQ ID No. 50 (see FIG. 58);

(j) the nucleotide sequence shown as SEQ ID No. 51 (see FIG. 59);

(k) the nucleotide sequence shown as SEQ ID No. 52 (see FIG. 60);

(l) the nucleotide sequence shown as SEQ ID No. 53 (see FIG. 61);

(m) the nucleotide sequence shown as SEQ ID No. 54 (see FIG. 62);

(n) the nucleotide sequence shown as SEQ ID No. 55 (see FIG. 63);

(o) the nucleotide sequence shown as SEQ ID No. 56 (see FIG. 64);

(p) the nucleotide sequence shown as SEQ ID No. 57 (see FIG. 65);

(q) the nucleotide sequence shown as SEQ ID No. 58 (see FIG. 66);

(r) the nucleotide sequence shown as SEQ ID No. 59 (see FIG. 67);

(s) the nucleotide sequence shown as SEQ ID No. 60 (see FIG. 68);

(t) the nucleotide sequence shown as SEQ ID No. 61 (see FIG. 69);

(u) the nucleotide sequence shown as SEQ ID No. 62 (see FIG. 70);

(v) the nucleotide sequence shown as SEQ ID No. 63 (see FIG. 71); or (w) the nucleotide sequence shown as SEQ ID No. 24 (see FIG. 72).

a nucleotide sequence which has 70% or more, preferably 75% or more, identity with any one of the sequences shown as SEQ ID No. 24, SEQ ID No. 36, SEQ ID No. 27, SEQ ID No. 39, SEQ ID No. 42, SEQ ID No. 44, SEQ ID No. 46, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62 or SEQ ID No. 63.

Suitably the nucleotide sequence may have 80% or more, preferably 85% or more, more preferably 90% or more and even more preferably 95% or more identity with any one of the sequences shown as SEQ ID No. 24, SEQ ID No. 36, SEQ ID No. 27, SEQ ID No. 39, SEQ ID No. 42, SEQ ID No. 44, SEQ ID No. 46, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62 or SEQ ID No. 63.

In one embodiment, the nucleotide sequence encoding a lipid acyltransferase enzyme for use any one of the host cells, vectors, methods and uses of the present invention is a nucleotide sequence which has 70% or more, preferably 75% or more, identity with any one of the sequences shown as: SEQ ID No. 49, SEQ ID No. 50, SEQ ID 20 No. 51, SEQ ID No. 62, and SEQ ID No. 63. Suitably the nucleotide sequence may have 80% or more, preferably 85% or more, more preferably 90% or more and even more preferably 95% or more identity with any one of the sequences shown as: SEQ ID No. 49, SEQ ID No. 50, SEQ ID No. 51, SEQ ID No. 62, and SEQ ID No. 63.

In one embodiment, the nucleotide sequence encoding a lipid acyltransferase enzyme for use in any one of the host cells, vectors, methods and uses of the present invention is a nucleotide sequence which has 70% or more, 75% or more, 80% or more, preferably 85% or more, more preferably 90% or more and even more preferably 95% or more identity the sequence shown as SEQ ID No. 49.

Suitably, the nucleotide sequence encoding a lipid acyl transferase enzyme for use any one of the host cells, vectors, methods and uses of the present invention may encode a lipid acyltransferase that comprises one or more of the following amino acid sequences:

(i) the amino acid sequence shown as SEQ ID No. 3
(ii) the amino acid sequence shown as SEQ ID No. 4
(iii) the amino acid sequence shown as SEQ ID No. 5
(iv) the amino acid sequence shown as SEQ ID No. 6
(v) the amino acid sequence shown as SEQ ID No. 7
(vi) the amino acid sequence shown as SEQ ID No. 8
(vii) the amino acid sequence shown as SEQ ID No. 19
(viii) the amino acid sequence shown as SEQ ID No. 10
(ix) the amino acid sequence shown as SEQ ID No. 11
(x) the amino acid sequence shown as SEQ ID No. 12
(xi) the amino acid sequence shown as SEQ ID No. 13
(xii) the amino acid sequence shown as SEQ ID No. 14
(xiii) the amino acid sequence shown as SEQ ID No. 1
(xiv) the amino acid sequence shown as SEQ ID No. 15 or
an amino acid sequence which has 75%, 80%, 85%, 90%, 95%, 98% or more identity with any one of the sequences shown as SEQ ID No. 1, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, or SEQ ID No. 15.

Suitably, nucleotide sequence encoding a lipid acyl transferase enzyme for use any one of the host cells, vectors, methods and uses of the present invention may encode a lipid acyltransferase that comprises either the amino acid sequence shown as SEQ ID No. 3 or as SEQ ID No. 4 or SEQ ID No. 1 or SEQ ID No. 15 or comprises an amino acid sequence which has 75% or more, preferably 80% or more, preferably 85% or more, preferably 90% or more, preferably 95% or more, identity with the amino acid sequence shown as SEQ ID No. 3 or the amino acid sequence shown as SEQ ID No. 4 or the amino acid sequence shown as SEQ ID No. 1 or the amino acid sequence shown as SEQ ID No. 15.

Suitably the nucleotide sequence encoding a lipid acyl transferase enzyme for use any one of the host cells, vectors, methods and uses of the present invention may encode a lipid acyltransferase that comprises an amino acid sequence which has 80% or more, preferably 85% or more, more preferably 90% or more and even more preferably 95% or more identity with any one of the sequences shown as SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, or SEQ ID No. 15.

Suitably, the nucleotide sequence encoding a lipid acyl transferase enzyme for use any one of the host cells, vectors, methods and uses of the present invention may encode a lipid acyltransferase that comprises one or more of the following amino acid sequences:

(a) an amino acid sequence shown as amino acid residues 1-100 of SEQ ID No. 3 or SEQ ID No. 1;
(b) an amino acid sequence shown as amino acids residues 101-200 of SEQ ID No. 3 or SEQ ID No. 1;
(c) an amino acid sequence shown as amino acid residues 201-300 of SEQ ID No. 3 or SEQ ID No. 1; or
(d) an amino acid sequence which has 75% or more, preferably 85% or more, more preferably 90% or more, even more preferably 95% or more identity to any one of the amino acid sequences defined in (a)-(c) above.

Suitably, lipid acyl transferase enzyme for use in methods and uses of the present invention may comprise one or more of the following amino acid sequences:
(a) an amino acid sequence shown as amino acid residues 28-39 of SEQ ID No. 3 or SEQ ID No. 1;
(b) an amino acid sequence shown as amino acids residues 77-88 of SEQ ID No. 3 or SEQ ID No. 1;
(c) an amino acid sequence shown as amino acid residues 126-136 of SEQ ID No. 3 or SEQ ID No. 1;
(d) an amino acid sequence shown as amino acid residues 163-175 of SEQ ID No. 3 or SEQ ID No. 1;
(e) an amino acid sequence shown as amino acid residues 304-311 of SEQ ID No. 3 or SEQ ID No. 1; or
(f) an amino acid sequence which has 75% or more, preferably 85% or more, more preferably 90% or more, even more preferably 95% or more identity to any one of the amino acid sequences defined in (a)-(e) above.

In one aspect, nucleotide sequence encoding a lipid acyl transferase enzyme for use any one of the host cells, vectors, methods and uses of the present invention encodes a lipid acyltransferase that may be the lipid acyl transferase from *Candida parapsilosis* as taught in EP 1 275 711. Thus in one aspect the lipid acyl transferase for use in the method and uses of the present invention may be a lipid acyl transferase comprising one of the amino acid sequences taught in SEQ ID No. 17 or SEQ ID No. 18.

Much by preference, the nucleotide sequence encoding a lipid acyl transferase enzyme for use in any one of the host cells, vectors, methods and uses of the present invention encodes a lipid acyltransferase that may be a lipid acyl transferase (lipid acyltransferase) comprising the amino acid sequence shown as SEQ ID No. 16 or SEQ ID No. 70, or an amino acid sequence which has 75% or more, preferably 85% or more, more preferably 90% or more, even more preferably 95% or more, even more preferably 98% or more, or even more preferably 99% or more identity to SEQ ID No. 16 or SEQ ID No. 70. This enzyme could be considered a variant enzyme.

In one aspect, the nucleotide sequence encoding a lipid acyltransferase enzyme for use any one of the host cells, vectors, methods and uses of the present invention encodes a lipid acyltransferase that may be a lecithin:cholesterol acyltransferase (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the nucleotide sequence encoding a lipid acyltransferase enzyme for use any one of the host cells, vectors, methods and uses of the present invention encodes a lipid acyltransferase that may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NCIMB 41204 and NCIMB 41205, respectively.

A nucleotide sequence encoding a lipid acyltransferase enzyme for use any one of the host cells, vectors, methods and uses of the present invention may encode a phospholipid glycerol acyl transferase. Phospholipid glycerol acyl transferases include those isolated from *Aeromonas* spp., preferably *Aeromonas hydrophila* or *A. salmonicida*, most preferable *A. salmonicida* or variants thereof. Most preferred lipid acyl transferases for use in the present invention are encoded by SEQ ID No.s 1, 3, 4, and 16. It will be recognised by the skilled person that it is preferable that the signal peptides of the acyl transferase has been cleaved during expression of the transferase. The signal peptide of SEQ ID 1, 3, 4, and 15 are amino acids 1-18. Therefore the most preferred regions are amino acids 19-335 for SEQ ID No. 1 and SEQ ID No. 3 (*A. hydrophila*) and amino acids 19-336 for SEQ ID No. 4 and SEQ ID No. 15. (*A. salmonicida*). When used to determine the homology of identity of the amino acid sequences, it is preferred that the alignments as herein described use the mature sequence.

Therefore the most preferred regions for determining homology (identity) are amino acids 19-335 for SEQ ID No. 1 and 3 (*A. hydrophilia*) and amino acids 19-336 for SEQ ID No.s 4 and 15 (*A. salmonicida*). SEQ ID 34 and 35 are mature protein sequences of a lipid acyl transferase from *A. hydrophilia* and *A. salmonicida* respectively.

A nucleotide sequence encoding a lipid acyltransferase enzyme for use any one of the host cells, vectors, methods and uses of the present invention encodes a lipid acyltransferase that may also be isolated from *Thermobifida*, preferably *T. fusca*, most preferably that encoded by SEQ ID No. 28.

A nucleotide sequence encoding a lipid acyltransferase enzyme for use any one of the host cells, vectors, methods and uses of the present invention encodes a lipid acyltransferase that may also be isolated from *Streptomyces*, preferable *S. avermitis*, most preferably that encoded by SEQ ID No. 32. Other possible enzymes for use in the present invention from *Streptomyces* include those encoded by SEQ ID No.s 5, 6, 19, 10, 11, 12, 13, 14, 31, and 26.

An enzyme for use in the invention may also be isolated from *Corynebacterium*, preferably *C. efficiens*, most preferably that encoded by SEQ ID No. 29.

Suitably, the nucleotide sequence encoding a lipid acyltransferase enzyme for use any one of the host cells, vectors, methods and uses of the present invention may encode a lipid acyltransferase that comprises any one of the amino acid sequences shown as SEQ ID No.s 26, 27, 40, 29, 31, 32, or 28 or an amino acid sequence which has at least 70%, 75%, 80%, 85%, 90%, 95%, 96%, 97% or 98% identity therewith, or encoded by any one of the nucleotide sequences shown as SEQ ID No.s 36, 39, 42, 44, 46, or 48 or a nucleotide sequence which has at least 70%, 75%, 80%, 85%, 90%, 95%, 96%, 97% or 98% identity therewith.

In one embodiment, the nucleic sequence encoding a lipid acyltransferase enzyme for use any one of the host cells, vectors, methods and uses of the present invention is selected from the group consisting of:
a) a nucleic acid comprising a nucleotide sequence shown in SEQ ID No. 36;
b) a nucleic acid which is related to the nucleotide sequence of SEQ ID No. 36 by the degeneration of the genetic code; and
c) a nucleic acid comprising a nucleotide sequence which has at least 70% identity with the nucleotide sequence shown in SEQ ID No. 36.

In one embodiment, a nucleotide sequence encoding a lipid acyltransferase enzyme for use any one of the host cells, vectors, methods and uses of the present invention encodes a lipid acyltransferase that comprises an amino acid sequence as shown in SEQ ID No. 26 or an amino acid sequence which has at least 60% identity thereto.

In a further embodiment the nucleotide sequence encoding a lipid acyltransferase enzyme for use any one of the host cells, vectors, methods and uses of the present invention may encode a lipid acyltransferase comprising any one of the amino acid sequences shown as SEQ ID No. 26, 27, 40, 29, 31, 32 or 28 or an amino acid sequence which has at least 70%, 75%, 80%, 85%, 90%, 95%, 96%, 97% or 98% identity therewith, or encoded by any one of the nucleotide sequences shown as SEQ ID No. 39, 42, 44, 46 or 48 or a nucleotide sequence which has at least 70%, 75%, 80%, 85%, 90%, 95%, 96%, 97% or 98% identity therewith.

In a further embodiment the nucleotide sequence encoding a lipid acyltransferase enzyme for use any one of the host cells, vectors, methods and uses of the present invention may encode a lipid acyltransferase comprising any one of amino sequences shown as SEQ ID No. 27, 40, 29, 32 or 28 or an amino acid sequence which has at least 70%, 75%, 80%, 85%, 90%, 95%, 96%, 97% or 98% identity therewith for the uses described herein.

In a further embodiment the nucleotide sequence encoding a lipid acyltransferase for use in any one of the host cells, vectors, methods and uses of the present invention may encode a lipid acyltransferase comprising any one of amino sequences shown as SEQ ID No. 27, 40, or 28 or an amino acid sequence which has at least 70%, 75%, 80%, 85%, 90%, 95%, 96%, 97% or 98% identity therewith for the uses described herein.

More preferably in one embodiment the nucleotide sequence encoding a lipid acyltransferase for use in any one of the host cells, vectors, methods and uses of the present invention may encode a lipid acyltransferase comprising the amino acid sequence shown as SEQ ID No. 28 or an amino acid sequence which has at least 70%, 75%, 80%, 85%, 90%, 95%, 96%, 97% or 98% identity therewith.

In another embodiment the nucleotide sequence encoding a lipid acyltransferase for use in any one of the host cells, vectors, methods and uses of the present invention may encode a lipid acyltransferase comprising the amino acid sequence shown as SEQ ID No. 31 or 44 or an amino acid sequence which has at least 80%, 85%, 90%, 95%, 96%, 97% or 98% identity therewith.

In another embodiment the nucleotide sequence encoding a lipid acyltransferase for use in any one of the host cells, vectors, methods and uses of the present invention may encode a lipid acyltransferase comprising the amino acid sequence shown as SEQ ID No. 29 or an amino acid sequence which has at least 70%, 75%, 80%, 85%, 90%, 95%, 96%, 97% or 98% identity therewith.

In one embodiment the nucleotide sequence encoding a lipid acyltransferase for use in any one of the host cells, vectors, methods and uses of the present invention is selected from the group consisting of:
  a) a nucleic acid comprising a nucleotide sequence shown in SEQ ID No. 36;
  b) a nucleic acid which is related to the nucleotide sequence of SEQ ID No. 36 by the degeneration of the genetic code; and
  c) a nucleic acid comprising a nucleotide sequence which has at least 70% identity with the nucleotide sequence shown in SEQ ID No. 36.

In one embodiment the lipid acyltransferase according to the present invention may be a lipid acyltransferase obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable nucleotide sequences encoding a lipid acyltransferase for use in any one of the host cells, vectors, methods and uses of the present invention may encode a polynucleotide encoding a lipid acyltransferase (SEQ ID No. 16 or SEQ ID No. 70); or may encode an amino acid sequence of a lipid acyltransferase (SEQ ID No. 17).

A suitable nucleotide sequence encoding a lipid acyltransferase for use in any one of the host cells, vectors, methods and uses of the present invention may encode an amino acid sequence which may be identified by alignment to the L131 (SEQ ID No. 26) sequence using Align X, the Clustal W pairwise alignment algorithm of VectorNTI using default settings.

An alignment of the L131 and homologues from *S. avermitilis* and *T. fusca* illustrates that the conservation of the GDSx motif (GDSY (SEQ ID NO: 78) in L131 and *S. avermitilis* and *T. fusca*), the GANDY (SEQ ID NO: 45) box, which is either GGNDA (SEQ ID NO: 76) or GGNDL (SEQ ID NO: 77), and the HPT block (considered to be the conserved catalytic histidine). These three conserved blocks are highlighted in FIG. 42.

When aligned to either the pfam Pfam00657 consensus sequence (as described in WO04/064987) and/or the L131 sequence herein disclosed (SEQ ID No 26) it is possible to identify three conserved regions, the GDSx block, the GANDY (SEQ ID NO: 45) block and the HTP block (see WO04/064987 for further details).

When aligned to either the pfam Pfam00657 consensus sequence (as described in WO04/064987) and/ or the L131 sequence herein disclosed (SEQ ID No 26)
  i) The nucleotide sequence encoding a lipid acyltransferase for use in any one of the host cells, vectors, methods and uses of the present invention may encode a lipid acyltransferase that, has a GDSx motif, more preferably a GDSx motif selected from GDSL (SEQ ID NO: 43) or GDSY (SEQ ID NO: 78) motif.
  and/or
  ii) The nucleotide sequence encoding a lipid acyltransferase for use in any one of the host cells, vectors, methods and uses of the present invention may encode a lipid acyltransferase that, has a GANDY (SEQ ID NO: 45) block, more preferably a GANDY (SEQ ID NO: 45) block comprising amino GGNDx (SEQ ID NO: 79), more preferably GGNDA (SEQ ID NO: 76) or GGNDL (SEQ ID NO: 77).
  and/or
  iii) The nucleotide sequence encoding a lipid acyltransferase for use in any one of the host cells, vectors, methods and uses of the present invention encodes a lipid acyltransferase that has preferably an HTP block.
  and preferably
  iv) nucleotide sequence encoding a lipid acyltransferase for use in any one of the host cells, vectors, methods and uses of the present invention may encode a lipid acyltransferase that has preferably a GDSx or GDSY (SEQ ID NO: 78) motif, and a GANDY (SEQ ID NO: 45) block comprising amino GGNDx (SEQ ID NO: 79), preferably GGNDA (SEQ ID NO: 76) or GGNDL (SEQ ID NO: 77), and a HTP block (conserved histidine).

Variant lipid acyl transferase

In a preferred embodiment the nucleotide sequence encoding a lipid acyltransferase for use in any one of the host cells, vectors, methods and uses of the present invention may encode a lipid acyltransferase that is a variant lipid acyl transferase. Variants which have an increased activity on phospholipids, such as increased hydrolytic activity and/or increased transferase activity, preferably increased transferase activity on phospholipids may be used.

Preferably the variant lipid acyltransferase is prepared by one or more amino acid modifications of the lipid acyl transferases as defined hereinabove.

Suitably, when the nucleotide sequence encoding a lipid acyltransferase for use in any one of the host cells, vectors, methods and uses of the present invention may encode a lipid acyltransferase that may be a variant lipid acyltransferase, in which case the enzyme may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7 (as defined WO2005/066347 and hereinbelow).

For instance the variant lipid acyltransferase may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues detailed in set 2 or set 4 or set 6 or set 7 (as defined in WO2005/066347 and hereinbelow) identified by said parent sequence being structurally aligned with the structural model of P10480 defined herein, which is preferably obtained by structural alignment of P10480 crystal structure coordinates with 1IVN.PDB and/or 1DEO.PDB as defined WO2005/066347 and hereinbelow.

In a further embodiment a nucleotide sequence encoding a lipid acyltransferase for use in any one of the host cells, vectors, methods and uses of the present invention may encode a variant lipid acyltransferase that may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues taught in set 2 identified when said parent sequence is aligned to the pfam consensus sequence (SEQ ID No. 2-FIG. 3) and modified according to a structural model of P10480 to ensure best fit overlap as defined WO2005/066347 and hereinbelow.

Suitably the nucleotide sequence encoding a lipid acyltransferase for use in any one of the host cells, vectors, methods and uses of the present invention may encode a variant lipid acyltransferase enzyme that may comprise an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 28, SEQ ID No. 29, SEQ ID No. 30, or SEQ ID No. 32, except for one or more amino acid modifications at any one or more of the amino acid residues defined in set 2 or set 4 or set 6 or set 7 (as defined WO2005/066347 and hereinbelow) identified by sequence alignment with SEQ ID No. 2.

Alternatively the nucleotide sequence encoding a lipid acyltransferase may encode a variant lipid acyltransferase enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 28, SEQ ID No. 29, SEQ ID No. 30, or SEQ ID No. 32 except for one or more amino acid modifications at any one or more of the amino acid residues defined in set 2 or set 4 or set 6 or set 7 as defined WO2005/066347 and hereinbelow, identified by said parent sequence being structurally aligned with the structural model of P10480 defined herein, which is preferably obtained by structural alignment of P10480 crystal structure coordinates with 1IVN.PDB and/or 1DEO.PDB as taught within WO2005/066347 and hereinbelow.

Alternatively, the nucleotide sequence encoding a lipid acyltransferase may encode a variant lipid acyltransferase enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 28, SEQ ID No. 29, SEQ ID No. 30, or SEQ ID No. 32, except for one or more amino acid modifications at any one or more of the amino acid residues taught in set 2 identified when said parent sequence is aligned to the pfam consensus sequence (SEQ ID No. 2) and modified according to a structural model of P10480 to ensure best fit overlap as taught within WO2005/066347 and hereinbelow.

Preferably, the parent enzyme is an enzyme which comprises, or is homologous to, the amino acid sequence shown as SEQ ID No. 2 and/or SEQ ID No. 15 and/or SEQ ID No. 35.

Preferably, the nucleotide sequence encoding a lipid acyltransferase may encode a variant enzyme which comprises an amino acid sequence, which amino acid sequence is shown as SEQ ID No. 2 or SEQ ID No. 35 except for one or more amino acid modifications at any one or more of the amino acid residues defined in set 2 or set 4 or set 6 or set 7 as defined in WO2005/066347 and hereinbelow.

Definition of Sets

Sets were determined as described in Example 1, herein, and are summarized here.

Amino acid set 1:

Amino acid set 1 (note that these are amino acids in 1IVN—FIG. 50 and FIG. 51)

Gly8 Asp9 Ser10, Leu11, Ser12, Tyr15, Gly44, Asp45, Thr46, Glu69, Leu70, Gly71, Gly72, Asn73 Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158

The highly conserved motifs, such as GDSx and catalytic residues, were deselected from set 1 (residues underlined). For the avoidance of doubt, set 1 defines the amino acid residues within 10 Å of the central carbon atom of a glycerol in the active site of the 1IVN model.

Amino acid set 2:

Amino acid set 2 (note that the numbering of the amino acids refers to the amino acids in the P10480 mature sequence)

Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

Table of selected residues in Set 1 compared with Set 2:

| IVN model | | | P10480 |
|---|---|---|---|
| | A. hyd homologue | | Mature sequence |
| IVN | PFAM | Structure | Residue Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |
| Pro110 | | 180 to 190 | Pro162 |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino acid set 3:

Amino acid set 3 is identical to set 2 but refers to the *Aeromonas salmonicida* (SEQ ID No. 4) coding sequence, i.e. the amino acid residue numbers are 18 higher in set 3 as this reflects the difference between the amino acid numbering in the mature protein (SEQ ID No. 34) compared with the protein including a signal sequence (SEQ ID No. 1).

The mature proteins of *Aeromonas salmonicida* GDSX (SEQ ID No. 4) and *Aeromonas hydrophila* GDSX (SEQ ID No. 34) differ in five amino acids. These are Thr3Ser, Gln182Lys, Glu309Ala, Ser310Asn, and Gly318-, where the *salmonicida* residue is listed first and the *hydrophila* residue is listed last. The *hydrophila* protein is only 317 amino acids long and lacks a residue in position 318. The *Aeromonas salmonicida* GDSX has considerably high activity on polar lipids such as galactolipid substrates than the *Aeromonas hydrophila* protein. Site scanning was performed on all five amino acid positions.

Amino acid set 4:
Amino acid set 4 is S3, Q182, E309, S310, and −318.

Amino acid set 5:
F13S, D15N, S18G, S18V, Y30F, D116N, D116E, D157N, Y226F, D228N Y230F.

Amino acid set 6:
Amino acid set 6 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, −318.

The numbering of the amino acids in set 6 refers to the amino acids residues in P10480 (SEQ ID No. 25)—corresponding amino acids in other sequence backbones can be determined by homology alignment and/or structural alignment to P10480 and/or 1IVN.

Amino acid set 7:
Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Lys187, Met209, Leu210, Arg211, Asn215, Lys284, Met285, Gln289, Val290, Glu309, Ser310, −318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y).

The numbering of the amino acids in set 7 refers to the amino acids residues in P10480 (SEQ ID No. 25)—corresponding amino acids in other sequence backbones can be determined by homology alignment and/or structural alignment to P10480 and/or 1IVN).

Suitably, the variant enzyme comprises one or more of the following amino acid modifications compared with the parent enzyme:

S3E, A, G, K, M, Y, R, P, N, T or G

E309Q, R or A, preferably Q or R

−318Y, H, S or Y, preferably Y.

Preferably, X of the GDSX motif is L. Thus, preferably the parent enzyme comprises the amino acid motif GDSL (SEQ ID NO: 43).

Suitably, said first parent lipid acyltransferase may comprise any one of the following amino acid sequences: SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 28, SEQ ID No. 29, SEQ ID No. 30, or SEQ ID No. 32.

Suitably, said second related lipid acyltransferase may comprise any one of the following amino acid sequences: SEQ ID No. 3, SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 16, SEQ ID No. 25, SEQ ID No. 26, SEQ ID No. 27, SEQ ID No. 28, SEQ ID No. 29, SEQ ID No. 30, or SEQ ID No. 32.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID No. 2 or SEQ ID No. 35.

In order to align a GDSx polypeptide sequence (parent sequence) with SEQ ID No. 2 (P01480), sequence alignment such as pairwise alignment can be used such as the align program available at web pages maintained by the European Bioinformatics Institute website. Thereby, the equivalent amino acids in alternative parental GDSx polypeptides, which correspond to one or more of the following amino acids (SET 7) of SEQ ID No. 2 can be determined and modified. As the skilled person will readily appreciate, when using the emboss pairwise alignment, standard settings usually suffice. Corresponding residues can be identified using "needle" in order to make an alignment that covers the whole length of both sequences. However, it is also possible to find the best region of similarity between two sequences, using "water".

Alternatively, particularly in instances where parent GDSx polypeptides share low homology with SEQ ID No. 2, the corresponding amino acids in alternative parental GDSx polypeptides which correspond to one or more of the following amino acids (SET 7) of SEQ ID No. 34 can be determined by structural alignment to the structural model of P10480, obtained by the structural alignment of P10480 crystal structure coordinates of 1IVN.PDB and 1DEO.PDB using the 'Deep View Swiss-PDB viewer' (obtained from web pages maintained by Glaxo Wellcome Experimental Research) (FIG. 46 and Example 1). Equivalent residues are identified as those overlapping or in closest proximity to the residues in the obtained structural model of P010480.

Alternatively, particularly in instances where a parent GDSx polypeptide shares a low homology with SEQ ID No. 2, the equivalent amino acids in alternative parental GDSx polypeptides, which correspond to one or more of the following amino acids (SET 7) of SEQ ID No. 34 can be determined from an alignment obtained from the PFAM database (PFAM consensus) modified based on the structural alignment as shown in Alignment 1 (FIG. 48). The modification based on the structural models may be necessary to slightly shift the alignment in order to ensure a best fit overlap. Alignment 1 (FIG. 48) provides guidance in this regard.

In one aspect preferably the variant enzyme comprises one or more of the following amino acid substitutions:

S3A, C, D, E, F, G, H, I, K, L, M, N, P, Q, R, T, V, W, or Y; and/or

L17A, C, D, E, F, G, H, I, K, M, N, P, Q, R, S, T, V, W, or Y; and/or

S18A, C, D, E, F, H, I, K, L, M, N, P, Q, R, T, W, or Y; and/or

K22A, C, D, E, F, G, H, I, L, M, N, P, Q, R, S, T, V, W, or Y; and/or

M23A, C, D, E, F, G, H, I, K, L, N, P, Q, R, S, T, V, W, or Y; and/or

Y30A, C, D, E, G, H, I, K, L, M, N, P, Q, R, S, T, V, or W; and/or

G40A, C, D, E, F, H, I, K, L, M, N, P, Q, R, S, T, V, W, or Y; and/or

N80A, C, D, E, F, G, H, I, K, L, M, P, Q, R, S, T, V, W, or Y; and/or

P81A, C, D, E, F, G, H, I, K, L, M, N, Q, R, S, T, V, W, or Y; and/or

K82A, C, D, E, F, G, H, I, L, M, N, P, Q, R, S, T, V, W, or Y; and/or

N87A, C, D, E, F, G, H, I, K, L, M, P, Q, R, S, T, V, W, or Y; and/or

N88A, C, D, E, F, G, H, I, K, L, M, P, Q, R, S, T, V, W, or Y; and/or

W111A, C, D, E, F, G, H, I, K, L, M, N, P, Q, R, S, T, V, W or Y; and/or

V112A, C, D, E, F, G, H, I, K, L, M, N, P, Q, R, S, T, W, or Y; and/or

A114C, D, E, F, G, H, I, K, L, M, N, P, Q, R, S, T, V, W, or Y; and/or

Y117A, C, D, E, F, G, H, I, K, L, M, N, P, Q, R, S, T, V, or W; and/or

L118A, C, D, E, F, G, H, I, K, M, N, P, Q, R, S, T, V, W, or Y; and/or

P156A, C, D, E, F, G, H, I, K, L, M, N, Q, R, S, T, V, W, or Y; and/or

D157A, C, E, F, G, H, I, K, L, M, P, Q, R, S, T, V, W, or Y; and/or

G159A, C, D, E, F, H, I, K, L, M, N, P, Q, R, S, T, V, W, or Y; and/or

Q160A, C, D, E, F, G, H, I, K, L, M, N, P, R, S, T, V, W, or Y; and/or

N161A, C, D, E, F, G, H, I, K, L, M P, Q, R, S, T, V, W, or Y; and/or

P162A, C, D, E, F, G, H, I, K, L, M, N, Q, R, S, T, V, W, or Y; and/or

S163A, C, D, E, F, G, H, I, K, L, M, N, P, Q, R, T, V, W, or Y; and/or

A164C, D, E, F, G, H, I, K, L, M, N, P, Q, R, S, T, V, W, or Y; and/or

R165A, C, D, E, F, G, H, I, K, L, M, N, P, Q, S, T, V, W, or Y; and/or

S166A, C, D, E, F, G, H, I, K, L, M, N, P, Q, R, T, V, W, or Y; and/or

Q167A, C, D, E, F, G, H, I, K, L, M, N, P, R, S, T, V, W, or Y; and/or

K168A, C, D, E, F, G, H, I, L, M, N, P, Q, R, S, T, V, W, or Y; and/or

V169A, C, D, E, F, G, H, I, K, L, M, N, P, Q, R, S, T, W, or Y; and/or

V170A, C, D, E, F, G, H, I, K, L, M, N, P, Q, R, S, T, W, or Y; and/or

E171A, C, D, F, G, H, I, K, L, M, N, P, Q, R, S, T, V, W, or Y; and/or

A172C, D, E, F, G, H, I, K, L, M, N, P, Q, R, S, T, V, W, or Y; and/or

Y179A, C, D, E, F, G, H, I, K, L, M, N, P, Q, R, S, T, V, or W; and/or

H180A, C, D, E, F, G, I, K, L, M, P, Q, R, S, T, V, W, or Y; and/or

N181A, C, D, E, F, G, H, I, K, L, M, P, Q, R, S, T, V, W, or Y; and/or

Q182A, C, D, E, F, G, H, I, K, L, M, N, P, R, S, T, V, W, or Y, preferably K; and/or M209A, C, D, E, F, G, H, I, K, L, N, P, Q, R, S, T, V, W, or Y; and/or L210A, C, D, E, F, G, H, I, K, M, N, P, Q, R, S, T, V, W, or Y; and/or R211A, C, D, E, F, G, H, I, K, L, M, N, P, Q, R, S, T, V, W, or Y; and/or N215A, C, D, E, F, G, H, I, K, L, M, N, P, Q, R, S, T, V, W, or Y; and/or Y226A, C, D, E, G, H, I, K, L, M, N, P, Q, R, S, T, V, or W; and/or Y230A, C, D, E, G, H, I, K, L, M, N, P, Q, R, S, T, V or W; and/or K284A, C, D, E, F, G, H, I, L, M, N, P, Q, R, S, T, V, W, or Y; and/or M285A, C, D, E, F, G, H, I, K, L, N, P, Q, R, S, T, V, W, or Y; and/or Q289A, C, D, E, F, G, H, I, K, L, M, N, P, R, S, T, V, W, or Y; and/or V290A, C, D, E, F, G, H, I, K, L, M, N, P, Q, R, S, T, W, or Y; and/or E309A, C, D, F, G, H, I, K, L, M, N, P, Q, R, S, T, V, W, or Y; and/or S310A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

When it is the case that the residues in the parent backbone differ from those in P10480 (SEQ ID No. 2), as determined by homology alignment and/or structural alignment to P10480 and/or 1IVN, it may be desirable to replace the residues which align to any one or more of the following amino acid residues in P10480 (SEQ ID No. 2): (SET 7, including Try30 and Tyr230), with the residue found in P10480.

Preferably, the His amino acid at residue 180 is substituted for one of the following A, D, E, F, G, I, K, L, P, R, V, W, or Y.

Preferably, the Gln amino acid at residue 182 is substituted for a polar amino acid, most preferably K, R, D, or E.

Preferably, the Tyr amino acid at residue 230 is substituted for one of the following amino acids A, C, D, E, G, I, K, L, M, N, P, Q, R, S, T, V, or Y In one aspect preferably the variant enzyme comprises one or more of the following amino acid substitutions: S3T, Q182K, E309A, S310E.

In a further aspect, preferably the variant enzyme comprises a C-terminal addition, namely –318G.

Suitably, the variant enzyme may comprise one or more of the following modifications: S3T, Q182K, E309A, S310E, –318G.

Variant enzymes which have an increased hydrolytic activity against a polar lipid may also have an increased transferase activity from a polar lipid.

Preferred variant enzymes may have a decreased hydrolytic activity against a phospholipid, such as phosphatidylcholine (PC), may also have an increased transferase activity from a phospholipid.

Preferred variant enzymes may have an increased transferase activity from a phospholipid, such as phosphatidylcholine (PC), these may also have an increased hydrolytic activity against a phospholipid.

The variant enzyme in accordance with the present invention may have one or more of the following functionalities compared with the parent enzyme:
i) improved activity towards a phospholipid, such as phosphatidylcholine;
ii) improved activity towards a galactolipid, such as DGDG;
iii) improved specificity towards a galactolipid, in particular DGDG;
iv) improved galactolipid:phospholipid ratio);
v) improved transferase activity with a phospholipid, such as phosphatidylcholine, as the lipid acyl donor;
vi) improved transferase activity with a galactolipid, such as DGDG, as the lipid acyl donor Modification of one or more of the following residues may result in a variant enzyme having an increased absolute transferase activity against phospholipid:

S3, D157, S310, E309, Y179, N215, K22, Q289, M23, H180, M209, L210, R211, P81, V112, N80, L82, N88; N87

Specific preferred modifications which may provide a variant enzyme having an improved transferase activity from a phospholipid may be selected from one or more of the following:

S3A, C, D, E, F, G, H, I, K, L, M, N, P, Q, R, T, V, W or Y; preferably N, E, K, R, A, P or M, most preferably S3A D157A, C, E, F, G, H, I, K, L, M, N, P, Q, R, S, T, V, W or Y; preferably D157S, R, E, N, G, T, V, Q, K or C S310A, C, D, E, F, G, H, I, K, L, M, N, P, Q, R, T, V, W or Y; preferably S310T –318 E E309A, C, D, E, F, G, H, I, K, L, M, N, P, Q, R, T, V, W or Y; preferably E309 R, E, L, R or A Y179A, C, D, E, F, G, H, I, K, L, M, N, P, Q, R, S, T, V or W; preferably Y179 D, T, E, R, N, V, K, Q or S, more preferably E, R, N, V, K or Q N215A, C, D, E, F, G, H, I, K, L, M, N, P, Q, R, S, T, V, W or Y; preferably N215 S, L, R or Y K22A, C, D, E, F, G, H, I, L, M, N, P, Q, R, S, T, V, W or Y; preferably K22 E, R, C or A Q289A, C, D, E, F, G, H, I, K, L, M, N, P, R, S, T, V, W or Y; preferably Q289 R, E, G, P or N M23A, C, D, E, F, G, H, I, K, L N, P, Q, R, S, T, V, W or Y; preferably M23 K, Q, L, G, T or S H180A, C, D, E, F, G, I, K, L, M, P, Q, R, S, T, V, W or Y; preferably H180 Q, R or K M209 A, C, D, E, F, G, H, I, K, L, N, P, Q, R, S, T, V, W or Y; preferably M209 Q, S, R, A, N, Y, E, V or L L210A, C, D, E, F, G, H, I, K, M, N, P, Q, R, S, T, V, W or Y; preferably L210 R, A, V, S, T, I, W or M R211A, C, D, E, F, G, H, I, K, L, M, N, P, Q, S, T, V, W or Y; preferably R211T P81A, C, D, E, F, G, H, I, K, L, M, N, Q, R, S, T, V, W or Y; preferably P81G V112A, C, D, E, F, G, H, I, K, L, M, N, P, Q, R, S, T, W or Y; preferably V112C N80A, C, D, E, F, G, H, I, K, L, M, P, Q, R, S, T, V, W or Y; preferably N80 R, G, N, D, P, T, E, V, A or G L82A, C, D, E, F, G, H, I, M, N, P, Q, R, S, T, V, W or Y; preferably L82N, S or E N88A, C, D, E, F, G, H, I, K, L, M, P, Q, R, S, T, V, W or Y; preferably N88C N87A, C, D, E, F, G, H, I, K, L, M, P, Q, R, S, T, V, W or Y; preferably N87M or G The following modifications may result in variants having an improved activity towards a galactolipid, such as DGDG:

S3A, C, D, E, F, G, H, I, K, L, M, N, P, Q, R, S, T, V, W, or Y, preferably S3 is substituted with an aliphatic amino acid or one of the following amino acid residues S3G, S3A, S3T, S3N, S3Q, S3K, S3R, S3P, S3M, or a polar charged amino acid, preferably C, S, T, M, N or Q, more preferably N or Q; and/or Y230A, C, D, E, G, H, I, K, L, M, N, P, Q, R, S, T, V, or W, preferably Y230 is substituted with an aliphatic amino acid or one of the following amino acid residues G, D, T, V, R or M, more preferably G, D, T, V, R or M, more preferably G or T; and/or Q182A, C, D, E, F, G, H, I, K, L, M, N, Q, P, R, S, T, V, W, or Y, preferably Q182 is substituted with an aliphatic amino acid, preferably a polar amino acid, preferably a polar charged amino acid, more preferably D or E, most preferably D; and/or A309A, C, D, E, F, G, H, I, K, L, M, N, P, Q, R, S, T, V, W, or Y, preferably A309 is substituted with an aliphatic amino acid, preferably a non-polar amino acid, preferably G, A, or P, more preferably A; and/or A C-terminal addition (−318) of at least one amino acid, preferably one amino acid, wherein the additional amino acid is preferably an aliphatic amino acid, preferably a non-polar amino acid, more preferably I, L or V.

The following modifications may result in variants having an improved specificity towards a galactolipid, in particular DGDG:

Y230A, C, D, E, G, H, I, K, L, M, N, P, Q, R, S, T, V, or W, preferably Y230 is substituted with an aliphatic amino acid or one of the following amino acid residues G, D, T, V, R or M, more preferably G, D, T, V, R or M;

The following modifications may result in variants having an improved galactolipid:phospholipid ratio:

Y230A, C, D, E, G, H, I, K, L, M, N, P, Q, R, S, T, V, or W, preferably Y230 is substituted with an aliphatic amino acid or one of the following amino acid residues G, D, T, V, R or M, more preferably G, D, T, V, R or M.

The following modifications may result in variants having an improved activity with a phospholipid, such as phosphatidylcholine, as the lipid acyl donor:

A309A, C, D, E, F, G, H, I, K, L, M, N, P, Q, R, S, T, V, W, or Y, preferably A309 is substituted with an aliphatic amino acid, preferably a non-polar amino acid, preferably G, A, or P, more preferably A; and/or S3A, C, D, E, F, G, H, I, K, L, M, N, P, Q, R, S, T, V, W, or Y, preferably SA is substituted with a polar uncharged and/or polar charged amino acid, preferably one of the following amino acids residues S3T, S3N, S3Q, S3K, S3R, S3P, S3M, more preferably S3Q, S3K, or S3R.

The following modifications may result in variants having an improved transferase activity with a phospholipid, such as phosphatidylcholine, as the lipid acyl donor:

S3A, C, D, E, F, G, H, I, K, L, M, N, P, Q, R, S, T, V, W, or Y, preferably SA is substituted with a polar uncharged and/or polar charged amino acid pore preferably one of the following amino acids residues S3T, S3N, S3Q, S3D, S3K, S3R, S3P, S3M; and/or Q182A, C, D, E, F, G, H, I, K, L, M, N, P, Q, R, S, T, V, W, or Y, preferably Q182 is substituted with an aliphatic amino acid residue, preferably a polar amino acid, preferably a polar charged amino acid, more preferably D or E, most preferably D; and/or A309A, C, D, E, F, G, H, I, K, L, M, N, P, Q, R, S, T, V, W, or Y, preferably A309 is substituted with an aliphatic residue, preferably a non-polar residue, preferable G, A, or P, more preferably A.

The following modifications may result in variants having an improved transferase activity using a galactolipid acyl, such as DGDG, as the lipid acyl donor:

Q182A, C, D, E, F, G, H, I, K, L, M, N, P, Q, R, S, T, V, W, or Y, preferably Q182 is substituted by an aliphatic amino acid residue, preferably a polar amino acid, preferably a polar charged amino acid, more preferably D or E, most preferably D; and/or Y230A, C, D, E, G, H, I, K, L, M, N, P, Q, R, S, T, V, or W, preferably Y230 is substituted with an aliphatic amino acid or one of the following amino acid residues G, D, T, V, R or M, more preferably G, D, T, V, R or M, more preferably G or T; and/or A309A, C, D, E, F, G, H, I, K, L, M, N, P, Q, R, S, T, V, W, or Y, preferably A309 is substituted with an aliphatic residue, preferably a non-polar residue, preferable G, A, or P, more preferably A.

The following modifications may result in variants having an improved transferase activity with a polar lipid, such as a galactolipid (e.g. DGDG) and/or a phospholipid (e.g. phosphatidylcholine) as the lipid acyl donor:

S3A, C, D, E, F, G, H, I, K, L, M, N, P, Q, R, S, T, V, W, or Y, preferably S3 is substituted with a polar uncharged and/or polar charged amino acid, more preferably one of the following amino acids residues S3T, S3N, S3Q, S3D, S3K, S3R, S3P, S3M; and/or Y230A, C, D, E, G, H, I, K, L, M, N, P, Q, R, S, T, V, or W, preferably Y230 is substituted with an aliphatic amino acid or one of the following amino acid residues G, D, T, V, R or M, more preferably G, D, T, V, R or M, more preferably G or T; and/or Q182A, C, D, E, F, G, H, I, K, L, M, N, P, Q, R, S, T, V, W, or Y, preferably an aliphatic amino acid residue, preferably a polar amino acid, preferably a polar charged amino acid, more preferably D or E, most preferably D; and/or S3A, C, D, E, F, G, H, I, K, L, M, N, P, Q, R, S, T, V, W, or Y, preferably S3 is substituted with a polar uncharged and/or polar charged amino acid, more preferably one of the following amino acids residues S3T, S3N, S3Q, S3D, S3K, S3R, S3P, S3M; and/or A309A, C, D, E, F, G, H, I, K, L, M, N, P, Q, R, S, T, V, W, or Y, preferably an aliphatic residue, preferably a non-polar residue, preferable G, A, or P, more preferably A.

The following modifications result in variants having improved activity towards PC:

S3N, Q, K, R, P, and/or M

The following modifications result in variants having improved activity towards DGDG:

K187D, E309A, Y230T, Y230G, S3Q

The following modifications result in variants having improved specificity towards DGDG:

K187D, K187D, Y230G, Y230T, Y230R, Y230M, Y230V, D157C, E309A, G218I

The following modifications result in variants having improved transferase activity with PC as the acyl donor:

S3K, S3R, S3Q, S3N, S3P, S3M

The following modifications result in variants having improved transferase activity with DGDG as the acyl donor:

Y230T, K187D, Y230G, E309A

Preferred modification of one or more of the following residues results in a variant enzyme having an increased absolute transferase activity against phospholipid:

S3 N, R, A, G
M23 K, Q, L, G, T, S
H180 R
L82 G
Y179 E, R, N, V, K or Q
E309 R, S, L or A

One preferred modification is N80D. This is particularly the case when using the reference sequence SEQ ID No. 35 as the backbone. Thus, the reference sequence may be SEQ ID No. 16. This modification may be in combination with one or more further modifications. Therefore in a preferred embodiment of the present invention the nucleotide sequence encoding a lipid acyltransferase for use in any one of the host cells, vectors, methods and uses of the present invention may encode a lipid acyltransferase that comprises SEQ ID No. 35 or an amino acid sequence which has 75% or more, preferably 85% or more, more preferably 90% or more, even more preferably 95% or more, even more preferably 98% or more, or even more preferably 99% or more identity to SEQ ID No. 35.

As noted above, when referring to specific amino acid residues herein the numbering is that obtained from alignment of the variant sequence with the reference sequence shown as SEQ ID No. 2 or SEQ ID No. 35.

For the avoidance of doubt, when a particular amino acid is taught at a specific site, for instance K187 for instance, this refers to the specific amino acid at residue number 187 in SEQ ID No. 2. However, the amino acid residue at site 187 in a different parent enzyme may be different from lysine.

Thus, when taught to substitute an amino acid at residue 187, although reference may be made to K187 it would be readily understood by the skilled person that when the parent enzyme is other than that shown in SEQ ID No. 2, the amino acid being substituted may not be lysine. It is, therefore, possible that when substituting an amino acid sequence in a parent enzyme which is not the enzyme having the amino acid sequence shown as SEQ ID No. 2, the new (substituting) amino acid may be the same as that taught in SEQ ID No. 2. This may be the case, for instance, where the amino acid at say residue 187 is not lysine and is, therefore different from the amino acid at residue 187 in SEQ ID No. 2. In other words, at residue 187 for example, if the parent enzyme has at that position an amino acid other than lysine, this amino acid may be substituted with lysine in accordance with the present invention.

Much by preference, the nucleotide sequence encoding a lipid acyltransferase for use in any one of the host cells, vectors, methods and uses of the present invention may encode a lipid comprising the amino acid sequence shown as SEQ ID No. 16 or SEQ ID No. 70, or an amino acid sequence which has 75% or more, preferably 85% or more, more preferably 90% or more, even more preferably 95% or more, even more preferably 98% or more, or even more preferably 99% or more identity to SEQ ID No. 16 or SEQ ID No. 70. This enzyme may be considered a variant enzyme.

For the purposes of the present invention, the degree of identity is based on the number of sequence elements which are the same. The degree of identity in accordance with the present invention for amino acid sequences may be suitably determined by means of computer programs known in the art, such as Vector NTI 10 (Invitrogen Corp.). For pairwise alignment the score used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

Suitably, the nucleotide sequence encoding a lipid acyltransferase/ lipid acyl transferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

Suitably, the nucleotide sequence encoding a lipid acyltransferase/lipid acyl transferase enzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus sp, Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis Candida parapsilosis Thermobifida fusca* and *Corynebacterium efficiens*.

In one aspect, preferably the nucleotide sequence encoding a nucleotide sequence encoding a lipid acyltransferase for use in any one of the host cells, vectors, methods and uses of the present invention encodes a lipid acyl transferase enzyme according to the present invention is obtainable, preferably obtained or derived, from one or more of *Aeromonas* spp., *Aeromonas hydrophila* or *Aeromonas salmonicida*.

Enzymes which function as lipid acyltransferases in accordance with the present invention can be routinely identified using the assay taught in Example 12 of WO2004/064537. Using this assay, in which there is a very high water content—approximately 95%, lipid acyltransferases/lipid acyl transferase in accordance with the present invention are those which have at least 2% acyltransferase activity (relative transferase activity), preferably at least 5% relative transferase activity, preferably at least 10% relative transferase activity, preferably at least 15%, 20%, 25% 26%, 28%, 30%, 40% 50%, 60% or 75% relative transferase activity.

Phospholipases may act as acyl-transferase enzymes in low water environments. Therefore it is considered that in place of or in addition to the phospholipid acyltransferase enzyme a phospholipase enzyme may be used when process for the modification of the edible oil of fat takes place in a low water environment.

The term "high water" as used herein means any substrate or foodstuff with more than 3% water content, preferably more than 4%, more than 5%, more than 6%, more than 7%, more than 8%, more than 9%, more than 10%, more than 20%, more than 30%, more than 40%, more than 50%, more than 60%, more than 70%, more than 80% or more than 90%.

The term "low water" as used herein means any substrate or foodstuff with less than 3% water content, preferably less than 2%, less than 1% or less than 0.5%, less than 0.3%, less than 0.2, less than 0.1, less than 0.05, or less than 0.01%

For avoidance of doubt milk is a high water environment where as butterfat is a low water environment.

Suitable phospholipases for use in the invention include phospholipase A1, phospholipase A2, or phospholipase B. Phospholipase A1, phospholipase A2, or phospholipase B may also be used in co-ordination with the lipid acyl transferase activity. Phospholipase C and/or D may also be used in co-ordination with the lipid acyl transferase activity/phospholipase A1, A2 and/or B activity in analogy with WO2005/089562. Preferred phospholipases may include phospholipase A2, such as Lecitase™ or the *Fusarium venenatum* and *Tuber albidum* phospholipase disclosed in WO2004/97012 (Novozymes/Chr. Hansen). A *Fusarium venenatum* phospholipase is sold by Novozymes as MAX YIELD™.

Isolated

In one aspect, the method of the present invention comprises the additional step of recovering/isolating the lipid acyltransferase. Thus, the lipid acyltransferase produced may be in an isolated form.

In another aspect, the nucleotide sequence encoding a lipid acyltransferase for use in the present invention may be in an isolated form.

The term "isolated" means that the sequence or protein is at least substantially free from at least one other component with which the sequence or protein is naturally associated in nature and as found in nature.

Purified

In one aspect, the method of the present invention comprises the additional step of purifying the lipid acyltransferase.

In another aspect, the nucleotide sequence encoding a lipid acyltransferase for use in the present invention may be in a purified form.

The term "purified" means that the sequence is in a relatively pure state—e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Suitably the variant enzyme may be prepared using site directed mutagenesis.

Mutations may be introduced using synthetic oligonucleotides. These oligonucleotides contain nucleotide sequences flanking the desired mutation sites.

A suitable method is disclosed in Morinaga et al (Biotechnology (1984) 2, p646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EPO 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the nucleotide sequence encoding a lipid acyltransferase used in the invention may encode a variant lipid acyltransferase, i.e. the lipid acyltransferase may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY (SEQ ID NO: 45) and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the nucleotide sequence encoding a lipid acyltransferase for use in any one of the vectors, host cells, methods and/or uses of the present invention may encode a lipid acyltransferase that may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J Biol. Chem. 1991 Jan. 15: 266 (2): 997-1000; Robertson et al J. Biol. Chem. 1994 Jan. 21; 269(3):2146-50; Brumlik et al J. Bacteriol 1996 Apr; 178 (7): 2060-4; Peelman et al Protein Sci. 1998 March; 7(3):587-99.

Amino Acid Sequences

The present invention also encompasses amino acid sequences encoded by a nucleotide sequence which encodes a lipid acyltransferase for use in any one of the vectors, host cells, methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST package (see Ausubel et al 1999 Short Protocols in Molecular Biology, 4$^{th}$ Ed—Chapter 18), and FASTA (Altschul et al 1990 J. Mol. Biol. 403-410). Both BLAST and FASTA are available for offline and online searching (see Ausubel et al 1999, pages 7-58 to 7-60). However, for some applications, it is preferred to use the Vector NTI program. A new tool, called BLAST 2 Sequences is also available for comparing protein and nucleotide sequence (see FEMS Microbiol Lett 1999 174(2): 247-50; FEMS Microbiol Lett 1999 177(1): 187-8.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins DG & Sharp PM (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
| --- | --- |
| GAP OPEN | 0 |
| GAP EXTENSION | 0 |

| FOR CLUSTAL | DNA | PROTEIN | |
| --- | --- | --- | --- |
| WORD SIZE | 2 | 1 | K triple |
| GAP PENALTY | 15 | 10 | |
| GAP EXTENSION | 6.66 | 0.1 | |

In one embodiment, preferably the sequence identity for the nucleotide sequences is determined using CLUSTAL with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

In one embodiment the degree of amino acid sequence identity in accordance with the present invention may be suitably determined by means of computer programs known in the art, such as Vector NTI 10 (Invitrogen Corp.). For pairwise alignment the matrix used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or O-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon RJ et al., PNAS (1992) 89(20), 9367-9371 and Horwell DC, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a lipid acyltransferase in nature.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts are well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Various methods are known for the transformation of *Bacillus* species.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech Mar./Apr. 1994 17-27). Further teachings on plant transformation may be found in EP-A-0449375.

General teachings on the transformation of fungi, yeasts and plants are presented in following sections.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g. from *Aspergillus*), the α-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

In the method of the present invention the lipid acyltransferase may be produced as a Fusion protein, for example to aid in extraction and purification thereof. Examples of fusion protein partners include glutathione-S-transferase (GST), 6×His, (SEQ ID NO: 41), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

In another embodiment of the invention, the amino acid sequence of a polypeptide having the specific properties as defined herein may be ligated to a non-native sequence to encode a fusion protein. For example, for screening of peptide libraries for agents capable of affecting the substance activity, it may be useful to encode a chimeric substance expressing a non-native epitope that is recognised by a commercially available antibody.

The invention will now be described, by way of example only, with reference to the following Figures and Examples.

FIG. 1 shows the amino acid sequence of a mutant *Aeromonas salmonicida* mature lipid acyltransferase (GCAT) with a mutation of Asn80Asp (notably, amino acid 80 is in the mature sequence) (SEQ ID No. 16);

FIG. 2 shows an amino acid sequence (SEQ ID No. 1) a lipid acyl transferase from *Aeromonas hydrophila* (ATCC #7965);

FIG. 3 shows a pfam00657 consensus sequence from database version 6 (SEQ ID No. 2);

FIG. 4 shows an amino acid sequence (SEQ ID No. 3) obtained from the organism *Aeromonas hydrophila* (P10480; GI:121051);

FIG. 5 shows an amino acid sequence (SEQ ID No. 4) obtained from the organism *Aeromonas salmonicida* (AAG098404; GI:9964017);

FIG. 6 shows an amino acid sequence (SEQ ID No. 5) obtained from the organism *Streptomyces coelicolor* A3(2) (Genbank accession number NP_631558);

FIG. 7 shows an amino acid sequence (SEQ ID No. 6) obtained from the organism *Streptomyces coelicolor* A3(2) (Genbank accession number: CAC42140);

FIG. 8 shows an amino acid sequence (SEQ ID No. 7) obtained from the organism *Saccharomyces cerevisiae* (Genbank accession number P41734);

FIG. 9 shows an amino acid sequence (SEQ ID No. 8) obtained from the organism *Ralstonia* (Genbank accession number: AL646052);

FIG. 10 shows SEQ ID No. 19. Scoe1 NCBI protein accession code CAB39707.1 GI:4539178 conserved hypothetical protein [*Streptomyces coelicolor* A3(2)];

FIG. 11 shows an amino acid shown as SEQ ID No. 10. Scoe2 NCBI protein accession code CAC01477.1 GI:9716139 conserved hypothetical protein [*Streptomyces coelicolor* A3(2)];

FIG. 12 shows an amino acid sequence (SEQ ID No. 11) Scoe3 NCBI protein accession code CAB88833.1 GI:7635996 putative secreted protein. [*Streptomyces coelicolor* A3(2)];

FIG. 13 shows an amino acid sequence (SEQ ID No. 12) Scoe4 NCBI protein accession code CAB89450.1 GI:7672261 putative secreted protein. [*Streptomyces coelicolor* A3(2)];

FIG. 14 shows an amino acid sequence (SEQ ID No. 13) Scoe5 NCBI protein accession code CAB62724.1 GI:6562793 putative lipoprotein [*Streptomyces coelicolor* A3(2)];

FIG. 15 shows an amino acid sequence (SEQ ID No. 14) Srim1 NCBI protein accession code AAK84028.1 GI:15082088 GDSL-lipase [*Streptomyces rimosus*];

FIG. 16 shows an amino acid sequence (SEQ ID No. 15) of a lipid acyltransferase from *Aeromonas salmonicida* subsp. *Salmonicida* (ATCC#14174);

FIG. 17 shows an alignment of selected sequences (SEQ ID NOS 80-84, respectively, in order of appearance) to pfam00657 consensus sequence (SEQ ID NO: 2);

FIG. 18 shows an amino acid sequence (SEQ ID No. 25) of the fusion construct used for mutagenesis of the *Aeromonas hydrophila* lipid acyltransferase gene in Example 7. The underlined amino acids is a xylanase signal peptide;

FIG. 19 shows a polypeptide sequence of a lipid acyltransferase enzyme from *Streptomyces thermosacchari* (SEQ ID No. 26);

FIG. 20 shows a polypeptide sequence of a lipid acyltransferase enzyme from *Thermobifida fusca* GDSX 548 amino acid (SEQ ID No. 27);

FIG. 21 shows a polypeptide sequence of a lipid acyltransferase enzyme from *Thermobifida fusca* GDSX (SEQ ID No. 28);

FIG. 22 shows a polypeptide of a lipid acyltransferase enzyme from *Corynebacterium efficiens* GDSx 300 amino acid (SEQ ID No. 29);

FIG. 23 shows a polypeptide of a lipid acyltransferase enzyme from *Novosphingobium aromaticivorans* GDSx 284 amino acid (SEQ ID No. 30);

FIG. 24 shows a polypeptide of a lipid acyltransferase enzyme from *Streptomyces coelicolor* GDSx 269 aa (SEQ ID No. 31);

FIG. 25 shows a polypeptide of a lipid acyltransferase enzyme from *Streptomyces avermitilis*\GDSx 269 amino acid (SEQ ID No. 32);

Figure 45:
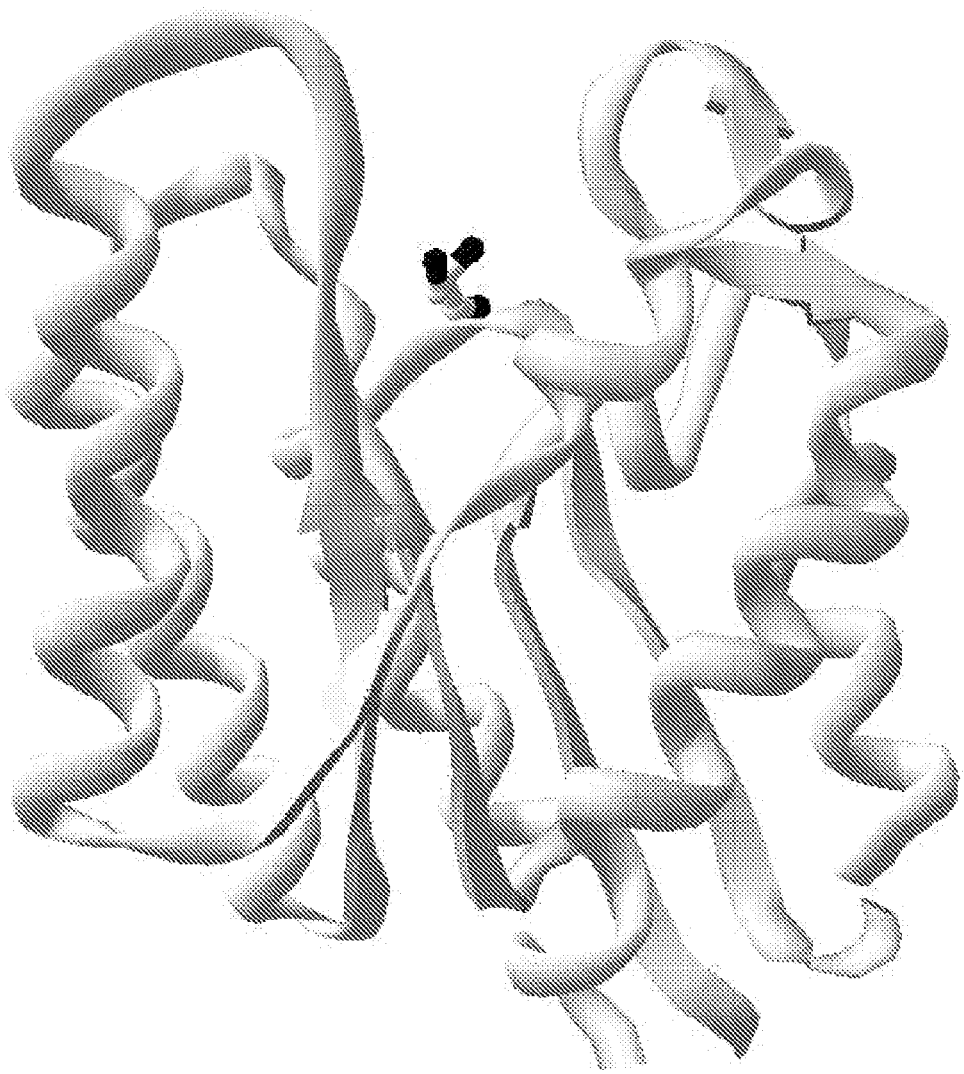

FIG. 26 shows a pairwise alignment of SEQ ID No. 3 (A. hyd sequence) with SEQ ID No. 4 (A. sal sequence) showing 93% amino acid sequence identity. The signal sequence is underlined. + denotes differences. The GDSX motif containing the active site serine 16, and the active sites aspartic acid 116 and histidine 291 are highlighted (see shaded regions). Numbers after the amino acid is minus the signal sequence;

FIG. 27 shows an amino acid sequence (SEQ ID No. 34) obtained from the organism *Aeromonas hydrophila* (P10480; GI:121051) (notably, this is the mature sequence). This amino acid sequence is a reference enzymes, which may be a parent enzyme in accordance with the present invention;

FIG. 28 shows the amino acid sequence (SEQ ID No. 35) of a mutant *Aeromonas salmonicida* mature lipid acyltransferase (GCAT) (notably, this is the mature sequence);

FIG. 29 shows a nucleotide sequence encoding a lipid acyltransferase enzyme (SEQ ID No. 36) from *Streptomyces thermosacchari*;

FIG. 30 shows that homologues of the *Aeromonas* genes can be identified using the basic local alignment search tool service at the National Center for Biotechnology Information, NIH, MD, USA and the completed genome databases. The GDSX motif was used in the database search and a number of sequences/genes potentially encoding enzymes with lipolytic activity were identified. Genes were identified from the genus *Streptomyces, Xanthomonas* and *Ralstonia*. As an example below, the *Ralstonia solanacearum* (SEQ ID NO: 86) was aligned to the *Aeromonas salmonicida* (satA) (SEQ ID NO: 85) gene. Pairwise alignment showed 23% identity. The active site serine is present at the amino terminus and the catalytic residues histidine and aspartic acid can be identified;

FIG. 31 shows the Pfam00657.11 [family 00657, database version 11] consensus sequence (hereafter called Pfam consensus) and the alignment of various sequences to the Pfam consensus sequence. The arrows indicate the active site residues, the underlined boxes indicate three of the homology boxes indicated by [Upton C and Buckley J T (1995) Trends Biochem Sci 20; 179-179]. Capital letters in the Pfam consensus indicate conserved residues in many family members. The - symbol indicates a position where the hidden Markov model of the Pfam consensus expected to find a residue but did not, so a gap is inserted. The . symbol indicates a residue without a corresponding residue in the Pfam consensus. The sequences listed from top to bottom correspond to those sequences listed in FIGS. 15 ("Srim1" disclosed as residues 38-263 of SEQ ID NO: 14), 10 ("Scoe1" disclosed as residues 5-186 of SEQ ID NO: 19), 11 ("Scoe2" disclosed as residues 10-188 of SEQ ID NO: 10), 12 ("Scoe3" disclosed as residues 239-441 of SEQ ID NO: 11), 13 ("Scoe4" disclosed as residues 75-262 of SEQ ID NO: 12), 14 ("Scoe5" disclosed as residues 66-296 of SEQ ID NO: 13), 4 ("Ahyd1" disclosed as residues 28-322 of SEQ ID NO: 3), 16 ("Asal1" disclosed as residues 28-322 of SEQ ID NO: 15), and 18 ("Ahyd2" disclosed as residues 40-334 of SEQ ID NO: 25), respectively. Additionally, "Pfam" is disclosed as SEQ ID NO: 33.

FIG. 32 shows a nucleotide sequence encoding a lipid acyltransferase enzyme (SEQ ID No. 39) from *Thermobifida fusca;*

FIG. 33 shows an amino acid sequence of a lipid acyltransferase enzyme (SEQ ID No. 40) from *Thermobifida fuscal* GDSx;

FIG. 34 shows the Pfam00657.11 [family 00657, database version 11] consensus sequence (hereafter called Pfam consensus) and the alignment of various sequences to the Pfam consensus sequence. The arrows indicate the active site residues, the underlined boxes indicate three of the homology boxes indicated by [Upton C and Buckley J T (1995) Trends Biochem Sci 20; 179-179]. Capital letters in the Pfam consensus indicate conserved residues in many family members. The - symbol indicates a position where the hidden Markov model of the Pfam consensus expected to find a residue but did not, so a gap is inserted. The . symbol indicates a residue without a corresponding residue in the Pfam consensus. The sequences listed from top to bottom correspond to those sequences listed in FIGS. 15 ("Srim1" disclosed as residues 38-263 of SEQ ID NO: 14), 10 ("Scoe1" disclosed as residues 5-186 of SEQ ID NO: 19), 11 ("Scoe2" disclosed as residues 10-188 of SEQ ID NO: 10), 4 ("Ahyd1" disclosed as residues 28-322 of SEQ ID NO: 3), 16 ("Asal1" disclosed as residues 28-322 of SEQ ID NO: 15), and 18 ("Ahyd2" disclosed as residues 40-334 of SEQ ID NO: 25), respectively. Additionally, the "Pfam" sequence is disclosed as SEQ ID NO: 33. All these proteins were found to be active against lipid substrates.

FIG. 35 shows a nucleotide sequence encoding a lipid acyltransferase enzyme (SEQ ID No. 42) from *Corynebacterium efficiens*\GDSx 300 aa;

FIG. 36 shows a nucleotide sequence encoding a lipid acyltransferase enzyme from *Novosphingobium\aromaticivorans*\GDSx 284 aa (SEQ ID NO: 69)

FIG. 37 shows a nucleotide sequence (SEQ ID No. 44) encoding a lipid acyltransferase enzyme from *S. coelicolor*\GDSx 268 aa;

FIG. 38 shows a typical set of 384 clones, the wild type control lies at the intersection of 0.9PC, 0.8DGDG; and FIG. 39 shows a nucleotide sequence (SEQ ID No. 46) encoding a lipid acyltransferase enzyme from *S. avermitilis*\GDSx 269 aa;

FIG. 40 shows three areas of interest. Section 1 contains mutants with an increased ratio R but lower activity towards DGDG. Region 2 contains mutants with an increased ratio R and an increased DGDG activity. Region 3 contains clones with an increased PC or DGDG activity, but no increase in the ratio R.

FIG. 41 shows a nucleotide sequence (SEQ ID No. 48) from *Thermobifida fusca*/GDSx;

FIG. 42 shows an alignment of the L131 (SEQ ID NO: 26) and homologues from *S. avermitilis* (SEQ ID NO: 32) and *T. fusca* (SEQ ID NO: 40) illustrates that the conservation of the GDSx motif (GDSY (SEQ ID NO: 78) in L131 and *S. avermitilis* and *T. fusca*), the GANDY (SEQ ID NO: 45) box, which is either GGNDA (SEQ ID NO: 76) or GGNDL (SEQ ID NO: 77), and the HPT block (considered to be the conserved catalytic histidine). These three conserved blocks are highlighted;

FIG. 43 shows SEQ ID No 17 which is the amino acid sequence of a lipid acyltransferase from *Candida parapsilosis;*

FIG. 44 shows SEQ ID No 18 which is the amino acid sequence of a lipid acyltransferase from *Candida parapsilosis;*

Figure 46:
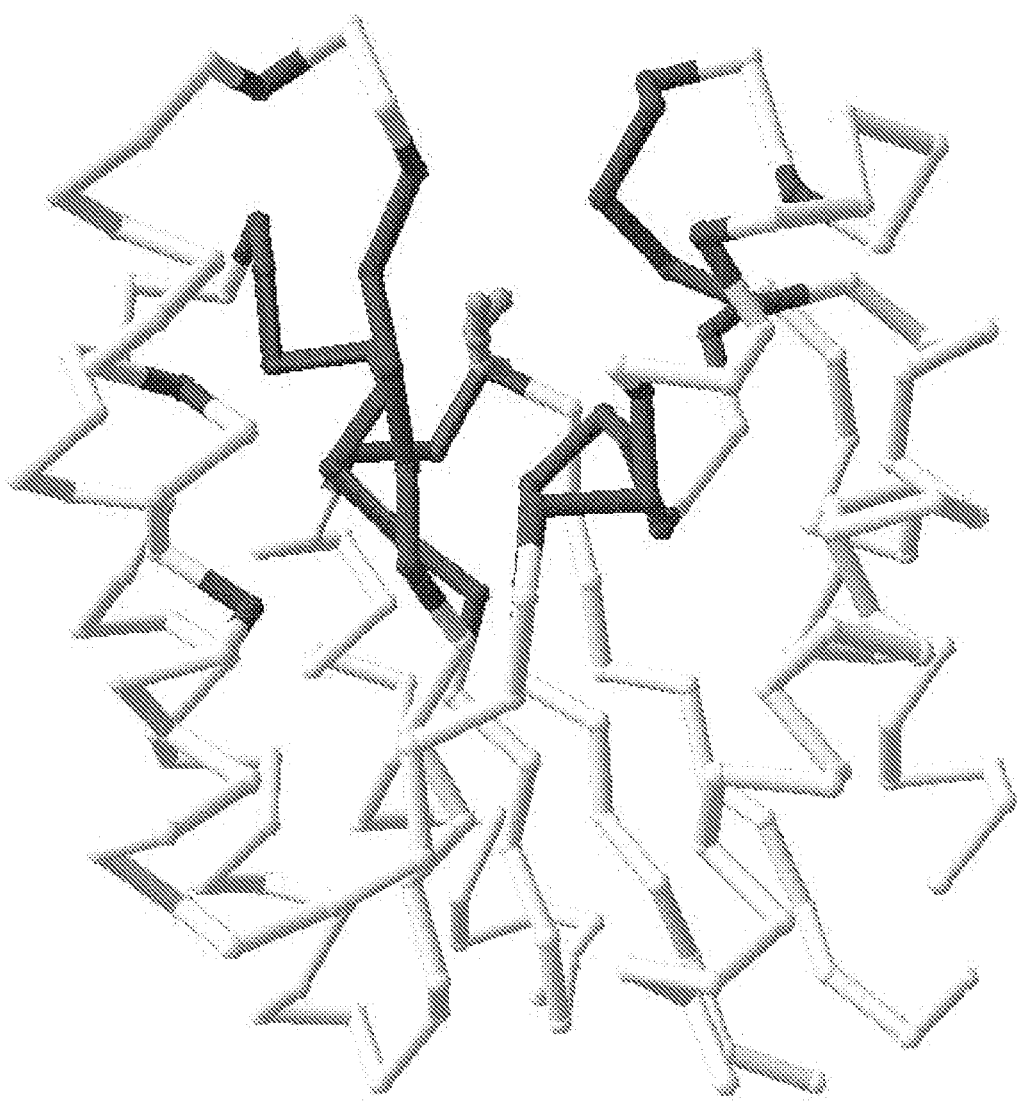
Figure 47:
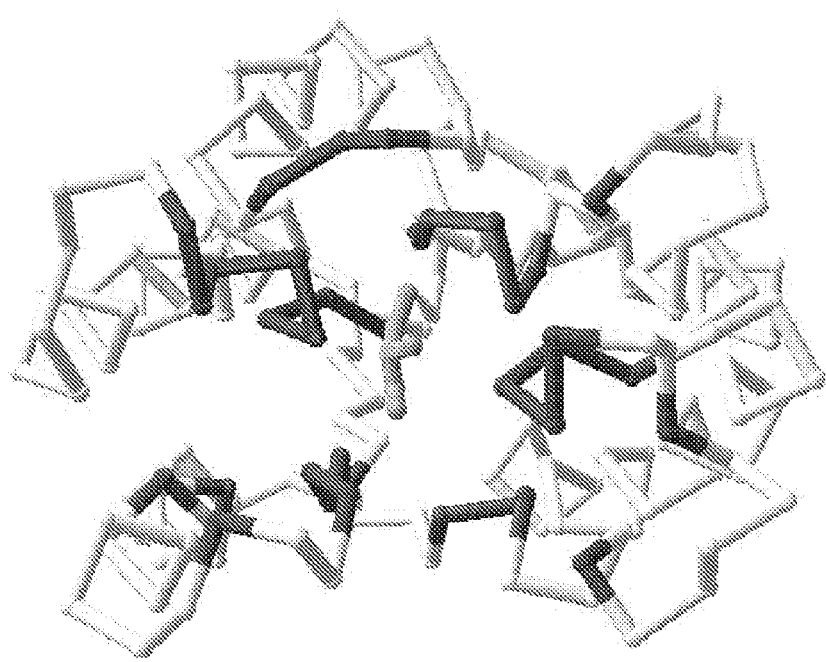

FIG. 45 shows a ribbon representation of the 1IVN.PDB crystal structure which has glycerol in the active site. The Figure was made using the Deep View Swiss-PDB viewer;

FIG. 46 shows 1IVN.PDB Crystal Structure—Side View using Deep View Swiss-PDB viewer, with glycerol in active site—residues within 10 Å of active site glycerol are coloured black;

FIG. 47 shows 1IVN.PDB Crystal Structure—Top View using Deep View Swiss-PDB viewer, with glycerol in active site—residues within 10 Å of active site glycerol are coloured black;

FIG. 48 shows alignment 1 (SEQ ID NOS 37-38 and 87, respectively, in order of appearance);

Figure 49:
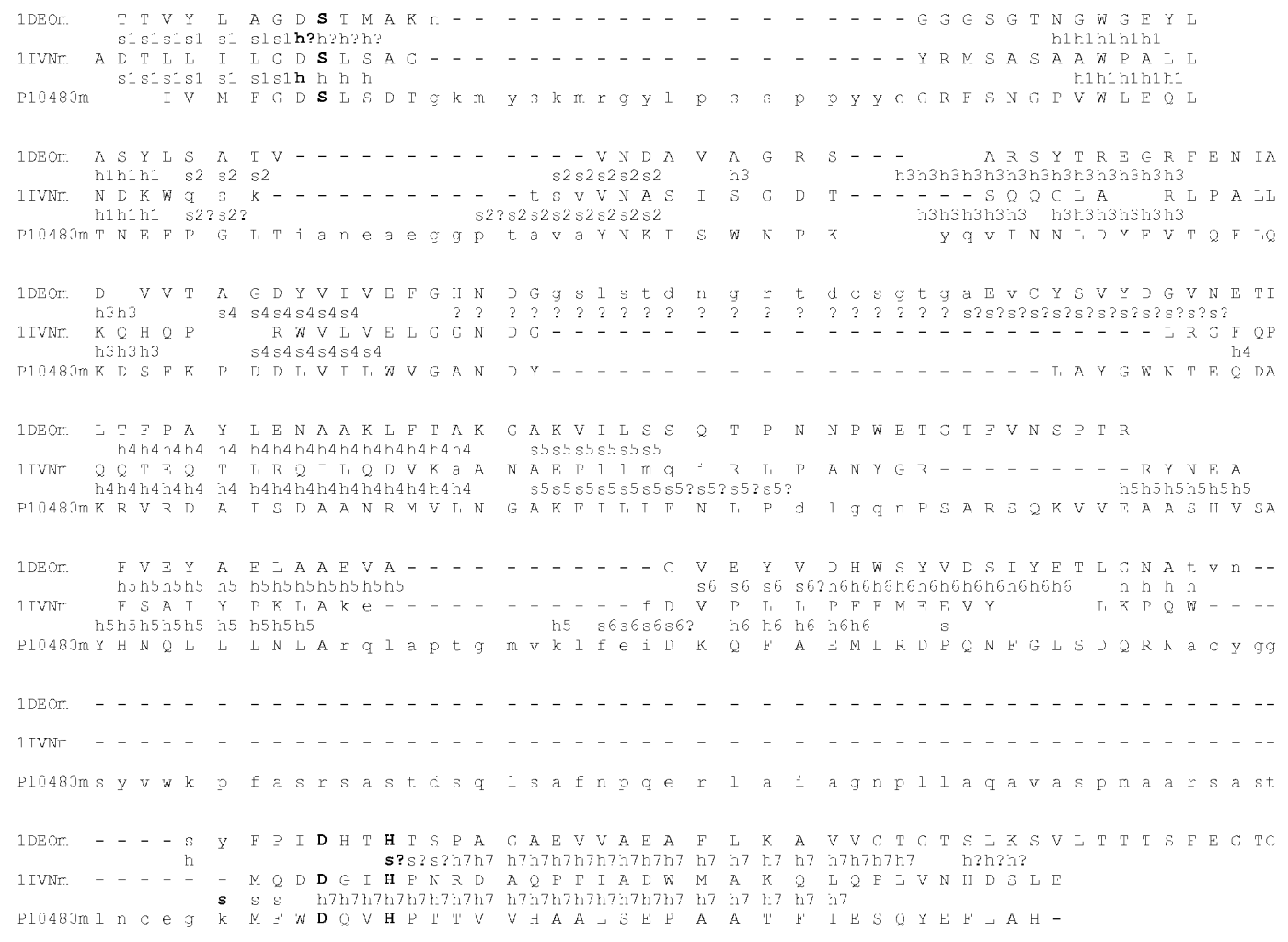

FIG. 49 shows alignment 2 (SEQ ID NOS 41, 38 and 87, respectively, in order of appearance);

FIGS. 50 and 51 show an alignment of 1IVN to P10480 (P10480 is the database sequence for *A. hydrophila* enzyme), this alignment was obtained from the PFAM database and used in the model building process. FIG. 50 discloses SEQ ID NOS 37-38, 87, 41, 38 and 87, respectively, in order of appearance and FIG. 51 discloses SEQ ID NOS 88-89, respectively, in order of appearance; and FIG. 52 shows an alignment where P10480 is the database sequence for *Aeromonas Hydrophila*. This sequence is used for the model construction and the site selection. Note that the full protein (SEQ ID No. 3) is depicted, the mature protein (equivalent to SEQ ID No. 34) starts at residue 19. A. sal is *Aeromonas salmonicida* (residues 19-336 of SEQ ID No. 15) GDSX lipase, A. hyd is *Aeromonas hydrophila* (residues 31-347 of SEQ ID No. 25) GDSX lipase. The consensus sequence contains a * at the position of a difference between the listed sequences.

Figure 54:
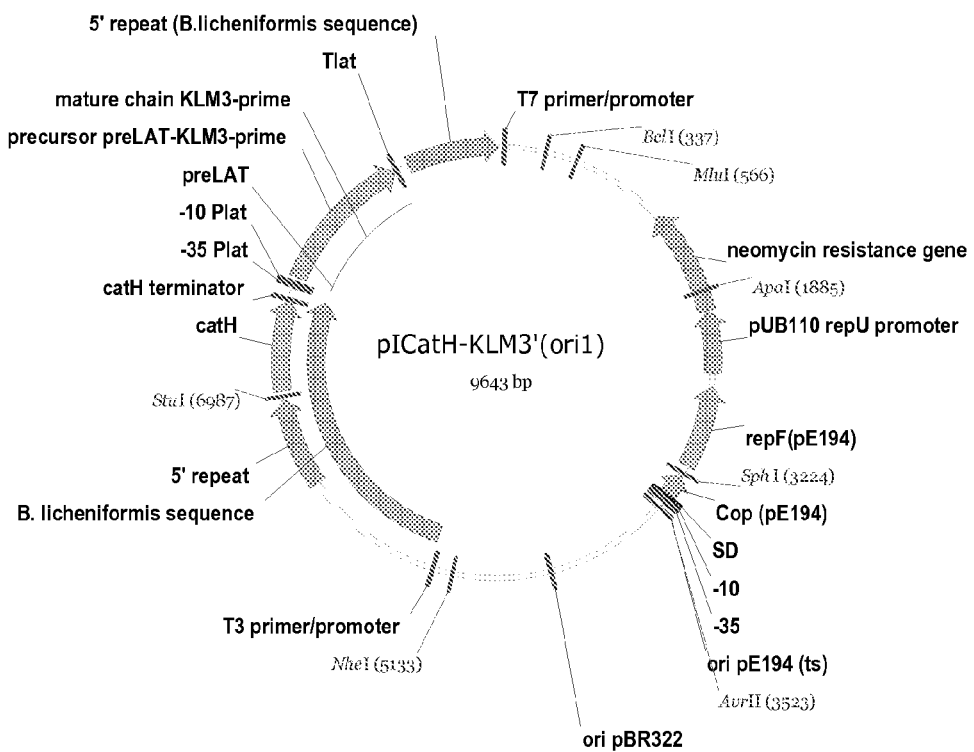
Figure 56:
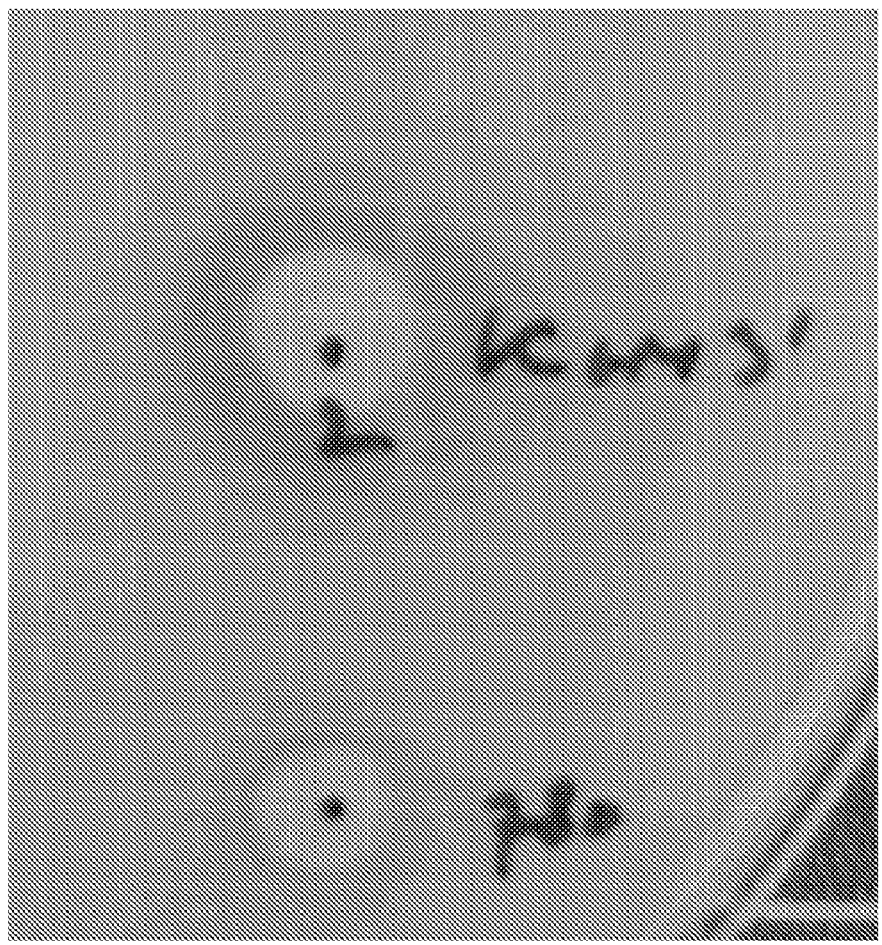

FIG. 53 shows a gene construct used in Example 7;

FIG. 54 shows a codon optimised gene construct (no. 052907) used in Example 8; and FIG. 55 shows the sequence (Nucleotide sequence disclosed as SEQ ID NO: 90 and amino acid sequence disclosed as SEQ ID NO: 91) of the XhoI insert containing the LAT-KLM3' precursor gene, the −35 and −10 boxes are underlined;

FIG. 56 shows BML780-KLM3'CAP50 (comprising SEQ ID No. 16—upper colony) and BML780 (the empty host strain—lower colony) after 48 h growth at 37° C. on 1% tributyrin agar;

FIG. 57 shows a nucleotide sequence from *Aeromonas salmonicida* (SEQ ID No. 49) including the signal sequence (preLAT—positions 1 to 87);

FIG. 58 shows a nucleotide sequence (SEQ ID No. 50) encoding a lipid acyl transferase according to the present invention obtained from the organism *Aeromonas hydrophila;*

FIG. 59 shows a nucleotide sequence (SEQ ID No. 51) encoding a lipid acyl transferase according to the present invention obtained from the organism *Aeromonas salmonicida;*

FIG. 60 shows a nucleotide sequence (SEQ ID No. 52) encoding a lipid acyl transferase according to the present invention obtained from the organism *Streptomyces coelicolor* A3(2) (Genbank accession number NC_003888.1: 8327480..8328367);

FIG. 61 shows a nucleotide sequence (SEQ ID No. 53) encoding a lipid acyl transferase according to the present invention obtained from the organism *Streptomyces coelicolor* A3(2) (Genbank accession number AL939131.1: 265480..266367);

FIG. 62 shows a nucleotide sequence (SEQ ID No. 54) encoding a lipid acyl transferase according to the present invention obtained from the organism *Saccharomyces cerevisiae* (Genbank accession number Z75034);

FIG. 63 shows a nucleotide sequence (SEQ ID No. 55) encoding a lipid acyl transferase according to the present invention obtained from the organism *Ralstonia*;

FIG. 64 shows a nucleotide sequence shown as SEQ ID No. 56 encoding NCBI protein accession code CAB39707.1 GI:4539178 conserved hypothetical protein [*Streptomyces coelicolor* A3(2)];

FIG. 65 shows a nucleotide sequence shown as SEQ ID No. 57 encoding Scoe2 NCBI protein accession code CAC01477.1 GI:9716139 conserved hypothetical protein [*Streptomyces coelicolor* A3(2)];

FIG. 66 shows a nucleotide sequence shown as SEQ ID No. 58 encoding Scoe3 NCBI protein accession code CAB88833.1 GI:7635996 putative secreted protein. [*Streptomyces coelicolor* A3(2)];

FIG. 67 shows a nucleotide sequence shown as SEQ ID No. 59 encoding Scoe4 NCBI protein accession code CAB89450.1 GI:7672261 putative secreted protein. [*Streptomyces coelicolor* A3(2)];

FIG. 68 shows a nucleotide sequence shown as SEQ ID No. 60, encoding Scoe5 NCBI protein accession code CAB62724.1 GI:6562793 putative lipoprotein [*Streptomyces coelicolor* A3(2)];

FIG. 69 shows a nucleotide sequence shown as SEQ ID No. 61 encoding Srim1 NCBI protein accession code AAK84028.1 GI:15082088 GDSL-lipase [*Streptomyces rimosus*];

FIG. 70 shows a nucleotide sequence (SEQ ID No. 62) encoding a lipid acyltransferase from *Aeromonas hydrophila* (ATCC #7965);

FIG. 71 shows a nucleotide sequence (SEQ ID No 63) encoding a lipid acyltransferase from *Aeromonas salmonicida* subsp. *Salmonicida* (ATCC#14174); and FIG. 72 shows a nucleotide sequence (SEQ ID No. 24) encoding a lipid acyltransferase enzyme from *Aeromonas hydrophila* including a xylanase signal peptide.

FIG. 73 shows an amino acid sequence of a mutant *Aeromonas salmonicida* mature lipid acyltransferase (GCAT) with a mutation of Asn80Asp (notably, amino acid 80 is in the mature sequence) (SEQ ID NO: 70) wherein the amino acid sequence has been subjected to post-translational modification resulting in the removal of 38 amino acids. FIG. 1 depicts SEQ ID NO: 16, which is the mature sequence prior to post-translational modification. Amino acid residue 236 of SEQ ID NO: 70 correspond to amino acid residue 274 in SEQ ID NO: 16.

EXAMPLE 1

Modelling of *Aeromonas hydrophila* GDSx Lipase on 1IVN

The alignment of the *Aeromonas hydrophila* GDSX lipase amino acid sequence (P10480) to the *Escherichia coli* Tioesterase amino acid sequence (1IVN) and the *Aspergillus aculeatus* rhamnogalacturonan acetylesterase amino acid sequence (1DEO) was obtained from the PFAM database in FASTA format. The alignment of P10480 and 1IVN was fed into an automated 3D structure modeller (SWISS-MODELLER server at web pages maintained by Glaxo Wellcome Experimental Research) together with the 1IVN.PDB crystal structure coordinates file FIG. 45). The obtained model for P10480 was structurally aligned to the crystal structures coordinates of 1IVN.PDB and 1DEO.PDB using the 'Deep View Swiss-PDB viewer' (obtained at web pages maintained by Glaxo Wellcome Experimental Research) (FIG. 46). The amino acid alignment obtained from the PFAM database (alignment 1—(FIG. 48)) was modified based on the structural alignment of 1DEO.PDB and 1IVN.PDB. This alternative amino acid alignment is called alignment 2 (FIG. 49).

The 1IVN.PDB structure contains a glycerol molecule. This molecule is considered to be in the active site it is in the vicinity of the catalytic residues. Therefore, a selection can be made of residues that are close to the active site which, due to their vicinity, are likely to have an influence on substrate binding, product release, and/or catalysis. In the 1IVN.PDB structure, all amino acids within a 10 Å sphere centered on the central carbon atom of the glycerol molecule in the active site were selected (amino acid set 1) (See FIG. 46 and FIG. 47).

The following amino acids were selected from the P10480 sequence; (1) all amino acids in P10480 corresponding to the amino acid set 1 in alignment 1; (2) all amino acids in P10480 corresponding to the amino acid set 1 in alignment 2; (3) from the overlay of the P10480 model and 1IVN all amino acids in the P10480 model within 12 Å from the glycerol molecule in 1IVN. All three groups combined give amino acid set 2.

Sequence P10480 was aligned to "AAG09804.1 GI:9964017 glycerophospholipid-cholesterol acyltransferase [*Aeromonas salmonicida*]" and the residues in AAG09804 corresponding to amino acid set 2 were selected in amino acid set 3.

Set 1, 2, and 3

Amino acid set 1 (note that these are amino acids in 1IVN—FIG. 50 and FIG. 51.) Gly8, Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, Gly155, Ile156, His157, Pro158

The highly conserved motifs, such as GDSx and catalytic residues, were deselected from set 1 (residues underlined). For the avoidance of doubt, set 1 defines the amino acid residues within 10 Å of the central carbon atom of a glycerol in the active site of the 1IVN model.

Amino acid set 2 (note that the numbering of the amino acids refers to the amino acids in the P10480 mature sequence)

Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289, Val290

Amino acid set 3 is identical to set 2 but refers to the *Aeromonas salmonicida* (SEQ ID No. 4) mature sequence, i.e. the amino acid residue numbers are 18 higher in set 3 as this reflects the difference between the amino acid numbering in the mature protein (SEQ ID No. 34) compared with the protein including a signal sequence (SEQ ID No. 1).

The mature proteins of *Aeromonas salmonicida* GDSX (SEQ ID No. 35) and *Aeromonas hydrophila* GDSX (SEQ ID No. 34) differ in five amino acids. These are Thr3Ser, Lys182Gln Glu309Ala, Thr310Asn, Gly318-, where the *salmonicida* residue is listed first and the *hydrophila* residue last (FIG. 52). The *hydrophila* protein is only 317 amino acids long and lacks a residue on position 318. The *Aeromonas salmonicidae* GDSX has considerably high activity on polar lipids such as galactolipid substrates than the *Aeromonas hydrophila* protein. Site scanning was performed on all five amino acid positions.

Amino acid set four=Thr3Ser, Lys182Gln Glu309Ala, Thr310Asn, –318Gly

The Alignments 1 and 2 used to obtain the sets

From the crystal structure one can obtain the secondary structure classification. That means, one can classify each amino acid as being part of an alpha-helix or a beta-sheet. FIG. 50 shows the PFAM alignment of 1DEO, 1IVN, and P10480 (the database *Aeromonas hydrophila*). Added below each line of sequence is the structural classification.

The PFAM database contains alignments of proteins with low sequence identity. Therefore, these alignments are not very good. Although the alignment algorithms (HAMMER profiles) are well suited for recognizing conserved motifs the algorithm is not very good on a detailed level. Therefore it is not surprising to find a disparity between the PFAM alignment and a structural alignment. As a skilled person would be readily aware, one can modify the PFAM alignment based on the structural data. Meaning that one can align those structural elements that overlap.

FIG. 48 shows the original PFAM alignment of 1DEO, 1IVN and P10480. Added to the alignment is the secondary structure information from the crystal structures of 1DEO and 1IVN. Alignment 2 in FIG. 49 shows a manually modified alignment where the match between the secondary structure elements is improved. Based on conserved residues between either 1DEO and P10480 or between 1IVN and P10480 the alignment was modified for P10480 as well. To easily distinguish the sequence blocks the sequence identifiers in alignment 2 have an extra m (1DEOm, 1IVNm, P10480m).

Alignment 3 is a mix of 1 and 2, it gives the alignment per block

EXAMPLE 2

Construction of Site Scan Libraries

The Quick Change Multi Site-Directed Mutagenesis Kit from Stratagene was used according to the manufacturers instruction. For each library a degenerate primer with one NNK or NNS (nucleotide abbreviations) codon was designed. Primer design was performed using the tools available on the Stratagene web site. Primer quality control was further confirmed using standard analysis tools which analyze the primer for the potential of forming hairpins or of forming primer-dimers.

The main concepts of the method are as follows; using a non-strand displacing high-fidelity DNA polymerase such as Pfu-Turbo and a single primer one will linearly amplify the DNA template. This is in contrast to the normal exponential amplification process of a PCR reaction. This linear amplification process ensures a low error frequency. The product is single stranded non-methylated DNA and double stranded hemi-methylated DNA. If the template is obtained from a suitable host organism, then the template is double stranded methylated DNA. This means that the template DNA can be digested with Dpn I endonuclease without digesting the product DNA. Therefore upon transformation of the DNA into a suitable host only a very low frequency of the transformants with non-mutagenized plasmid.

EXAMPLE 3

Selection of Winners From a Site Scan Library

Two alternative approaches are described; library sequencing followed by analysis of unique amino acids, or library analysis followed by sequencing of the winners.

Selection of winners method 1; library sequencing followed by analysis of unique amino acids.

Site scan libraries were constructed using a degenerate oligo containing one NNK codon, where K stands for G or T and N stands for A, C, G, or T. This means that a set of clones constructed from an amplification reaction using an NNK primer (also known as 'a site scan library') contains in principle 32 unique codons (4×4×2=32 combination options). Assuming no bias due, the number of clones that one needs to pick to have a 95% chance of picking every one of the 32 codons at least once is 95. This can be calculated using the following formula $$n=\{\log(1-c)\}/\{\log(1-f)\}$$  Formula 1;

Where n is the number of clones, c is the fraction value of the confidence interval, for example the 95% confidence interval has a value of 0.95 and the 99% confidence interval has a fraction value of 0.99, and f is the frequency with which each individual codon occurs, which for an NNK primer is ⅟32 or 0.03125. Solving the formula for n gives 94.36 or 95 clones. If a 95% confidence interval is deemed to be too low, or if one is unable to avoid bias in one or more steps of the library construction process, one can decide to assay or sequence more clones. For example, in formula 1, if n is set to 384, f to ⅟32 or 0.03125 then the confidence interval c is much larger than 99%. Even if 60% of the clones contain the same mutation or the wild type codon, then 363 clones will give a 99% confidence of obtaining all 32 codons. From this one can conclude that, 384 clones will have a 99% confidence of containing each of the 32 codons at least once.

A colony PCR was performed (a PCR reaction on a bacterial colony or on a bacterial liquid culture to amplify a fragment from a plasmid inside a bacterium, and subsequently sequencing that part of the fragment which has been mutagenised is an established procedure. Colony PCR can be routinely performed for sets of 96 due to the availability of prefabricated material (also known as kits) for colony PCR, sequencing, and sequence purification. This entire procedure is offered as a service by several commercial companies such as AGOWA GmbH, Glienicker weg 185, D-12489 Berlin, Germany.

After analysing the 96 sequence reactions, the individual clones were selected representing one for each codon that is available in the set of 96 sequences. Subsequently, the individual clones were grown and the recombinant protein expressed. The unit activity per quantity of protein in the assays described in Example 4 was performed.

Selection of winners method 2; library screening followed by sequencing of the winners Although one could choose to sequence 384 clones, one may also assay them and select improved variants before sequencing.

A number of issues should be considered when such a number of samples are screened. Without being exhaustive, although it is possible to select variants with altered activity on one substrate, the difference in expression level between 384 cultures can be substantial even if one uses a 384 well microtiter plate, resulting in a high background. Therefore, measuring two activities and selecting winners based on a change in ratio is a preferred method. To illustrate, if two activities have a certain ratio R then regardless of the absolute amount of enzyme present, the ratio between the two activities will always be R. A change in the R value indicates a mutation that changed one activity relative to the second activity.

FIG. 38 shows a data set obtained from the site scan library. The clones are all tested for activity towards phosphatidyl choline (PC) and digalactosyl diglyceride (DGDG). All clones, which can be mutated or not, that exhibit no change in the R value will lie on a straight line with a certain margin of error. Disregarding these clones three groups of interest appear in FIG. 40.

Section 1 in FIG. 40 contains all the clones that have a significantly higher R than the wild-type (not mutated) but lower overall DGDG activity. Section 2 contains those clones that have both a higher R value and a higher DGDG activity than the wild type. Section 3 contains clones that do not have a higher R value, but that do have a significantly higher DGDG or PC activity.

If one is interested in variants with an increased activity towards DGDG then section 2 contains the most interesting variants and section 3 contains variants of interest as well. The variants in Section 3 which show a large increase in hydrolytic activity may be accompanied by a decrease in transferase activity.

One thing is worth noticing, if a specificity determining residue is hit, most of the 20 possible amino acids could yield a very different R value. However, if the library contains a large bias towards a single amino acid (for example 60% is Tyrosine) then all those variants will still lie on a straight line.

EXAMPLE 4

Assays for PC and DGDG Activity in a 384 Well Microtiter Plate

Start Material
EM media
Plate with transformants
Plate with wild type
384 plates
colony picker
Waco NEFA-C kit
PC and DGDG solutions in a 384 plate
Part 1—Picking Colonies
Pick colonies into a 384 plate filled with EM medium
Skip 4 wells and inoculate those with colonies containing the non-mutated backbone
Grow o/n at 30° C., 200 rpm shaking speed
Part 2—Incubation on Substrate
Centrifuge the o/n grown plates; 2500 rpm, 20 min
Transfer 10 µl supernatant from each well to 2 empty 384 plates
Add 5 µl 12.5 mM DGDG to one of the plates, add 5 µl 12.5 mM PC to the other plate
Incubate both plates 2 hrs at 37° C., shake at start to mix then stop the shaking
Continue with the NEFA C procedure
Part 3—NEFA-C Procedure
Add 10 µl A solution
Incubate 10 min 37° C., 300 rpm
Add 20 µl B solution
Incubate 10 min 37° C., 300 rpm
Read the plate at 550 nm
Substrate Composition—in mM
25 mM PC eller DGDG
10 mM $CaCl_2$
60 mM Triton X 100
15 mM $NaN_3$
20 mM Briton Robinson pH 5.0

EXAMPLE 5

Selected Variants

Determination of enzyme activity

To determine the enzymatic activity towards various substrates 4 µl enzyme solution was incubated with 11 µl substrate for 60 minutes at 37° C. Subsequently the amount of free fatty acids was determined using the WACO NEFA-C kit. To the 15 µl enzyme+substrate mix 75 µl NEFA solution A was added and incubated for 15 minutes at 37° C. Subsequently 150 µl NEFA solution B was added and incubated for 15 minutes. Subsequently the optical density (OD) of the sample was measured at 550 nm.

As a control, from each variant 4 µl enzyme solution was incubated with 11 µl HEPES buffer for 60 min at 37° C. Subsequently the amount of free fatty acids was determined as described above. The OD values of this control sample was deducted from the observed OD on each substrate to obtain a corrected activity.

Four different substrates were used, the composition was in general 30 mg lipid, 4.75 ml 50 mM HEPES buffer pH 7, 42.5 µl 0.6 M CaCl2, 200 µl 10% Triton X-100 H202-free. The 30 mg lipid was either phosphatidyl choline (PC), PC with cholesterol in a 9 to 1 ratio, digalactosyl diglyceride (DGDG), or DGDG with cholesterol in a 9 to 1 ratio.

Selection of Improved Variants

Variants with Improved Activity Towards PC

Those variants that showed an increase in the OD relative to the wild type enzyme when incubated on PC were selected as variants with improved phospholipase activity.

Variants with Improved Activity Towards DGDG

Those variants that showed an increase in the OD relative to the wild type enzyme when incubated on DGDG were selected as variants with improved activity towards DGDG.

Variants with Improved Specificity Towards DGDG

The specificity towards DGDG is the ratio between the activity towards DGDG and the activity towards phosphatidylcholine (PC). Those variants that showed a higher ratio between DGDG and PC than the wild type were selected as variants with improved specificity towards DGDG.

Variants with Improved Transferase Activity with PC as the Acyl Donor

The difference in the amount of free fatty acids formed when one incubates an enzyme on PC and on PC with cholesterol is an indication of the amount of transferase activity relative to the amount of hydrolytic activity. Transferase activity will not cause the formation of free fatty acids. The transferase preference is the ratio between the free fatty acids formed when PC is used as a substrate and the free fatty acids formed when PC with cholesterol is used as a substrate. Those variants that show an increase in the transferase preference and show a higher than wild type activity towards PC were selected as having improved transferase activity.

Variants with Improved Transferase Activity with DGDG as the Acyl Donor

The difference in the amount of free fatty acids formed when one incubates an enzyme on DGDG and on DGDG with cholesterol is an indication of the amount of transferase activity relative to the amount of hydrolytic activity. Transferase activity will not cause the formation of free fatty acids. The transferase preference is the ratio between the free fatty acids formed when DGDG is used as a substrate and the free fatty acids formed when DGDG with cholesterol is used as a substrate. Those variants that show an increase in the transferase preference and show a higher than wild type activity towards DGDG were selected as having improved transferase activity.

Selected Variants

For each of the four selection criteria above a number of variants were selected. The "wild type" enzyme in this example is *A. salmonicida* (SEQ ID No. 15). Variants with improved activity towards PC:

|  | PC |
| --- | --- |
| Thr3Asn | 158.0 |
| Thr3Gln | 151.5 |
| Thr3Lys | 141.5 |
| Thr3Arg | 133.0 |
| Glu309Ala | 106.0 |
| Thr3Pro | 101.5 |
| Thr3Met | 96.0 |
| wild-type | 86.5 |

Variants with improved activity towards DGDG:

|  | DGDG |
| --- | --- |
| Lys182Asp | 66.5 |
| Glu309Ala | 60 |
| Tyr230Thr | 59 |
| Tyr230Gly | 57.5 |
| Tyr230Gly | 51 |
| Thr3Gln | 44.5 |
| wild-type | 43.5 |

Variants with improved specificity towards DGDG:

|  | $R_{DGDG/PC}$ | PC | DGDG |
| --- | --- | --- | --- |
| Lys182Asp | 1.02 | 65.5 | 66.5 |
| Tyr230Gly | 0.79 | 72.5 | 57.5 |
| Tyr230Gly | 0.78 | 65.0 | 51.0 |
| Tyr230Thr | 0.75 | 78.5 | 59.0 |
| Tyr230Val | 0.71 | 58.0 | 41.0 |
| Asp157Cys | 0.69 | 48.0 | 33.0 |
| Glu309Pro | 0.58 | 73.5 | 42.5 |
| Glu309Ala | 0.57 | 106.0 | 60.0 |
| Gly318Ile | 0.53 | 69.5 | 36.5 |
| Tyr230Arg | 0.50 | 63.5 | 32.0 |
| Tyr230Met | 0.50 | 64.5 | 32.5 |
| wild-type | 0.50 | 86.5 | 43.5 |

Variants with improved transferase activity with PC as the acyl donor:

|  | $R_{PC+Cho/PC}$ | PC | PC + Cho |
| --- | --- | --- | --- |
| Thr3Lys | 0.54 | 142 | 76 |
| Thr3Arg | 0.55 | 133 | 73 |
| Thr3Gln | 0.63 | 152 | 96 |
| Thr3Asn | 0.64 | 158 | 101 |
| Thr3Pro | 0.67 | 102 | 68 |
| Thr3Met | 0.78 | 96 | 75 |
| wild-type | 0.83 | 87 | 72 |

Variants with improved transferase activity with DGDG as the acyl donor:

|  | $R_{DGDG+Cho/DGDG}$ | DGDG |
| --- | --- | --- |
| Tyr230Thr | 1.10 | 59 |
| Lys182Asp | 1.39 | 67 |
| Tyr230Gly | 1.55 | 58 |
| Glu309Ala | 1.78 | 60 |
| wild-type | 1.78 | 44 |

EXAMPLE 6

Transferase assay Phospholipid:cholesterol

Phospholipid can be replaced by DGDG to provide a transferase assay from a galacolipid. Other acceptors for example, glycerol, glucose, hydroxy acids, proteins or maltose can also be used in the same assay. 300 mg Phosphatidylcholine (Avanti #441601):Cholesterol(Sigma C8503) 9:1 is scaled in a Wheaton glass. 10 ml 50 mM HEPES buffer pH 7.0 is added and stirring at 40° C. disperses the substrate 0.5 ml substrate is transferred to a 4 ml vial and placed in a heating block at 40° C. 0.050 ml transferase solution is added, also a control with 0.050 ml water is analysed in the same way. The reaction mixture is agitated for 4 hours at 40° C. The sample is then frozen and lyophilised and analysed by GLC.

Calculation:

From the GLC analysis the content of free fatty acids and cholesterol ester is calculated.

The enzymatic activity is calculated as:

$$\% \text{ Transferase activity} = \frac{\Delta \% \text{ cholesterol ester}/(Mv \text{ sterol ester}) \times 100}{\Delta \% \text{ cholesterol ester}/(Mv \text{ cholesterol ester}) + \Delta \% \text{ fatty acid}/(Mv \text{ fatty acid})}$$

$$\% \text{ Hydrolyse activity} = \frac{\Delta \% \text{ fatty acid}/(Mv \text{ fatty acid}) \times 100}{\Delta \% \text{ cholesterol ester}/(Mv \text{ cholesterol ester}) + \Delta \% \text{ fatty acid}/(Mv \text{ fatty acid})}$$

Ratio Transferase/Hydrolyse=% transferase activity/% Hydrolyse activity

Where:

Δ% cholesterol ester=% cholesterol ester(sample)−% cholesterol ester(control).

Δ% fatty acid=% fatty acid(sample)−% fatty acid(control).

Transferase assay Galactolipid:cholesterol.

300 mg Digalactosyldiglyceride (>95%, from Wheat lipid):Cholesterol(Sigma) 9:1 is scaled in a Wheaton glass. 10 ml 50 mM HEPES buffer pH 7.0 is added and stirring at 40° C. disperses the substrate.

0.5 ml substrate is transferred to a 4 ml vial and placed in a heating block at 40° C. 0.050 ml transferase solution is added, also a control with 0.050 ml water is analysed in the same way. The reaction mixture is agitated for 4 hours at 40° C. The sample is then frozen and lyophilised and analysed by GLC.

Calculation:
From the GLC analysis the content of free fatty acids and cholesterol ester is calculated.
The enzymatic activity is calculated as:

$$\% \text{ Transferase activity} = \frac{\Delta \% \text{ cholesterol ester}/(Mv \text{ sterol ester}) \times 100}{\Delta \% \text{ cholesterol ester}/(Mv \text{ cholesterol ester}) + \Delta \% \text{ fatty acid}/(Mv \text{ fatty acid})}$$

$$\% \text{ Hydrolyse activity} = \frac{\Delta \% \text{ fatty acid}/(Mv \text{ fatty acid}) \times 100}{\Delta \% \text{ cholesterol ester}/(Mv \text{ cholesterol ester}) + \Delta \% \text{ fatty acid}/(Mv \text{ fatty acid})}$$

Ratio Transferase/Hydrolyse=% transferase activity/% Hydrolyse activity
Where:
Δ% cholesterol ester=% cholesterol ester(sample)–% cholesterol ester(control).
Δ% fatty acid=% fatty acid(sample)–% fatty acid(control)

EXAMPLE 7

Variants of a Lipid Acyltransferase for *Aeromonas hydrophila* (SEQ ID No. 1)

Mutations were introduced using the QuikChange™ Multi-Site Directed Mutagenesis kit from Stratagene, La Jolla, Calif. 92037, USA following the instructions provided by Stratagene.

Variants at Tyr256 showed an increased activity towards phospholipids.

Variants at Tyr256 and Tyr260 showed an increased activity towards galactolipids.

Suitably the variant enzyme may have an enhanced ratio of activity on galactolipids to either phospholipids and/or triglycerides when compared with the parent enzyme.

The term "enhanced activity towards galactolipids" means the enzyme has an enhanced (i.e. higher) hydrolytic activity towards galactolipids and/or an enhanced (i.e. higher) transferase activity wherein the lipid acyl donor is a galactolipid.

Variants at Tyr265 showed an increased transferase activity with galactolipids as the acyl donor.

The numbers indicate positions on the following sequence: An enzyme from *Aeromonas hydrophila* the amino acid sequence of which is shown as SEQ ID No. 1. The nucleotide sequence is as shown as SEQ ID No. 62.

EXAMPLE 8

Expression of KLM3' in *Bacillus licheniformis*

A nucleotide sequence (SEQ ID No. 49) encoding a lipid acyltransferase (SEQ. ID No. 16, hereinafter KLM3') was expressed in *Bacillus licheniformis* as a fusion protein with the signal peptide of *B. licheniformis* [alpha]-amylase (LAT) (see FIGS. 53 and 54). For optimal expression in *Bacillus*, a codon optimized gene construct (no. 052907) was ordered at Geneart (Geneart AG, Regensburg, Germany).

Construct no. 052907 contains an incomplete LAT promoter (only the –10 sequence) in front of the LAT-KLM3' precursor gene and the LAT transcription (Tlat) downstream of the LAT-KLM3' precursor gene (see FIGS. 53 and 55). To create a XhoI fragment that contains the LAT-KLM3' precursor gene flanked by the complete LAT promoter at the 5' end and the LAT terminator at the 3' end, a PCR (polymerase chain reaction) amplification was performed with the primers Plat5XhoI_FW and EBS2XhoI_RV and gene construct 052907 as template.

```
Plat5XhoI_FW:
ccccgctcgaggcttttcttttggaagaaaatatagggaaaatggtactt gttaaaaattcggaatatttatacaatatcatatgtttcacattgaaagg gg EBS2XhoI_RV:
tggaatctcgaggttttatcctttaccttgtctcc
```

PCR was performed on a thermocycler with Phusion High Fidelity DNA polymerase (Finnzymes OY, Espoo, Finland) according to the instructions of the manufacturer (annealing temperature of 55[deg.] C.).

The resulting PCR fragment was digested with restriction enzyme XhoI and ligated with T4 DNA ligase into XhoI digested plCatH according to the instructions of the supplier (Invitrogen, Carlsbad, Calif. USA).

The ligation mixture was transformed into *B. subtilis* strain SC6.1 as described in U.S. Patent Application US20020182734 (International Publication WO 02/14490). The sequence of the XhoI insert containing the LAT-KLM3' precursor gene was confirmed by DNA sequencing (BaseClear, Leiden, The Netherlands) and one of the correct plasmid clones was designated plCatH-KLM3'(ori1) (FIG. 53). plCatH-KLM3'(ori1) was transformed into *B. licheniformis* strain BML780 (a derivative of BRA7 and BML612, see WO2005111203) at the permissive temperature (37[deg.] C.).

One neomycin resistant (neoR) and chloramphenicol resistant (CmR) transformant was selected and designated BML780(plCatH-KLM3'(ori1)). The plasmid in BML780 (plCatH-KLM3'(ori1)) was integrated into the catH region on the *B. licheniformis* genome by growing the strain at a non-permissive temperature (50[deg.] C.) in medium with 5 [mu] g/ml chloramphenicol. One CmR resistant clone was selected and designated BML780-plCatH-KLM3'(ori1). BML780-plCatH- KLM3'(ori1) was grown again at the permissive temperature for several generations without antibiotics to loop-out vector sequences and then one neomycin sensitive (neoS), CmR clone was selected. In this clone, vector sequences of plCatH on the chromosome are excised (including the neomycin resistance gene) and only the catH-LATKLM3' cassette is left. Next, the catH-LATKLM3' cassette on the chromosome was amplified by growing the strain in/on media with increasing concentrations of chloramphenicol. After various rounds of amplification, one clone (resistant against 50 [mu]g/ml chloramphenicol) was selected and designated BML780-KLM3' CAP50. To verify KLM3'expression, BML780-KLM3' CAP50 and BML780 (the empty host strain) were grown for 48 h at 37 [deg.] C. on a Heart Infusion (Bacto) agar plate with 1% tributyrin. A clearing zone, indicative for lipid acyltransferase activity, was clearly visible around the colony of BML780-KLM3' CAP50 but not around the host strain BML780 (see FIG. 56). This result shows that a substantial amount of KLM3' is expressed in *B. licheniformis* strain BML780-KLM3' CAP50 and that these KLM3' molecules are functional.

COMPARATIVE EXAMPLE 9

Vector Construct

The plasmid construct is pCS32new N80D, which is a pCCmini derivative carrying the sequence encoding the mature form of the native *Aeromonas salmonicida* Glycerophospholipid-cholesterol acyltransferase with a Asn to Asp substitution at position 80 (KLM3'), under control of the p32 promoter and with a CGTase signal sequence.

The host strain used for the expression, is in the *bacillus subtilis* OS21ΔAprE strain The expression level is measured as transferase activity, expressed as % cholesterol esterified, calculated from the difference in free cholesterol in the reference sample and free cholesterol in the enzyme sample in reactions with PC ($T_{PC}$) as donor and cholesterol as acceptor molecule.

Culture Conditions 5 ml of LB broth (Casein enzymatic digest, 10 g/l; low-sodium Yeast extract, 5 g/l; Sodium Chloride, 5 g/l; Inert tableting aids, 2 g/l) supplemented with 50 mg/l kanamycin, was inoculated with a single colony and incubated at 30° C. for 6 hours at 205 rpm. 0.7 ml of this culture was used to inoculate 50 ml of SAS media ($K_2HPO_4$, 10 g/l; MOPS (3-morpholinopropane sulfonic acid), 40 g/l; Sodium Chloride, 5 g/l; Antifoam (Sin 260), 5 drops/l; Soy flour degreased, 20 g/l; Biospringer 106 (100% dw YE), 20 g/l) supplemented with 50 mg/l kanamycin and a solution of high maltose starch hydrolysates (60 g/l). Incubation was continued for 40 hours at 30° C. and 180 rpm before the culture supernatant was separated by centrifugation at 19000 rpm for 30 min. The supernatant was transferred into a clean tube and directly used for transferase activity measurement.

Preparation of Substrates and Enzymatic Reaction

PC (Avanti Polar Lipids #441601) and cholesterol (Sigma C8503) was scaled in the ratio 9:1, dissolved in chloroform, and evaporated to dryness.

The substrate was prepared by dispersion of 3% PC:Cholesterol 9:1 in 50 mM Hepes buffer pH 7.

0.250 ml substrate solution was transferred into a 3 ml glass tube with screw lid. 0.025 ml culture supernatant was added and the mixture was incubated at 40° C. for 2 hours. A reference sample with water instead of enzyme was also prepared. Heating the reaction mixture in a boiling water bath for 10 minutes stopped the enzyme reaction. 2 ml of 99% ethanol was added to the reaction mixture before submitted to cholesterol assay analysis.

Cholesterol Assay

100 μl substrate containing 1.4 U/ml Cholesterol oxidase( SERVA Electrophoresis GmbH cat. No 17109), 0.4 mg/ml ABTS (Sigma A-1888), 6 U/ml Peroxidase (Sigma 6782) in 0.1 M Tris-HCl, pH 6.6 and 0.5% Triton X-100 (Sigma X-100) was incubated at 37° C. for 5 minutes before 5 μl enzyme reaction sample was added and mixed. The reaction mixture was incubated for further 5 minutes and $OD_{405}$ was measured. The content of cholesterol was calculated from the analyses of standard solutions of cholesterol containing 0.4 mg/ml, 0.3 mg/ml, 0.20 mg/ml, 0.1 mg/ml, 0.05 mg/ml, and 0 mg/ml cholesterol in 99% EtOH.

Results

The table shows the average of 8 separate expression cultures

| Strain | $T_{PC}{}^{a}$ |
|---|---|
| OS21ΔAprE[pCS32new] | $74.2 \pm 10.1^{b}$ |

[a]$T_{PC}$ is the transferase activity, expressed as % cholesterol esterified, calculated from the difference in free cholesterol in the reference sample and free cholesterol in the enzyme sample in reactions with PC as donor molecule and cholesterol as acceptor molecule.
[b]Average of 8 separate expression cultures All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An isolated lipid acyltransferase comprising: the amino acid sequence of SEQ ID No. 16.

2. The isolated lipid acyltransferase of claim 1, wherein the amino acid sequence undergoes post-translational modification.

3. The isolated lipid acyltransferase of claim 2, wherein the post-translational modification is a truncation.

4. The isolated lipid acyltransferase of claim 2, wherein the post-translational modification comprises removal of amino acids from position 235 to position 273 of SEQ ID No. 16.

5. An isolated lipid acyltransferase comprising:
(i) the amino acid sequence of SEQ ID No. 70; or
(ii) an amino acid sequence having at least 90% identity to SEQ ID No. 70 along its full length;
wherein the amino acid sequence possesses acyltransferase activity, and wherein the amino acid sequence contains the motif GDSX, wherein X is one of amino acid residues L, A, V, I, F, Y, H, Q, T, N, M or S.

6. The isolated lipid acyltransferase of claim 5, wherein the amino acid sequence has at least 95% identity to SEQ ID No. 70.

7. The isolated lipid acyltransferase of claim 5, wherein the amino acid sequence has at least 98% identity to SEQ ID No. 70.

8. The isolated lipid acyltransferase of claim 5, wherein the amino acid sequence is SEQ ID No. 70.

9. The isolated lipid acyltransferase of claim 5, wherein X is L or Y.

10. The isolated lipid acyltransferase of claim 5, wherein X is L.

11. A method of preparing a lyso-glycolipid comprising treating a foodstuff or an oil comprising a glycolipid with the lipid acyltransferase of claim 1, thereby preparing a lyso-glycolipid.

12. The method of claim 11, wherein the lyso-glycolipid is digalactosyl monoglyceride (DGMG) and the glycolipid is digalactosyl diglyceride (DGDG).

13. The method of claim 11, wherein the lyso-glycolipid is monogalactosyl monoglyceride (MGMG) and the glycolipid is monogalactosyl diglyceride (MGDG).

14. The method of claim 11, wherein the foodstuff is a dough.

15. The method of claim 11, wherein the foodstuff is or comprises an egg.

16. The method of claim 11, wherein an oil is treated with the lipid acyltransferase.

17. The method of claim 16, wherein the method is a degumming process.

18. A method of preparing a lyso-glycolipid comprising treating a foodstuff or an oil comprising a glycolipid with the lipid acyltransferase of claim 5, thereby preparing a lyso-glycolipid.

19. The method of claim 18, wherein the lyso-glycolipid is digalactosyl monoglyceride (DGMG) and the glycolipid is digalactosyl diglyceride (DGDG).

20. The method of claim 18, wherein the lyso-glycolipid is monogalactosyl monoglyceride (MGMG) and the glycolipid is monogalactosyl diglyceride (MGDG).

21. The method of claim 18, wherein the foodstuff is a dough.

22. The method of claim 18, wherein the foodstuff is or comprises an egg.

23. The method of claim 18, wherein an oil is treated with the lipid acyltransferase.

24. The method of claim 23, wherein the method is a degumming process.

* * * * *

SEQUENCE LISTING

```
<160> NUMBER OF SEQ ID NOS: 91

<210> SEQ ID NO 1
<211> LENGTH: 335
<212> TYPE: PRT
<213> ORGANISM: Aeromonas hydrophila

<400> SEQUENCE: 1

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
```

```
                    85                  90                  95
Trp Asn Pro Lys Tyr Gln Val Ile Asn Asn Leu Asp Tyr Glu Val Thr
            100                 105                 110
Gln Phe Leu Gln Lys Asp Ser Phe Lys Pro Asp Asp Leu Val Ile Leu
            115                 120                 125
Trp Val Gly Ala Asn Asp Tyr Leu Ala Tyr Gly Trp Asn Thr Glu Gln
            130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
                180                 185                 190
His Val Ser Ala Tyr His Asn Gln Leu Leu Leu Asn Leu Ala Arg Gln
                195                 200                 205
Leu Ala Pro Thr Gly Met Val Lys Leu Phe Glu Ile Asp Lys Gln Phe
            210                 215                 220
Ala Glu Met Leu Arg Asp Pro Gln Asn Phe Gly Leu Ser Asp Val Glu
225                 230                 235                 240
Asn Pro Cys Tyr Asp Gly Gly Tyr Val Trp Lys Pro Phe Ala Thr Arg
                245                 250                 255
Ser Val Ser Thr Asp Arg Gln Leu Ser Ala Phe Ser Pro Gln Glu Arg
                260                 265                 270
Leu Ala Ile Ala Gly Asn Pro Leu Leu Ala Gln Ala Val Ala Ser Pro
                275                 280                 285
Met Ala Arg Arg Ser Ala Ser Pro Leu Asn Cys Glu Gly Lys Met Phe
            290                 295                 300
Trp Asp Gln Val His Pro Thr Thr Val Val His Ala Ala Leu Ser Glu
305                 310                 315                 320
Arg Ala Ala Thr Phe Ile Ala Asn Gln Tyr Glu Phe Leu Ala His
                325                 330                 335

<210> SEQ ID NO 2
<211> LENGTH: 361
<212> TYPE: PRT
<213> ORGANISM: Unknown
<220> FEATURE:
<223> OTHER INFORMATION: Description of Unknown: pfam00657 consensus
      sequence

<400> SEQUENCE: 2

Ile Val Ala Phe Gly Asp Ser Leu Thr Asp Gly Glu Ala Tyr Tyr Gly
1               5                   10                  15
Asp Ser Asp Gly Gly Gly Trp Gly Ala Gly Leu Ala Asp Arg Leu Thr
                20                  25                  30
Ala Leu Leu Arg Leu Arg Ala Arg Pro Arg Gly Val Asp Val Phe Asn
            35                  40                  45
Arg Gly Ile Ser Gly Arg Thr Ser Asp Gly Arg Leu Ile Val Asp Ala
        50                  55                  60
Leu Val Ala Leu Leu Phe Leu Ala Gln Ser Leu Gly Leu Pro Asn Leu
65                  70                  75                  80
Pro Pro Tyr Leu Ser Gly Asp Phe Leu Arg Gly Ala Asn Phe Ala Ser
                85                  90                  95
Ala Gly Ala Thr Ile Leu Pro Thr Ser Gly Pro Phe Leu Ile Gln Val
            100                 105                 110
Gln Phe Lys Asp Phe Lys Ser Gln Val Leu Glu Leu Arg Gln Ala Leu
```

```
            115                 120                 125
Gly Leu Leu Gln Glu Leu Leu Arg Leu Leu Pro Val Leu Asp Ala Lys
    130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
                165                 170                 175

Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
        195                 200                 205

Asn Leu Gly Pro Leu Gly Cys Leu Pro Leu Lys Leu Ala Leu Ala Leu
    210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
        275                 280                 285

Gly Ile Gln Asn Pro Ser Ala Tyr Val Tyr Gly Phe Glu Thr Thr Lys
    290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
            340                 345                 350

Gly Tyr Lys Ala Val Ala Glu Ala Leu
        355                 360

<210> SEQ ID NO 3
<211> LENGTH: 335
<212> TYPE: PRT
<213> ORGANISM: Aeromonas hydrophila

<400> SEQUENCE: 3

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
```

```
            130                 135                 140
Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Asn Leu Ala Arg Gln
                195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
                275                 280                 285

Met Ala Arg Ser Ala Ser Thr Leu Asn Cys Glu Gly Lys Met Phe
290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 4
<211> LENGTH: 336
<212> TYPE: PRT
<213> ORGANISM: Aeromonas salmonicida

<400> SEQUENCE: 4

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
```

```
                         180                 185                 190
His Val Ser Ala Tyr His Asn Lys Leu Leu Asn Leu Ala Arg Gln
            195                 200                 205
Leu Ala Pro Thr Gly Met Val Lys Leu Phe Glu Ile Asp Lys Gln Phe
            210                 215                 220
Ala Glu Met Leu Arg Asp Pro Gln Asn Phe Gly Leu Ser Asp Val Glu
225                 230                 235                 240
Asn Pro Cys Tyr Asp Gly Gly Tyr Val Trp Lys Pro Phe Ala Thr Arg
            245                 250                 255
Ser Val Ser Thr Asp Arg Gln Leu Ser Ala Phe Ser Pro Gln Glu Arg
            260                 265                 270
Leu Ala Ile Ala Gly Asn Pro Leu Leu Ala Gln Ala Val Ala Ser Pro
            275                 280                 285
Met Ala Arg Arg Ser Ala Ser Pro Leu Asn Cys Glu Gly Lys Met Phe
            290                 295                 300
Trp Asp Gln Val His Pro Thr Thr Val Val His Ala Ala Leu Ser Glu
305                 310                 315                 320
Arg Ala Ala Thr Phe Ile Glu Thr Gln Tyr Glu Phe Leu Ala His Gly
            325                 330                 335

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
1               5                   10                  15
Val Gly Thr Leu Ala Leu Gly Leu Thr Asp Ala Thr Ala His Ala Ala
            20                  25                  30
Pro Ala Gln Ala Thr Pro Thr Leu Asp Tyr Val Ala Leu Gly Asp Ser
            35                  40                  45
Tyr Ser Ala Gly Ser Gly Val Leu Pro Val Asp Pro Ala Asn Leu Leu
        50                  55                  60
Cys Leu Arg Ser Thr Ala Asn Tyr Pro His Val Ile Ala Asp Thr Thr
65                  70                  75                  80
Gly Ala Arg Leu Thr Asp Val Thr Cys Gly Ala Ala Gln Thr Ala Asp
                85                  90                  95
Phe Thr Arg Ala Gln Tyr Pro Gly Val Ala Pro Gln Leu Asp Ala Leu
            100                 105                 110
Gly Thr Gly Thr Asp Leu Val Thr Leu Thr Ile Gly Gly Asn Asp Asn
            115                 120                 125
Ser Thr Phe Ile Asn Ala Ile Thr Ala Cys Gly Thr Ala Gly Val Leu
        130                 135                 140
Ser Gly Gly Lys Gly Ser Pro Cys Lys Asp Arg His Gly Thr Ser Phe
145                 150                 155                 160
Asp Asp Glu Ile Glu Ala Asn Thr Tyr Pro Ala Leu Lys Glu Ala Leu
                165                 170                 175
Leu Gly Val Arg Ala Arg Ala Pro His Ala Arg Val Ala Ala Leu Gly
            180                 185                 190
Tyr Pro Trp Ile Thr Pro Ala Thr Ala Asp Pro Ser Cys Phe Leu Lys
            195                 200                 205
Leu Pro Leu Ala Ala Gly Asp Val Pro Tyr Leu Arg Ala Ile Gln Ala
        210                 215                 220
His Leu Asn Asp Ala Val Arg Arg Ala Ala Glu Glu Thr Gly Ala Thr
```

```
                225                 230                 235                 240
Tyr Val Asp Phe Ser Gly Val Ser Asp Gly His Asp Ala Cys Glu Ala
                    245                 250                 255
Pro Gly Thr Arg Trp Ile Glu Pro Leu Leu Phe Gly His Ser Leu Val
                260                 265                 270
Pro Val His Pro Asn Ala Leu Gly Glu Arg Arg Met Ala Glu His Thr
            275                 280                 285
Met Asp Val Leu Gly Leu Asp
        290                 295

<210> SEQ ID NO 6
<211> LENGTH: 295
<212> TYPE: PRT
<213> ORGANISM: Streptomyces coelicolor

<400> SEQUENCE: 6

Met Pro Lys Pro Ala Leu Arg Arg Val Met Thr Ala Thr Val Ala Ala
1               5                   10                  15
Val Gly Thr Leu Ala Leu Gly Leu Thr Asp Ala Thr Ala His Ala Ala
                20                  25                  30
Pro Ala Gln Ala Thr Pro Thr Leu Asp Tyr Val Ala Leu Gly Asp Ser
            35                  40                  45
Tyr Ser Ala Gly Ser Gly Val Leu Pro Val Asp Pro Ala Asn Leu Leu
        50                  55                  60
Cys Leu Arg Ser Thr Ala Asn Tyr Pro His Val Ile Ala Asp Thr Thr
65                  70                  75                  80
Gly Ala Arg Leu Thr Asp Val Thr Cys Gly Ala Ala Gln Thr Ala Asp
                85                  90                  95
Phe Thr Arg Ala Gln Tyr Pro Gly Val Ala Pro Gln Leu Asp Ala Leu
            100                 105                 110
Gly Thr Gly Thr Asp Leu Val Thr Leu Thr Ile Gly Gly Asn Asp Asn
        115                 120                 125
Ser Thr Phe Ile Asn Ala Ile Thr Ala Cys Gly Thr Ala Gly Val Leu
    130                 135                 140
Ser Gly Gly Lys Gly Ser Pro Cys Lys Asp Arg His Gly Thr Ser Phe
145                 150                 155                 160
Asp Asp Glu Ile Glu Ala Asn Thr Tyr Pro Ala Leu Lys Glu Ala Leu
                165                 170                 175
Leu Gly Val Arg Ala Arg Ala Pro His Ala Arg Val Ala Ala Leu Gly
            180                 185                 190
Tyr Pro Trp Ile Thr Pro Ala Thr Ala Asp Pro Ser Cys Phe Leu Lys
        195                 200                 205
Leu Pro Leu Ala Ala Gly Asp Val Pro Tyr Leu Arg Ala Ile Gln Ala
    210                 215                 220
His Leu Asn Asp Ala Val Arg Arg Ala Ala Glu Glu Thr Gly Ala Thr
225                 230                 235                 240
Tyr Val Asp Phe Ser Gly Val Ser Asp Gly His Asp Ala Cys Glu Ala
                    245                 250                 255
Pro Gly Thr Arg Trp Ile Glu Pro Leu Leu Phe Gly His Ser Leu Val
                260                 265                 270
Pro Val His Pro Asn Ala Leu Gly Glu Arg Arg Met Ala Glu His Thr
            275                 280                 285
Met Asp Val Leu Gly Leu Asp
        290                 295
```

<210> SEQ ID NO 7
<211> LENGTH: 238
<212> TYPE: PRT
<213> ORGANISM: Saccharomyces cerevisiae

<400> SEQUENCE: 7

```
Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Ile Gly Pro Gly Leu Val Asp Arg Glu Lys
        115                 120                 125

Trp Glu Lys Glu Lys Ser Glu Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235
```

<210> SEQ ID NO 8
<211> LENGTH: 347
<212> TYPE: PRT
<213> ORGANISM: Ralstonia solanacearum

<400> SEQUENCE: 8

```
Met Asn Leu Arg Gln Trp Met Gly Ala Ala Thr Ala Ala Leu Ala Leu
1               5                   10                  15

Gly Leu Ala Ala Cys Gly Gly Gly Gly Thr Asp Gln Ser Gly Asn Pro
            20                  25                  30

Asn Val Ala Lys Val Gln Arg Met Val Val Phe Gly Asp Ser Leu Ser
        35                  40                  45

Asp Ile Gly Thr Tyr Thr Pro Val Ala Gln Ala Val Gly Gly Gly Lys
    50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95

Gln Asn Cys Pro Lys Ala Gly Cys Phe Asp Tyr Ala Gln Gly Gly Ser
            100                 105                 110
```

Arg Val Thr Asp Pro Asn Gly Ile Gly His Asn Gly Gly Ala Gly Ala
            115                 120                 125

Leu Thr Tyr Pro Val Gln Gln Gln Leu Ala Asn Phe Tyr Ala Ala Ser
            130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Ala Thr Ser Gly Ser
                165                 170                 175

Gly Val Thr Pro Ala Ile Ala Thr Ala Gln Val Gln Gln Ala Ala Thr
            180                 185                 190

Asp Leu Val Gly Tyr Val Lys Asp Met Ile Ala Lys Gly Ala Thr Gln
            195                 200                 205

Val Tyr Val Phe Asn Leu Pro Asp Ser Ser Leu Thr Pro Asp Gly Val
            210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
            260                 265                 270

Phe Gly Phe Ala Asn Thr Ser Ala Arg Ala Cys Asp Ala Thr Lys Ile
            275                 280                 285

Asn Ala Leu Val Pro Ser Ala Gly Gly Ser Ser Leu Phe Cys Ser Ala
            290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
            340                 345

<210> SEQ ID NO 9
<211> LENGTH: 335
<212> TYPE: PRT
<213> ORGANISM: Aeromonas salmonicida

<400> SEQUENCE: 9

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
            50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
            115                 120                 125

Trp Val Gly Ala Asn Asp Tyr Leu Ala Tyr Gly Trp Asn Thr Glu Gln
            130                 135                 140

```
Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
            165                 170                 175

Gly Gln Asn Pro Ser Ala Arg Ser Gln Lys Val Val Glu Ala Val Ser
        180                 185                 190

His Val Ser Ala Tyr His Asn Lys Leu Leu Asn Leu Ala Arg Gln
    195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His
                325                 330                 335

<210> SEQ ID NO 10
<211> LENGTH: 260
<212> TYPE: PRT
<213> ORGANISM: Streptomyces coelicolor

<400> SEQUENCE: 10

Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
        35                  40                  45

Arg Tyr Ala Asn Leu Ala Val Arg Gly Lys Leu Ile Gly Gln Ile Val
    50                  55                  60

Asp Glu Gln Val Asp Val Ala Ala Ala Met Gly Ala Asp Val Ile Thr
65                  70                  75                  80

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
            180                 185                 190
```

```
Gly His Glu Pro Glu Asp Pro Glu Trp His Ala Pro Ile Pro Ala Thr
            195                 200                 205

Pro Pro Pro Gly Trp Val Thr Arg Arg Thr Ala Asp Val Arg Phe Ala
210                 215                 220

Arg Gln His Leu Leu Pro Trp Ile Gly Arg Arg Leu Thr Gly Arg Ser
225                 230                 235                 240

Ser Gly Asp Gly Leu Pro Ala Lys Arg Pro Asp Leu Leu Pro Tyr Glu
            245                 250                 255

Asp Pro Ala Arg
            260

<210> SEQ ID NO 11
<211> LENGTH: 454
<212> TYPE: PRT
<213> ORGANISM: Streptomyces coelicolor

<400> SEQUENCE: 11

Met Thr Arg Gly Arg Asp Gly Gly Ala Gly Ala Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
        35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Ala Glu
65                  70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
            100                 105                 110

Leu Tyr Gly Gln Ser Pro Leu Thr Val Thr His Ala Ser Ile Ala Leu
        115                 120                 125

Ala Ala Gly Pro Asp Thr Ala Ala Ile Ala Asp Thr Met Arg Arg
    130                 135                 140

Leu Thr Phe Gly Gly Ser Ala Arg Val Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
        195                 200                 205

Asp Val Thr Ala Val Ala Tyr Thr Thr Pro Thr Pro Tyr Trp Arg Tyr
    210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
                245                 250                 255

Asn His Arg Trp Thr Asp Val Leu Ala Ala Arg Leu His Glu Ala Ala
            260                 265                 270

Gly Asp Gly Arg Asp Thr Pro Arg Tyr Ser Val Val Asn Glu Gly Ile
        275                 280                 285

Ser Gly Asn Arg Leu Leu Thr Ser Arg Pro Gly Arg Pro Ala Asp Asn
    290                 295                 300
```

```
Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
            325                 330                 335

Pro Glu Leu Ala Asp Arg Asp Ala Ile Leu Thr Gly Leu Arg Thr Leu
                340                 345                 350

Val Asp Arg Ala His Ala Arg Gly Leu Arg Val Val Gly Ala Thr Ile
                355                 360                 365

Thr Pro Phe Gly Gly Tyr Gly Gly Tyr Thr Glu Ala Arg Glu Thr Met
        370                 375                 380

Arg Gln Glu Val Asn Glu Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415

Met Arg Ser Asp Tyr Asp Ser Gly Asp His Leu His Pro Gly Asp Lys
                420                 425                 430

Gly Tyr Ala Arg Met Gly Ala Val Ile Asp Leu Ala Ala Leu Lys Gly
                435                 440                 445

Ala Ala Pro Val Lys Ala
        450

<210> SEQ ID NO 12
<211> LENGTH: 340
<212> TYPE: PRT
<213> ORGANISM: Streptomyces coelicolor

<400> SEQUENCE: 12

Met Thr Ser Met Ser Arg Ala Arg Val Ala Arg Arg Ile Ala Ala Gly
1               5                   10                  15

Ala Ala Tyr Gly Gly Gly Gly Ile Gly Leu Ala Gly Ala Ala Ala Val
                20                  25                  30

Gly Leu Val Val Ala Glu Val Gln Leu Ala Arg Arg Arg Val Gly Val
            35                  40                  45

Gly Thr Pro Thr Arg Val Pro Asn Ala Gln Gly Leu Tyr Gly Gly Thr
        50                  55                  60

Leu Pro Thr Ala Gly Asp Pro Leu Arg Leu Met Met Leu Gly Asp
65                  70                  75                  80

Ser Thr Ala Ala Gly Gln Gly Val His Arg Ala Gly Gln Thr Pro Gly
                85                  90                  95

Ala Leu Leu Ala Ser Gly Leu Ala Val Ala Glu Arg Pro Val Arg
                100                 105                 110

Leu Gly Ser Val Ala Gln Pro Gly Ala Cys Ser Asp Asp Leu Asp Arg
            115                 120                 125

Gln Val Ala Leu Val Leu Ala Glu Pro Asp Arg Val Pro Asp Ile Cys
130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Leu Arg Thr Ala
                165                 170                 175

Gly Ala Glu Val Val Gly Thr Cys Pro Asp Leu Gly Thr Ile Glu
                180                 185                 190

Arg Val Arg Gln Pro Leu Arg Trp Leu Ala Arg Ala Ser Arg Gln
            195                 200                 205

Leu Ala Ala Ala Gln Thr Ile Gly Ala Val Glu Gln Gly Gly Arg Thr
210                 215                 220
```

```
Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala
            245                 250                 255

Thr Ala Ala Met Ala Val Leu Pro Ser Val Cys Ala Ala Leu Gly Leu
                260                 265                 270

Trp Pro Ala Asp Glu Glu His Pro Asp Ala Leu Arg Arg Glu Gly Phe
            275                 280                 285

Leu Pro Val Ala Arg Ala Ala Glu Ala Ala Ser Glu Ala Gly Thr
        290                 295                 300

Glu Val Ala Ala Ala Met Pro Thr Gly Pro Arg Gly Pro Trp Ala Leu
305                 310                 315                 320

Leu Lys Arg Arg Arg Arg Arg Val Ser Glu Ala Gly Pro Ser Ser
                325                 330                 335

Pro Ser Gly Val
            340

<210> SEQ ID NO 13
<211> LENGTH: 305
<212> TYPE: PRT
<213> ORGANISM: Streptomyces coelicolor

<400> SEQUENCE: 13

Met Gly Arg Gly Thr Asp Gln Arg Thr Arg Tyr Gly Arg Arg Arg Ala
1               5                   10                  15

Arg Val Ala Leu Ala Ala Leu Thr Ala Ala Val Leu Gly Val Gly Val
                20                  25                  30

Ala Gly Cys Asp Ser Val Gly Gly Asp Ser Pro Ala Pro Ser Gly Ser
            35                  40                  45

Pro Ser Lys Arg Thr Arg Thr Ala Pro Ala Trp Asp Thr Ser Pro Ala
        50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
                85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255
```

```
Arg Arg Cys Arg Ser Asp Asp Gly Ala Val His Glu Phe Arg Phe Gly
            260                 265                 270

Thr Asp Gln Leu Ser His Trp Asp Trp Phe His Pro Ser Val Asp Gly
            275                 280                 285

Gln Ala Arg Leu Ala Glu Ile Ala Tyr Arg Ala Val Thr Ala Lys Asn
            290                 295                 300

Pro
305

<210> SEQ ID NO 14
<211> LENGTH: 268
<212> TYPE: PRT
<213> ORGANISM: Streptomyces rimosus

<400> SEQUENCE: 14

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
            35                  40                  45

Val Gly Ala Gly Ser Tyr Asp Ser Ser Gly Ser Cys Lys Arg Ser
    50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
            115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Val Leu Gly Tyr Pro
                165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Ala Asp Asp Ile Asn Ala Val Thr
    195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
    260                 265

<210> SEQ ID NO 15
<211> LENGTH: 336
<212> TYPE: PRT
<213> ORGANISM: Aeromonas salmonicida

<400> SEQUENCE: 15
```

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 16
<211> LENGTH: 318
<212> TYPE: PRT
<213> ORGANISM: Aeromonas salmonicida

<400> SEQUENCE: 16

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Tyr Tyr Glu Gly Arg Phe Ser Asn Gly Pro Val Trp
        35                  40                  45

```
Leu Glu Gln Leu Thr Lys Gln Phe Pro Gly Leu Thr Ile Ala Asn Glu
 50                  55                  60

Ala Glu Gly Gly Ala Thr Ala Val Ala Tyr Asn Lys Ile Ser Trp Asp
 65                  70                  75                  80

Pro Lys Tyr Gln Val Ile Asn Asn Leu Asp Tyr Glu Val Thr Gln Phe
                 85                  90                  95

Leu Gln Lys Asp Ser Phe Lys Pro Asp Leu Val Ile Leu Trp Val
            100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
                180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
                260                 265                 270

Arg Arg Ser Ala Ser Pro Leu Asn Cys Glu Gly Lys Met Phe Trp Asp
                275                 280                 285

Gln Val His Pro Thr Thr Val Val His Ala Ala Leu Ser Glu Arg Ala
            290                 295                 300

Ala Thr Phe Ile Glu Thr Gln Tyr Glu Phe Leu Ala His Gly
305                 310                 315

<210> SEQ ID NO 17
<211> LENGTH: 465
<212> TYPE: PRT
<213> ORGANISM: Candida parapsilosis

<400> SEQUENCE: 17

Met Arg Tyr Phe Ala Ile Ala Phe Leu Leu Ile Asn Thr Ile Ser Ala
 1               5                  10                  15

Phe Val Leu Ala Pro Lys Lys Pro Ser Gln Asp Asp Phe Tyr Thr Pro
                20                  25                  30

Pro Gln Gly Tyr Glu Ala Gln Pro Leu Gly Ser Ile Leu Lys Thr Arg
            35                  40                  45

Asn Val Pro Asn Pro Leu Thr Asn Val Phe Thr Pro Val Lys Val Gln
 50                  55                  60

Asn Ala Trp Gln Leu Leu Val Arg Ser Glu Asp Thr Phe Gly Asn Pro
 65                  70                  75                  80

Asn Ala Ile Val Thr Thr Ile Ile Gln Pro Phe Asn Ala Lys Lys Asp
                 85                  90                  95

Lys Leu Val Ser Tyr Gln Thr Phe Glu Asp Ser Gly Leu Asp Cys
            100                 105                 110
```

```
Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe
465

<210> SEQ ID NO 18
<211> LENGTH: 471
<212> TYPE: PRT
<213> ORGANISM: Candida parapsilosis

<400> SEQUENCE: 18

Met Arg Tyr Phe Ala Ile Ala Phe Leu Leu Ile Asn Thr Ile Ser Ala
1               5                   10                  15
```

-continued

```
Phe Val Leu Ala Pro Lys Lys Pro Ser Gln Asp Asp Phe Tyr Thr Pro
            20              25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
50                      55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
                100                 105                 110

Ala Pro Ser Tyr Ala Ile Gln Tyr Gly Ser Asp Ile Ser Thr Leu Thr
            115                 120                 125

Thr Gln Gly Glu Met Tyr Tyr Ile Ser Ala Leu Leu Asp Gln Gly Tyr
130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
                180                 185                 190

Trp Gly Tyr Ser Gly Gly Ser Leu Ala Ser Gly Trp Ala Ala Ala Ile
            195                 200                 205

Gln Lys Glu Tyr Ala Pro Glu Leu Ser Lys Asn Leu Leu Gly Ala Ala
            210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
            275                 280                 285

Gly Gly Ile Ala Tyr Phe Gly Lys Ser Phe Phe Ser Arg Ile Ile Arg
290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
            355                 360                 365

Lys Ser Gly Glu Tyr Asn Glu Asp Leu Thr Asn Gly His Ile Thr Glu
            370                 375                 380

Ser Ile Val Gly Ala Pro Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
            435                 440                 445
```

Arg Asp Lys Val Thr Leu Gly Gly Leu Leu Lys Leu Glu Arg Phe Ala
    450                 455                 460

Phe His His His His His
465                 470

<210> SEQ ID NO 19
<211> LENGTH: 261
<212> TYPE: PRT
<213> ORGANISM: Streptomyces coelicolor

<400> SEQUENCE: 19

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 20

<400> SEQUENCE: 20

000

<210> SEQ ID NO 21
<211> LENGTH: 18
<212> TYPE: PRT
<213> ORGANISM: Bacillus licheniformis

<400> SEQUENCE: 21

```
Met Lys Lys Trp Phe Val Cys Leu Leu Gly Leu Ile Ala Leu Thr Val
1               5                   10                  15

Gln Ala

<210> SEQ ID NO 22
<211> LENGTH: 29
<212> TYPE: PRT
<213> ORGANISM: Bacillus subtilis

<400> SEQUENCE: 22

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 23
<211> LENGTH: 29
<212> TYPE: PRT
<213> ORGANISM: Bacillus licheniformis

<400> SEQUENCE: 23

Met Met Arg Lys Lys Ser Phe Trp Phe Gly Met Leu Thr Ala Phe Met
1               5                   10                  15

Leu Val Phe Thr Met Glu Phe Ser Asp Ser Ala Ser Ala
            20                  25

<210> SEQ ID NO 24
<211> LENGTH: 1047
<212> TYPE: DNA
<213> ORGANISM: Aeromonas hydrophila

<400> SEQUENCE: 24
atgtttaagt ttaaaaagaa tttcttagtt ggattatcgg cagctttaat gagtattagc      60
ttgttttcgg caaccgcctc tgcagctagc gccgacagcc gtcccgcctt tcccggatc     120
gtgatgttcg cgacagcct ctccgatacc ggcaaaatgt acagcaagat gcgcggttac     180
ctcccctcca gcccgcccta ctatgagggc cgtttctcca acggacccgt ctggctggag     240
cagctgacca aacagttccc gggtctgacc atcgccaacg aagcggaagg cggtgccact     300
gccgtggctt acaacaagat ctcctggaat cccaagtatc aggtcatcaa caacctggac     360
tacgaggtca cccagttctt gcagaaagac agcttcaagc cggacgatct ggtgatcctc     420
tgggtcggtg ccaatgacta tctggcctat ggctggaaca cggagcagga tgccaagcgg     480
gttcgcgatg ccatcagcga tgcggccaac cgcatggtac tgaacggtgc caagcagata     540
ctgctgttca acctgccgga tctgggccag aaccccgtcag ctcgcagtca gaaggtggtc     600
gaggcggtca gccatgtctc cgcctatcac aaccagctgc tgctgaacct ggcacgccag     660
ctggcccca ccggcatggt aaagctgttc gagatcgaca gcaatttgc cgagatgctg     720
cgtgatccgc agaacttcgg cctgagcgac gtcgagaacc cctgctacga cggcggctat     780
gtgtggaagc cgtttgccac ccgcagcgtc agcaccgacc gccagctctc cgccttcagt     840
ccgcaggaac gcctcgccat cgccggcaac ccgctgctgg cacaggccgt tgccagtcct     900
atggcccgcc gcagcgccag ccccctcaac tgtgagggca agtgttctg ggatcaggta     960
cacccgacca ctgtcgtgca cgcagccctg agcgagcgcg ccgccacctt catcgcgaac    1020
cagtacgagt cctcgcccca ctgatga                                       1047

<210> SEQ ID NO 25
```

```
<211> LENGTH: 347
<212> TYPE: PRT
<213> ORGANISM: Aeromonas hydrophila

<400> SEQUENCE: 25

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
        35                  40                  45

Asp Thr Gly Lys Met Tyr Ser Lys Met Arg Gly Tyr Leu Pro Ser Ser
    50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
        115                 120                 125

Lys Asp Ser Phe Lys Pro Asp Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255

Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
    290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
            340                 345

<210> SEQ ID NO 26
<211> LENGTH: 267
<212> TYPE: PRT
<213> ORGANISM: Streptomyces thermosacchari

<400> SEQUENCE: 26
```

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65              70                  75                  80

Ala Cys Ser Gly Ala Val Thr Thr Asp Val Ile Asn Asn Gln Leu Gly
            85                  90                  95

Ala Leu Asn Ala Ser Thr Gly Leu Val Ser Ile Thr Ile Gly Gly Asn
        100                 105                 110

Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
                260                 265

<210> SEQ ID NO 27
<211> LENGTH: 548
<212> TYPE: PRT
<213> ORGANISM: Thermobifida fusca

<400> SEQUENCE: 27

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65              70                  75                  80

Pro Asp Gly Gly Phe Arg Pro His Leu Gly Val Gly Cys Leu Leu Ala
            85                  90                  95

Gly Gln Gly Ser Pro Gly Val Leu Trp Cys Gly Arg Glu Gly Cys Arg
        100                 105                 110
```

```
Phe Glu Val Cys Arg Arg Asp Thr Pro Gly Leu Ser Arg Thr Arg Asn
            115                 120                 125

Gly Asp Ser Ser Pro Pro Phe Arg Ala Gly Trp Ser Leu Pro Pro Lys
        130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Arg Leu Phe Leu Gly
                180                 185                 190

Ile Pro Ala Leu Val Leu Val Thr Ala Leu Thr Leu Val Leu Ala Val
                195                 200                 205

Pro Thr Gly Arg Glu Thr Leu Trp Arg Met Trp Cys Glu Ala Thr Gln
        210                 215                 220

Asp Trp Cys Leu Gly Val Pro Val Asp Ser Arg Gly Gln Pro Ala Glu
225                 230                 235                 240

Asp Gly Glu Phe Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
        260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
        290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
                340                 345                 350

Val Leu Lys Thr Cys Met Val Arg Val Pro Leu Leu Asp Ser Lys Ala
                355                 360                 365

Cys Thr Asp Gln Glu Asp Ala Ile Arg Lys Arg Met Ala Lys Phe Glu
        370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
                420                 425                 430

Glu Thr Ile Gln Glu Phe Asn Gln Gln Leu Ala Glu Ala Val Ala Val
        435                 440                 445

His Asp Glu Glu Ile Ala Ala Ser Gly Gly Val Gly Ser Val Glu Phe
        450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
            515                 520                 525

Tyr Ala Thr Phe Ala Val Val Ala Gly Ala Thr Val Asp Thr Leu Ala
        530                 535                 540
```

Gly Glu Val Gly
545

<210> SEQ ID NO 28
<211> LENGTH: 372
<212> TYPE: PRT
<213> ORGANISM: Thermobifida fusca

<400> SEQUENCE: 28

Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
        50                  55                  60

Asp Gly Glu Phe Leu Leu Ser Pro Val Gln Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 29
<211> LENGTH: 300
<212> TYPE: PRT
<213> ORGANISM: Corynebacterium efficiens

<400> SEQUENCE: 29

Met Arg Thr Thr Val Ile Ala Ala Ser Ala Leu Leu Leu Leu Ala Gly
1               5                   10                  15

Cys Ala Asp Gly Ala Arg Glu Glu Thr Ala Gly Ala Pro Pro Gly Glu
            20                  25                  30

Ser Ser Gly Gly Ile Arg Glu Glu Gly Ala Glu Ala Ser Thr Ser Ile
        35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
        275                 280                 285

Val Arg Asp Ala Leu Gly Leu Glu Pro Val Gln Pro
    290                 295                 300

<210> SEQ ID NO 30
<211> LENGTH: 284
<212> TYPE: PRT
<213> ORGANISM: Novosphingobium aromaticivorans

<400> SEQUENCE: 30

Met Gly Gln Val Lys Leu Phe Ala Arg Arg Cys Ala Pro Val Leu Leu
1               5                   10                  15

```
Ala Leu Ala Gly Leu Ala Pro Ala Thr Val Ala Arg Glu Ala Pro
            20                  25                  30

Leu Ala Glu Gly Ala Arg Tyr Val Ala Leu Gly Ser Ser Phe Ala Ala
        35                  40                  45

Gly Pro Gly Val Gly Pro Asn Ala Pro Gly Ser Pro Glu Arg Cys Gly
    50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
            100                 105                 110

Thr Arg Leu Val Thr Leu Thr Ile Gly Gly Asn Asp Val Ser Phe Val
        115                 120                 125

Gly Asn Ile Phe Ala Ala Ala Cys Glu Lys Met Ala Ser Pro Asp Pro
    130                 135                 140

Arg Cys Gly Lys Trp Arg Glu Ile Thr Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Val Asp Tyr Ile Thr Val Leu Pro Pro Ser
        180                 185                 190

Gly Thr Cys Ala Ala Met Ala Ile Ser Pro Asp Arg Leu Ala Gln Ser
    195                 200                 205

Arg Ser Ala Ala Lys Arg Leu Ala Arg Ile Thr Ala Arg Val Ala Arg
210                 215                 220

Glu Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
        260                 265                 270

Ala Ala Ala Leu Val Lys Leu Val Lys Leu Met Lys
    275                 280
```

<210> SEQ ID NO 31
<211> LENGTH: 268
<212> TYPE: PRT
<213> ORGANISM: Streptomyces coelicolor

<400> SEQUENCE: 31

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110
```

```
Ile Gly Gly Asn Asp Ala Gly Phe Ala Asp Thr Met Thr Thr Cys Val
            115                 120                 125

Leu Gln Ser Glu Ser Ser Cys Leu Ser Arg Ile Ala Thr Ala Glu Ala
        130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
            165                 170                 175

Arg Phe Tyr Lys Leu Gly Thr Thr Cys Ile Gly Leu Ser Glu Thr Lys
                180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
            245                 250                 255

Ser Gly Gly Tyr Leu Pro Val Leu Asn Gly Ala Ala
            260                 265

<210> SEQ ID NO 32
<211> LENGTH: 269
<212> TYPE: PRT
<213> ORGANISM: Streptomyces avermitilis

<400> SEQUENCE: 32

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
            115                 120                 125

Leu Gln Ser Asp Ser Ala Cys Leu Ser Arg Ile Asn Thr Ala Lys Ala
        130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
            165                 170                 175

Arg Phe Tyr Lys Leu Gly Gly Ser Cys Leu Ala Gly Leu Ser Glu Thr
                180                 185                 190

Lys Arg Ser Ala Ile Asn Asp Ala Asp Tyr Leu Asn Ser Ala Ile
        195                 200                 205

Ala Lys Arg Ala Ala Asp His Gly Phe Thr Phe Gly Asp Val Lys Ser
    210                 215                 220
```

```
Thr Phe Thr Gly His Glu Ile Cys Ser Ser Ser Thr Trp Leu His Ser
225                 230                 235                 240

Leu Asp Leu Leu Asn Ile Gly Gln Ser Tyr His Pro Thr Ala Ala Gly
            245                 250                 255

Gln Ser Gly Gly Tyr Leu Pro Val Met Asn Ser Val Ala
        260                 265
```

<210> SEQ ID NO 33
<211> LENGTH: 367
<212> TYPE: PRT
<213> ORGANISM: Artificial Sequence
<220> FEATURE:
<223> OTHER INFORMATION: Description of Artificial Sequence: Synthetic
      Pfam00657.11 consensus polypeptide

<400> SEQUENCE: 33

```
Ile Val Ala Phe Gly Asp Ser Leu Thr Asp Gly Gly Ala Tyr Tyr
1               5                   10                  15

Gly Asp Ser Asp Gly Gly Trp Gly Ala Gly Leu Ala Asp Arg Leu
                20                  25                  30

Thr Ser Leu Ala Arg Leu Arg Ala Arg Gly Arg Gly Val Asp Val Phe
            35                  40                  45

Asn Arg Gly Ile Ser Gly Arg Thr Ser Asp Gly Arg Leu Val Val Asp
50                  55                  60

Ala Arg Leu Val Ala Thr Leu Leu Phe Leu Ala Gln Phe Leu Gly Leu
65                  70                  75                  80

Asn Leu Pro Pro Tyr Leu Ser Gly Asp Phe Leu Arg Gly Ala Asn Phe
                85                  90                  95

Ala Ser Ala Gly Ala Thr Ile Leu Gly Thr Ser Leu Ile Pro Phe Leu
                100                 105                 110

Asn Ile Gln Val Gln Phe Lys Asp Phe Lys Ser Lys Val Leu Glu Leu
            115                 120                 125

Arg Gln Ala Leu Gly Leu Leu Gln Glu Leu Leu Arg Leu Val Pro Val
                130                 135                 140

Leu Asp Ala Lys Ser Pro Asp Leu Val Thr Ile Met Ile Gly Thr Asn
145                 150                 155                 160

Asp Leu Ile Thr Val Ala Lys Phe Gly Pro Lys Ser Thr Lys Ser Asp
                165                 170                 175

Arg Asn Val Ser Val Pro Glu Phe Arg Asp Asn Leu Arg Lys Leu Ile
                180                 185                 190

Lys Arg Leu Arg Ser Ala Asn Gly Ala Arg Ile Ile Leu Ile Thr
            195                 200                 205

Leu Val Leu Leu Asn Leu Pro Leu Pro Leu Gly Cys Leu Pro Gln Lys
210                 215                 220

Leu Ala Leu Ala Leu Ala Ser Ser Lys Asn Val Asp Ala Thr Gly Cys
225                 230                 235                 240

Leu Glu Arg Leu Asn Glu Ala Val Ala Asp Tyr Asn Glu Ala Leu Arg
                245                 250                 255

Glu Leu Ala Glu Ile Glu Lys Leu Gln Ala Gln Leu Arg Lys Asp Gly
                260                 265                 270

Leu Pro Asp Leu Lys Glu Ala Asn Val Pro Tyr Val Asp Leu Tyr Ser
            275                 280                 285

Ile Phe Gln Asp Leu Asp Gly Ile Gln Asn Pro Ser Ala Tyr Val Tyr
                290                 295                 300

Gly Phe Glu Glu Thr Lys Ala Cys Cys Gly Tyr Gly Gly Arg Tyr Asn
305                 310                 315                 320
```

```
Tyr Asn Arg Val Cys Gly Asn Ala Gly Leu Cys Lys Val Thr Ala Lys
                325                 330                 335

Ala Cys Asp Ala Ser Ser Tyr Leu Leu Ala Thr Leu Phe Trp Asp Gly
            340                 345                 350

Phe His Pro Ser Glu Lys Gly Tyr Lys Ala Val Ala Glu Ala Leu
        355                 360                 365

<210> SEQ ID NO 34
<211> LENGTH: 317
<212> TYPE: PRT
<213> ORGANISM: Aeromonas hydrophila

<400> SEQUENCE: 34

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Gln Arg Asn Ala
    210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
        275                 280                 285

Gln Val His Pro Thr Thr Val Val His Ala Ala Leu Ser Glu Pro Ala
    290                 295                 300

Ala Thr Phe Ile Glu Ser Gln Tyr Glu Phe Leu Ala His
305                 310                 315

<210> SEQ ID NO 35
<211> LENGTH: 318
```

```
<212> TYPE: PRT
<213> ORGANISM: Aeromonas salmonicida

<400> SEQUENCE: 35

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
                20                  25                  30

Ser Ser Pro Pro Tyr Tyr Glu Gly Arg Phe Ser Asn Gly Pro Val Trp
            35                  40                  45

Leu Glu Gln Leu Thr Lys Gln Phe Pro Gly Leu Thr Ile Ala Asn Glu
        50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
                100                 105                 110

Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
        290                 295                 300

Ala Thr Phe Ile Glu Thr Gln Tyr Glu Phe Leu Ala His Gly
305                 310                 315

<210> SEQ ID NO 36
<211> LENGTH: 1371
<212> TYPE: DNA
<213> ORGANISM: Streptomyces thermosacchari

<400> SEQUENCE: 36
acaggccgat gcacggaacc gtacctttcc gcagtgaagc gctctccccc catcgttcgc      60
cgggacttca tccgcgattt tggcatgaac acttccttca acgcgcgtag cttgctacaa     120
gtgcggcagc agaccgctc gttggaggct cagtgagatt gacccgatcc ctgtcggccg      180
catccgtcat cgtcttcgcc ctgctgctcg cgctgctggg catcagcccg gcccaggcag     240
```

```
ccggcccggc ctatgtggcc ctgggggatt cctattcctc gggcaacggc gccggaagtt      300
acatcgattc gagcggtgac tgtcaccgca gcaacaacgc gtaccccgcc cgctgggcgg      360
cggccaacgc accgtcctcc ttcaccttcg cggcctgctc gggagcggtg accacggatg      420
tgatcaacaa tcagctgggc gccctcaacg cgtccaccgg cctggtgagc atcaccatcg      480
gcggcaatga cgcgggcttc gcggacgcga tgaccacctg cgtcaccagc tcggacagca      540
cctgcctcaa ccggctggcc accgccacca actacatcaa caccaccctg ctcgcccggc      600
tcgacgcggt ctacagccag atcaaggccg tgcccccaa cgcccgcgtg gtcgtcctcg       660
gctacccgcg catgtacctg gcctcgaacc cctggtactg cctgggcctg agcaacacca      720
agcgcgcggc catcaacacc accgccgaca ccctcaactc ggtgatctcc tcccgggcca      780
ccgcccacgg attccgattc ggcgatgtcc gcccgacctt caacaaccac gaactgttct      840
tcggcaacga ctggctgcac tcactcaccc tgccggtgtg ggagtcgtac caccccacca      900
gcacgggcca tcagagcggc tatctgccgg tcctcaacgc caacagctcg acctgatcaa      960
cgcacggccg tgcccgcccc gcgcgtcacg ctcggcgcgg gcgccgcagc gcgttgatca     1020
gcccacagtg ccggtgacgg tcccaccgtc acggtcgagg gtgtacgtca cggtggcgcc     1080
gctccagaag tggaacgtca gcaggaccgt ggagccgtcc ctgacctcgt cgaagaactc     1140
cggggtcagc gtgatcaccc ctcccccgta gccggggggcg aaggcggcgc cgaactcctt    1200
gtaggacgtc cagtcgtgcg gcccggcgtt gccaccgtcc gcgtagaccg cttccatggt     1260
cgccagccgc tccccgcgga actcggtggg gatgtccgtg cccaaggtgg tcccggtggt    1320
gtccgagagc accgggggct cgtaccggat gatgtgcaga tccaaagaat t             1371

<210> SEQ ID NO 37
<211> LENGTH: 230
<212> TYPE: PRT
<213> ORGANISM: Aspergillus aculeatus

<400> SEQUENCE: 37

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
                20                  25                  30

Ala Thr Val Val Asn Asp Ala Val Ala Gly Arg Ser Ala Arg Ser Tyr
            35                  40                  45

Thr Arg Glu Gly Arg Phe Glu Asn Ile Ala Asp Val Val Thr Ala Gly
        50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175
```

```
Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
            195                 200                 205

Leu Lys Ala Val Val Cys Thr Gly Thr Ser Leu Lys Ser Val Leu Thr
            210                 215                 220

Thr Thr Ser Phe Glu Gly
225                 230

<210> SEQ ID NO 38
<211> LENGTH: 184
<212> TYPE: PRT
<213> ORGANISM: Escherichia coli

<400> SEQUENCE: 38

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 39
<211> LENGTH: 3000
<212> TYPE: DNA
<213> ORGANISM: Thermobifida fusca

<400> SEQUENCE: 39
ggtggtgaac cagaacaccc ggtcgtcggc gtgggcgtcc aggtgcaggt gcaggttctt      60
caactgctcc agcaggatgc cgccgtggcc gtgcacgatg gccttgggca ggcctgtggt     120
ccccgacgag tacagcaccc atagcggatg gtcgaacggc agcggggtga actccagttc     180
cgcgccttcg cccgcggctt cgaactccgc ccaggacagg gtgtcggcga cagggccgca     240
gcccaggtac ggcaggacga cggtgtgctg caggctgggc atgccgtcgc gcagggcttt     300
gagcacgtca cggcggtcga agtccttacc gccgtagcgg tagccgtcca cggccagcag     360
cactttcggt tcgatctgcg cgaaccggtc gaggacgctg cgcaccccga agtcggggga     420
acaggacgac caggtcgcac cgatcgcggg gcaggcgagg aatgcggccg tcgcctcggc     480
```

```
gatgttcggc aggtaggcca cgacccggtc gccggggccc accccgaggc tgcggagggc      540
cgcagcgatc gcggcggtgc gggtccgcag ttctccccag gtccactcgg tcaacggccg      600
gagttcggac gcgtgccgga tcgccacggc tgatgggtca cggtcgcgga agatgtgctc      660
ggcgtagttg agggtggcgc cggggaacca gacggcgccg gcatggcgt cggaggcgag       720 cactgtggtg tacggggtgg cggcgcgcac ccggtagtac tcccagatcg cggaccagaa      780
tccttcgagg tcggttaccg accagcgcca cagtgcctcg tagtccggtg cgtccacacc      840
gcggtgctcc cgcacccagc gggtgaacgc ggtgaggttg gcgcgttctt tgcgctcctc      900
gtcgggactc cacaggatcg gcggctgcgg cttgagtgtc atgaaacgcg accccttcgt      960
ggacggtgcg gatgcggtga gcgtcgggtg cctcccctaa cgctcccgg tgacggagtg      1020 ttgtgcacca catctagcac gcgggacgcg gaaaccgtat ggagaaaaca cctacaaccc     1080
cggccggacg gtgggtttcg gccacactta ggggtcgggt gcctgcttgc cgggcagggc     1140
agtcccgggg tgctgtggtg cgggcgggag ggctgtcgct tcgaggtgtg ccggcgggac     1200
actccgggcc tcagccgtac ccgcaacggg gacagttctc ctcccttccg ggctggatgg     1260
tcccttcccc cgaaatgcgg cgagatctcc cagtcagccc ggaaaacacc cgctgtgccc     1320
aggtactctt tgcttcgaac agacaggccg gacggtccac gggggaggtt tgtgggcagc     1380
ggaccacgtg cggcgaccag acgacggttg ttcctcggta tccccgctct tgtacttgtg     1440
acagcgctca cgctggtctt ggctgtcccg acggggcgcg agacgctgtg gcgcatgtgg     1500
tgtgaggcca cccaggactg gtgcctgggg gtgccggtcg actccgcgg acagcctgcg      1560 gaggacggcg agtttctgct gctttctccg gtccaggcag cgacctgggg gaactattac     1620
gcgctcgggg attcgtactc ttcgggggac ggggcccgcg actactatcc cggcaccgcg     1680
gtgaagggcg gttgctggcg gtccgctaac gcctatccgg agctggtcgc cgaagcctac     1740
gacttcgccg gacacttgtc gttcctggcc tgcagcggcc agcgcggcta cgccatgctt     1800
gacgctatcg acgaggtcgg ctcgcagctg gactggaact cccctcacac gtcgctggtg     1860
acgatcggga tcggcggcaa cgatctgggg ttctccacgg ttttgaagac ctgcatggtg     1920
cgggtgccgc tgctggacag caaggcgtgc acggaccagg aggacgctat ccgcaagcgg     1980
atggcgaaat tcgagacgac gtttgaagag ctcatcagcg aagtgcgcac ccgcgcgccg     2040
gacgcccgga tccttgtcgt gggctacccc cggattttc cggaggaacc gaccggcgcc      2100
tactacacgc tgaccgcgag caaccagcgg tggctcaacg aaaccattca ggagttcaac     2160
cagcagctcg ccgaggctgt cgcggtccac gacgaggaga ttgccgcgtc gggcggggtg     2220
ggcagcgtgg agttcgtgga cgtctaccac gcgttggacg gccacgagat cggctcggac     2280
gagccgtggg tgaacggggt gcagttgcgg gacctcgcca ccggggtgac tgtgaccgcc     2340
agtaccttcc accccaacgc cgctgggcac cgggcggtcg gtgagcgggt catcgagcag     2400
atcgaaaccg gcccggggcg tccgctctat gccactttcg cggtggtggc gggggcgacc     2460
gtggacactc tcgcgggcga ggtggggtga cccggcttac cgtccggccc gcaggtctgc     2520
gagcactgcg gcgatctggt ccactgccca gtgcagttcc tcttcggtga tgaccagcgg     2580
cggggagagc cggatcgttg agccgtgcgt gtctttgacg agcacacccc gctgcaggag     2640
ccgttcgcac agttctcttc cggtggccag agtcgggtcg acgtcgatcc cagcccacag     2700
gccgatgctg cgggccgcga ccacgccgtt gccgaccagt tggtcgaggc gggcgcgcag     2760 cacggggggcg agggcgcgga catggtccag gtaaggccg tcgcggacga ggctcaccac      2820
ggcagtgccg accgcgcagg cgagggcgtt gccgccgaag gtgctgccgt gctggccggg     2880
```

```
gcggatcacg tcgaagactt ccgcgtcgcc taccgccgcc gccacgggca ggatgccgcc    2940
gcccagcgct tgccgaaca  ggtagatatc ggcgtcgact ccgctgtggt cgcaggcccg    3000
```

<210> SEQ ID NO 40
<211> LENGTH: 372
<212> TYPE: PRT
<213> ORGANISM: Thermobifida fusca

<400> SEQUENCE: 40

```
Val Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln
        35                  40                  45

Asp Trp Cys Leu Gly Val Pro Val Asp Ser Arg Gly Gln Pro Ala Glu
    50                  55                  60

Asp Gly Glu Phe Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365
```

Gly Glu Val Gly
    370

<210> SEQ ID NO 41
<211> LENGTH: 232
<212> TYPE: PRT
<213> ORGANISM: Aspergillus aculeatus

<400> SEQUENCE: 41

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Ala Glu Ala Phe
        195                 200                 205

Leu Lys Ala Val Val Cys Thr Gly Thr Ser Leu Lys Ser Val Leu Thr
    210                 215                 220

Thr Thr Ser Phe Glu Gly Thr Cys
225                 230

<210> SEQ ID NO 42
<211> LENGTH: 3000
<212> TYPE: DNA
<213> ORGANISM: Corynebacterium efficiens

<400> SEQUENCE: 42
ttctggggtg ttatggggtt gttatcggct cgtcctgggt ggatcccgcc aggtggggta      60
ttcacggggg acttttgtgt ccaacagccg agaatgagtg ccctgagcgg tgggaatgag     120
gtgggcgggg ctgtgtcgcc atgagggggc ggcgggctct gtggtgcccc gcgacccccg     180
gccccggtga gcggtgaatg aaatccggct gtaatcagca tcccgtgccc accccgtcgg     240
ggaggtcagc gcccggagtg tctacgcagt cggatcctct cggactcggc catgctgtcg     300
gcagcatcgc gctcccgggt cttggcgtcc ctcggctgtt ctgcctgctg tccctggaag     360
gcgaaatgat caccggggag tgatacaccg gtggtctcat cccggatgcc acttcggcg      420 ccatccggca attcgggcag ctccgggtgg aagtaggtgg catccgatgc gtcggtgacg     480

```
ccatagtggg cgaagatctc atcctgctcg agggtgctca ggccactctc cggatcgata     540
tcgggggcgt ccttgatggc gtccttgctg aaaccgaggt gcagcttgtg ggcttccaat     600
ttcgcaccac ggagcgggac gaggctggaa tgacggccga agagcccgtg gtggacctca     660
acgaaggtgg gtagtcccgt gtcatcattg aggaacacgc cctccaccgc acccagcttg     720
tggccggagt tgtcgtaggc gctggcatcc agaagggaaa cgatctcata tttgtcggtg     780
tgctcagaca tgatcttcct ttgctgtcgg tgtctggtac taccacggta gggctgaatg     840
caactgttat ttttctgtta ttttaggaat tggtccatat cccacaggct ggctgtggtc     900
aaatcgtcat caagtaatcc ctgtcacaca aatgggtgg tgggagccct ggtcgcggtt     960
ccgtgggagg cgccgtgccc cgcaggatcg tcggcatcgg cggatctggc cggtaccccg    1020
cggtgaataa aatcattctg taaccttcat cacggttggt tttaggtatc cgccccttc    1080 gtcctgaccc cgtccccggc gcgcgggagc ccgcggttg cggtagacag gggagacgtg    1140
gacaccatga ggacaacggt catcgcagca agcgcattac tccttctcgc cggatgcgcg    1200
gatgggcccc gggaggagac cgccggtgca ccgccgggtg agtcctccgg gggcatccgg    1260
gaggaggggg cggaggcgtc gacaagcatc accgacgtct acatcgccct cggggattcc    1320
tatgcggcga tgggcgggcg ggatcagccg ttacggggtg agccgttctg cctgcgctcg    1380
tccggtaatt acccggaact cctccacgca gaggtcaccg atctcacctg ccaggggggcg   1440 gtgaccgggg atctgctcga acccaggacg ctggggagc gcacgctgcc ggcgcaggtg    1500
gatgcgctga cggaggacac caccctggtc accctctcca tcgggggcaa tgacctcgga    1560
ttcggggagg tggcgggatg catccgggaa cggatcgccg gggagaacgc tgatgattgc    1620
gtggacctgc tgggggaaac catcggggag cagctcgatc agcttccccc gcagctggac    1680
cgcgtgcacg aggctatccg ggaccgcgcc ggggacgcgc aggttgtggt caccggttac    1740
ctgccgctcg tgtctgccgg ggactgcccc gaactggggg atgtctccga gcggatcgt    1800 cgttgggcgg ttgagctgac cgggcagatc aacgagaccg tgcgcgaggc ggccgaacga    1860
cacgatgccc tctttgtcct gcccgacgat gccgatgagc acaccagttg tgcaccccca    1920
cagcagcgct gggcggatat ccagggccaa cagaccgatg cctatccgct gcacccgacc    1980
tccgccggcc atgaggcgat ggccgccgcc gtccggacg cgctgggcct ggaaccggtc    2040
cagccgtagc gccgggcgcg cgcttgtcga cgaccaaccc atgccaggct gcagtcacat    2100
ccgcacatag cgcgcgcggg cgatggagta cgcaccatag aggatgagcc cgatgccgac    2160
gatgatgagc agcacactgc cgaagggttg ttccccgagg gtgcgcagag ccgagtccag    2220
acctgcggcc tgctccggat catgggccca accggcgatg acgatcaaca cccccaggat    2280
cccgaaggcg ataccacggg cgacataacc ggctgttccg gtgatgatga tcgcggtccc    2340
gacctgccct gaccccgcac ccgcctccag atcctcccgg aaatcccggg tggccccctt    2400
ccagaggttg tagacacccg ccccagtac caccagcccg cgaccacaa ccagcaccac    2460 accccagggt tgggatagga cggtggcggt gacatcggtg gcggtctccc catcggaggt   2520
gctgccgccc cgggcgaagg tggaggtggt caccgccagg gagaagtaga ccatggccat    2580
gaccgccccc ttggcccttt ccttgaggtc ctcgcccgcc agcagctggc tcaattgcca    2640
gagtcccagg gccgccaggg cgatgacggc aaccacagg gaactgcc cacccggagc    2700 ctccgcgatg gtggccaggg cacctgaatt cgaggcctca tcacccgaac cgccggatcc    2760
agtggcgatg cgcaccgcga tccacccgat gaggatgtgc agtatgccca ggacaatgaa    2820
accacctctg gccagggtgg tcagcgcggg gtggtcctcg gcctggtcgg cagcccgttc    2880
```

```
gatcgtccgt tcgcggatc tggtgtcgcc cttatccata gctcccattg aaccgccttg    2940
aggggtgggc ggccactgtc agggcggatt gtgatctgaa ctgtgatgtt ccatcaaccc    3000
```

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 43

Gly Asp Ser Leu
1

<210> SEQ ID NO 44
<211> LENGTH: 2000
<212> TYPE: DNA
<213> ORGANISM: Streptomyces coelicolor

<400> SEQUENCE: 44

```
cccggcggcc cgtgcaggag cagcagccgg cccgcgatgt cctcgggcgt cgtcttcatc     60
aggccgtcca tcgcgtcggc gaccggcgcc gtgtagttgg cccggacctc gtcccaggtg    120
cccgcggcga tctggcgggt ggtgcggtgc gggccgcgcc gagggagac gtaccagaag     180 cccatcgtca cgttctccgg ctgcggttcg ggctcgtccg ccgctccgtc cgtcgcctcg    240
ccgagcacct tctcggcgag gtcggcgctg gtcgccgtca ccgtgacgtc ggcgccccgg    300
ctccagcgcg agatcagcag cgtccagccg tcgccctccg ccagcgtcgc gctgcggtcg    360
tcgtcgcggg cgatccgcag cacgcgcgcg cgggcggca gcagcgtggc gccggaccgt     420
acgcggtcga tgttcgccgc gtgcgagtac ggctgctcac ccgtggcgaa acggccgagg    480
aacagcgcgt cgacgacgtc ggacggggag tcgctgtcgt ccacgttgag ccggatcggc    540
agggcttcgt gcgggttcac ggacatgtcg ccatgatcgg gcacccggcc gccgcgtgca    600
cccgctttcc cgggcacgca cgacaggggc tttctcgccg tcttccgtcc gaacttgaac    660
gagtgtcagc catttcttgg catggacact tccagtcaac gcgcgtagct gctaccacgg    720
ttgtggcagc aatcctgcta agggaggttc catgagacgt ttccgacttg tcggcttcct    780
gagttcgctc gtcctcgccg ccggcgccgc cctcaccggg gcagcgaccg cccaggcggc    840
ccaacccgcc gccgccgacg gctatgtggc cctcggcgac tcctactcct cggggtcgg    900 agcgggcagc tacatcagct cgagcggcga ctgcaagcgc agcacgaagg cccatcccta    960
cctgtgggcg gccgcccact cgccctccac gttcgacttc accgcctgtt ccggcgcccg    1020
tacgggtgat gttctctccg gacagctcgg cccgctcagc tccggcaccg gcctcgtctc    1080
gatcagcatc ggcggcaacg acgccggttt cgccgacacc atgacgacct gtgtgctcca    1140
gtccgagagc tcctgcctgt cgcggatcgc caccgccgag gcgtacgtcg actcgacgct    1200
gcccggcaag ctcgacggcg tctactcggc aatcagcgac aaggcgccga acgcccacgt    1260
cgtcgtcatc ggctacccgc gcttctacaa gctcggcacc acctgcatcg gcctgtccga    1320
gaccaagcgg acggcgatca acaaggcctc gaccaccctc aacaccgtcc tcgcccagcg    1380
cgccgccgcc cacggcttca ccttcggcga cgtacgcacc accttcaccg gccacgagct    1440
gtgctccggc agccctggc tgcacagcgt caactggctg aacatcggcg agtcgtacca    1500
ccccaccgcg gccggccagt ccggtggcta cctgccggtc ctcaacgcg ccgcctgacc    1560 tcaggcggaa ggagaagaag aaggagcgga gggagacgag gagtgggagg ccccgcccga    1620
```

-continued

```
cggggtcccc gtcccgtct ccgtctccgt cccggtcccg caagtcaccg agaacgccac    1680
cgcgtcggac gtggcccgca ccggactccg cacctccacg cgcacggcac tctcgaacgc    1740
gccggtgtcg tcgtgcgtcg tcaccaccac gccgtcctgg cgcgagcgct cgccgcccga    1800
cgggaaggac agcgtccgcc accccggatc ggagaccgac ccgtccgcgg tcacccaccg    1860
gtagccgacc tccgcgggca gccgcccgac cgtgaacgtc gccgtgaacg cgggtgcccg    1920
gtcgtgcggc ggcggacagg cccccgagta gtgggtgcgc gagcccacca cggtcacctc    1980
caccgactgc gctgcggggc                                                2000
```

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic peptide motif

<400> SEQUENCE: 45

Gly Ala Asn Asp Tyr
1               5

<210> SEQ ID NO 46
<211> LENGTH: 1980
<212> TYPE: DNA
<213> ORGANISM: Streptomyces avermitilis

<400> SEQUENCE: 46

```
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggcccct    120 tgcccttgct cgacgcggcc ttgaagccgg tgcccttctt gagcgtgacg atgtagctgc     180
ccttgatcgc ggtgggggag ccggcggcga gcaccgtgcc ctcggccggg gtggcctggg     240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacgggggt ggctcaaggg     480
agttgagacc ctgtcatgag tctgacatga gcacgcaatc aacggggccg tgagcacccc     540
ggggcgaccc cggaaagtgc cgagaagtct tggcatggac acttcctgtc aacacgcgta     600
gctggtacga cggttacggc agagatcctg ctaaagggag gttccatgag acgttcccga     660
attacggcat acgtgacctc actcctcctc gccgtcggct cgcccctcac cggggcagcg     720
acggcgcagg cgtcccagc cgccgcggcc acgggctatg tggccctcgg cgactcgtac      780
tcgtccggtg tcggcgccgg cagctacctc agctccagcg gcgactgcaa gcgcagttcg     840
aaggcctatc cgtacctctg gcaggccgcg cattcaccct cgtcgttcag tttcatggct     900
tgctcgggcg ctcgtacggg tgatgtcctg gccaatcagc tcggcaccct gaactcgtcc     960
accggcctgg tctccctcac catcggaggc aacgacgcgg gcttctccga cgtcatgacg    1020
acctgtgtgc tccagtccga cagcgcctgc ctctccccgca tcaacacggc gaaggcgtac    1080
gtcgactcca ccctgcccgg ccaactcgac agcgtgtaca cggcgatcag cacgaaggcc    1140
ccgtcggccc atgtggccgt gctgggctac ccccgcttct acaaactggg cggctcctgc    1200
ctcgcgggcc tctcggagac caagcggtcc gccatcaacg acgcggccga ctatctgaac    1260
agcgccatcg ccaagcgcgc cgccgaccac ggcttcacct tcggcgacgt caagagcacc    1320
```

```
ttcaccggcc atgagatctg ctccagcagc acctggctgc acagtctcga cctgctgaac   1380
atcggccagt cctaccaccc gaccgcggcc ggccagtccg gcggctatct gccggtcatg   1440
aacagcgtgg cctgagctcc cacggcctga attttttaagg cctgaatttt taaggcgaag   1500
gtgaaccgga agcggaggcc ccgtccgtcg gggtctccgt cgcacaggtc accgagaacg   1560
gcacggagtt ggacgtcgtg cgcaccgggt cgcgcacctc gacggcgatc tcgttcgaga   1620
tcgttccgct cgtgtcgtac gtggtgacga acacctgctt ctgctgggtc tttccgccgc   1680
tcgccgggaa ggacagcgtc ttccagcccg atccgggac ctcgcccttc ttggtcaccc    1740
agcggtactc cacctcgacc ggcacccggc ccaccgtgaa ggtcgccgtg aacgtgggcg   1800
cctgggcggt gggcggcggg caggcaccgg agtagtcggt gtgcacgccg gtgaccgtca   1860
ccttcacgga ctgggccggc ggggtcgtcg taccgccgcc gccaccgccg cctcccggag   1920
tggagcccga gctgtggtcg ccccccgccgt cggcgttgtc gtcctcgggg gttttcgaac   1980
```

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 47

His His His His His His
1               5

<210> SEQ ID NO 48
<211> LENGTH: 968
<212> TYPE: DNA
<213> ORGANISM: Thermobifida fusca

<400> SEQUENCE: 48

```
ctgcagacac ccgccccgcc ttctcccgga tcgtcatgtt cggcgactcc ctcagcgaca     60
ccggcaagat gtactccaag atgcgcggct acctgccgtc ctccccgccg tactacgagg    120
gccgcttctc gaacggcccg gtctggctgg agcagctgac gaagcagttc cccggcctga    180
cgatcgccaa cgaggccgag gggggcgcga ccgcagtcgc ctacaacaag atctcctgga    240
acccgaagta ccaggtcatt aacaacctcg actacgaggt cacccagttc ttgcagaagg    300
actcgttcaa gcccgacgac ctggtcatcc tgtgggtggg cgccaacgac tacctggcct    360
acggttggaa cacggagcag gacgccaagc gggtgcgcga cgccatctcg gacgcggcaa    420
accgcatggt cctgaacggc gcgaagcaga tcctgctgtt caacctgccc gacctgggcc    480
agaacccgtc cgcccgctcc cagaaggtcg tcgaggccgt ctcgcacgtg tccgcctacc    540
acaacaagct gctcctcaac ctcgcccggc agctcgcccc gacgggcatg gtcaagctgt    600
tcgagatcga caagcagttc gcggagatgc tgcgcgaccc ccagaacttc ggcctgagcg    660
acgtggagaa cccgtgctac gacgcggct acgtgtggaa gccgttcgcc acccggtccg    720
tctcgaccga ccggcagctg tcggccttct cgccccagga gcgcctggcg atcgctggca    780
acccgctcct ggcacaggcg gtagcttcgc cgatggcccg ccgctcggcc tcgcccctca    840
actgcgaggg caagatgttc tgggaccagg tccaccccac caccgtggtc cacgccgccc    900
tctcggagcg cgccgccacc ttcatcgaga cccagtacga gttcctcgcc cactagtcta    960
gaggatcc                                                            968
```

```
<210> SEQ ID NO 49
<211> LENGTH: 1044
<212> TYPE: DNA
<213> ORGANISM: Aeromonas salmonicida

<400> SEQUENCE: 49
atgaaacaac aaaaacggct ttacgcccga ttgctgacgc tgttatttgc gctcatcttc    60
ttgctgcctc attctgcagc ttcagcagca gatacaagac cggcgtttag ccggatcgtc   120
atgtttggag atagcctgag cgatacgggc aaaatgtata gcaaaatgag aggctatctt   180
ccgtcaagcc cgccgtatta tgaaggccgc tttagcaatg gaccggtctg gctggaacaa   240
ctgacgaaac aatttccggg actgacgatc gctaatgaag cagaaggagg agcaacagcg   300
gtcgcctata caaaatcag ctgggaccccg aaatatcagg tcatcaacaa cctggactat   360
gaagtcacac agtttcttca gaaagacagc tttaaaccgg atgatctggt catcctttgg   420
gtcggcgcca atgattatct ggcgtatggc tggaacacag aacaagatgc caaaagagtc   480
agagatgcca tcagcgatgc cgctaataga atggtcctga cggcgccaa acaaatcctg   540 ctgtttaacc tgccggatct gggacaaaat ccgagcgcca aagccaaaa agtcgtcgaa   600 gcagtcagcc atgtcagcgc ctatcataac aaactgctgc tgaacctggc aagacaattg   660
gcaccgacgg gaatggttaa attgtttgaa attgacaaac agtttgccga atgctgaga   720 gatccgcaaa attttggcct gagcgatgtc gaaaacccgt gctatgatgg cggatatgtc   780
tggaaaccgt tgccacaag aagcgtcagc acggatagac aactgtcagc gtttagcccg   840
caagaaagac tggcaatcgc cggaaatccg cttttggcac aagcagttgc ttcaccgatg   900
gcaagaagat cagcaagccc gctgaattgc gaaggcaaaa tgttttggga tcaggtccat   960
ccgacaacag ttgtccatgc tgccctttca gaaagagcgg cgacgtttat cgaaacacag  1020
tatgaatttc tggcccatgg ctga                                        1044

<210> SEQ ID NO 50
<211> LENGTH: 1005
<212> TYPE: DNA
<213> ORGANISM: Aeromonas hydrophila

<400> SEQUENCE: 50
atgaaaaaat ggtttgtgtg tttattggga ttggtcgcgc tgacagttca ggcagccgac    60
agccgtcccg ccttctcccg gatcgtgatg tttggcgaca gcctctccga taccggcaag   120
atgtacagca agatgcgcgg ttacctcccc tccagccccc cctactatga gggccgcttc   180
tccaacgggc ccgtctggct ggagcagctg accaacgagt tcccgggcct gaccatagcc   240
aacgaggcgg aaggcggacc gaccgccgtg gcttacaaca agatctcctg gaatcccaag   300
tatcaggtca tcaacaacct ggactacgag gtcacccagt tcctgcaaaa agacagcttc   360
aagccggacg atctggtgat cctctgggtc ggcgccaacg actatctggc ctatggctgg   420
aacacagagc aggatgccaa gcgggtgcgc gacgccatca gcgatgcggc caaccgcatg   480
gtgctgaacg cgccaaggga gatactgctg ttcaacctgc cggatctggg ccagaaccc    540 tcggcccgca gccagaaggt ggtcgaggcg ccagccatg tctccgccta ccacaaccag   600
ctgctgctga acctggcacg ccagctggct cccaccggca tggtgaagct gttcgagatc   660
gacaagcagt ttgccgagat gctgcgtgat ccgcagaact tcggcctgag cgaccagagg   720
aacgcctgct acggtggcag ctatgtatgg aagccgtttg cctcccgcag cgccagcacc   780
gacagccagc tctccgcctt caaccccgca gagcgcctcg ccatcgccgg caaccccgctg   840 ctggcccagg ccgtcgccag ccccatggct gcccgcagcg ccagcaccct caactgtgag   900
```

```
ggcaagatgt tctgggatca ggtccacccc accactgtcg tgcacgccgc cctgagcgag      960
cccgccgcca ccttcatcga gagccagtac gagttcctcg cccac                    1005

<210> SEQ ID NO 51
<211> LENGTH: 1011
<212> TYPE: DNA
<213> ORGANISM: Aeromonas salmonicida

<400> SEQUENCE: 51
atgaaaaaat ggtttgtttg tttattgggg ttgatcgcgc tgacagttca ggcagccgac       60
actcgccccg ccttctcccg gatcgtgatg ttcggcgaca gcctctccga taccggcaaa      120
atgtacagca agatgcgcgg ttacctcccc tccagcccgc cctactatga ggccgtttc       180 tccaacggac ccgtctggct ggagcagctg accaagcagt tcccgggtct gaccatcgcc      240
aacgaagcgg aaggcggtgc cactgccgtg gcttacaaca agatctcctg gaatcccaag      300
tatcaggtct acaacaacct ggactacgag gtcacccagt tcttgcagaa agacagcttc      360
aagccggacg atctggtgat cctctgggtc ggtgccaatg actatctggc atatggctgg      420
aatacggagc aggatgccaa gcgagttcgc gatgccatca gcgatgcggc caaccgcatg      480
gtactgaacg gtgccaagca gatactgctg ttcaacctgc cggatctggg ccagaacccg      540
tcagcccgca gtcagaaggt ggtcgaggcg gtcagccatg tctccgccta tcacaacaag      600
ctgctgctga acctggcacg ccagctggcc ccaccggca tggtaaagct gttcgagatc       660
gacaagcaat tgccgagat gctgcgtgat ccgcagaact tcggcctgag cgacgtcgag       720 aaccccctgct acgacggcgg ctatgtgtgg aagccgtttg ccacccgcag cgtcagcacc      780
gaccgccagc tctccgcctt cagtccgcag gaacgcctcg ccatcgccgg caacccgctg      840
ctggcacagg ccgttgccag tcctatggcc cgccgcagcg ccagcccct caactgtgag       900 ggcaagatgt tctgggatca ggtacacccg accactgtcg tgcacgcagc cctgagcgag      960
cgcgccgcca ccttcatcga gacccagtac gagttcctcg cccacggatg a             1011

<210> SEQ ID NO 52
<211> LENGTH: 888
<212> TYPE: DNA
<213> ORGANISM: Streptomyces coelicolor

<400> SEQUENCE: 52
atgccgaagc ctgcccttcg ccgtgtcatg accgcgacag tcgccgccgt cggcacgctc       60
gccctcggcc tcaccgacgc caccgcccac gccgcgcccg cccaggccac tccgaccctg      120
gactacgtcg ccctcggcga cagctacagc gccggctccg gcgtcctgcc cgtcgacccc      180
gccaacctgc tctgtctgcg ctcgacggcc aactacccc acgtcatcgc ggacacgacg       240
ggcgcccgcc tcacggacgt cacctgcggc gccgcgcaga ccgccgactt cacgcgggcc      300
cagtacccgg gcgtcgcacc ccagttggac gcgctcggca ccggcacgga cctggtcacg      360
ctcaccatcg gcggcaacga caacagcacc ttcatcaacg ccatcacggc ctgcggcacg      420
gcgggtgtcc tcagcggcgg caagggcagc ccctgcaagg acaggcacgg cacctccttc      480
gacgacgaga tcgaggccaa cacgtacccc gcgctcaagg aggcgctgct cggcgtccgc      540
gccagggctc cccacgccag ggtggcggct ctcggctacc cgtggatcac cccggccacc      600 gccgaccgt cctgcttcct gaagctcccc ctcgccgcg gtgacgtgcc ctacctgcgg       660
gccatccagg cacacctcaa cgacgcggtc cggcgggccg ccgaggagac cggagccacc      720
tacgtggact tctccggggt gtccgacggc cacgacgcct gcgaggcccc cggcacccgc      780
```

```
tggatcgaac cgctgctctt cgggcacagc ctcgttcccg tccacccccaa cgccctgggc    840 gagcggcgca tggccgagca cacgatggac gtcctcggcc tggactga                 888
```

<210> SEQ ID NO 53
<211> LENGTH: 888
<212> TYPE: DNA
<213> ORGANISM: Streptomyces coelicolor

<400> SEQUENCE: 53

```
tcagtccagg ccgaggacgt ccatcgtgtg ctcggccatg cgccgctcgc ccagggcgtt     60
ggggtggacg ggaacgaggc tgtgcccgaa gagcagcggt tcgatccagc gggtgccggg    120
ggcctcgcag gcgtcgtggc cgtcggacac cccggagaag tccacgtagg tggctccggt    180
ctcctcggcg gcccgccgga ccgcgtcgtt gaggtgtgcc tggatggccc gcaggtaggg    240
cacgtcaccg gcggcgaggg ggagcttcag gaagcaggac gggtcggcgg tggccggggt    300
gatccacggg tagccgagag ccgccaccct ggcgtgggga gccctggcgc ggacgccgag    360
cagcgcctcc ttgagcgcgg ggtacgtgtt ggcctcgatc tcgtcgtcga aggaggtgcc    420
gtgcctgtcc ttgcagggc tgcccttgcc gccgctgagg acacccgccg tgccgcaggc    480
cgtgatggcg ttgatgaagg tgctgttgtc gttgccgccg atggtgagcg tgaccaggtc    540
cgtgccggtg ccgagcgcgt ccaactgggg tgcgacgccc gggtactggg cccgcgtgaa    600
gtcggcggtc tgcgcggcgc cgcaggtgac gtccgtgagg cgggcgcccg tcgtgtccgc    660
gatgacgtgg gggtagttgg ccgtcgagcg cagacagagc aggttggcgg ggtcgacggg    720
caggacgccg gagccggcgc tgtagctgtc gccgagggcg acgtagtcca gggtcggagt    780
ggcctgggcg ggcgcggcgt gggcggttggc gtcggtgagg ccgagggcga gcgtgccgac    840
ggcggcgact gtcgcggtca tgacacggcg aagggcaggc ttcggcat                 888
```

<210> SEQ ID NO 54
<211> LENGTH: 717
<212> TYPE: DNA
<213> ORGANISM: Saccharomyces cerevisiae

<400> SEQUENCE: 54

```
atggattacg agaagtttct gttatttggg gattccatta ctgaatttgc ttttaatact     60
aggcccattg aagatggcaa agatcagtat gctcttggag ccgcattagt caacgaatat    120
acgagaaaaa tggatattct tcaaagaggg ttcaaagggt acacttctag atgggcgttg    180
aaaatacttc ctgagatttt aaagcatgaa tccaatattg tcatggccac aatattttg     240 ggtgccaacg atgcatgctc agcaggtccc caaagtgtcc ccctccccga atttatcgat    300
aatattcgtc aaatggtatc tttgatgaag tcttaccata tccgtcctat tataatagga    360
ccggggctag tagatagaga gaagtgggaa aagagaaaaat ctgaagaaat agctctcgga    420
tacttccgta ccaacgagaa cttttgccatt tattccgatg ccttagcaaa actagccaat    480
gaggaaaaag ttcccttcgt ggctttgaat aaggcgtttc aacaggaagg tggtgatgct    540
tggcaacaac tgctaacaga tggactgcac ttttccggaa aagggtacaa aattttttcat    600 gacgaattat tgaaggtcat tgagacattc tacccccaat atcatcccaa aaacatgcag    660
tacaaactga agattggag agatgtgcta atgatggat ctaacataat gtcttga        717
```

<210> SEQ ID NO 55
<211> LENGTH: 1044
<212> TYPE: DNA
<213> ORGANISM: Ralstonia sp.

<400> SEQUENCE: 55

```
atgaacctgc gtcaatggat gggcgccgcc acggctgccc ttgccttggg cttggccgcg      60
tgcgggggcg gtgggaccga ccagagcggc aatcccaatg tcgccaaggt gcagcgcatg     120
gtggtgttcg gcgacagcct gagcgatatc ggcacctaca ccccgtcgc gcaggcggtg     180
ggcggcggca agttcaccac caacccgggc ccgatctggg ccgagaccgt ggccgcgcaa     240
ctgggcgtga cgctcacgcc ggcggtgatg ggctacgcca cctccgtgca gaattgcccc     300
aaggccggct gcttcgacta tgcgcagggc ggctcgcgcg tgaccgatcc gaacggcatc     360
ggccacaacg gcgcgcgggg ggcgctgacc tacccggttc agcagcagct cgccaacttc     420
tacgcggcca gcaacaacac attcaacggc aataacgatg tcgtcttcgt gctggccggc     480
agcaacgaca tttttcttctg gaccactgcg gcggccacca gcggctccgg cgtgacgccc     540
gccattgcca cggcccaggt gcagcaggcc gcgacggacc tggtcggcta tgtcaaggac     600
atgatcgcca agggtgcgac gcaggtctac gtgttcaacc tgcccgacag cagcctgacg     660
ccggacggcg tggcaagcgg cacgaccggc caggcgctgc tgcacgcgct ggtgggcacg     720
ttcaacacga cgctgcaaag cgggctggcc ggcacctcgg cgcgcatcat cgacttcaac     780
gcacaactga ccgcggcgat ccagaatggc gcctcgttcg gcttcgccaa caccagcgcc     840
cgggcctgcg acgccaccaa gatcaatgcc ctggtgccga gcgccggcgg cagctcgctg     900
ttctgctcgg ccaacacgct ggtggcttcc ggtgcggacc agagctacct gttcgccgac     960
ggcgtgcacc cgaccacggc cggccatcgc ctgatcgcca gcaacgtgct ggcgcgcctg    1020
ctggcggata acgtcgcgca ctga                                           1044
```

<210> SEQ ID NO 56
<211> LENGTH: 786
<212> TYPE: DNA
<213> ORGANISM: Streptomyces coelicolor

<400> SEQUENCE: 56

```
gtgatcgggt cgtacgtggc ggtgggggac agcttcaccg agggcgtcgg cgaccccggc      60
cccgacgggg cgttcgtcgg ctgggccgac cggctcgccg tactgctcgc ggaccggcgc     120
cccgagggcg acttcacgta cacgaacctc gccgtgcgcg gcaggctcct cgaccagatc     180
gtggcggaac aggtcccgcg ggtcgtcgga ctcgcgcccg acctcgtctc gttcgcggcg     240
ggcggcaacg acatcatccg gcccggcacc gatcccgacg aggtcgccga gcggttcgag     300
ctggcggtgg ccgcgctgac cgccgcggcc ggaaccgtcc tggtgaccac cgggttcgac     360
acccggggggg tgcccgtcct caagcacctg cgcggcaaga tcgccacgta caacgggcac     420
gtccgcgcca tcgccgaccg ctacggctgc ccggtgctcg acctgtggtc gctgcggagc     480
gtccaggacc gcagggcgtg ggacgccgac cggctgcacc tgtcgccgga ggggcacacc     540
cgggtggcgc tgcgcgcggg gcaggccctg gcctgcgcg tccggccga ccctgaccag     600
ccctggccgc ccctgccgcc gcgcggcacg ctcgacgtcc ggcgcgacga cgtgcactgg     660
gcgcgcgagt acctggtgcc gtggatcggg cgccggctgc ggggcgagtc gtcgggcgac     720
cacgtgacgg ccaagggggac gctgtcgccg gacgccatca agacgcggat cgccgcggtg     780
gcctga                                                                786
```

<210> SEQ ID NO 57
<211> LENGTH: 783
<212> TYPE: DNA
<213> ORGANISM: Streptomyces coelicolor

<400> SEQUENCE: 57

```
atgcagacga accccgcgta caccagtctc gtcgccgtcg gcgactcctt caccgagggc      60
atgtcggacc tgctgcccga cggctcctac cgtggctggg ccgacctcct cgccacccgg     120
atggcggccc gctccccgg cttccggtac gccaacctgg cggtgcgcgg aagctgatc       180
ggacagatcg tcgacgagca ggtggacgtg ccgccgcca tgggagccga cgtgatcacg      240
ctggtcggcg ggctcaacga cacgctgcgg cccaagtgcg acatggcccg ggtgcgggac     300
ctgctgaccc aggccgtgga acggctcgcc ccgcactgcg agcagctggt gctgatgcgc     360
agtcccggtc gccagggtcc ggtgctggag cgcttccggc cccgcatgga ggccctgttc     420
gccgtgatcg acgacctggc cgggcggcac ggcgccgtgg tcgtcgacct gtacggggcc     480
cagtcgctgg ccgaccctcg gatgtgggac gtggaccggc tgcacctgac cgccgagggc     540
caccgccggg tcgcggaggc ggtgtggcag tcgctcggcc acgagcccga ggaccccgag     600
tggcacgcgc cgatcccggc gacgccgccg ccggggtggg tgacgcgcag gaccgcggac     660
gtccggttcg cccggcagca cctgctgccc tggataggcc gcaggctgac cgggcgctcg     720
tccggggacg gcctgccggc caagcgcccg gacctgctgc cctacgagga ccccgcacgg     780
tga                                                                   783
```

<210> SEQ ID NO 58
<211> LENGTH: 1365
<212> TYPE: DNA
<213> ORGANISM: Streptomyces coelicolor

<400> SEQUENCE: 58

```
atgacccggg gtcgtgacgg gggtgcgggg gcgccccca ccaagcaccg tgccctgctc       60
gcggcgatcg tcaccctgat agtggcgatc tccgcggcca tatacgccgg agcgtccgcg     120
gacgacggca gcagggacca cgcgctgcag gccgaggcc gtctcccacg aggagacgcc      180
gcccccgcgt ccaccggtgc ctgggtgggc gcctgggcca ccgcaccggc cgcggccgag     240
ccgggcaccg agacgaccgg cctggcgggc cgctccgtgc gcaacgtcgt gcacacctcg     300
gtcggcggca ccggcgcgcg gatcaccctc tcgaacctgt acgggcagtc gccgctgacc     360
gtcacacacg cctcgatcgc cctggccgcc gggcccgaca ccgccgccgc gatcgccgac     420
accatgcgcc ggctcacctt cggcggcagc gcccgggtga tcatcccggc gggcggccag     480
gtgatgagcg acaccgcccg cctcgccatc ccctacgggg cgaacgtcct ggtcaccacg     540
tactcccca tcccgtccgg gccggtgacc taccatccgc aggcccggca gaccagctac     600
ctggccgacg cgaccgcac ggcggacgtc accgccgtcg cgtacaccac ccccacgccc      660
tactggcgct acctgaccgc cctcgacgtg ctgagccacg aggccgacgg cacggtcgtg     720
gcgttcggcg actccatcac cgacggcgcc cgctcgcaga gcgacgccaa ccaccgctgg     780
accgacgtcc tcgccgcacg cctgcacgag gcggcgggcg acggccggga cacgccccgc     840
tacagcgtcg tcaacgaggg catcagcggc aacggctccc tgaccagcag gccggggcgg     900
ccggccgaca cccgagcgg actgagccgg ttcagcgggc acgtgctgga acgcaccaac     960
gtcaaggccg tcgtcgtcgt cctcggcgtc aacgacgtcc tgaacagccc ggaactcgcc    1020
gaccgcgacg ccatcctgac cggcctgcgc accctcgtcg accgggcgca cgcccgggga    1080
ctgcgggtcg tcgccgccac gatcacgccg ttcggcggct acggcggcta caccgaggcc    1140
cgcgagacga tgcggcagga ggtcaacgag gagatccgct ccggccgggt cttcgacacg    1200
gtcgtcgact tcgacaaggc cctgcgcgac ccgtacgacc cgcgccggat gcgctccgac    1260
```

| | |
|---|---:|
| tacgacagcg cgaccacct gcaccccggc gacaaggggt acgcgcgcat gggcgcggtc | 1320 |
| atcgacctgg ccgcgctgaa gggcgcggcg ccggtcaagg cgtag | 1365 |

<210> SEQ ID NO 59
<211> LENGTH: 1023
<212> TYPE: DNA
<213> ORGANISM: Streptomyces coelicolor

<400> SEQUENCE: 59

| | |
|---|---:|
| atgacgagca tgtcgagggc gagggtggcg cggcggatcg cggccggcgc ggcgtacggc | 60 |
| ggcggcggca tcggcctggc gggagcggcg gcggtcggtc tggtggtggc cgaggtgcag | 120 |
| ctggccagac gcagggtggg ggtgggcacg ccgacccggg tgccgaacgc gcagggactg | 180 |
| tacgcggca ccctgcccac ggccggcgac ccgccgctgc ggctgatgat gctgggcgac | 240 |
| tccacggccg ccgggcaggg cgtgcaccgg gccgggcaga cgccgggcgc gctgctggcg | 300 |
| tccgggctcg cggcggtggc ggagcggccg gtgcggctgg ggtcggtcgc ccagccgggg | 360 |
| gcgtgctcgg acgacctgga ccggcaggtg gcgctggtgc tcgccgagcc ggaccgggtg | 420 |
| cccgacatct gcgtgatcat ggtcggcgcc aacgacgtca cccaccggat gccggcgacc | 480 |
| cgctcggtgc ggcacctgtc ctcggcggta cggcggctgc gcacggccgg tgcggaggtg | 540 |
| gtggtcggca cctgtccgga cctgggcacg atcgagcggg tgcggcagcc gctgcgctgg | 600 |
| ctggcccggc gggcctcacg gcagctcgcg gcggcacaga ccatcggcgc cgtcgagcag | 660 |
| ggcgggcgca cggtgtcgct gggcgacctg ctgggtccgg agttcgcgca gaacccgcgg | 720 |
| gagctcttcg gccccgacaa ctaccacccc tccgccgagg ggtacgccac ggccgcgatg | 780 |
| gcggtactgc cctcggtgtg cgccgcgctc ggcctgtggc cggccgacga ggagcacccg | 840 |
| gacgcgctgc gccgcgaggg cttcctgccg gtggcgcgcg cggcggcgga ggcggcgtcc | 900 |
| gaggcgggta cggaggtcgc cgccgccatg cctacggggc ctcggggggcc ctgggcgctg | 960 |
| ctgaagcgcc ggagacggcg tcgggtgtcg gaggcggaac cgtccagccc gtccggcgtt | 1020 |
| tga | 1023 |

<210> SEQ ID NO 60
<211> LENGTH: 918
<212> TYPE: DNA
<213> ORGANISM: Streptomyces coelicolor

<400> SEQUENCE: 60

| | |
|---|---:|
| atgggtcgag ggacggacca gcggacgcgg tacggccgtc gccgggcgcg tgtcgcgctc | 60 |
| gccgccctga ccgccgccgt cctgggcgtg ggcgtggcgg gctgcgactc cgtgggcggc | 120 |
| gactcacccg ctccttccgg cagcccgtcg aagcggacga ggacggcgcc cgcctgggac | 180 |
| accagcccgg cgtccgtcgc cgccgtgggc gactccatca cgcgcggctt cgacgcctgt | 240 |
| gcggtgctgt cggactgccc ggaggtgtcg tgggcgaccg gcagcagcgc gaaggtcgac | 300 |
| tcgctggccg tacggctgct ggggaaggcg gacgcggccg agcacagctg gaactacgcg | 360 |
| gtcaccgggg cccggatggc ggacctgacc gctcaggtga cgcgggcggc gcagcgcgag | 420 |
| ccggagctgg tggcggtgat ggccggggcg aacgacgcgt gccggtccac gacctcggcg | 480 |
| atgacgccgg tggcggactt ccgggcgcag ttcgaggagg cgatggccac cctgcgcaag | 540 |
| aagctcccca aggcgcaggt gtacgtgtcg agcatcccgg acctcaagcg gctctggtcc | 600 |
| cagggccgca ccaacccgct gggcaagcag gtgtggaagc tcggcctgtg cccgtcgatg | 660 |
| ctgggcgacg cggactccct ggactcggcg gcgaccctgc ggcgcaacac ggtgcgcgac | 720 |

```
cgggtggcgg actacaacga ggtgctgcgg gaggtctgcg cgaaggaccg gcggtgccgc    780
agcgacgacg gcgcggtgca cgagttccgg ttcggcacgg accagttgag ccactgggac    840
tggttccacc cgagtgtgga cggccaggcc cggctggcgg agatcgccta ccgcgcggtc    900
accgcgaaga atccctga                                                  918
```

<210> SEQ ID NO 61
<211> LENGTH: 1068
<212> TYPE: DNA
<213> ORGANISM: Streptomyces rimosus

<400> SEQUENCE: 61

```
ttcatcacaa cgatgtcaca acaccggcca tccgggtcat ccctgatcgt gggaatgggt     60
gacaagcctt cccgtgacga aagggtcctg ctacatcaga aatgacagaa atcctgctca    120
gggaggttcc atgagactgt cccgacgcgc ggccacggcg tccgcgctcc tcctcacccc    180
ggcgctcgcg ctcttcggcg cgagcgccgc cgtgtccgcg ccgcgaatcc aggccaccga    240
ctacgtggcc ctcggcgact cctactcctc ggggtcggc gcgggcagct acgacagcag    300
cagtggctcc tgtaagcgca gcaccaagtc ctacccggcc ctgtgggccg cctcgcacac    360
cggtacgcgg ttcaacttca ccgcctgttc gggcgcccgc acaggagacg tgctggccaa    420
gcagctgacc ccgtcaact ccggcaccga cctggtcagc attaccatcg gcggcaacga    480
cgcgggcttc gccgacacca tgaccacctg caacctccag ggcgagagcg cgtgcctggc    540
gcggatcgcc aaggcgcgcg cctacatcca gcagacgctg cccgcccagc tggaccaggt    600
ctacgacgcc atcgacagcc gggcccccgc agcccaggtc gtcgtcctgg gctacccgcg    660
cttctacaag ctgggcggca gctgcgccgt cggtctctcg gagaagtccc gcgcggccat    720
caacgccgcc gccgacgaca tcaacgccgt caccgccaag cgcgccgccg accacggctt    780
cgccttcggg gacgtcaaca cgaccttcgc cgggcacgag ctgtgctccg gcgccccctg    840
gctgcacagc gtcaccccttc ccgtggagaa ctcctaccac cccacggcca acggacagtc    900
caagggctac ctgcccgtcc tgaactccgc cacctgatct cgcggctact ccgcccctga    960
cgaagtcccg ccccggggcg gggcttcgcc gtaggtgcgc gtaccgccgt cgcccgtcgc   1020
gccggtggcc ccgccgtacg tgccgccgcc cccggacgcg gtcggttc                1068
```

<210> SEQ ID NO 62
<211> LENGTH: 1008
<212> TYPE: DNA
<213> ORGANISM: Aeromonas hydrophila

<400> SEQUENCE: 62

```
atgaaaaaat ggtttgtgtg tttattggga ttggtcgcgc tgacagttca ggcagccgac     60
agtcgccccg ccttttcccg gatcgtgatg ttcggcgaca gcctctccga taccggcaaa    120
atgtacagca agatgcgcgg ttacctcccc tccagcccgc cctactatga gggccgtttc    180
tccaacggac ccgtctggct ggagcagctg accaaacagt tcccgggtct gaccatcgcc    240
aacgaagcgg aaggcggtgc cactgccgtg gcttacaaca agatctcctg gaatcccaag    300
tatcaggtca tcaacaacct ggactacgag gtcacccagt tcttgcagaa agacagcttc    360
aagccggacg atctggtgat cctctgggtc ggtgccaatg actatctggc ctatggctgg    420
aacacggagc aggatgccaa gcgggttcgc gatgccatca gcgatgcggc caaccgcatg    480
gtactgaacg gtgccaagca gatactgctg ttcaacctgc cggatctggg ccagaacccg    540
tcagctcgca gtcagaaggt ggtcgaggcg gtcagccatg tctccgccta tcacaaccag    600
```

```
ctgctgctga acctggcacg ccagctggcc cccaccggca tggtaaagct gttcgagatc    660
gacaagcaat ttgccgagat gctgcgtgat ccgcagaact tcggcctgag cgacgtcgag    720 aaccctgct acgacggcgg ctatgtgtgg aagccgtttg ccacccgcag cgtcagcacc     780
gaccgccagc tctccgcctt cagtccgcag gaacgcctcg ccatcgccgg caacccgctg    840
ctggcacagg ccgttgccag tcctatggcc cgccgcagcg ccagcccct caactgtgag     900 ggcaagatgt tctgggatca ggtacacccg accactgtcg tgcacgcagc cctgagcgag    960
cgcgccgcca ccttcatcgc gaaccagtac gagttcctcg cccactga                1008
```

<210> SEQ ID NO 63
<211> LENGTH: 1011
<212> TYPE: DNA
<213> ORGANISM: Aeromonas salmonicida

<400> SEQUENCE: 63

```
atgaaaaaat ggtttgtttg tttattgggg ttgatcgcgc tgacagttca ggcagccgac     60
actcgccccg ccttctcccg gatcgtgatg ttcggcgaca gcctctccga taccggcaaa    120
atgtacagca gatgcgcgg ttacctcccc tccagcccgc cctactatga gggccgtttc     180
tccaacggac ccgtctggct ggagcagctg accaagcagt tcccgggtct gaccatcgcc    240
aacgaagcgg aaggcggtgc cactgccgtg gcttacaaca gatctcctg gaatcccaag     300 tatcaggtca tcaacaacct ggactacgag gtcacccagt tcttgcagaa agacagcttc    360
aagccggaca tctggtgat cctctgggtc ggtgccaatg actatctggc atatggctgg     420
aatacggagc aggatgccaa gcgagttcgc gatgccatca gcgatgcggc caaccgcatg    480
gtactgaacg gtgccaagca gatactgctg ttcaacctgc cggatctggg ccagaacccg    540
tcagcccgca gtcagaaggt ggtcgaggcg gtcagccatg tctccgccta tcacaacaag    600
ctgctgctga acctggcacg ccagctggcc cccaccggca tggtaaagct gttcgagatc    660
gacaagcaat ttgccgagat gctgcgtgat ccgcagaact tcggcctgag cgacgtcgag    720 aaccctgct acgacggcgg ctatgtgtgg aagccgtttg ccacccgcag cgtcagcacc     780
gaccgccagc tctccgcctt cagtccgcag gaacgcctcg ccatcgccgg caacccgctg    840
ctggcacagg ccgttgccag tcctatggcc cgccgcagcg ccagcccct caactgtgag     900 ggcaagatgt tctgggatca ggtacacccg accactgtcg tgcacgcagc cctgagcgag    960
cgcgccgcca ccttcatcga gacccagtac gagttcctcg cccacggatg a            1011
```

<210> SEQ ID NO 64
<211> LENGTH: 51
<212> TYPE: DNA
<213> ORGANISM: Unknown
<220> FEATURE:
<223> OTHER INFORMATION: Description of Unknown: Alpha-amylase
      terminator oligonucleotide

<400> SEQUENCE: 64

```
cgggacttac cgaaagaaac catcaatgat ggtttctttt tgttcataa a                51
```

<210> SEQ ID NO 65
<211> LENGTH: 59
<212> TYPE: DNA
<213> ORGANISM: Unknown
<220> FEATURE:
<223> OTHER INFORMATION: Description of Unknown: Alkaline protease
      terminator oligonucleotide

<400> SEQUENCE: 65

```
caagactaaa gaccgttcgc ccgttttgc aataagcggg cgaatcttac ataaaaata      59

<210> SEQ ID NO 66
<211> LENGTH: 61
<212> TYPE: DNA
<213> ORGANISM: Unknown
<220> FEATURE:
<223> OTHER INFORMATION: Description of Unknown: Glutamic-acid specific
      terminator oligonucleotide

<400> SEQUENCE: 66
acggccgtta gatgtgacag cccgttccaa aaggaagcgg gctgtcttcg tgtattattg     60
t                                                                    61

<210> SEQ ID NO 67
<211> LENGTH: 54
<212> TYPE: DNA
<213> ORGANISM: Unknown
<220> FEATURE:
<223> OTHER INFORMATION: Description of Unknown: Levanase terminator
      oligonucleotide

<400> SEQUENCE: 67
tcttttaaag gaaaggctgg aatgcccggc attccagcca catgatcatc gttt           54

<210> SEQ ID NO 68
<211> LENGTH: 56
<212> TYPE: DNA
<213> ORGANISM: Unknown
<220> FEATURE:
<223> OTHER INFORMATION: Description of Unknown: Subtilisin E terminator
      oligonucleotide

<400> SEQUENCE: 68
gctgacaaat aaaagaagc aggtatggag gaacctgctt cttttacta ttattg           56

<210> SEQ ID NO 69
<211> LENGTH: 1500
<212> TYPE: DNA
<213> ORGANISM: Novosphingobium aromaticivorans

<400> SEQUENCE: 69
tgccggaact caagcggcgt ctagccgaac tcatgcccga aagcgcgtgg cactatcccg     60
aagaccaggt ctcggacgcc agcgagcgcc tgatggccgc cgaaatcacg cgcgaacagc    120
tctaccgcca gctccacgac gagctgccct atgacagtac cgtacgtccc gagaagtacc    180
tccatcgcaa ggacggttcg atcgagatcc accagcagat cgtgattgcc cgcgagacac    240
agcgtccgat cgtgctgggc aagggtggcg cgaagatcaa ggcgatcgga gaggccgcac    300
gcaaggaact ttcgcaattg ctcgacacca aggtgcacct gttcctgcat gtgaaggtcg    360
acgagcgctg ggccgacgcc aaggaaatct acgaggaaat cggcctcgaa tgggtcaagt    420
gaagctcttc gcgcgccgct gcgccccagt acttctcgcc cttgccgggc tggctccggc    480
ggctacggtc gcgcgggaag caccgctggc cgaaggcgcg cgttacgttg cgctgggaag    540
ctccttcgcc gcaggtccgg gcgtggggcc caacgcgccc ggatcgcccg aacgctgcgg    600
ccggggcacg ctcaactacc cgcacctgct cgccgaggcg ctcaagctcg atctcgtcga    660
tgcgacctgc agcggcgcga cgacccacca cgtgctgggc ccctggaacg aggttccccc    720
tcagatcgac agcgtgaatg cgacacccg cctcgtcacc ctgaccatcg gcggaaacga    780
tgtgtcgttc gtcggcaaca tcttcgccgc cgcttgcgag aagatggcgt cgcccgatcc    840
```

```
gcgctgcggc aagtggcggg agatcaccga ggaagagtgg caggccgacg aggagcggat    900
gcgctccatc gtacgccaga tccacgcccg cgcgcctctc gcccgggtgg tggtggtcga    960
ttacatcacg gtcctgccgc catcaggcac ttgcgctgcc atggcgattt cgccggaccg   1020
gctggcccag agccgcagcg ccgcgaaacg gcttgcccgg attaccgcac gggtcgcgcg   1080
agaagagggt gcatcgctgc tcaagttctc gcatatctcg cgccggcacc atccatgctc   1140
tgccaagccc tggagcaacg gccttccgc cccggccgac gacggcatcc cggtccatcc   1200
gaaccggctc ggacatgctg aagcggcagc ggcgctggtc aagcttgtga aattgatgaa   1260
gtagctactg cactgatttc aaatagtatt gcctgtcagc tttccagccc ggattgttgc   1320
agcgcaacag aaacttgtcc gtaatggatt gatggtttat gtcgctcgca aattgccgtc   1380
gaagggaacg ggcgcgtcgc tcgttaacgt cctgggtgca gcagtgacgg agcgcgtgga   1440
tgagtgatac tggcggtgtc atcggtgtac gcgccgccat tcccatgcct gtacgcgccg   1500
```

<210> SEQ ID NO 70
<211> LENGTH: 280
<212> TYPE: PRT
<213> ORGANISM: Aeromonas salmonicida

<400> SEQUENCE: 70

```
Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Arg Ser Ala Ser Pro
225                 230                 235                 240

Leu Asn Cys Glu Gly Lys Met Phe Trp Asp Gln Val His Pro Thr Thr
                245                 250                 255

Val Val His Ala Ala Leu Ser Glu Arg Ala Ala Thr Phe Ile Glu Thr
            260                 265                 270
```

```
Gln Tyr Glu Phe Leu Ala His Gly
        275                 280

<210> SEQ ID NO 71
<211> LENGTH: 56
<212> TYPE: DNA
<213> ORGANISM: Unknown
<220> FEATURE:
<223> OTHER INFORMATION: Description of Unknown: Subtilisin E terminator
      oligonucleotide

<400> SEQUENCE: 71
gctgacaaat aaaaagaagc aggtatggag gaacctgctt ctttttacta ttattg      56

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Met, Ile, Leu, Val, Ala, Gly, Cys, His, Lys,
      Trp, Tyr or Phe
<220> FEATURE:
<221> NAME/KEY: MOD_RES
<222> LOCATION: (8)..(8)
<223> OTHER INFORMATION: Met, Ile, Leu, Val, Ala, Gly, Cys, His, Lys,
      Trp, Tyr or Phe

<400> SEQUENCE: 72

Xaa Xaa Xaa Xaa Gly Asp Ser Xaa
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Ile, Leu, Val, Ala, Gly, Cys, His, Lys,
      Trp, Tyr or Phe
<220> FEATURE:
<221> NAME/KEY: MOD_RES
<222> LOCATION: (3)..(3)
<223> OTHER INFORMATION: Met, Ile, Leu, Val, Ala, Gly, Cys, His, Lys,
      Trp, Tyr or Phe
<220> FEATURE:
<221> NAME/KEY: MOD_RES
<222> LOCATION: (6)..(6)
<223> OTHER INFORMATION: Met, Ile, Leu, Val, Ala, Gly, Cys, His, Lys,
      Trp, Tyr or Phe

<400> SEQUENCE: 73

Xaa Gly Xaa Asn Asp Xaa
1               5

<210> SEQ ID NO 74
<211> LENGTH: 102
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
```

```
cccgctcga ggcttttctt ttggaagaaa atatagggaa aatggtactt gttaaaaatt    60
cggaatattt atacaatatc atatgtttca cattgaaagg gg                     102
```

<210> SEQ ID NO 75
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

```
tggaatctcg aggttttatc ctttaccttg tctcc                              35
```

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Asn Asp Ala
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Asn Asp Leu
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Asp Ser Tyr
1

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Leu, Ala, Val, Ile, Phe, Tyr, His, Gln, Thr,
      Asn, Met or Ser

<400> SEQUENCE: 79

Gly Gly Asn Asp Xaa
1               5

-continued

```
<210> SEQ ID NO 80
<211> LENGTH: 295
<212> TYPE: PRT
<213> ORGANISM: Aeromonas hydrophila

<400> SEQUENCE: 80

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295

<210> SEQ ID NO 81
<211> LENGTH: 295
<212> TYPE: PRT
<213> ORGANISM: Aeromonas salmonicida

<400> SEQUENCE: 81

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Lys Gln Phe Pro
        35                  40                  45
```

```
Gly Leu Thr Ile Ala Asn Glu Ala Glu Gly Ala Thr Ala Val Ala
    50                  55                  60

Tyr Asn Lys Ile Ser Trp Asn Pro Lys Tyr Gln Val Tyr Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Gln Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Val Ser His Val Ser Ala Tyr His Asn Lys Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
    195                 200                 205

Leu Ser Asp Val Glu Asn Pro Cys Tyr Asp Gly Gly Tyr Val Trp Lys
210                 215                 220

Pro Phe Ala Thr Arg Ser Val Ser Thr Asp Arg Gln Leu Ser Ala Phe
225                 230                 235                 240

Ser Pro Gln Glu Arg Leu Ala Ile Ala Gly Asn Pro Leu Leu Ala Gln
                245                 250                 255

Ala Val Ala Ser Pro Met Ala Arg Arg Ser Ala Ser Pro Leu Asn Cys
            260                 265                 270

Glu Gly Lys Met Phe Trp Asp Gln Val His Pro Thr Thr Val Val His
    275                 280                 285

Ala Ala Leu Ser Glu Arg Ala
    290                 295

<210> SEQ ID NO 82
<211> LENGTH: 247
<212> TYPE: PRT
<213> ORGANISM: Streptomyces coelicolor

<400> SEQUENCE: 82

Tyr Val Ala Leu Gly Asp Ser Tyr Ser Ala Gly Ser Gly Val Leu Pro
1               5                   10                  15

Val Asp Pro Ala Asn Leu Leu Cys Leu Arg Ser Thr Ala Asn Tyr Pro
            20                  25                  30

His Val Ile Ala Asp Thr Thr Gly Ala Arg Leu Thr Asp Val Thr Cys
        35                  40                  45

Gly Ala Ala Gln Thr Ala Asp Phe Thr Arg Ala Gln Tyr Pro Gly Val
    50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Gly Lys Gly Ser Pro Cys Lys
            100                 105                 110

Asp Arg His Gly Thr Ser Phe Asp Asp Glu Ile Glu Ala Asn Thr Tyr
        115                 120                 125
```

```
Pro Ala Leu Lys Glu Ala Leu Leu Gly Val Arg Ala Arg Ala Pro His
    130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
        195                 200                 205

Gly His Asp Ala Cys Glu Ala Pro Gly Thr Arg Trp Ile Glu Pro Leu
210                 215                 220

Leu Phe Gly His Ser Leu Val Pro Val His Pro Asn Ala Leu Gly Glu
225                 230                 235                 240

Arg Arg Met Ala Glu His Thr
                245

<210> SEQ ID NO 83
<211> LENGTH: 247
<212> TYPE: PRT
<213> ORGANISM: Streptomyces coelicolor

<400> SEQUENCE: 83

Tyr Val Ala Leu Gly Asp Ser Tyr Ser Ala Gly Ser Gly Val Leu Pro
1               5                   10                  15

Val Asp Pro Ala Asn Leu Leu Cys Leu Arg Ser Thr Ala Asn Tyr Pro
                20                  25                  30

His Val Ile Ala Asp Thr Thr Gly Ala Arg Leu Thr Asp Val Thr Cys
            35                  40                  45

Gly Ala Ala Gln Thr Ala Asp Phe Thr Arg Ala Gln Tyr Pro Gly Val
        50                  55                  60

Ala Pro Gln Leu Asp Ala Leu Gly Thr Gly Thr Asp Leu Val Thr Leu
65                  70                  75                  80

Thr Ile Gly Gly Asn Asp Asn Ser Thr Phe Ile Asn Ala Ile Thr Ala
                85                  90                  95

Cys Gly Thr Ala Gly Val Leu Ser Gly Gly Lys Gly Ser Pro Cys Lys
            100                 105                 110

Asp Arg His Gly Thr Ser Phe Asp Asp Glu Ile Glu Ala Asn Thr Tyr
        115                 120                 125

Pro Ala Leu Lys Glu Ala Leu Leu Gly Val Arg Ala Arg Ala Pro His
    130                 135                 140

Ala Arg Val Ala Ala Leu Gly Tyr Pro Trp Ile Thr Pro Ala Thr Ala
145                 150                 155                 160

Asp Pro Ser Cys Phe Leu Lys Leu Pro Leu Ala Ala Gly Asp Val Pro
                165                 170                 175

Tyr Leu Arg Ala Ile Gln Ala His Leu Asn Asp Ala Val Arg Arg Ala
            180                 185                 190

Ala Glu Glu Thr Gly Ala Thr Tyr Val Asp Phe Ser Gly Val Ser Asp
        195                 200                 205

Gly His Asp Ala Cys Glu Ala Pro Gly Thr Arg Trp Ile Glu Pro Leu
210                 215                 220

Leu Phe Gly His Ser Leu Val Pro Val His Pro Asn Ala Leu Gly Glu
225                 230                 235                 240

Arg Arg Met Ala Glu His Thr
                245
```

<210> SEQ ID NO 84
<211> LENGTH: 198
<212> TYPE: PRT
<213> ORGANISM: Saccharomyces cerevisiae

<400> SEQUENCE: 84

Phe Leu Leu Phe Gly Asp Ser Ile Thr Glu Phe Ala Phe Asn Thr Arg
1               5                   10                  15

Pro Ile Glu Asp Gly Lys Asp Gln Tyr Ala Leu Gly Ala Ala Leu Val
            20                  25                  30

Asn Glu Tyr Thr Arg Lys Met Asp Ile Leu Gln Arg Gly Phe Lys Gly
        35                  40                  45

Tyr Thr Ser Arg Trp Ala Leu Lys Ile Leu Pro Glu Ile Leu Lys His
    50                  55                  60

Glu Ser Asn Ile Val Met Ala Thr Ile Phe Leu Gly Ala Asn Asp Ala
65                  70                  75                  80

Cys Ser Ala Gly Pro Gln Ser Val Pro Leu Pro Glu Phe Ile Asp Asn
                85                  90                  95

Ile Arg Gln Met Val Ser Leu Met Lys Ser Tyr His Ile Arg Pro Ile
            100                 105                 110

Ile Ile Gly Pro Gly Leu Val Asp Arg Glu Lys Trp Glu Lys Glu Lys
        115                 120                 125

Ser Glu Glu Ile Ala Leu Gly Tyr Phe Arg Thr Asn Glu Asn Phe Ala
    130                 135                 140

Ile Tyr Ser Asp Ala Leu Ala Lys Leu Ala Asn Glu Glu Lys Val Pro
145                 150                 155                 160

Phe Val Ala Leu Asn Lys Ala Phe Gln Gln Glu Gly Gly Asp Ala Trp
                165                 170                 175

Gln Gln Leu Leu Thr Asp Gly Leu His Phe Ser Gly Lys Gly Tyr Lys
            180                 185                 190

Ile Phe His Asp Glu Leu
        195

<210> SEQ ID NO 85
<211> LENGTH: 317
<212> TYPE: PRT
<213> ORGANISM: Aeromonas salmonicida

<400> SEQUENCE: 85

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

```
Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His
305                 310                 315

<210> SEQ ID NO 86
<211> LENGTH: 320
<212> TYPE: PRT
<213> ORGANISM: Ralstonia solanacearum

<400> SEQUENCE: 86

Gln Ser Gly Asn Pro Asn Val Ala Lys Val Gln Arg Met Val Val Phe
1               5                   10                  15

Gly Asp Ser Leu Ser Asp Ile Gly Thr Tyr Thr Pro Val Ala Gln Ala
            20                  25                  30

Val Gly Gly Gly Lys Phe Thr Thr Asn Pro Gly Pro Ile Trp Ala Glu
        35                  40                  45

Thr Val Ala Ala Gln Leu Gly Val Thr Leu Thr Pro Ala Val Met Gly
    50                  55                  60

Tyr Ala Thr Ser Val Gln Asn Cys Pro Lys Ala Gly Cys Phe Asp Tyr
65                  70                  75                  80

Ala Gln Gly Gly Ser Arg Val Thr Asp Pro Asn Gly Ile Gly His Asn
                85                  90                  95

Gly Gly Ala Gly Ala Leu Thr Tyr Pro Val Gln Gln Gln Leu Ala Asn
            100                 105                 110

Phe Tyr Ala Ala Ser Asn Asn Thr Phe Asn Gly Asn Asn Asp Val Val
        115                 120                 125

Phe Val Leu Ala Gly Ser Asn Asp Ile Phe Phe Trp Thr Thr Ala Ala
    130                 135                 140

Ala Thr Ser Gly Ser Gly Val Thr Pro Ala Ile Ala Thr Ala Gln Val
145                 150                 155                 160

Gln Gln Ala Ala Thr Asp Leu Val Gly Tyr Val Lys Asp Met Ile Ala
                165                 170                 175

Lys Gly Ala Thr Gln Val Tyr Val Phe Asn Leu Pro Asp Ser Ser Leu
            180                 185                 190
```

```
Thr Pro Asp Gly Val Ala Ser Gly Thr Thr Gly Gln Ala Leu Leu His
        195                 200                 205

Ala Leu Val Gly Thr Phe Asn Thr Thr Leu Gln Ser Gly Leu Ala Gly
        210                 215                 220

Thr Ser Ala Arg Ile Ile Asp Phe Asn Ala Gln Leu Thr Ala Ala Ile
225                 230                 235                 240

Gln Asn Gly Ala Ser Phe Gly Phe Ala Asn Thr Ser Ala Arg Ala Cys
                245                 250                 255

Asp Ala Thr Lys Ile Asn Ala Leu Val Pro Ser Ala Gly Gly Ser Ser
                260                 265                 270

Leu Phe Cys Ser Ala Asn Thr Leu Val Ala Ser Gly Ala Asp Gln Ser
                275                 280                 285

Tyr Leu Phe Ala Asp Gly Val His Pro Thr Thr Ala Gly His Arg Leu
                290                 295                 300

Ile Ala Ser Asn Val Leu Ala Arg Leu Leu Ala Asp Asn Val Ala His
305                 310                 315                 320

<210> SEQ ID NO 87
<211> LENGTH: 308
<212> TYPE: PRT
<213> ORGANISM: Aeromonas hydrophila

<400> SEQUENCE: 87

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
                20                  25                  30

Phe Ser Asn Gly Pro Val Trp Leu Glu Gln Leu Thr Asn Glu Phe Pro
                35                  40                  45

Gly Leu Thr Ile Ala Asn Glu Ala Glu Gly Gly Pro Thr Ala Val Ala
        50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
                100                 105                 110

Trp Asn Thr Glu Gln Asp Ala Lys Arg Val Arg Asp Ala Ile Ser Asp
                115                 120                 125

Ala Ala Asn Arg Met Val Leu Asn Gly Ala Lys Glu Ile Leu Leu Phe
        130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
                180                 185                 190

Ile Asp Lys Gln Phe Ala Glu Met Leu Arg Asp Pro Gln Asn Phe Gly
                195                 200                 205

Leu Ser Asp Gln Arg Asn Ala Cys Tyr Gly Gly Ser Tyr Val Trp Lys
        210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255
```

-continued

```
Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala Ala Thr Phe Ile Glu Ser Gln Tyr Glu
    290                 295                 300

Phe Leu Ala His
305

<210> SEQ ID NO 88
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Leu Ile Leu Gly Asp Ser Leu Ser Ala Gly Tyr Arg Met Ser Ala
1               5                   10                  15

Ser Ala Ala Trp Pro Ala Leu Leu Asn Asp Lys Trp Gln Ser Lys Thr
            20                  25                  30

Ser Val Val Asn Ala Ser Ile Ser Gly Asp Thr Ser Gln Gln Gly Leu
        35                  40                  45

Ala Arg Leu Pro Ala Leu Leu Lys Gln His Gln Pro Arg Trp Val Leu
    50                  55                  60

Val Glu Leu Gly Gly Asn Asp Gly Leu Arg Gly Phe Gln Pro Gln Gln
65                  70                  75                  80

Thr Glu Gln Thr Leu Arg Gln Ile Leu Gln Asp Val Lys Ala Ala Asn
                85                  90                  95

Ala Glu Pro Leu Leu Met Gln Ile Arg Leu Pro Ala Asn Tyr Gly Arg
            100                 105                 110

Arg Tyr Asn Glu Ala Phe Ser Ala Ile Tyr Pro Lys Leu Ala Lys Glu
        115                 120                 125

Phe Asp Val Pro Leu Leu Pro Phe Phe Met Glu Glu Val Tyr Leu Lys
    130                 135                 140

Pro Gln Trp Met Gln Asp Asp Gly Ile His Pro Asn Arg Asp Ala Gln
145                 150                 155                 160

Pro Phe Ile Ala Asp Trp Met
                165

<210> SEQ ID NO 89
<211> LENGTH: 295
<212> TYPE: PRT
<213> ORGANISM: Aeromonas hydrophila

<400> SEQUENCE: 89

Ile Val Met Phe Gly Asp Ser Leu Ser Asp Thr Gly Lys Met Tyr Ser
1               5                   10                  15

Lys Met Arg Gly Tyr Leu Pro Ser Ser Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
```

```
                85                  90                  95
Asp Leu Val Ile Leu Trp Val Gly Ala Asn Asp Tyr Leu Ala Tyr Gly
    100                 105                 110

Trp Asn Thr Glu Gln Asp Ala Lys Arg Val Arg Asp Ala Ile Ser Asp
            115                 120                 125

Ala Ala Asn Arg Met Val Leu Asn Gly Ala Lys Glu Ile Leu Leu Phe
130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
    290                 295

<210> SEQ ID NO 90
<211> LENGTH: 1225
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (101)..(1141)

<400> SEQUENCE: 90
gcttttcttt tggaagaaaa tatagggaaa atggtacttg ttaaaaattc ggaatattta      60
tacaatatca tatgtttcac attgaaaggg gaggagaatc atg aaa caa caa aaa      115
                                             Met Lys Gln Gln Lys
                                             1               5 cgg ctt tac gcc cga ttg ctg acg ctg tta ttt gcg ctc atc ttc ttg      163
Arg Leu Tyr Ala Arg Leu Leu Thr Leu Leu Phe Ala Leu Ile Phe Leu
             10                  15                  20 ctg cct cat tct gca gct tca gca gca gat aca aga ccg gcg ttt agc      211
Leu Pro His Ser Ala Ala Ser Ala Ala Asp Thr Arg Pro Ala Phe Ser
         25                  30                  35 cgg atc gtc atg ttt gga gat agc ctg agc gat acg ggc aaa atg tat      259
Arg Ile Val Met Phe Gly Asp Ser Leu Ser Asp Thr Gly Lys Met Tyr
     40                  45                  50 agc aaa atg aga ggc tat ctt ccg tca agc ccg ccg tat tat gaa ggc      307
Ser Lys Met Arg Gly Tyr Leu Pro Ser Ser Pro Pro Tyr Tyr Glu Gly
 55                  60                  65 cgc ttt agc aat gga ccg gtc tgg ctg gaa caa ctg acg aaa caa ttt      355
Arg Phe Ser Asn Gly Pro Val Trp Leu Glu Gln Leu Thr Lys Gln Phe
 70                  75                  80                  85
```

```
ccg gga ctg acg atc gct aat gaa gca gaa gga gga gca aca gcg gtc    403
Pro Gly Leu Thr Ile Ala Asn Glu Ala Glu Gly Gly Ala Thr Ala Val
             90                  95                 100 gcc tat aac aaa atc agc tgg gac ccg aaa tat cag gtc atc aac aac    451
Ala Tyr Asn Lys Ile Ser Trp Asp Pro Lys Tyr Gln Val Ile Asn Asn
            105                 110                 115 ctg gac tat gaa gtc aca cag ttt ctt cag aaa gac agc ttt aaa ccg    499
Leu Asp Tyr Glu Val Thr Gln Phe Leu Gln Lys Asp Ser Phe Lys Pro
            120                 125                 130 gat gat ctg gtc atc ctt tgg gtc ggc gcc aat gat tat ctg gcg tat    547
Asp Asp Leu Val Ile Leu Trp Val Gly Ala Asn Asp Tyr Leu Ala Tyr
            135                 140                 145 ggc tgg aac aca gaa caa gat gcc aaa aga gtc aga gat gcc atc agc    595
Gly Trp Asn Thr Glu Gln Asp Ala Lys Arg Val Arg Asp Ala Ile Ser
150                 155                 160                 165 gat gcc gct aat aga atg gtc ctg aac ggc gcc aaa caa atc ctg ctg    643
Asp Ala Ala Asn Arg Met Val Leu Asn Gly Ala Lys Gln Ile Leu Leu
                170                 175                 180 ttt aac ctg ccg gat ctg gga caa aat ccg agc gcc aga agc caa aaa    691
Phe Asn Leu Pro Asp Leu Gly Gln Asn Pro Ser Ala Arg Ser Gln Lys
            185                 190                 195 gtc gtc gaa gca gtc agc cat gtc agc gcc tat cat aac aaa ctg ctg    739
Val Val Glu Ala Val Ser His Val Ser Ala Tyr His Asn Lys Leu Leu
            200                 205                 210 ctg aac ctg gca aga caa ttg gca ccg acg gga atg gtt aaa ttg ttt    787
Leu Asn Leu Ala Arg Gln Leu Ala Pro Thr Gly Met Val Lys Leu Phe
            215                 220                 225 gaa att gac aaa cag ttt gcc gaa atg ctg aga gat ccg caa aat ttt    835
Glu Ile Asp Lys Gln Phe Ala Glu Met Leu Arg Asp Pro Gln Asn Phe
230                 235                 240                 245 ggc ctg agc gat gtc gaa aac ccg tgc tat gat ggc gga tat gtc tgg    883
Gly Leu Ser Asp Val Glu Asn Pro Cys Tyr Asp Gly Gly Tyr Val Trp
                250                 255                 260 aaa ccg ttt gcc aca aga agc gtc agc acg gat aga caa ctg tca gcg    931
Lys Pro Phe Ala Thr Arg Ser Val Ser Thr Asp Arg Gln Leu Ser Ala
            265                 270                 275 ttt agc ccg caa gaa aga ctg gca atc gcc gga aat ccg ctt ttg gca    979
Phe Ser Pro Gln Glu Arg Leu Ala Ile Ala Gly Asn Pro Leu Leu Ala
            280                 285                 290 caa gca gtt gct tca ccg atg gca aga aga tca gca agc ccg ctg aat    1027
Gln Ala Val Ala Ser Pro Met Ala Arg Arg Ser Ala Ser Pro Leu Asn
            295                 300                 305 tgc gaa ggc aaa atg ttt tgg gat cag gtc cat ccg aca aca gtt gtc    1075
Cys Glu Gly Lys Met Phe Trp Asp Gln Val His Pro Thr Thr Val Val
310                 315                 320                 325 cat gct gcc ctt tca gaa aga gcg gcg acg ttt atc gaa aca cag tat    1123
His Ala Ala Leu Ser Glu Arg Ala Ala Thr Phe Ile Glu Thr Gln Tyr
                330                 335                 340 gaa ttt ctg gcc cat ggc tgagttaaca gaggacggat ttcctgaagg           1171
Glu Phe Leu Ala His Gly
            345 aaatccgttt ttttatttta agcttggaga caaggtaaag gataaaacct cgag       1225

<210> SEQ ID NO 91
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 91

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Asp Thr
            20                  25                  30

Arg Pro Ala Phe Ser Arg Ile Val Met Phe Gly Asp Ser Leu Ser Asp
            35                  40                  45

Thr Gly Lys Met Tyr Ser Lys Met Arg Gly Tyr Leu Pro Ser Ser Pro
    50                  55                  60

Pro Tyr Tyr Glu Gly Arg Phe Ser Asn Gly Pro Val Trp Leu Glu Gln
65                      70                  75                  80

Leu Thr Lys Gln Phe Pro Gly Leu Thr Ile Ala Asn Glu Ala Glu Gly
                85                  90                  95

Gly Ala Thr Ala Val Ala Tyr Asn Lys Ile Ser Trp Asp Pro Lys Tyr
            100                 105                 110

Gln Val Ile Asn Asn Leu Asp Tyr Glu Val Thr Gln Phe Leu Gln Lys
            115                 120                 125

Asp Ser Phe Lys Pro Asp Asp Leu Val Ile Leu Trp Val Gly Ala Asn
    130                 135                 140

Asp Tyr Leu Ala Tyr Gly Trp Asn Thr Glu Gln Asp Ala Lys Arg Val
145                 150                 155                 160

Arg Asp Ala Ile Ser Asp Ala Ala Asn Arg Met Val Leu Asn Gly Ala
                165                 170                 175

Lys Gln Ile Leu Leu Phe Asn Leu Pro Asp Leu Gly Gln Asn Pro Ser
            180                 185                 190

Ala Arg Ser Gln Lys Val Val Glu Ala Val Ser His Val Ser Ala Tyr
    195                 200                 205

His Asn Lys Leu Leu Leu Asn Leu Ala Arg Gln Leu Ala Pro Thr Gly
    210                 215                 220

Met Val Lys Leu Phe Glu Ile Asp Lys Gln Phe Ala Glu Met Leu Arg
225                 230                 235                 240

Asp Pro Gln Asn Phe Gly Leu Ser Asp Val Glu Asn Pro Cys Tyr Asp
            245                 250                 255

Gly Gly Tyr Val Trp Lys Pro Phe Ala Thr Arg Ser Val Ser Thr Asp
            260                 265                 270

Arg Gln Leu Ser Ala Phe Ser Pro Gln Glu Arg Leu Ala Ile Ala Gly
    275                 280                 285

Asn Pro Leu Leu Ala Gln Ala Val Ala Ser Pro Met Ala Arg Arg Ser
    290                 295                 300

Ala Ser Pro Leu Asn Cys Glu Gly Lys Met Phe Trp Asp Gln Val His
305                 310                 315                 320

Pro Thr Thr Val Val His Ala Ala Leu Ser Glu Arg Ala Ala Thr Phe
                325                 330                 335

Ile Glu Thr Gln Tyr Glu Phe Leu Ala His Gly
            340                 345
```